US007385123B2

(12) United States Patent
Sauer et al.

(10) Patent No.: US 7,385,123 B2
(45) Date of Patent: Jun. 10, 2008

(54) PROCESS FOR PREPARING KETOCAROTENOIDS IN GENETICALLY MODIFIED ORGANISMS

(75) Inventors: Matt Sauer, Quedlinburg (DE); Ralf Flachmann, Quedlinburg (DE); Martin Klebsattel, Quedlinburg (DE); Christel Renate Schopfer, Quedlinburg (DE)

(73) Assignee: SunGene GmbH & Co. KGaA (DE)

( * ) Notice: Subject to any disclaimer, the term of this patent is extended or adjusted under 35 U.S.C. 154(b) by 0 days.

(21) Appl. No.: 10/524,827

(22) PCT Filed: Aug. 18, 2003

(86) PCT No.: PCT/EP03/09106

§ 371 (c)(1),
(2), (4) Date: Feb. 18, 2005

(87) PCT Pub. No.: WO2004/018694

PCT Pub. Date: Mar. 4, 2004

(65) Prior Publication Data

US 2006/0112451 A1   May 25, 2006

(30) Foreign Application Priority Data

Aug. 20, 2002 (DE) ............................... 102 38 978
Aug. 20, 2002 (DE) ............................... 102 38 979
Aug. 20, 2002 (DE) ............................... 102 38 980
Nov. 13, 2002 (DE) ............................... 102 53 112
Dec. 16, 2002 (DE) ............................... 102 58 971

(51) Int. Cl.
*C12N 15/29* (2006.01)
*C12N 15/31* (2006.01)
*C12N 15/52* (2006.01)
*C12N 15/82* (2006.01)
*A01H 5/00* (2006.01)

(52) U.S. Cl. ................... 800/323; 800/282; 800/298
(58) Field of Classification Search ............... 800/282, 800/298, 323; 435/419, 465; 536/23.1, 536/23.2, 23.6, 23.7
See application file for complete search history.

(56) References Cited

U.S. PATENT DOCUMENTS 6,232,530 B1 * 5/2001 DellaPenna et al. ........ 800/282

FOREIGN PATENT DOCUMENTS

| EP | 0 735 137 A1 | 10/1996 |
|---|---|---|
| WO | WO-9818910 | 5/1998 |
| WO | WO 99/07867 * | 2/1999 |
| WO | WO-9907867 | 2/1999 |
| WO | WO-9961652 | 12/1999 |
| WO | WO-0120011 A1 | 3/2001 |

OTHER PUBLICATIONS

Ronen G. et al. The Plant Journal, 1999; vol. 17, No. 4, pp. 341-351.*
Kaneko T. et al. "beta-carotene ketolase [Nostoc sp. PCC 7120]" *Database NCBI* Accession No. BAB74888, Oct. 22, 2004.
Kaneko T. et al. "Beta-carotene ketolase" *Data Uniprot 'Online!* Accession No. Q8YSA0, Mar. 1, 2002, XP-002275240.
Kaneko T. et al. "Nostoc sp. PCC 7120 DNA, complete genome, section 12/19." *Database EM_PRO 'Online!* Accession No. AP003592, Nov. 28, 2001, XP-002275241.
Misawa N. et al. "Paracoccus sp. MBIC1143 crtW, crtZ, crtY, crtI, crtB genes, complete cds." *Database NCBI* Accession No. D58420, Aug. 28, 2002.
Misawa N. et al. "Alcaligenes sp. crtW and crtZ genes for beta-carotene hydroxylase and beta-Carotene ketolase, complete cds." *Database NCBI* Accession No. D58422, Feb. 1, 2003.
Lotan T. "Cloning and expression in *Escherichia coli* of the gene encoding β-C-4-oxygenase, that converts β-carotene to the ketocarotenoid canthaxanthin in *Haematococcus pluvialis*" FEBS Letters 364 (1995), pp. 125-128.
Harker M. et al. "*H. pluvialis* mRNA for beta-carotene C-4 oxygenase" *Database NCBI* Accession No. X86782, Sep. 9, 2004.
Kajiwara S. et al. "*Haematococcus pluvialis* mRNA for beta-carotene ketolase, complete cds." *Database NCBI* Accession No. D45881, Feb. 1, 1999.
Harker M. et al. "*Paracoccus marcusii* crtW, crtZ, crtY, crtI, crtB & crtE genes." *Database NCBI* Accession No. Y15112, Sep. 15, 1999.
Kaneko T. et al. "b-carotene ketolase [*Synechocystis* sp. PCC 6803]." *Database NCBI* Accession No. NP_442491, Nov. 9, 2004.
Hannibal L. et al. "*Bradyrhizobium* sp. ORS278 geranylgeranyl synthase (crtE), lycopene cyclase (crtY), phytoene desaturase (crtI), phytoene synthase (crtB), and beta-carotene ketolase (crtW) genes, complete cds." *Database NCBI* Accession No. AF218415, Jun. 22, 2000.
Kaneko T. et al. "Complete genomic sequence of the filamentous nitrogen-fixing cyanobacterium *Anabaena* sp. strain PCC 7120" *DNA Research* 8, (2001) pp. 205.213.
Kaneko T. et al. "Nostoc sp. PCC 7120 DNA, complete genome, section 12/19" *Database NCBI* Accession No. AP003592, Nov. 28, 2001.
Kajiwara S. et al. "Isolation and functional identification of a novel cDNA for astaxanthin biosynthesis from *Haematococcus pluvialis*, and astaxanthin synthesis in *Escherichia coli*" Plant Molecular Biology 29, (1995), pp. 343-352.

(Continued)

*Primary Examiner*—Russell P. Kallis
(74) *Attorney, Agent, or Firm*—Connolly Bove Lodge & Hutz LLP

(57) ABSTRACT

The present invention relates to a process for preparing ketocarotenoids by cultivation of genetically modified organisms which, compared with the wild type, have a modified ketolase activity, to the genetically modified organisms, and to the use thereof as human and animal foods and for producing ketocarotenoid extracts.

30 Claims, 18 Drawing Sheets

OTHER PUBLICATIONS

Harker M. et al. "Biosynthesis of ketocarotenoids in transgenic cyanobacteria expressing the algal gene for β-C-4-oxygenase, *crtO*" *FEBS Letters* 404, (1997), pp. 129-134.

Albrecht M. et al. "Expression of a ketolase gene mediates the synthesis of canthaxanthin in *Synechococcus* leading to tolerance against photoinhibition, pigment degradation and UV-B sensitivity of photosynthesis" *Photochemistry and Photobiology*, 73(5), (2001), pp. 551-555.

Mann V. et al. "Metabolic engineering of astaxanthin production in tobacco flowers" *Nature Biotechnology*, vol. 18, (Aug. 2000), pp. 888-892.

* cited by examiner

SEQUENCE LISTING

```
<160> NUMBER OF SEQ ID NOS: 74

<210> SEQ ID NO 1
<211> LENGTH: 777
<212> TYPE: DNA
<213> ORGANISM: Nostoc sp. Strain PCC7120
<220> FEATURE:
<221> NAME/KEY: CDS

<400> SEQUENCE: 1 atg gtt cag tgt caa cca tca tct ctg cat tca gaa aaa ctg gtg tta      48
Met Val Gln Cys Gln Pro Ser Ser Leu His Ser Glu Lys Leu Val Leu
1               5                   10                  15 ttg tca tcg aca atc aga gat gat aaa aat att aat aag ggt ata ttt      96
Leu Ser Ser Thr Ile Arg Asp Asp Lys Asn Ile Asn Lys Gly Ile Phe
            20                  25                  30 att gcc tgc ttt atc tta ttt tta tgg gca att agt tta atc tta tta     144
Ile Ala Cys Phe Ile Leu Phe Leu Trp Ala Ile Ser Leu Ile Leu Leu
        35                  40                  45 ctc tca ata gat aca tcc ata att cat aag agc tta tta ggt ata gcc     192
Leu Ser Ile Asp Thr Ser Ile Ile His Lys Ser Leu Leu Gly Ile Ala
    50                  55                  60
```

```
atg ctt tgg cag acc ttc tta tat aca ggt tta ttt att act gct cat       240
Met Leu Trp Gln Thr Phe Leu Tyr Thr Gly Leu Phe Ile Thr Ala His
 65                  70                  75                  80 gat gcc atg cac ggc gta gtt tat ccc aaa aat ccc aga ata aat aat       288
Asp Ala Met His Gly Val Val Tyr Pro Lys Asn Pro Arg Ile Asn Asn
                 85                  90                  95 ttt ata ggt aag ctc act cta atc ttg tat gga cta ctc cct tat aaa       336
Phe Ile Gly Lys Leu Thr Leu Ile Leu Tyr Gly Leu Leu Pro Tyr Lys
            100                 105                 110 gat tta ttg aaa aaa cat tgg tta cac cac gga cat cct ggt act gat       384
Asp Leu Leu Lys Lys His Trp Leu His His Gly His Pro Gly Thr Asp
        115                 120                 125 tta gac cct gat tat tac aat ggt cat ccc caa aac ttc ttt ctt tgg       432
Leu Asp Pro Asp Tyr Tyr Asn Gly His Pro Gln Asn Phe Phe Leu Trp
130                 135                 140 tat cta cat ttt atg aag tct tat tgg cga tgg acg caa att ttc gga       480
Tyr Leu His Phe Met Lys Ser Tyr Trp Arg Trp Thr Gln Ile Phe Gly
145                 150                 155                 160 tta gtg atg att ttt cat gga ctt aaa aat ctg gtg cat ata cca gaa       528
Leu Val Met Ile Phe His Gly Leu Lys Asn Leu Val His Ile Pro Glu
                165                 170                 175 aat aat tta att ata ttt tgg atg ata cct tct att tta agt tca gta       576
Asn Asn Leu Ile Ile Phe Trp Met Ile Pro Ser Ile Leu Ser Ser Val
            180                 185                 190 caa cta ttt tat ttt ggt aca ttt ttg cct cat aaa aag cta gaa ggt       624
Gln Leu Phe Tyr Phe Gly Thr Phe Leu Pro His Lys Lys Leu Glu Gly
        195                 200                 205 ggt tat act aac ccc cat tgt gcg cgc agt atc cca tta cct ctt ttt       672
Gly Tyr Thr Asn Pro His Cys Ala Arg Ser Ile Pro Leu Pro Leu Phe
210                 215                 220 tgg tct ttt gtt act tgt tat cac ttc ggc tac cac aag gaa cat cac       720
Trp Ser Phe Val Thr Cys Tyr His Phe Gly Tyr His Lys Glu His His
225                 230                 235                 240 gaa tac cct caa ctt cct tgg tgg aaa tta cct gaa gct cac aaa ata       768
Glu Tyr Pro Gln Leu Pro Trp Trp Lys Leu Pro Glu Ala His Lys Ile
                245                 250                 255 tct tta taa                                                           777
Ser Leu <210> SEQ ID NO 2
<211> LENGTH: 258
<212> TYPE: PRT
<213> ORGANISM: Nostoc sp. Strain PCC7120

<400> SEQUENCE: 2

Met Val Gln Cys Gln Pro Ser Ser Leu His Ser Glu Lys Leu Val Leu
1               5                   10                  15

Leu Ser Ser Thr Ile Arg Asp Asp Lys Asn Ile Asn Lys Gly Ile Phe
            20                  25                  30

Ile Ala Cys Phe Ile Leu Phe Leu Trp Ala Ile Ser Leu Ile Leu Leu
        35                  40                  45

Leu Ser Ile Asp Thr Ser Ile Ile His Lys Ser Leu Leu Gly Ile Ala
    50                  55                  60

Met Leu Trp Gln Thr Phe Leu Tyr Thr Gly Leu Phe Ile Thr Ala His
65                  70                  75                  80

Asp Ala Met His Gly Val Val Tyr Pro Lys Asn Pro Arg Ile Asn Asn
                85                  90                  95

Phe Ile Gly Lys Leu Thr Leu Ile Leu Tyr Gly Leu Leu Pro Tyr Lys
            100                 105                 110
```

```
Asp Leu Leu Lys Lys His Trp Leu His Gly His Pro Gly Thr Asp
        115                 120                 125

Leu Asp Pro Asp Tyr Tyr Asn Gly His Pro Gln Asn Phe Phe Leu Trp
        130                 135                 140

Tyr Leu His Phe Met Lys Ser Tyr Trp Arg Trp Thr Gln Ile Phe Gly
145                 150                 155                 160

Leu Val Met Ile Phe His Gly Leu Lys Asn Leu Val His Ile Pro Glu
                165                 170                 175

Asn Asn Leu Ile Ile Phe Trp Met Ile Pro Ser Ile Leu Ser Ser Val
            180                 185                 190

Gln Leu Phe Tyr Phe Gly Thr Phe Leu Pro His Lys Lys Leu Glu Gly
        195                 200                 205

Gly Tyr Thr Asn Pro His Cys Ala Arg Ser Ile Pro Leu Pro Leu Phe
    210                 215                 220

Trp Ser Phe Val Thr Cys Tyr His Phe Gly Tyr His Lys Glu His His
225                 230                 235                 240

Glu Tyr Pro Gln Leu Pro Trp Trp Lys Leu Pro Glu Ala His Lys Ile
                245                 250                 255

Ser Leu

<210> SEQ ID NO 3
<211> LENGTH: 789
<212> TYPE: DNA
<213> ORGANISM: Nostoc punctiforme
<220> FEATURE:
<221> NAME/KEY: CDS

<400> SEQUENCE: 3
```

| | | | | | | | | | | | | | | | | |
|---|---|---|---|---|---|---|---|---|---|---|---|---|---|---|---|---|
| ttg | aat | ttt | tgt | gat | aaa | cca | gtt | agc | tat | tat | gtt | gca | ata | gag | caa | 48 |
| Leu | Asn | Phe | Cys | Asp | Lys | Pro | Val | Ser | Tyr | Tyr | Val | Ala | Ile | Glu | Gln | |
| 1 | | | | 5 | | | | | 10 | | | | | 15 | | |
| tta | agt | gct | aaa | gaa | gat | act | gtt | tgg | ggg | ctg | gtg | att | gtc | ata | gta | 96 |
| Leu | Ser | Ala | Lys | Glu | Asp | Thr | Val | Trp | Gly | Leu | Val | Ile | Val | Ile | Val | |
| | | | 20 | | | | | 25 | | | | | 30 | | | |
| att | att | agt | ctt | tgg | gta | gct | agt | ttg | gct | ttt | tta | cta | gct | att | aat | 144 |
| Ile | Ile | Ser | Leu | Trp | Val | Ala | Ser | Leu | Ala | Phe | Leu | Leu | Ala | Ile | Asn | |
| | | 35 | | | | | 40 | | | | | 45 | | | | |
| tat | gcc | aaa | gtc | cca | att | tgg | ttg | ata | cct | att | gca | ata | gtt | tgg | caa | 192 |
| Tyr | Ala | Lys | Val | Pro | Ile | Trp | Leu | Ile | Pro | Ile | Ala | Ile | Val | Trp | Gln | |
| | 50 | | | | | 55 | | | | | 60 | | | | | |
| atg | ttc | ctt | tat | aca | ggg | cta | ttt | att | act | gca | cat | gat | gct | atg | cat | 240 |
| Met | Phe | Leu | Tyr | Thr | Gly | Leu | Phe | Ile | Thr | Ala | His | Asp | Ala | Met | His | |
| 65 | | | | | 70 | | | | | 75 | | | | | 80 | |
| ggg | tca | gtt | tat | cgt | aaa | aat | ccc | aaa | att | aat | aat | ttt | atc | ggt | tca | 288 |
| Gly | Ser | Val | Tyr | Arg | Lys | Asn | Pro | Lys | Ile | Asn | Asn | Phe | Ile | Gly | Ser | |
| | | | | 85 | | | | | 90 | | | | | 95 | | |
| cta | gct | gta | gcg | ctt | tac | gct | gtg | ttt | cca | tat | caa | cag | atg | tta | aag | 336 |
| Leu | Ala | Val | Ala | Leu | Tyr | Ala | Val | Phe | Pro | Tyr | Gln | Gln | Met | Leu | Lys | |
| | | | 100 | | | | | 105 | | | | | 110 | | | |
| aat | cat | tgc | tta | cat | cat | cgt | cat | cct | gct | agc | gaa | gtt | gac | cca | gat | 384 |
| Asn | His | Cys | Leu | His | His | Arg | His | Pro | Ala | Ser | Glu | Val | Asp | Pro | Asp | |
| | | 115 | | | | | 120 | | | | | 125 | | | | |
| ttt | cat | gat | ggt | aag | aga | aca | aac | gct | att | ttc | tgg | tat | ctc | cat | ttc | 432 |
| Phe | His | Asp | Gly | Lys | Arg | Thr | Asn | Ala | Ile | Phe | Trp | Tyr | Leu | His | Phe | |
| | 130 | | | | | 135 | | | | | 140 | | | | | |
| atg | ata | gaa | tac | tcc | agt | tgg | caa | cag | tta | ata | gta | cta | act | atc | cta | 480 |
| Met | Ile | Glu | Tyr | Ser | Ser | Trp | Gln | Gln | Leu | Ile | Val | Leu | Thr | Ile | Leu | |
| 145 | | | | | 150 | | | | | 155 | | | | | 160 | |

```
ttt aat tta gct aaa tac gtt ttg cac atc cat caa ata aat ctc atc    528
Phe Asn Leu Ala Lys Tyr Val Leu His Ile His Gln Ile Asn Leu Ile
            165                 170                 175 tta ttt tgg agt att cct cca att tta agt tcc att caa ctg ttt tat    576
Leu Phe Trp Ser Ile Pro Pro Ile Leu Ser Ser Ile Gln Leu Phe Tyr
    180                 185                 190 ttc gga aca ttt ttg cct cat cga gaa ccc aag aaa gga tat gtt tat    624
Phe Gly Thr Phe Leu Pro His Arg Glu Pro Lys Lys Gly Tyr Val Tyr
195                 200                 205 ccc cat tgc agc caa aca ata aaa ttg cca act ttt ttg tca ttt atc    672
Pro His Cys Ser Gln Thr Ile Lys Leu Pro Thr Phe Leu Ser Phe Ile
    210                 215                 220 gct tgc tac cac ttt ggt tat cat gaa gaa cat cat gag tat ccc cat    720
Ala Cys Tyr His Phe Gly Tyr His Glu Glu His His Glu Tyr Pro His
225                 230                 235                 240 gta cct tgg tgg caa ctt cca tct gta tat aag cag aga gta ttc aac    768
Val Pro Trp Trp Gln Leu Pro Ser Val Tyr Lys Gln Arg Val Phe Asn
                245                 250                 255 aat tca gta acc aat tcg taa                                        789
Asn Ser Val Thr Asn Ser
            260

<210> SEQ ID NO 4
<211> LENGTH: 262
<212> TYPE: PRT
<213> ORGANISM: Nostoc punctiforme

<400> SEQUENCE: 4

Leu Asn Phe Cys Asp Lys Pro Val Ser Tyr Tyr Val Ala Ile Glu Gln
1               5                   10                  15

Leu Ser Ala Lys Glu Asp Thr Val Trp Gly Leu Val Ile Val Ile Val
            20                  25                  30

Ile Ile Ser Leu Trp Val Ala Ser Leu Ala Phe Leu Leu Ala Ile Asn
        35                  40                  45

Tyr Ala Lys Val Pro Ile Trp Leu Ile Pro Ile Ala Ile Val Trp Gln
    50                  55                  60

Met Phe Leu Tyr Thr Gly Leu Phe Ile Thr Ala His Asp Ala Met His
65                  70                  75                  80

Gly Ser Val Tyr Arg Lys Asn Pro Lys Ile Asn Asn Phe Ile Gly Ser
                85                  90                  95

Leu Ala Val Ala Leu Tyr Ala Val Phe Pro Tyr Gln Gln Met Leu Lys
            100                 105                 110

Asn His Cys Leu His His Arg His Pro Ala Ser Glu Val Asp Pro Asp
        115                 120                 125

Phe His Asp Gly Lys Arg Thr Asn Ala Ile Phe Trp Tyr Leu His Phe
    130                 135                 140

Met Ile Glu Tyr Ser Ser Trp Gln Gln Leu Ile Val Leu Thr Ile Leu
145                 150                 155                 160

Phe Asn Leu Ala Lys Tyr Val Leu His Ile His Gln Ile Asn Leu Ile
                165                 170                 175

Leu Phe Trp Ser Ile Pro Pro Ile Leu Ser Ser Ile Gln Leu Phe Tyr
            180                 185                 190

Phe Gly Thr Phe Leu Pro His Arg Glu Pro Lys Lys Gly Tyr Val Tyr
        195                 200                 205

Pro His Cys Ser Gln Thr Ile Lys Leu Pro Thr Phe Leu Ser Phe Ile
    210                 215                 220
```

```
Ala Cys Tyr His Phe Gly Tyr His Glu Glu His His Glu Tyr Pro His
225                 230                 235                 240

Val Pro Trp Trp Gln Leu Pro Ser Val Tyr Lys Gln Arg Val Phe Asn
                245                 250                 255

Asn Ser Val Thr Asn Ser
                260

<210> SEQ ID NO 5
<211> LENGTH: 762
<212> TYPE: DNA
<213> ORGANISM: Nostoc punctiforme
<220> FEATURE:
<221> NAME/KEY: CDS

<400> SEQUENCE: 5 gtg atc cag tta gaa caa cca ctc agt cat caa gca aaa ctg act cca      48
Val Ile Gln Leu Glu Gln Pro Leu Ser His Gln Ala Lys Leu Thr Pro
  1               5                  10                  15 gta ctg aga agt aaa tct cag ttt aag ggg ctt ttc att gct att gtc      96
Val Leu Arg Ser Lys Ser Gln Phe Lys Gly Leu Phe Ile Ala Ile Val
             20                  25                  30 att gtt agc gca tgg gtc att agc ctg agt tta tta ctt tcc ctt gac     144
Ile Val Ser Ala Trp Val Ile Ser Leu Ser Leu Leu Leu Ser Leu Asp
         35                  40                  45 atc tca aag cta aaa ttt tgg atg tta ttg cct gtt ata cta tgg caa     192
Ile Ser Lys Leu Lys Phe Trp Met Leu Leu Pro Val Ile Leu Trp Gln
     50                  55                  60 aca ttt tta tat acg gga tta ttt att aca tct cat gat gcc atg cat     240
Thr Phe Leu Tyr Thr Gly Leu Phe Ile Thr Ser His Asp Ala Met His
 65                  70                  75                  80 ggc gta gta ttt ccc caa aac acc aag att aat cat ttg att gga aca     288
Gly Val Val Phe Pro Gln Asn Thr Lys Ile Asn His Leu Ile Gly Thr
                 85                  90                  95 ttg acc cta tcc ctt tat ggt ctt tta cca tat caa aaa cta ttg aaa     336
Leu Thr Leu Ser Leu Tyr Gly Leu Leu Pro Tyr Gln Lys Leu Leu Lys
            100                 105                 110 aaa cat tgg tta cac cac cac aat cca gca agc tca ata gac ccg gat     384
Lys His Trp Leu His His His Asn Pro Ala Ser Ser Ile Asp Pro Asp
        115                 120                 125 ttt cac aat ggt aaa cac caa agt ttc ttt gct tgg tat ttt cat ttt     432
Phe His Asn Gly Lys His Gln Ser Phe Phe Ala Trp Tyr Phe His Phe
    130                 135                 140 atg aaa ggt tac tgg agt tgg ggg caa ata att gcg ttg act att att     480
Met Lys Gly Tyr Trp Ser Trp Gly Gln Ile Ile Ala Leu Thr Ile Ile
145                 150                 155                 160 tat aac ttt gct aaa tac ata ctc cat atc cca agt gat aat cta act     528
Tyr Asn Phe Ala Lys Tyr Ile Leu His Ile Pro Ser Asp Asn Leu Thr
                165                 170                 175 tac ttt tgg gtg cta ccc tcg ctt tta agt tca tta caa tta ttc tat     576
Tyr Phe Trp Val Leu Pro Ser Leu Leu Ser Ser Leu Gln Leu Phe Tyr
            180                 185                 190 ttt ggt act ttt tta ccc cat agt gaa cca ata ggg ggt tat gtt cag     624
Phe Gly Thr Phe Leu Pro His Ser Glu Pro Ile Gly Gly Tyr Val Gln
        195                 200                 205 cct cat tgt gcc caa aca att agc cgt cct att tgg tgg tca ttt atc     672
Pro His Cys Ala Gln Thr Ile Ser Arg Pro Ile Trp Trp Ser Phe Ile
    210                 215                 220 acg tgc tat cat ttt ggc tac cac gag gaa cat cac gaa tat cct cat     720
Thr Cys Tyr His Phe Gly Tyr His Glu Glu His His Glu Tyr Pro His
225                 230                 235                 240
```

-continued

```
att tct tgg tgg cag tta cca gaa att tac aaa gca aaa tag          762
Ile Ser Trp Trp Gln Leu Pro Glu Ile Tyr Lys Ala Lys
            245                 250
```

<210> SEQ ID NO 6
<211> LENGTH: 253
<212> TYPE: PRT
<213> ORGANISM: Nostoc punctiforme

<400> SEQUENCE: 6

Val Ile Gln Leu Glu Gln Pro Leu Ser His Gln Ala Lys Leu Thr Pro
1               5                   10                  15

Val Leu Arg Ser Lys Ser Gln Phe Lys Gly Leu Phe Ile Ala Ile Val
            20                  25                  30

Ile Val Ser Ala Trp Val Ile Ser Leu Ser Leu Leu Ser Leu Asp
        35                  40                  45

Ile Ser Lys Leu Lys Phe Trp Met Leu Leu Pro Val Ile Leu Trp Gln
    50                  55                  60

Thr Phe Leu Tyr Thr Gly Leu Phe Ile Thr Ser His Asp Ala Met His
65                  70                  75                  80

Gly Val Val Phe Pro Gln Asn Thr Lys Ile Asn His Leu Ile Gly Thr
                85                  90                  95

Leu Thr Leu Ser Leu Tyr Gly Leu Leu Pro Tyr Gln Lys Leu Leu Lys
            100                 105                 110

Lys His Trp Leu His His His Asn Pro Ala Ser Ser Ile Asp Pro Asp
        115                 120                 125

Phe His Asn Gly Lys His Gln Ser Phe Phe Ala Trp Tyr Phe His Phe
    130                 135                 140

Met Lys Gly Tyr Trp Ser Trp Gly Gln Ile Ile Ala Leu Thr Ile Ile
145                 150                 155                 160

Tyr Asn Phe Ala Lys Tyr Ile Leu His Ile Pro Ser Asp Asn Leu Thr
                165                 170                 175

Tyr Phe Trp Val Leu Pro Ser Leu Leu Ser Ser Leu Gln Leu Phe Tyr
            180                 185                 190

Phe Gly Thr Phe Leu Pro His Ser Glu Pro Ile Gly Gly Tyr Val Gln
        195                 200                 205

Pro His Cys Ala Gln Thr Ile Ser Arg Pro Ile Trp Trp Ser Phe Ile
    210                 215                 220

Thr Cys Tyr His Phe Gly Tyr His Glu Glu His His Glu Tyr Pro His
225                 230                 235                 240

Ile Ser Trp Trp Gln Leu Pro Glu Ile Tyr Lys Ala Lys
                245                 250

<210> SEQ ID NO 7
<211> LENGTH: 789
<212> TYPE: DNA
<213> ORGANISM: Unknown
<220> FEATURE:
<221> NAME/KEY: CDS
<223> OTHER INFORMATION: Artificial sequence

<400> SEQUENCE: 7

```
atg aat ttt tgt gat aaa cca gtt agc tat tat gtt gca ata gag caa    48
Met Asn Phe Cys Asp Lys Pro Val Ser Tyr Tyr Val Ala Ile Glu Gln
1               5                   10                  15 tta agt gct aaa gaa gat act gtt tgg ggg ctg gtg att gtc ata gta    96
Leu Ser Ala Lys Glu Asp Thr Val Trp Gly Leu Val Ile Val Ile Val
            20                  25                  30
```

```
att att agt ctt tgg gta gct agt ttg gct ttt tta cta gct att aat      144
Ile Ile Ser Leu Trp Val Ala Ser Leu Ala Phe Leu Leu Ala Ile Asn
         35                  40                  45 tat gcc aaa att cat aag tgg ttg ata cct att gca ata gtt tgg caa      192
Tyr Ala Lys Ile His Lys Trp Leu Ile Pro Ile Ala Ile Val Trp Gln
 50                  55                  60 atg ttc ctt tat aca ggg cta ttt att act gca cat gat gct atg cat      240
Met Phe Leu Tyr Thr Gly Leu Phe Ile Thr Ala His Asp Ala Met His
 65                  70                  75                  80 ggg tca gtt tat cgt aaa aat ccc aaa att aat aat ttt atc ggt tca      288
Gly Ser Val Tyr Arg Lys Asn Pro Lys Ile Asn Asn Phe Ile Gly Ser
                 85                  90                  95 cta gct gta gcg ctt tac gct gtg ttt cca tat caa cag atg tta aag      336
Leu Ala Val Ala Leu Tyr Ala Val Phe Pro Tyr Gln Gln Met Leu Lys
                100                 105                 110 aat cat tgc tta cat cat cgt cat cct gct agc gaa gtt gac cca gat      384
Asn His Cys Leu His His Arg His Pro Ala Ser Glu Val Asp Pro Asp
            115                 120                 125 ttt cat gat ggt aag aga aca aac gct att ttc tgg tat ctc cat ttc      432
Phe His Asp Gly Lys Arg Thr Asn Ala Ile Phe Trp Tyr Leu His Phe
130                 135                 140 atg ata gaa tac tcc agt tgg caa cag tta ata gta cta act atc cta      480
Met Ile Glu Tyr Ser Ser Trp Gln Gln Leu Ile Val Leu Thr Ile Leu
145                 150                 155                 160 ttt aat tta gct aaa tac gtt ttg cac atc cat caa ata aat ctc atc      528
Phe Asn Leu Ala Lys Tyr Val Leu His Ile His Gln Ile Asn Leu Ile
                165                 170                 175 tta ttt tgg agt att cct cca att tta agt tcc att caa ctg ttt tat      576
Leu Phe Trp Ser Ile Pro Pro Ile Leu Ser Ser Ile Gln Leu Phe Tyr
                180                 185                 190 ttc gga aca ttt ttg cct cat cga gaa ccc aag aaa gga tat gtt tat      624
Phe Gly Thr Phe Leu Pro His Arg Glu Pro Lys Lys Gly Tyr Val Tyr
            195                 200                 205 ccc cat tgc agc caa aca ata aaa ttg cca act ttt ttg tca ttt atc      672
Pro His Cys Ser Gln Thr Ile Lys Leu Pro Thr Phe Leu Ser Phe Ile
210                 215                 220 gct tgc tac cac ttt ggt tat cat gaa gaa cat cat gag tat ccc cat      720
Ala Cys Tyr His Phe Gly Tyr His Glu Glu His His Glu Tyr Pro His
225                 230                 235                 240 gta cct tgg tgg caa ctt cca tct gta tat aag cag aga gta ttc aac      768
Val Pro Trp Trp Gln Leu Pro Ser Val Tyr Lys Gln Arg Val Phe Asn
                245                 250                 255 aat tca gta acc aat tcg taa                                          789
Asn Ser Val Thr Asn Ser
            260
```

<210> SEQ ID NO 8
<211> LENGTH: 262
<212> TYPE: PRT
<213> ORGANISM: Unknown
<220> FEATURE:
<223> OTHER INFORMATION: Artificial sequence

<400> SEQUENCE: 8

```
Met Asn Phe Cys Asp Lys Pro Val Ser Tyr Tyr Val Ala Ile Glu Gln
1               5                   10                  15

Leu Ser Ala Lys Glu Asp Thr Val Trp Gly Leu Val Ile Val Ile Val
                20                  25                  30

Ile Ile Ser Leu Trp Val Ala Ser Leu Ala Phe Leu Leu Ala Ile Asn
         35                  40                  45
```

```
Tyr Ala Lys Ile His Lys Trp Leu Ile Pro Ile Ala Ile Val Trp Gln
 50                  55                  60

Met Phe Leu Tyr Thr Gly Leu Phe Ile Thr Ala His Asp Ala Met His
 65                  70                  75                  80

Gly Ser Val Tyr Arg Lys Asn Pro Lys Ile Asn Asn Phe Ile Gly Ser
                 85                  90                  95

Leu Ala Val Ala Leu Tyr Ala Val Phe Pro Tyr Gln Gln Met Leu Lys
            100                 105                 110

Asn His Cys Leu His His Arg His Pro Ala Ser Glu Val Asp Pro Asp
        115                 120                 125

Phe His Asp Gly Lys Arg Thr Asn Ala Ile Phe Trp Tyr Leu His Phe
    130                 135                 140

Met Ile Glu Tyr Ser Ser Trp Gln Gln Leu Ile Val Leu Thr Ile Leu
145                 150                 155                 160

Phe Asn Leu Ala Lys Tyr Val Leu His Ile His Gln Ile Asn Leu Ile
                165                 170                 175

Leu Phe Trp Ser Ile Pro Pro Ile Leu Ser Ser Ile Gln Leu Phe Tyr
            180                 185                 190

Phe Gly Thr Phe Leu Pro His Arg Glu Pro Lys Lys Gly Tyr Val Tyr
        195                 200                 205

Pro His Cys Ser Gln Thr Ile Lys Leu Pro Thr Phe Leu Ser Phe Ile
    210                 215                 220

Ala Cys Tyr His Phe Gly Tyr His Glu Glu His His Glu Tyr Pro His
225                 230                 235                 240

Val Pro Trp Trp Gln Leu Pro Ser Val Tyr Lys Gln Arg Val Phe Asn
                245                 250                 255

Asn Ser Val Thr Asn Ser
            260

<210> SEQ ID NO 9
<211> LENGTH: 789
<212> TYPE: DNA
<213> ORGANISM: Unknown
<220> FEATURE:
<221> NAME/KEY: CDS
<223> OTHER INFORMATION: Artificial sequence

<400> SEQUENCE: 9 atg aat ttt tgt gat aaa cca gtt agc tat tat gtt gca ata gag caa      48
Met Asn Phe Cys Asp Lys Pro Val Ser Tyr Tyr Val Ala Ile Glu Gln
  1               5                  10                  15 tta agt gct aaa gaa gat act gtt tgg ggg ctg gtg att gtc ata gta      96
Leu Ser Ala Lys Glu Asp Thr Val Trp Gly Leu Val Ile Val Ile Val
             20                  25                  30 att att agt ctt tgg gta gct agt ttg gct ttt tta cta gct att aat     144
Ile Ile Ser Leu Trp Val Ala Ser Leu Ala Phe Leu Leu Ala Ile Asn
         35                  40                  45 tat gcc aaa gtc cca att tgg ttg ata cct att gca ata gtt tgg caa     192
Tyr Ala Lys Val Pro Ile Trp Leu Ile Pro Ile Ala Ile Val Trp Gln
     50                  55                  60 atg ttc ctt tat aca ggg cta ttt att act gca cat gat gct atg cat     240
Met Phe Leu Tyr Thr Gly Leu Phe Ile Thr Ala His Asp Ala Met His
 65                  70                  75                  80 ggg tca gtt tat cgt aaa aat ccc aaa att aat aat ttt atc ggt tca     288
Gly Ser Val Tyr Arg Lys Asn Pro Lys Ile Asn Asn Phe Ile Gly Ser
                 85                  90                  95 cta gct gta gcg ctt tac gct gtg ttt cca tat caa cag atg tta aag     336
Leu Ala Val Ala Leu Tyr Ala Val Phe Pro Tyr Gln Gln Met Leu Lys
            100                 105                 110
```

```
                    100                 105                 110
aat cat tgc tta cat cat cgt cat cct gct agc gat tta gac cca gat       384
Asn His Cys Leu His His Arg His Pro Ala Ser Asp Leu Asp Pro Asp
        115                 120                 125 ttt cat gat ggt aag aga aca aac gct att ttc tgg tat ctc cat ttc       432
Phe His Asp Gly Lys Arg Thr Asn Ala Ile Phe Trp Tyr Leu His Phe
    130                 135                 140 atg ata gaa tac tcc agt tgg caa cag tta ata gta cta act atc cta       480
Met Ile Glu Tyr Ser Ser Trp Gln Gln Leu Ile Val Leu Thr Ile Leu
145                 150                 155                 160 ttt aat tta gct aaa tac gtt ttg cac atc cat caa ata aat ctc atc       528
Phe Asn Leu Ala Lys Tyr Val Leu His Ile His Gln Ile Asn Leu Ile
                165                 170                 175 tta ttt tgg agt att cct cca att tta agt tcc att caa ctg ttt tat       576
Leu Phe Trp Ser Ile Pro Pro Ile Leu Ser Ser Ile Gln Leu Phe Tyr
            180                 185                 190 ttc gga aca ttt ttg cct cat cga gaa ccc aag aaa gga tat gtt tat       624
Phe Gly Thr Phe Leu Pro His Arg Glu Pro Lys Lys Gly Tyr Val Tyr
        195                 200                 205 ccc cat tgc agc caa aca ata aaa ttg cca act ttt ttg tca ttt atc       672
Pro His Cys Ser Gln Thr Ile Lys Leu Pro Thr Phe Leu Ser Phe Ile
    210                 215                 220 gct tgc tac cac ttt ggt tat cat gaa gaa cat cat gag tat ccc cat       720
Ala Cys Tyr His Phe Gly Tyr His Glu Glu His His Glu Tyr Pro His
225                 230                 235                 240 gta cct tgg tgg caa ctt cca tct gta tat aag cag aga gta ttc aac       768
Val Pro Trp Trp Gln Leu Pro Ser Val Tyr Lys Gln Arg Val Phe Asn
                245                 250                 255 aat tca gta acc aat tcg taa                                           789
Asn Ser Val Thr Asn Ser
            260

<210> SEQ ID NO 10
<211> LENGTH: 262
<212> TYPE: PRT
<213> ORGANISM: Unknown
<220> FEATURE:
<223> OTHER INFORMATION: Artificial sequence

<400> SEQUENCE: 10

Met Asn Phe Cys Asp Lys Pro Val Ser Tyr Tyr Val Ala Ile Glu Gln
1               5                   10                  15

Leu Ser Ala Lys Glu Asp Thr Val Trp Gly Leu Val Ile Val Ile Val
                20                  25                  30

Ile Ile Ser Leu Trp Val Ala Ser Leu Ala Phe Leu Leu Ala Ile Asn
            35                  40                  45

Tyr Ala Lys Val Pro Ile Trp Leu Ile Pro Ile Ala Ile Val Trp Gln
        50                  55                  60

Met Phe Leu Tyr Thr Gly Leu Phe Ile Thr Ala His Asp Ala Met His
65                  70                  75                  80

Gly Ser Val Tyr Arg Lys Asn Pro Lys Ile Asn Asn Phe Ile Gly Ser
                85                  90                  95

Leu Ala Val Ala Leu Tyr Ala Val Phe Pro Tyr Gln Gln Met Leu Lys
                100                 105                 110

Asn His Cys Leu His His Arg His Pro Ala Ser Asp Leu Asp Pro Asp
            115                 120                 125

Phe His Asp Gly Lys Arg Thr Asn Ala Ile Phe Trp Tyr Leu His Phe
        130                 135                 140
```

```
Met Ile Glu Tyr Ser Ser Trp Gln Gln Leu Ile Val Leu Thr Ile Leu
145                 150                 155                 160

Phe Asn Leu Ala Lys Tyr Val Leu His Ile His Gln Ile Asn Leu Ile
                165                 170                 175

Leu Phe Trp Ser Ile Pro Pro Ile Leu Ser Ser Ile Gln Leu Phe Tyr
            180                 185                 190

Phe Gly Thr Phe Leu Pro His Arg Glu Pro Lys Lys Gly Tyr Val Tyr
        195                 200                 205

Pro His Cys Ser Gln Thr Ile Lys Leu Pro Thr Phe Leu Ser Phe Ile
    210                 215                 220

Ala Cys Tyr His Phe Gly Tyr His Glu Glu His Glu Tyr Pro His
225                 230                 235                 240

Val Pro Trp Trp Gln Leu Pro Ser Val Tyr Lys Gln Arg Val Phe Asn
                245                 250                 255

Asn Ser Val Thr Asn Ser
            260

<210> SEQ ID NO 11
<211> LENGTH: 762
<212> TYPE: DNA
<213> ORGANISM: Unknown
<220> FEATURE:
<221> NAME/KEY: CDS
<223> OTHER INFORMATION: Artificial sequence

<400> SEQUENCE: 11 atg atc cag tta gaa caa cca ctc agt cat caa gca aaa ctg act cca       48
Met Ile Gln Leu Glu Gln Pro Leu Ser His Gln Ala Lys Leu Thr Pro
1               5                   10                  15 gta ctg aga agt aaa tct cag ttt aag ggg ctt ttc att gct att gtc       96
Val Leu Arg Ser Lys Ser Gln Phe Lys Gly Leu Phe Ile Ala Ile Val
                20                  25                  30 att gtt agc gca tgg gtc att agc ctg agt tta tta ctt tcc ctt gac      144
Ile Val Ser Ala Trp Val Ile Ser Leu Ser Leu Leu Leu Ser Leu Asp
            35                  40                  45 atc tca aag att cat aag tgg atg tta ttg cct gtt ata cta tgg caa      192
Ile Ser Lys Ile His Lys Trp Met Leu Leu Pro Val Ile Leu Trp Gln
        50                  55                  60 aca ttt tta tat acg gga tta ttt att aca tct cat gat gcc atg cat      240
Thr Phe Leu Tyr Thr Gly Leu Phe Ile Thr Ser His Asp Ala Met His
65                  70                  75                  80 ggc gta gta ttt ccc caa aac acc aag att aat cat ttg att gga aca      288
Gly Val Val Phe Pro Gln Asn Thr Lys Ile Asn His Leu Ile Gly Thr
                85                  90                  95 ttg acc cta tcc ctt tat ggt ctt tta cca tat caa aaa cta ttg aaa      336
Leu Thr Leu Ser Leu Tyr Gly Leu Leu Pro Tyr Gln Lys Leu Leu Lys
            100                 105                 110 aaa cat tgg tta cac cac cac aat cca gca agc tca ata gac ccg gat      384
Lys His Trp Leu His His His Asn Pro Ala Ser Ser Ile Asp Pro Asp
        115                 120                 125 ttt cac aat ggt aaa cac caa agt ttc ttt gct tgg tat ttt cat ttt      432
Phe His Asn Gly Lys His Gln Ser Phe Phe Ala Trp Tyr Phe His Phe
    130                 135                 140 atg aaa ggt tac tgg agt tgg ggg caa ata att gcg ttg act att att      480
Met Lys Gly Tyr Trp Ser Trp Gly Gln Ile Ile Ala Leu Thr Ile Ile
145                 150                 155                 160 tat aac ttt gct aaa tac ata ctc cat atc cca agt gat aat cta act      528
Tyr Asn Phe Ala Lys Tyr Ile Leu His Ile Pro Ser Asp Asn Leu Thr
                165                 170                 175
```

```
tac ttt tgg gtg cta ccc tcg ctt tta agt tca tta caa tta ttc tat      576
Tyr Phe Trp Val Leu Pro Ser Leu Leu Ser Ser Leu Gln Leu Phe Tyr
            180                 185                 190 ttt ggt act ttt tta ccc cat agt gaa cca ata ggg ggt tat gtt cag      624
Phe Gly Thr Phe Leu Pro His Ser Glu Pro Ile Gly Gly Tyr Val Gln
        195                 200                 205 cct cat tgt gcc caa aca att agc cgt cct att tgg tgg tca ttt atc      672
Pro His Cys Ala Gln Thr Ile Ser Arg Pro Ile Trp Trp Ser Phe Ile
    210                 215                 220 acg tgc tat cat ttt ggc tac cac gag gaa cat cac gaa tat cct cat      720
Thr Cys Tyr His Phe Gly Tyr His Glu Glu His His Glu Tyr Pro His
225                 230                 235                 240 att tct tgg tgg cag tta cca gaa att tac aaa gca aaa tag              762
Ile Ser Trp Trp Gln Leu Pro Glu Ile Tyr Lys Ala Lys
                245                 250

<210> SEQ ID NO 12
<211> LENGTH: 253
<212> TYPE: PRT
<213> ORGANISM: Unknown
<220> FEATURE:
<223> OTHER INFORMATION: Artificial sequence

<400> SEQUENCE: 12

Met Ile Gln Leu Glu Gln Pro Leu Ser His Gln Ala Lys Leu Thr Pro
1               5                   10                  15

Val Leu Arg Ser Lys Ser Gln Phe Lys Gly Leu Phe Ile Ala Ile Val
            20                  25                  30

Ile Val Ser Ala Trp Val Ile Ser Leu Ser Leu Leu Ser Leu Asp
        35                  40                  45

Ile Ser Lys Ile His Lys Trp Met Leu Leu Pro Val Ile Leu Trp Gln
    50                  55                  60

Thr Phe Leu Tyr Thr Gly Leu Phe Ile Thr Ser His Asp Ala Met His
65                  70                  75                  80

Gly Val Val Phe Pro Gln Asn Thr Lys Ile Asn His Leu Ile Gly Thr
                85                  90                  95

Leu Thr Leu Ser Leu Tyr Gly Leu Leu Pro Tyr Gln Lys Leu Leu Lys
            100                 105                 110

Lys His Trp Leu His His His Asn Pro Ala Ser Ser Ile Asp Pro Asp
        115                 120                 125

Phe His Asn Gly Lys His Gln Ser Phe Phe Ala Trp Tyr Phe His Phe
    130                 135                 140

Met Lys Gly Tyr Trp Ser Trp Gly Gln Ile Ile Ala Leu Thr Ile Ile
145                 150                 155                 160

Tyr Asn Phe Ala Lys Tyr Ile Leu His Ile Pro Ser Asp Asn Leu Thr
                165                 170                 175

Tyr Phe Trp Val Leu Pro Ser Leu Leu Ser Ser Leu Gln Leu Phe Tyr
            180                 185                 190

Phe Gly Thr Phe Leu Pro His Ser Glu Pro Ile Gly Gly Tyr Val Gln
        195                 200                 205

Pro His Cys Ala Gln Thr Ile Ser Arg Pro Ile Trp Trp Ser Phe Ile
    210                 215                 220

Thr Cys Tyr His Phe Gly Tyr His Glu Glu His His Glu Tyr Pro His
225                 230                 235                 240

Ile Ser Trp Trp Gln Leu Pro Glu Ile Tyr Lys Ala Lys
                245                 250
```

<210> SEQ ID NO 13
<211> LENGTH: 762
<212> TYPE: DNA
<213> ORGANISM: Unknown
<220> FEATURE:
<221> NAME/KEY: CDS
<223> OTHER INFORMATION: Artificial sequence

<400> SEQUENCE: 13

| | | | | | | | | | | | | | | | | |
|---|---|---|---|---|---|---|---|---|---|---|---|---|---|---|---|---|
| atg | atc | cag | tta | gaa | caa | cca | ctc | agt | cat | caa | gca | aaa | ctg | act | cca | 48 |
| Met | Ile | Gln | Leu | Glu | Gln | Pro | Leu | Ser | His | Gln | Ala | Lys | Leu | Thr | Pro | |
| 1 | | | | 5 | | | | | 10 | | | | | 15 | | |
| gta | ctg | aga | agt | aaa | tct | cag | ttt | aag | ggg | ctt | ttc | att | gct | att | gtc | 96 |
| Val | Leu | Arg | Ser | Lys | Ser | Gln | Phe | Lys | Gly | Leu | Phe | Ile | Ala | Ile | Val | |
| | | | 20 | | | | | 25 | | | | | 30 | | | |
| att | gtt | agc | gca | tgg | gtc | att | agc | ctg | agt | tta | tta | ctt | tcc | ctt | gac | 144 |
| Ile | Val | Ser | Ala | Trp | Val | Ile | Ser | Leu | Ser | Leu | Leu | Leu | Ser | Leu | Asp | |
| | | | | 35 | | | | | 40 | | | | | 45 | | |
| atc | tca | aag | cta | aaa | ttt | tgg | atg | tta | ttg | cct | gtt | ata | cta | tgg | caa | 192 |
| Ile | Ser | Lys | Leu | Lys | Phe | Trp | Met | Leu | Leu | Pro | Val | Ile | Leu | Trp | Gln | |
| | 50 | | | | | 55 | | | | | 60 | | | | | |
| aca | ttt | tta | tat | acg | gga | tta | ttt | att | aca | tct | cat | gat | gcc | atg | cat | 240 |
| Thr | Phe | Leu | Tyr | Thr | Gly | Leu | Phe | Ile | Thr | Ser | His | Asp | Ala | Met | His | |
| 65 | | | | | 70 | | | | | 75 | | | | | 80 | |
| ggc | gta | gta | ttt | ccc | caa | aac | acc | aag | att | aat | cat | ttg | att | gga | aca | 288 |
| Gly | Val | Val | Phe | Pro | Gln | Asn | Thr | Lys | Ile | Asn | His | Leu | Ile | Gly | Thr | |
| | | | | 85 | | | | | 90 | | | | | 95 | | |
| ttg | acc | cta | tcc | ctt | tat | ggt | ctt | tta | cca | tat | caa | aaa | cta | ttg | aaa | 336 |
| Leu | Thr | Leu | Ser | Leu | Tyr | Gly | Leu | Leu | Pro | Tyr | Gln | Lys | Leu | Leu | Lys | |
| | | | 100 | | | | | 105 | | | | | 110 | | | |
| aaa | cat | tgg | tta | cac | cac | cac | aat | cca | gca | agc | gat | tta | gac | ccg | gat | 384 |
| Lys | His | Trp | Leu | His | His | His | Asn | Pro | Ala | Ser | Asp | Leu | Asp | Pro | Asp | |
| | | | | 115 | | | | | 120 | | | | | 125 | | |
| ttt | cac | aat | ggt | aaa | cac | caa | agt | ttc | ttt | gct | tgg | tat | ttt | cat | ttt | 432 |
| Phe | His | Asn | Gly | Lys | His | Gln | Ser | Phe | Phe | Ala | Trp | Tyr | Phe | His | Phe | |
| | 130 | | | | | 135 | | | | | 140 | | | | | |
| atg | aaa | ggt | tac | tgg | agt | tgg | ggg | caa | ata | att | gcg | ttg | act | att | att | 480 |
| Met | Lys | Gly | Tyr | Trp | Ser | Trp | Gly | Gln | Ile | Ile | Ala | Leu | Thr | Ile | Ile | |
| 145 | | | | | 150 | | | | | 155 | | | | | 160 | |
| tat | aac | ttt | gct | aaa | tac | ata | ctc | cat | atc | cca | agt | gat | aat | cta | act | 528 |
| Tyr | Asn | Phe | Ala | Lys | Tyr | Ile | Leu | His | Ile | Pro | Ser | Asp | Asn | Leu | Thr | |
| | | | | 165 | | | | | 170 | | | | | 175 | | |
| tac | ttt | tgg | gtg | cta | ccc | tcg | ctt | tta | agt | tca | tta | caa | tta | ttc | tat | 576 |
| Tyr | Phe | Trp | Val | Leu | Pro | Ser | Leu | Leu | Ser | Ser | Leu | Gln | Leu | Phe | Tyr | |
| | | | 180 | | | | | 185 | | | | | 190 | | | |
| ttt | ggt | act | ttt | tta | ccc | cat | agt | gaa | cca | ata | ggg | ggt | tat | gtt | cag | 624 |
| Phe | Gly | Thr | Phe | Leu | Pro | His | Ser | Glu | Pro | Ile | Gly | Gly | Tyr | Val | Gln | |
| | | | | 195 | | | | | 200 | | | | | 205 | | |
| cct | cat | tgt | gcc | caa | aca | att | agc | cgt | cct | att | tgg | tgg | tca | ttt | atc | 672 |
| Pro | His | Cys | Ala | Gln | Thr | Ile | Ser | Arg | Pro | Ile | Trp | Trp | Ser | Phe | Ile | |
| | 210 | | | | | 215 | | | | | 220 | | | | | |
| acg | tgc | tat | cat | ttt | ggc | tac | cac | gag | gaa | cat | cac | gaa | tat | cct | cat | 720 |
| Thr | Cys | Tyr | His | Phe | Gly | Tyr | His | Glu | Glu | His | His | Glu | Tyr | Pro | His | |
| 225 | | | | | 230 | | | | | 235 | | | | | 240 | |
| att | tct | tgg | tgg | cag | tta | cca | gaa | att | tac | aaa | gca | aaa | tag | | | 762 |
| Ile | Ser | Trp | Trp | Gln | Leu | Pro | Glu | Ile | Tyr | Lys | Ala | Lys | | | | |
| | | | | 245 | | | | | 250 | | | | | | | |

<210> SEQ ID NO 14
<211> LENGTH: 253
<212> TYPE: PRT
<213> ORGANISM: Unknown

```
<220> FEATURE:
<223> OTHER INFORMATION: Artificial sequence

<400> SEQUENCE: 14

Met Ile Gln Leu Glu Gln Pro Leu Ser His Gln Ala Lys Leu Thr Pro
1               5                   10                  15

Val Leu Arg Ser Lys Ser Gln Phe Lys Gly Leu Phe Ile Ala Ile Val
            20                  25                  30

Ile Val Ser Ala Trp Val Ile Ser Leu Ser Leu Leu Ser Leu Asp
        35                  40                  45

Ile Ser Lys Leu Lys Phe Trp Met Leu Pro Val Ile Leu Trp Gln
50                  55                  60

Thr Phe Leu Tyr Thr Gly Leu Phe Ile Thr Ser His Asp Ala Met His
65                  70                  75                  80

Gly Val Val Phe Pro Gln Asn Thr Lys Ile Asn His Leu Ile Gly Thr
                85                  90                  95

Leu Thr Leu Ser Leu Tyr Gly Leu Leu Pro Tyr Gln Lys Leu Leu Lys
                100                 105                 110

Lys His Trp Leu His His His Asn Pro Ala Ser Asp Leu Asp Pro Asp
            115                 120                 125

Phe His Asn Gly Lys His Gln Ser Phe Phe Ala Trp Tyr Phe His Phe
    130                 135                 140

Met Lys Gly Tyr Trp Ser Trp Gly Gln Ile Ile Ala Leu Thr Ile Ile
145                 150                 155                 160

Tyr Asn Phe Ala Lys Tyr Ile Leu His Ile Pro Ser Asp Asn Leu Thr
                165                 170                 175

Tyr Phe Trp Val Leu Pro Ser Leu Leu Ser Ser Leu Gln Leu Phe Tyr
            180                 185                 190

Phe Gly Thr Phe Leu Pro His Ser Glu Pro Ile Gly Gly Tyr Val Gln
        195                 200                 205

Pro His Cys Ala Gln Thr Ile Ser Arg Pro Ile Trp Trp Ser Phe Ile
210                 215                 220

Thr Cys Tyr His Phe Gly Tyr His Glu Glu His His Glu Tyr Pro His
225                 230                 235                 240

Ile Ser Trp Trp Gln Leu Pro Glu Ile Tyr Lys Ala Lys
                245                 250

<210> SEQ ID NO 15
<211> LENGTH: 1608
<212> TYPE: DNA
<213> ORGANISM: Haematococcus pluvialis
<220> FEATURE:
<221> NAME/KEY: CDS
<222> LOCATION: (3)..(971)

<400> SEQUENCE: 15 ct aca ttt cac aag ccc gtg agc ggt gca agc gct ctg ccc cac atc      47
   Thr Phe His Lys Pro Val Ser Gly Ala Ser Ala Leu Pro His Ile
   1               5                   10                  15 ggc cca cct cct cat ctc cat cgg tca ttt gct gct acc acg atg ctg    95
Gly Pro Pro Pro His Leu His Arg Ser Phe Ala Ala Thr Thr Met Leu
                20                  25                  30 tcg aag ctg cag tca atc agc gtc aag gcc cgc cgc gtt gaa cta gcc   143
Ser Lys Leu Gln Ser Ile Ser Val Lys Ala Arg Arg Val Glu Leu Ala
            35                  40                  45 cgc gac atc acg cgg ccc aaa gtc tgc ctg cat gct cag cgg tgc tcg   191
Arg Asp Ile Thr Arg Pro Lys Val Cys Leu His Ala Gln Arg Cys Ser
        50                  55                  60
```

```
tta gtt cgg ctg cga gtg gca gca cca cag aca gag gag gcg ctg gga      239
Leu Val Arg Leu Arg Val Ala Ala Pro Gln Thr Glu Glu Ala Leu Gly
     65                  70                  75 acc gtg cag gct gcc ggc gcg ggc gat gag cac agc gcc gat gta gca      287
Thr Val Gln Ala Ala Gly Ala Gly Asp Glu His Ser Ala Asp Val Ala
 80                  85                  90                  95 ctc cag cag ctt gac cgg gct atc gca gag cgt cgt gcc cgg cgc aaa      335
Leu Gln Gln Leu Asp Arg Ala Ile Ala Glu Arg Arg Ala Arg Arg Lys
                100                 105                 110 cgg gag cag ctg tca tac cag gct gcc gcc att gca gca tca att ggc      383
Arg Glu Gln Leu Ser Tyr Gln Ala Ala Ala Ile Ala Ala Ser Ile Gly
            115                 120                 125 gtg tca ggc att gcc atc ttc gcc acc tac ctg aga ttt gcc atg cac      431
Val Ser Gly Ile Ala Ile Phe Ala Thr Tyr Leu Arg Phe Ala Met His
        130                 135                 140 atg acc gtg ggc ggc gca gtg cca tgg ggt gaa gtg gct ggc act ctc      479
Met Thr Val Gly Gly Ala Val Pro Trp Gly Glu Val Ala Gly Thr Leu
145                 150                 155 ctc ttg gtg gtt ggt ggc gcg ctc ggc atg gag atg tat gcc cgc tat      527
Leu Leu Val Val Gly Gly Ala Leu Gly Met Glu Met Tyr Ala Arg Tyr
160                 165                 170                 175 gca cac aaa gcc atc tgg cat gag tcg cct ctg ggc tgg ctg ctg cac      575
Ala His Lys Ala Ile Trp His Glu Ser Pro Leu Gly Trp Leu Leu His
                180                 185                 190 aag agc cac cac aca cct cgc act gga ccc ttt gaa gcc aac gac ttg      623
Lys Ser His His Thr Pro Arg Thr Gly Pro Phe Glu Ala Asn Asp Leu
            195                 200                 205 ttt gca atc atc aat gga ctg ccc gcc atg ctc ctg tgt acc ttt ggc      671
Phe Ala Ile Ile Asn Gly Leu Pro Ala Met Leu Leu Cys Thr Phe Gly
        210                 215                 220 ttc tgg ctg ccc aac gtc ctg ggg gcg gcc tgc ttt gga gcg ggg ctg      719
Phe Trp Leu Pro Asn Val Leu Gly Ala Ala Cys Phe Gly Ala Gly Leu
225                 230                 235 ggc atc acg cta tac ggc atg gca tat atg ttt gta cac gat ggc ctg      767
Gly Ile Thr Leu Tyr Gly Met Ala Tyr Met Phe Val His Asp Gly Leu
240                 245                 250                 255 gtg cac agg cgc ttt ccc acc ggg ccc atc gct ggc ctg ccc tac atg      815
Val His Arg Arg Phe Pro Thr Gly Pro Ile Ala Gly Leu Pro Tyr Met
                260                 265                 270 aag cgc ctg aca gtg gcc cac cag cta cac cac agc ggc aag tac ggt      863
Lys Arg Leu Thr Val Ala His Gln Leu His His Ser Gly Lys Tyr Gly
            275                 280                 285 ggc gcg ccc tgg ggt atg ttc ttg ggt cca cag gag ctg cag cac att      911
Gly Ala Pro Trp Gly Met Phe Leu Gly Pro Gln Glu Leu Gln His Ile
        290                 295                 300 cca ggt gcg gcg gag gag gtg gag cga ctg gtc ctg gaa ctg gac tgg      959
Pro Gly Ala Ala Glu Glu Val Glu Arg Leu Val Leu Glu Leu Asp Trp
305                 310                 315 tcc aag cgg tag ggtgcggaac caggcacgct ggtttcacac ctcatgcctg         1011
Ser Lys Arg
320 tgataaggtg tggctagagc gatgcgtgtg agacgggtat gtcacggtcg actggtctga   1071 tggccaatgg catcggccat gtctggtcat cacgggctgg ttgcctgggt gaaggtgatg   1131 cacatcatca tgtgcggttg gaggggctgg cacagtgtgg gctgaactgg agcagttgtc   1191 caggctggcg ttgaatcagt gagggtttgt gattggcggt tgtgaagcaa tgactccgcc   1251 catattctat ttgtgggagc tgagatgatg gcatgcttgg gatgtgcatg gatcatggta   1311
```

-continued

```
gtgcagcaaa ctatattcac ctagggctgt tggtaggatc aggtgaggcc ttgcacattg      1371
catgatgtac tcgtcatggt gtgttggtga gaggatggat gtggatggat gtgtattctc      1431
agacgtagac cttgactgga ggcttgatcg agagagtggg ccgtattctt tgagagggga      1491
ggctcgtgcc agaaatggtg agtggatgac tgtgacgctg tacattgcag gcaggtgaga      1551
tgcactgtct cgattgtaaa atacattcag atgcaaaaaa aaaaaaaaaa aaaaaaa         1608
```

<210> SEQ ID NO 16
<211> LENGTH: 322
<212> TYPE: PRT
<213> ORGANISM: Haematococcus pluvialis

<400> SEQUENCE: 16

```
Thr Phe His Lys Pro Val Ser Gly Ala Ser Ala Leu Pro His Ile Gly
1               5                   10                  15

Pro Pro Pro His Leu His Arg Ser Phe Ala Ala Thr Thr Met Leu Ser
            20                  25                  30

Lys Leu Gln Ser Ile Ser Val Lys Ala Arg Arg Val Glu Leu Ala Arg
        35                  40                  45

Asp Ile Thr Arg Pro Lys Val Cys Leu His Ala Gln Arg Cys Ser Leu
    50                  55                  60

Val Arg Leu Arg Val Ala Ala Pro Gln Thr Glu Glu Ala Leu Gly Thr
65                  70                  75                  80

Val Gln Ala Ala Gly Ala Gly Asp Glu His Ser Ala Asp Val Ala Leu
                85                  90                  95

Gln Gln Leu Asp Arg Ala Ile Ala Glu Arg Ala Arg Arg Lys Arg
            100                 105                 110

Glu Gln Leu Ser Tyr Gln Ala Ala Ala Ile Ala Ala Ser Ile Gly Val
        115                 120                 125

Ser Gly Ile Ala Ile Phe Ala Thr Tyr Leu Arg Phe Ala Met His Met
    130                 135                 140

Thr Val Gly Gly Ala Val Pro Trp Gly Glu Val Ala Gly Thr Leu Leu
145                 150                 155                 160

Leu Val Val Gly Gly Ala Leu Gly Met Glu Met Tyr Ala Arg Tyr Ala
                165                 170                 175

His Lys Ala Ile Trp His Glu Ser Pro Leu Gly Trp Leu Leu His Lys
            180                 185                 190

Ser His His Thr Pro Arg Thr Gly Pro Phe Glu Ala Asn Asp Leu Phe
        195                 200                 205

Ala Ile Ile Asn Gly Leu Pro Ala Met Leu Leu Cys Thr Phe Gly Phe
    210                 215                 220

Trp Leu Pro Asn Val Leu Gly Ala Ala Cys Phe Gly Ala Gly Leu Gly
225                 230                 235                 240

Ile Thr Leu Tyr Gly Met Ala Tyr Met Phe Val His Asp Gly Leu Val
                245                 250                 255

His Arg Arg Phe Pro Thr Gly Pro Ile Ala Gly Leu Pro Tyr Met Lys
            260                 265                 270

Arg Leu Thr Val Ala His Gln Leu His Ser Gly Lys Tyr Gly Gly
        275                 280                 285

Ala Pro Trp Gly Met Phe Leu Gly Pro Gln Glu Leu Gln His Ile Pro
    290                 295                 300

Gly Ala Ala Glu Glu Val Glu Arg Leu Val Leu Glu Leu Asp Trp Ser
305                 310                 315                 320

Lys Arg
```

<210> SEQ ID NO 17
<211> LENGTH: 1650
<212> TYPE: DNA
<213> ORGANISM: Lycopersicon esculentum
<220> FEATURE:
<221> NAME/KEY: CDS
<222> LOCATION: (112)..(1614)

<400> SEQUENCE: 17

```
ggcacgagga aactttctc tcttcactag ctgtttacat gcttgaaatt tcaagatttt        60
aggaccccat tgaagtttt cttgaaacaa atattaccct gttggaaaaa g atg gat      117
                                                         Met Asp
                                                           1 act ttg ttg aaa acc cca aat aac ctt gaa ttt ctg aac cca cat cat      165
Thr Leu Leu Lys Thr Pro Asn Asn Leu Glu Phe Leu Asn Pro His His
        5                  10                  15 ggt ttt gct gtt aaa gct agt acc ttt aga tct gag aag cat cat aat      213
Gly Phe Ala Val Lys Ala Ser Thr Phe Arg Ser Glu Lys His His Asn
 20                  25                  30 ttt ggt tct agg aag ttt tgt gaa act ttg ggt aga agt gtt tgt gtt      261
Phe Gly Ser Arg Lys Phe Cys Glu Thr Leu Gly Arg Ser Val Cys Val
35                  40                  45                  50 aag ggt agt agt agt gct ctt tta gag ctt gta cct gag acc aaa aag      309
Lys Gly Ser Ser Ser Ala Leu Leu Glu Leu Val Pro Glu Thr Lys Lys
                55                  60                  65 gag aat ctt gat ttt gag ctt cct atg tat gac cct tca aaa ggg gtt      357
Glu Asn Leu Asp Phe Glu Leu Pro Met Tyr Asp Pro Ser Lys Gly Val
            70                  75                  80 gtt gtg gat ctt gct gtg gtt ggt ggt ggc cct gca gga ctt gct gtt      405
Val Val Asp Leu Ala Val Val Gly Gly Gly Pro Ala Gly Leu Ala Val
         85                  90                  95 gca cag caa gtt tct gaa gca gga ctc tct gtt tgt tca att gat ccg      453
Ala Gln Gln Val Ser Glu Ala Gly Leu Ser Val Cys Ser Ile Asp Pro
    100                 105                 110 aat cct aaa ttg ata tgg cct aat aac tat ggt gtt tgg gtg gat gaa      501
Asn Pro Lys Leu Ile Trp Pro Asn Asn Tyr Gly Val Trp Val Asp Glu
115                 120                 125                 130 ttt gag gct atg gac ttg tta gat tgt cta gat gct acc tgg tct ggt      549
Phe Glu Ala Met Asp Leu Leu Asp Cys Leu Asp Ala Thr Trp Ser Gly
                135                 140                 145 gca gca gtg tac att gat gat aat acg gct aaa gat ctt cat aga cct      597
Ala Ala Val Tyr Ile Asp Asp Asn Thr Ala Lys Asp Leu His Arg Pro
            150                 155                 160 tat gga agg gtt aac cgg aaa cag ctg aaa tcg aaa atg atg cag aaa      645
Tyr Gly Arg Val Asn Arg Lys Gln Leu Lys Ser Lys Met Met Gln Lys
        165                 170                 175 tgt ata atg aat ggt gtt aaa ttc cac caa gcc aaa gtt ata aag gtg      693
Cys Ile Met Asn Gly Val Lys Phe His Gln Ala Lys Val Ile Lys Val
    180                 185                 190 att cat gag gaa tcg aaa tcc atg ttg ata tgc aat gat ggt att act      741
Ile His Glu Glu Ser Lys Ser Met Leu Ile Cys Asn Asp Gly Ile Thr
195                 200                 205                 210 att cag gca acg gtg gtg ctc gat gca act ggc ttc tct aga tct ctt      789
Ile Gln Ala Thr Val Val Leu Asp Ala Thr Gly Phe Ser Arg Ser Leu
                215                 220                 225 gtt cag tat gat aag cct tat aac ccc ggg tat caa gtt gct tat ggc      837
Val Gln Tyr Asp Lys Pro Tyr Asn Pro Gly Tyr Gln Val Ala Tyr Gly
            230                 235                 240 att ttg gct gaa gtg gaa gag cac ccc ttt gat gta aac aag atg gtt      885
Ile Leu Ala Glu Val Glu Glu His Pro Phe Asp Val Asn Lys Met Val
```

-continued

```
                Ile Leu Ala Glu Val Glu Glu His Pro Phe Asp Val Asn Lys Met Val
                    245                 250                 255 ttc atg gat tgg cga gat tct cat ttg aag aac aat act gat ctc aag        933
Phe Met Asp Trp Arg Asp Ser His Leu Lys Asn Asn Thr Asp Leu Lys
    260                 265                 270 gag aga aat agt aga ata cca act ttt ctt tat gca atg cca ttt tca        981
Glu Arg Asn Ser Arg Ile Pro Thr Phe Leu Tyr Ala Met Pro Phe Ser
275                 280                 285                 290 tcc aac agg ata ttt ctt gaa gaa aca tca ctc gta gct cgt cct ggc       1029
Ser Asn Arg Ile Phe Leu Glu Glu Thr Ser Leu Val Ala Arg Pro Gly
                295                 300                 305 ttg cgt ata gat gat att caa gaa cga atg gtg gct cgt tta aac cat       1077
Leu Arg Ile Asp Asp Ile Gln Glu Arg Met Val Ala Arg Leu Asn His
        310                 315                 320 ttg ggg ata aaa gtg aag agc att gaa gaa gat gaa cat tgt cta ata       1125
Leu Gly Ile Lys Val Lys Ser Ile Glu Glu Asp Glu His Cys Leu Ile
    325                 330                 335 cca atg ggt ggt cca ctt cca gta tta cct cag aga gtc gtt gga atc       1173
Pro Met Gly Gly Pro Leu Pro Val Leu Pro Gln Arg Val Val Gly Ile
340                 345                 350 ggt ggt aca gct ggc atg gtt cat cca tcc acc ggt tat atg gtg gca       1221
Gly Gly Thr Ala Gly Met Val His Pro Ser Thr Gly Tyr Met Val Ala
355                 360                 365                 370 agg aca cta gct gcg gct cct gtt gtt gcc aat gcc ata att caa tac       1269
Arg Thr Leu Ala Ala Ala Pro Val Val Ala Asn Ala Ile Ile Gln Tyr
                375                 380                 385 ctc ggt tct gaa aga agt cat tcg ggt aat gaa tta tcc aca gct gtt       1317
Leu Gly Ser Glu Arg Ser His Ser Gly Asn Glu Leu Ser Thr Ala Val
        390                 395                 400 tgg aaa gat ttg tgg cct ata gag agg aga cgt caa aga gag ttc ttc       1365
Trp Lys Asp Leu Trp Pro Ile Glu Arg Arg Arg Gln Arg Glu Phe Phe
    405                 410                 415 tgc ttc ggt atg gat att ctt ctg aag ctt gat tta cct gct aca aga       1413
Cys Phe Gly Met Asp Ile Leu Leu Lys Leu Asp Leu Pro Ala Thr Arg
420                 425                 430 agg ttc ttt gat gca ttc ttt gac tta gaa cct cgt tat tgg cat ggc       1461
Arg Phe Phe Asp Ala Phe Phe Asp Leu Glu Pro Arg Tyr Trp His Gly
435                 440                 445                 450 ttc tta tcg tct cga ttg ttt cta cct gaa ctc ata gtt ttt ggg ctg       1509
Phe Leu Ser Ser Arg Leu Phe Leu Pro Glu Leu Ile Val Phe Gly Leu
                455                 460                 465 tct cta ttc tct cat gct tca aat act tct aga ttt gag ata atg aca       1557
Ser Leu Phe Ser His Ala Ser Asn Thr Ser Arg Phe Glu Ile Met Thr
        470                 475                 480 aag gga act gtt cca tta gta aat atg atc aac aat ttg tta cag gat       1605
Lys Gly Thr Val Pro Leu Val Asn Met Ile Asn Asn Leu Leu Gln Asp
    485                 490                 495 aaa gaa tga atccgagtaa ttcggaatct tgtccaatct cgtgcc                   1650
Lys Glu
    500

<210> SEQ ID NO 18
<211> LENGTH: 500
<212> TYPE: PRT
<213> ORGANISM: Lycopersicon esculentum

<400> SEQUENCE: 18

Met Asp Thr Leu Leu Lys Thr Pro Asn Asn Leu Glu Phe Leu Asn Pro
1               5                   10                  15

His His Gly Phe Ala Val Lys Ala Ser Thr Phe Arg Ser Glu Lys His
```

-continued

```
                 20                  25                  30
His Asn Phe Gly Ser Arg Lys Phe Cys Glu Thr Leu Gly Arg Ser Val
             35                  40                  45
Cys Val Lys Gly Ser Ser Ser Ala Leu Leu Glu Leu Val Pro Glu Thr
 50                  55                  60
Lys Lys Glu Asn Leu Asp Phe Glu Leu Pro Met Tyr Asp Pro Ser Lys
 65                  70                  75                  80
Gly Val Val Val Asp Leu Ala Val Val Gly Gly Pro Ala Gly Leu
                 85                  90                  95
Ala Val Ala Gln Gln Val Ser Glu Ala Gly Leu Ser Val Cys Ser Ile
                100                 105                 110
Asp Pro Asn Pro Lys Leu Ile Trp Pro Asn Asn Tyr Gly Val Trp Val
                115                 120                 125
Asp Glu Phe Glu Ala Met Asp Leu Leu Asp Cys Leu Asp Ala Thr Trp
                130                 135                 140
Ser Gly Ala Ala Val Tyr Ile Asp Asp Asn Thr Ala Lys Asp Leu His
145                 150                 155                 160
Arg Pro Tyr Gly Arg Val Asn Arg Lys Gln Leu Lys Ser Lys Met Met
                165                 170                 175
Gln Lys Cys Ile Met Asn Gly Val Lys Phe His Gln Ala Lys Val Ile
                180                 185                 190
Lys Val Ile His Glu Glu Ser Lys Ser Met Leu Ile Cys Asn Asp Gly
                195                 200                 205
Ile Thr Ile Gln Ala Thr Val Val Leu Asp Ala Thr Gly Phe Ser Arg
                210                 215                 220
Ser Leu Val Gln Tyr Asp Lys Pro Tyr Asn Pro Gly Tyr Gln Val Ala
225                 230                 235                 240
Tyr Gly Ile Leu Ala Glu Val Glu His Pro Phe Asp Val Asn Lys
                245                 250                 255
Met Val Phe Met Asp Trp Arg Asp Ser His Leu Lys Asn Asn Thr Asp
                260                 265                 270
Leu Lys Glu Arg Asn Ser Arg Ile Pro Thr Phe Leu Tyr Ala Met Pro
                275                 280                 285
Phe Ser Ser Asn Arg Ile Phe Leu Glu Glu Thr Ser Leu Val Ala Arg
                290                 295                 300
Pro Gly Leu Arg Ile Asp Asp Ile Gln Glu Arg Met Val Ala Arg Leu
305                 310                 315                 320
Asn His Leu Gly Ile Lys Val Lys Ser Ile Glu Glu Asp Glu His Cys
                325                 330                 335
Leu Ile Pro Met Gly Gly Pro Leu Pro Val Leu Pro Gln Arg Val Val
                340                 345                 350
Gly Ile Gly Gly Thr Ala Gly Met Val His Pro Ser Thr Gly Tyr Met
                355                 360                 365
Val Ala Arg Thr Leu Ala Ala Ala Pro Val Val Ala Asn Ala Ile Ile
                370                 375                 380
Gln Tyr Leu Gly Ser Glu Arg Ser His Ser Gly Asn Glu Leu Ser Thr
385                 390                 395                 400
Ala Val Trp Lys Asp Leu Trp Pro Ile Glu Arg Arg Gln Arg Glu
                405                 410                 415
Phe Phe Cys Phe Gly Met Asp Ile Leu Leu Lys Leu Asp Leu Pro Ala
                420                 425                 430
Thr Arg Arg Phe Phe Asp Ala Phe Phe Asp Leu Glu Pro Arg Tyr Trp
                435                 440                 445
```

His Gly Phe Leu Ser Ser Arg Leu Phe Leu Pro Glu Leu Ile Val Phe
    450                 455                 460

Gly Leu Ser Leu Phe Ser His Ala Ser Asn Thr Ser Arg Phe Glu Ile
465                 470                 475                 480

Met Thr Lys Gly Thr Val Pro Leu Val Asn Met Ile Asn Asn Leu Leu
                485                 490                 495

Gln Asp Lys Glu
        500

<210> SEQ ID NO 19
<211> LENGTH: 33
<212> TYPE: DNA
<213> ORGANISM: Unknown
<220> FEATURE:
<221> NAME/KEY: primer_bind
<223> OTHER INFORMATION: Artificial sequence

<400> SEQUENCE: 19
gcatgctcta gaccttataa agatattttg tga                            33

<210> SEQ ID NO 20
<211> LENGTH: 33
<212> TYPE: DNA
<213> ORGANISM: Unknown
<220> FEATURE:
<221> NAME/KEY: primer_bind
<223> OTHER INFORMATION: Artificial sequence

<400> SEQUENCE: 20
gcatgcatct agaaatggtt cagtgtcaac cat                            33

<210> SEQ ID NO 21
<211> LENGTH: 805
<212> TYPE: DNA
<213> ORGANISM: Nostoc sp. Strain PCC7120
<220> FEATURE:
<221> NAME/KEY: variation

<400> SEQUENCE: 21
gcatgcatct agaaatggtt cagtgtcaac catcatctct gcattcagaa aaactggtgt     60
tattgtcatc gacaatcaga gatgataaaa atattaataa gggtatattt attgcctgct    120
ttatcttatt tttatgggca attagtttaa tcttattact ctcaatagat acatccataa    180
ttcataagag cttattaggt atagccatgc tttggcagac cttcttatat acaggtttat    240
ttattactgc tcatgatgcc atgcacggcg tagtttatcc caaaaatccc agaataaata    300
attttatagg taagctcact ctaatcttgt atggactact cccttataaa gatttattga    360
aaaaacattg gttacaccac ggacatcctg gtactgattt agaccctgat tattacaatg    420
gtcatcccca aaacttcttt cttttggtatc tacatttta gaagtcttat tggcgatgga    480
cgcaaatttt cggattagtg atgattttc atggacttaa aaatctggtg catataccag    540
aaaataattt aattatattt tggatgatac cttctatttt aagttcagta caactatttt    600
attttggtac attttttgcct cataaaaagc tagaaggtgg ttatactaac ccccattgtg    660
cgcgcagtat cccattacct cttttttggt cttttgttac ttgttatcac ttcggctacc    720
acaaggaaca tcacgaatac cctcaacttc cttggtggaa attacctgaa gctcacaaaa    780
tatctttata aggtctagag catgc                                        805

<210> SEQ ID NO 22

-continued

```
<211> LENGTH: 24
<212> TYPE: DNA
<213> ORGANISM: Unknown
<220> FEATURE:
<221> NAME/KEY: primer_bind
<223> OTHER INFORMATION: Artificial sequence

<400> SEQUENCE: 22
aggtaccgca cggtctgcca atcc                                            24

<210> SEQ ID NO 23
<211> LENGTH: 26
<212> TYPE: DNA
<213> ORGANISM: Unknown
<220> FEATURE:
<221> NAME/KEY: primer_bind
<223> OTHER INFORMATION: Artificial sequence

<400> SEQUENCE: 23
aagcttgacc tgattatcag cacggt                                          26

<210> SEQ ID NO 24
<211> LENGTH: 4624
<212> TYPE: DNA
<213> ORGANISM: Erwinia uredovora
<220> FEATURE:
<221> NAME/KEY: CDS
<222> LOCATION: (128)..(1267)
<220> FEATURE:
<221> NAME/KEY: CDS
<222> LOCATION: (1288)..(2766)
<220> FEATURE:
<221> NAME/KEY: CDS
<222> LOCATION: (2802)..(3689)
<220> FEATURE:
<221> NAME/KEY: iDNA
<222> LOCATION: (3631)..(4158)

<400> SEQUENCE: 24
gtcgactttc agcagcgcat ggcgaaaatc cagacagccc ttcgtttggc aggggggcacc     60 atggccgctg ccgatatcat tgagcaggtt atgtgcaccg tcagcctgt cttaagtggg     120 agcggct atg caa ccg cat tat gat ctg att ctc gtg ggg gct gga ctc     169
        Met Gln Pro His Tyr Asp Leu Ile Leu Val Gly Ala Gly Leu
        1               5                   10 gcg aat ggc ctt atc gcc ctg cgt ctt cag cag cag caa cct gat atg     217
Ala Asn Gly Leu Ile Ala Leu Arg Leu Gln Gln Gln Gln Pro Asp Met
15                  20                  25                  30 cgt att ttg ctt atc gac gcc gca ccc cag gcg ggc ggg aat cat acg     265
Arg Ile Leu Leu Ile Asp Ala Ala Pro Gln Ala Gly Gly Asn His Thr
                35                  40                  45 tgg tca ttt cac cac gat gat ttg act gag agc caa cat cgt tgg ata     313
Trp Ser Phe His His Asp Asp Leu Thr Glu Ser Gln His Arg Trp Ile
            50                  55                  60 gct ccg ctg gtg gtt cat cac tgg ccc gac tat cag gta cgc ttt ccc     361
Ala Pro Leu Val Val His His Trp Pro Asp Tyr Gln Val Arg Phe Pro
        65                  70                  75 aca cgc cgt cgt aag ctg aac agc ggc tac ttt tgt att act tct cag     409
Thr Arg Arg Arg Lys Leu Asn Ser Gly Tyr Phe Cys Ile Thr Ser Gln
    80                  85                  90 cgt ttc gct gag gtt tta cag cga cag ttt ggc ccg cac ttg tgg atg     457
Arg Phe Ala Glu Val Leu Gln Arg Gln Phe Gly Pro His Leu Trp Met
95                  100                 105                 110 gat acc gcg gtc gca gag gtt aat gcg gaa tct gtt cgg ttg aaa aag     505
Asp Thr Ala Val Ala Glu Val Asn Ala Glu Ser Val Arg Leu Lys Lys
                115                 120                 125
```

```
ggt cag gtt atc ggt gcc cgc gcg gtg att gac ggg cgg ggt tat gcg      553
Gly Gln Val Ile Gly Ala Arg Ala Val Ile Asp Gly Arg Gly Tyr Ala
            130                 135                 140 gca aat tca gca ctg agc gtg ggc ttc cag gcg ttt att ggc cag gaa      601
Ala Asn Ser Ala Leu Ser Val Gly Phe Gln Ala Phe Ile Gly Gln Glu
        145                 150                 155 tgg cga ttg agc cac ccg cat ggt tta tcg tct ccc att atc atg gat      649
Trp Arg Leu Ser His Pro His Gly Leu Ser Ser Pro Ile Ile Met Asp
160                 165                 170 gcc acg gtc gat cag caa aat ggt tat cgc ttc gtg tac agc ctg ccg      697
Ala Thr Val Asp Gln Gln Asn Gly Tyr Arg Phe Val Tyr Ser Leu Pro
175                 180                 185                 190 ctc tcg ccg acc aga ttg tta att gaa gac acg cac tat att gat aat      745
Leu Ser Pro Thr Arg Leu Leu Ile Glu Asp Thr His Tyr Ile Asp Asn
                195                 200                 205 gcg aca tta gat cct gaa tgc gcg cgg caa aat att tgc gac tat gcc      793
Ala Thr Leu Asp Pro Glu Cys Ala Arg Gln Asn Ile Cys Asp Tyr Ala
        210                 215                 220 gcg caa cag ggt tgg cag ctt cag aca ctg ctg cga gaa gaa cag ggc      841
Ala Gln Gln Gly Trp Gln Leu Gln Thr Leu Leu Arg Glu Glu Gln Gly
    225                 230                 235 gcc tta ccc att act ctg tcg ggc aat gcc gac gca ttc tgg cag cag      889
Ala Leu Pro Ile Thr Leu Ser Gly Asn Ala Asp Ala Phe Trp Gln Gln
240                 245                 250 cgc ccc ctg gcc tgt agt gga tta cgt gcc ggt ctg ttc cat cct acc      937
Arg Pro Leu Ala Cys Ser Gly Leu Arg Ala Gly Leu Phe His Pro Thr
255                 260                 265                 270 acc ggc tat tca ctg ccg ctg gcg gtt gcc gtg gcc gac cgc ctg agt      985
Thr Gly Tyr Ser Leu Pro Leu Ala Val Ala Val Ala Asp Arg Leu Ser
                275                 280                 285 gca ctt gat gtc ttt acg tcg gcc tca att cac cat gcc att acg cat     1033
Ala Leu Asp Val Phe Thr Ser Ala Ser Ile His His Ala Ile Thr His
            290                 295                 300 ttt gcc cgc gag cgc tgg cag cag cag ggc ttt ttc cgc atg ctg aat     1081
Phe Ala Arg Glu Arg Trp Gln Gln Gln Gly Phe Phe Arg Met Leu Asn
        305                 310                 315 cgc atg ctg ttt tta gcc gga ccc gcc gat tca cgc tgg cgg gtt atg     1129
Arg Met Leu Phe Leu Ala Gly Pro Ala Asp Ser Arg Trp Arg Val Met
320                 325                 330 cag cgt ttt tat ggt tta cct gaa gat tta att gcc cgt ttt tat gcg     1177
Gln Arg Phe Tyr Gly Leu Pro Glu Asp Leu Ile Ala Arg Phe Tyr Ala
335                 340                 345                 350 gga aaa ctc acg ctg acc gat cgg cta cgt att ctg agc ggc aag ccg     1225
Gly Lys Leu Thr Leu Thr Asp Arg Leu Arg Ile Leu Ser Gly Lys Pro
                355                 360                 365 cct gtt ccg gta tta gca gca ttg caa gcc att atg acg act             1267
Pro Val Pro Val Leu Ala Ala Leu Gln Ala Ile Met Thr Thr
            370                 375                 380 catcgttaaa gagcgactac atg aaa cca act acg gta att ggt gca ggc ttc   1320
                     Met Lys Pro Thr Thr Val Ile Gly Ala Gly Phe
                                     385                 390 ggt ggc ctg gca ctg gca att cgt cta caa gct gcg ggg atc ccc gtc     1368
Gly Gly Leu Ala Leu Ala Ile Arg Leu Gln Ala Ala Gly Ile Pro Val
        395                 400                 405 tta ctg ctt gaa caa cgt gat aaa ccc ggc ggt cgg gct tat gtc tac     1416
Leu Leu Leu Glu Gln Arg Asp Lys Pro Gly Gly Arg Ala Tyr Val Tyr
    410                 415                 420 gag gat cag ggg ttt acc ttt gat gca ggc ccg acg gtt atc acc gat     1464
Glu Asp Gln Gly Phe Thr Phe Asp Ala Gly Pro Thr Val Ile Thr Asp
```

-continued

```
              425                 430                 435
ccc agt gcc att gaa gaa ctg ttt gca ctg gca gga aaa cag tta aaa        1512
Pro Ser Ala Ile Glu Glu Leu Phe Ala Leu Ala Gly Lys Gln Leu Lys
440                 445                 450                 455 gag tat gtc gaa ctg ctg ccg gtt acg ccg ttt tac cgc ctg tgt tgg        1560
Glu Tyr Val Glu Leu Leu Pro Val Thr Pro Phe Tyr Arg Leu Cys Trp
                460                 465                 470 gag tca ggg aag gtc ttt aat tac gat aac gat caa acc cgg ctc gaa        1608
Glu Ser Gly Lys Val Phe Asn Tyr Asp Asn Asp Gln Thr Arg Leu Glu
            475                 480                 485 gcg cag att cag cag ttt aat ccc cgc gat gtc gaa ggt tat cgt cag        1656
Ala Gln Ile Gln Gln Phe Asn Pro Arg Asp Val Glu Gly Tyr Arg Gln
        490                 495                 500 ttt ctg gac tat tca cgc gcg gtg ttt aaa gaa ggc tat cta aag ctc        1704
Phe Leu Asp Tyr Ser Arg Ala Val Phe Lys Glu Gly Tyr Leu Lys Leu
    505                 510                 515 ggt act gtc cct ttt tta tcg ttc aga gac atg ctt cgc gcc gca cct        1752
Gly Thr Val Pro Phe Leu Ser Phe Arg Asp Met Leu Arg Ala Ala Pro
520                 525                 530                 535 caa ctg gcg aaa ctg cag gca tgg aga agc gtt tac agt aag gtt gcc        1800
Gln Leu Ala Lys Leu Gln Ala Trp Arg Ser Val Tyr Ser Lys Val Ala
                540                 545                 550 agt tac atc gaa gat gaa cat ctg cgc cag gcg ttt tct ttc cac tcg        1848
Ser Tyr Ile Glu Asp Glu His Leu Arg Gln Ala Phe Ser Phe His Ser
            555                 560                 565 ctg ttg gtg ggc ggc aat ccc ttc gcc acc tca tcc att tat acg ttg        1896
Leu Leu Val Gly Gly Asn Pro Phe Ala Thr Ser Ser Ile Tyr Thr Leu
        570                 575                 580 ata cac gcg ctg gag cgt gag tgg ggc gtc tgg ttt ccg cgt ggc ggc        1944
Ile His Ala Leu Glu Arg Glu Trp Gly Val Trp Phe Pro Arg Gly Gly
    585                 590                 595 acc ggc gca tta gtt cag ggg atg ata aag ctg ttt cag gat ctg ggt        1992
Thr Gly Ala Leu Val Gln Gly Met Ile Lys Leu Phe Gln Asp Leu Gly
600                 605                 610                 615 ggc gaa gtc gtg tta aac gcc aga gtc agc cat atg gaa acg aca gga        2040
Gly Glu Val Val Leu Asn Ala Arg Val Ser His Met Glu Thr Thr Gly
                620                 625                 630 aac aag att gaa gcc gtg cat tta gag gac ggt cgc agg ttc ctg acg        2088
Asn Lys Ile Glu Ala Val His Leu Glu Asp Gly Arg Arg Phe Leu Thr
            635                 640                 645 caa gcc gtc gcg tca aat gca gat gtg gtt cat acc tat cgc gac ctg        2136
Gln Ala Val Ala Ser Asn Ala Asp Val Val His Thr Tyr Arg Asp Leu
        650                 655                 660 tta agc cag cac cct gcc gcg gtt aag cag tcc aac aaa ctg cag act        2184
Leu Ser Gln His Pro Ala Ala Val Lys Gln Ser Asn Lys Leu Gln Thr
    665                 670                 675 aag cgc atg agt aac tct ctg ttt gtg ctc tat ttt ggt ttg aat cac        2232
Lys Arg Met Ser Asn Ser Leu Phe Val Leu Tyr Phe Gly Leu Asn His
680                 685                 690                 695 cat cat gat cag ctc gcg cat cac acg gtt tgt ttc ggc ccg cgt tac        2280
His His Asp Gln Leu Ala His His Thr Val Cys Phe Gly Pro Arg Tyr
                700                 705                 710 cgc gag ctg att gac gaa att ttt aat cat gat ggc ctc gca gag gac        2328
Arg Glu Leu Ile Asp Glu Ile Phe Asn His Asp Gly Leu Ala Glu Asp
            715                 720                 725 ttc tca ctt tat ctg cac gcg ccc tgt gtc acg gat tcg tca ctg gcg        2376
Phe Ser Leu Tyr Leu His Ala Pro Cys Val Thr Asp Ser Ser Leu Ala
        730                 735                 740 cct gaa ggt tgc ggc agt tac tat gtg ttg gcg ccg gtg ccg cat tta        2424
```

```
                Pro Glu Gly Cys Gly Ser Tyr Tyr Val Leu Ala Pro Val Pro His Leu
                    745                 750                 755 ggc acc gcg aac ctc gac tgg acg gtt gag ggg cca aaa cta cgc gac      2472
Gly Thr Ala Asn Leu Asp Trp Thr Val Glu Gly Pro Lys Leu Arg Asp
760                 765                 770                 775 cgt att ttt gcg tac ctt gag cag cat tac atg cct ggc tta cgg agt      2520
Arg Ile Phe Ala Tyr Leu Glu Gln His Tyr Met Pro Gly Leu Arg Ser
                780                 785                 790 cag ctg gtc acg cac cgg atg ttt acg ccg ttt gat ttt cgc gac cag      2568
Gln Leu Val Thr His Arg Met Phe Thr Pro Phe Asp Phe Arg Asp Gln
            795                 800                 805 ctt aat gcc tat cat ggc tca gcc ttt tct gtg gag ccc gtt ctt acc      2616
Leu Asn Ala Tyr His Gly Ser Ala Phe Ser Val Glu Pro Val Leu Thr
        810                 815                 820 cag agc gcc tgg ttt cgg ccg cat aac cgc gat aaa acc att act aat      2664
Gln Ser Ala Trp Phe Arg Pro His Asn Arg Asp Lys Thr Ile Thr Asn
    825                 830                 835 ctc tac ctg gtc ggc gca ggc acg cat ccc ggc gca ggc att cct ggc      2712
Leu Tyr Leu Val Gly Ala Gly Thr His Pro Gly Ala Gly Ile Pro Gly
840                 845                 850                 855 gtc atc ggc tcg gca aaa gcg aca gca ggt ttg atg ctg gag gat ctg      2760
Val Ile Gly Ser Ala Lys Ala Thr Ala Gly Leu Met Leu Glu Asp Leu
                860                 865                 870 att tga ataatccgtc gttactcaat catgcggtcg aaacg atg gca gtt ggc      2813
Ile                                            Met Ala Val Gly
                                                       875 tcg aaa agt ttt gcg aca gcc tca aag tta ttt gat gca aaa acc cgg      2861
Ser Lys Ser Phe Ala Thr Ala Ser Lys Leu Phe Asp Ala Lys Thr Arg
        880                 885                 890 cgc agc gta ctg atg ctc tac gcc tgg tgc cgc cat tgt gac gat gtt      2909
Arg Ser Val Leu Met Leu Tyr Ala Trp Cys Arg His Cys Asp Asp Val
    895                 900                 905 att gac gat cag acg ctg ggc ttt cag gcc cgg cag cct gcc tta caa      2957
Ile Asp Asp Gln Thr Leu Gly Phe Gln Ala Arg Gln Pro Ala Leu Gln
910                 915                 920 acg ccc gaa caa cgt ctg atg caa ctt gag atg aaa acg cgc cag gcc      3005
Thr Pro Glu Gln Arg Leu Met Gln Leu Glu Met Lys Thr Arg Gln Ala
925                 930                 935                 940 tat gca gga tcg cag atg cac gaa ccg gcg ttt gcg gct ttt cag gaa      3053
Tyr Ala Gly Ser Gln Met His Glu Pro Ala Phe Ala Ala Phe Gln Glu
                945                 950                 955 gtg gct atg gct cat gat atc gcc ccg gct tac gcg ttt gat cat ctg      3101
Val Ala Met Ala His Asp Ile Ala Pro Ala Tyr Ala Phe Asp His Leu
            960                 965                 970 gaa ggc ttc gcc atg gat gta cgc gaa gcg caa tac agc caa ctg gat      3149
Glu Gly Phe Ala Met Asp Val Arg Glu Ala Gln Tyr Ser Gln Leu Asp
        975                 980                 985 gat acg ctg cgc tat tgc tat cac gtt gca ggc gtt  gtc ggc ttg atg    3197
Asp Thr Leu Arg Tyr Cys Tyr His Val Ala Gly Val  Val Gly Leu Met
    990                 995                 1000 atg gcg caa atc atg ggc  gtg cgg gat aac gcc  acg ctg gac cgc       3242
Met Ala Gln Ile Met Gly  Val Arg Asp Asn Ala  Thr Leu Asp Arg
1005                     1010                 1015 gcc tgt gac ctt ggg ctg  gca ttt cag ttg acc  aat att gct cgc       3287
Ala Cys Asp Leu Gly Leu  Ala Phe Gln Leu Thr  Asn Ile Ala Arg
1020                     1025                 1030 gat att gtg gac gat gcg  cat gcg ggc cgc tgt  tat ctg ccg gca       3332
Asp Ile Val Asp Asp Ala  His Ala Gly Arg Cys  Tyr Leu Pro Ala
1035                     1040                 1045
```

| | |
|---|---|
| agc tgg ctg gag cat gaa ggt ctg aac aaa gag aat tat gcg gca<br>Ser Trp Leu Glu His Glu Gly Leu Asn Lys Glu Asn Tyr Ala Ala<br>1050                         1055                       1060 | 3377 |
| cct gaa aac cgt cag gcg ctg agc cgt atc gcc cgt cgt ttg gtg<br>Pro Glu Asn Arg Gln Ala Leu Ser Arg Ile Ala Arg Arg Leu Val<br>1065                         1070                       1075 | 3422 |
| cag gaa gca gaa cct tac tat ttg tct gcc aca gcc ggc ctg gca<br>Gln Glu Ala Glu Pro Tyr Tyr Leu Ser Ala Thr Ala Gly Leu Ala<br>1080                         1085                       1090 | 3467 |
| ggg ttg ccc ctg cgt tcc gcc tgg gca atc gct acg gcg aag cag<br>Gly Leu Pro Leu Arg Ser Ala Trp Ala Ile Ala Thr Ala Lys Gln<br>1095                         1100                       1105 | 3512 |
| gtt tac cgg aaa ata ggt gtc aaa gtt gaa cag gcc ggt cag caa<br>Val Tyr Arg Lys Ile Gly Val Lys Val Glu Gln Ala Gly Gln Gln<br>1110                         1115                       1120 | 3557 |
| gcc tgg gat cag cgg cag tca acg acc acg ccc gaa aaa tta acg<br>Ala Trp Asp Gln Arg Gln Ser Thr Thr Thr Pro Glu Lys Leu Thr<br>1125                         1130                       1135 | 3602 |
| ctg ctg ctg gcc gcc tct ggt cag gcc ctt act tcc cgg atg cgg<br>Leu Leu Leu Ala Ala Ser Gly Gln Ala Leu Thr Ser Arg Met Arg<br>1140                         1145                       1150 | 3647 |
| gct cat cct ccc cgc cct gcg cat ctc tgg cag cgc ccg ctc<br>Ala His Pro Pro Arg Pro Ala His Leu Trp Gln Arg Pro Leu<br>1155                         1160                       1165 | 3689 |
| tagcgccatg tctttcccgg agcgtcgcct gaagttttga caggggcggc gcatagagga | 3749 |
| agccaaaaga aacacaacct tctttgcccc tgacggcgtg atgcatacgg tgcgccatat | 3809 |
| acaaccgttt gaggtagccc ttgcgtggaa tatagcggaa tggccaacgt tgatgcacca | 3869 |
| gcccgtcgtg caccataaaa tagagtaatc catacgccgt catacctgcg ccaatccact | 3929 |
| ggagcggcca cattcctgta ctgcccagat aaatcagcag gatcgataat gcagcaaaaa | 3989 |
| ccacggcata aagatcgtta acttcaaacg cacctttacg cggttcatga tgtgaaagat | 4049 |
| gccatcccca accccagccg tgcatgatgt atttgtgtgc cagtgcagca atcacttcca | 4109 |
| tgccaatcac ggtaacgaaa acgatcaggg cattccaaat ccacaacata atttctccgg | 4169 |
| tagagacgtc tggcagcagg cttaaggatt caattttaac agagattagc cgatctggcg | 4229 |
| gcgggaaggg aaaaaggcgc gccagaaagg cgcgccaggg atcagaagtc ggctttcaga | 4289 |
| accacacggt agttggcttt acctgcacga acatggtcca gtgcatcgtt gattttcgac | 4349 |
| atcgggaagt actccactgt cggcgcaata tctgtacggc cagccagctt cagcagtgaa | 4409 |
| cgcagctgcg caggtgaacc ggttgaagaa cccgtcacgg cgcggtcgcc taaaatcagg | 4469 |
| ctgaaagccg ggcacgtcaa acggcttcag tacggcaccc acggtatgga acttaccgcg | 4529 |
| aggcgccagg gccgcaaagt aggggttgcca gtcgagatcg acggcgaccg tgctgataat | 4589 |
| caggtcaaac tggcccgcca ggcttttttaa agctt | 4624 |

<210> SEQ ID NO 25
<211> LENGTH: 380
<212> TYPE: PRT
<213> ORGANISM: Erwinia uredovora

<400> SEQUENCE: 25

Met Gln Pro His Tyr Asp Leu Ile Leu Val Gly Ala Gly Leu Ala Asn
1               5                  10                 15

Gly Leu Ile Ala Leu Arg Leu Gln Gln Gln Gln Pro Asp Met Arg Ile
              20                  25                 30

Leu Leu Ile Asp Ala Ala Pro Gln Ala Gly Gly Asn His Thr Trp Ser

-continued

```
                35                  40                  45
Phe His His Asp Asp Leu Thr Glu Ser Gln His Arg Trp Ile Ala Pro
             50                  55                  60
Leu Val Val His His Trp Pro Asp Tyr Gln Val Arg Phe Pro Thr Arg
 65                  70                  75                  80
Arg Arg Lys Leu Asn Ser Gly Tyr Phe Cys Ile Thr Ser Gln Arg Phe
                 85                  90                  95
Ala Glu Val Leu Gln Arg Gln Phe Gly Pro His Leu Trp Met Asp Thr
            100                 105                 110
Ala Val Ala Glu Val Asn Ala Glu Ser Val Arg Leu Lys Lys Gly Gln
            115                 120                 125
Val Ile Gly Ala Arg Ala Val Ile Asp Gly Arg Gly Tyr Ala Ala Asn
130                 135                 140
Ser Ala Leu Ser Val Gly Phe Gln Ala Phe Ile Gly Gln Glu Trp Arg
145                 150                 155                 160
Leu Ser His Pro His Gly Leu Ser Ser Pro Ile Ile Met Asp Ala Thr
                165                 170                 175
Val Asp Gln Gln Asn Gly Tyr Arg Phe Val Tyr Ser Leu Pro Leu Ser
            180                 185                 190
Pro Thr Arg Leu Leu Ile Glu Asp Thr His Tyr Ile Asp Asn Ala Thr
            195                 200                 205
Leu Asp Pro Glu Cys Ala Arg Gln Asn Ile Cys Asp Tyr Ala Ala Gln
            210                 215                 220
Gln Gly Trp Gln Leu Gln Thr Leu Leu Arg Glu Glu Gln Gly Ala Leu
225                 230                 235                 240
Pro Ile Thr Leu Ser Gly Asn Ala Asp Ala Phe Trp Gln Gln Arg Pro
                245                 250                 255
Leu Ala Cys Ser Gly Leu Arg Ala Gly Leu Phe His Pro Thr Thr Gly
            260                 265                 270
Tyr Ser Leu Pro Leu Ala Val Ala Val Ala Asp Arg Leu Ser Ala Leu
            275                 280                 285
Asp Val Phe Thr Ser Ala Ser Ile His His Ala Ile Thr His Phe Ala
            290                 295                 300
Arg Glu Arg Trp Gln Gln Gln Gly Phe Phe Arg Met Leu Asn Arg Met
305                 310                 315                 320
Leu Phe Leu Ala Gly Pro Ala Asp Ser Arg Trp Arg Val Met Gln Arg
                325                 330                 335
Phe Tyr Gly Leu Pro Glu Asp Leu Ile Ala Arg Phe Tyr Ala Gly Lys
            340                 345                 350
Leu Thr Leu Thr Asp Arg Leu Arg Ile Leu Ser Gly Lys Pro Pro Val
            355                 360                 365
Pro Val Leu Ala Ala Leu Gln Ala Ile Met Thr Thr
            370                 375                 380

<210> SEQ ID NO 26
<211> LENGTH: 492
<212> TYPE: PRT
<213> ORGANISM: Erwinia uredovora

<400> SEQUENCE: 26

Met Lys Pro Thr Thr Val Ile Gly Ala Gly Phe Gly Gly Leu Ala Leu
  1               5                  10                  15
Ala Ile Arg Leu Gln Ala Ala Gly Ile Pro Val Leu Leu Leu Glu Gln
             20                  25                  30
```

-continued

```
Arg Asp Lys Pro Gly Gly Arg Ala Tyr Val Tyr Glu Asp Gln Gly Phe
        35                  40                  45

Thr Phe Asp Ala Gly Pro Thr Val Ile Thr Asp Pro Ser Ala Ile Glu
 50                  55                  60

Glu Leu Phe Ala Leu Ala Gly Lys Gln Leu Lys Glu Tyr Val Glu Leu
 65                  70                  75                  80

Leu Pro Val Thr Pro Phe Tyr Arg Leu Cys Trp Glu Ser Gly Lys Val
                 85                  90                  95

Phe Asn Tyr Asp Asn Asp Gln Thr Arg Leu Glu Ala Gln Ile Gln Gln
                100                 105                 110

Phe Asn Pro Arg Asp Val Glu Gly Tyr Arg Gln Phe Leu Asp Tyr Ser
                115                 120                 125

Arg Ala Val Phe Lys Glu Gly Tyr Leu Lys Leu Gly Thr Val Pro Phe
        130                 135                 140

Leu Ser Phe Arg Asp Met Leu Arg Ala Ala Pro Gln Leu Ala Lys Leu
145                 150                 155                 160

Gln Ala Trp Arg Ser Val Tyr Ser Lys Val Ala Ser Tyr Ile Glu Asp
                165                 170                 175

Glu His Leu Arg Gln Ala Phe Ser Phe His Ser Leu Leu Val Gly Gly
                180                 185                 190

Asn Pro Phe Ala Thr Ser Ser Ile Tyr Thr Leu Ile His Ala Leu Glu
        195                 200                 205

Arg Glu Trp Gly Val Trp Phe Pro Arg Gly Gly Thr Gly Ala Leu Val
        210                 215                 220

Gln Gly Met Ile Lys Leu Phe Gln Asp Leu Gly Gly Glu Val Val Leu
225                 230                 235                 240

Asn Ala Arg Val Ser His Met Glu Thr Thr Gly Asn Lys Ile Glu Ala
                245                 250                 255

Val His Leu Glu Asp Gly Arg Arg Phe Leu Thr Gln Ala Val Ala Ser
                260                 265                 270

Asn Ala Asp Val Val His Thr Tyr Arg Asp Leu Leu Ser Gln His Pro
        275                 280                 285

Ala Ala Val Lys Gln Ser Asn Lys Leu Gln Thr Lys Arg Met Ser Asn
        290                 295                 300

Ser Leu Phe Val Leu Tyr Phe Gly Leu Asn His His His Asp Gln Leu
305                 310                 315                 320

Ala His His Thr Val Cys Phe Gly Pro Arg Tyr Arg Glu Leu Ile Asp
                325                 330                 335

Glu Ile Phe Asn His Asp Gly Leu Ala Glu Asp Phe Ser Leu Tyr Leu
                340                 345                 350

His Ala Pro Cys Val Thr Asp Ser Ser Leu Ala Pro Glu Gly Cys Gly
        355                 360                 365

Ser Tyr Tyr Val Leu Ala Pro Val Pro His Leu Gly Thr Ala Asn Leu
        370                 375                 380

Asp Trp Thr Val Glu Gly Pro Lys Leu Arg Asp Arg Ile Phe Ala Tyr
385                 390                 395                 400

Leu Glu Gln His Tyr Met Pro Gly Leu Arg Ser Gln Leu Val Thr His
                405                 410                 415

Arg Met Phe Thr Pro Phe Asp Phe Arg Asp Gln Leu Asn Ala Tyr His
                420                 425                 430

Gly Ser Ala Phe Ser Val Glu Pro Val Leu Thr Gln Ser Ala Trp Phe
        435                 440                 445

Arg Pro His Asn Arg Asp Lys Thr Ile Thr Asn Leu Tyr Leu Val Gly
```

-continued

```
    450                 455                 460

Ala Gly Thr His Pro Gly Ala Gly Ile Pro Gly Val Ile Gly Ser Ala
465                 470                 475                 480

Lys Ala Thr Ala Gly Leu Met Leu Glu Asp Leu Ile
                485                 490

<210> SEQ ID NO 27
<211> LENGTH: 296
<212> TYPE: PRT
<213> ORGANISM: Erwinia uredovora

<400> SEQUENCE: 27

Met Ala Val Gly Ser Lys Ser Phe Ala Thr Ala Ser Lys Leu Phe Asp
1               5                   10                  15

Ala Lys Thr Arg Arg Ser Val Leu Met Leu Tyr Ala Trp Cys Arg His
            20                  25                  30

Cys Asp Asp Val Ile Asp Asp Gln Thr Leu Gly Phe Gln Ala Arg Gln
        35                  40                  45

Pro Ala Leu Gln Thr Pro Glu Gln Arg Leu Met Gln Leu Glu Met Lys
    50                  55                  60

Thr Arg Gln Ala Tyr Ala Gly Ser Gln Met His Glu Pro Ala Phe Ala
65                  70                  75                  80

Ala Phe Gln Glu Val Ala Met Ala His Asp Ile Ala Pro Ala Tyr Ala
                85                  90                  95

Phe Asp His Leu Glu Gly Phe Ala Met Asp Val Arg Glu Ala Gln Tyr
            100                 105                 110

Ser Gln Leu Asp Asp Thr Leu Arg Tyr Cys Tyr His Val Ala Gly Val
        115                 120                 125

Val Gly Leu Met Met Ala Gln Ile Met Gly Val Arg Asp Asn Ala Thr
    130                 135                 140

Leu Asp Arg Ala Cys Asp Leu Gly Leu Ala Phe Gln Leu Thr Asn Ile
145                 150                 155                 160

Ala Arg Asp Ile Val Asp Asp Ala His Ala Gly Arg Cys Tyr Leu Pro
                165                 170                 175

Ala Ser Trp Leu Glu His Glu Gly Leu Asn Lys Glu Asn Tyr Ala Ala
            180                 185                 190

Pro Glu Asn Arg Gln Ala Leu Ser Arg Ile Ala Arg Arg Leu Val Gln
        195                 200                 205

Glu Ala Glu Pro Tyr Tyr Leu Ser Ala Thr Ala Gly Leu Ala Gly Leu
    210                 215                 220

Pro Leu Arg Ser Ala Trp Ala Ile Ala Thr Ala Lys Gln Val Tyr Arg
225                 230                 235                 240

Lys Ile Gly Val Lys Val Glu Gln Ala Gly Gln Gln Ala Trp Asp Gln
                245                 250                 255

Arg Gln Ser Thr Thr Thr Pro Glu Lys Leu Thr Leu Leu Leu Ala Ala
            260                 265                 270

Ser Gly Gln Ala Leu Thr Ser Arg Met Arg Ala His Pro Pro Arg Pro
        275                 280                 285

Ala His Leu Trp Gln Arg Pro Leu
    290                 295

<210> SEQ ID NO 28
<211> LENGTH: 32
<212> TYPE: DNA
<213> ORGANISM: Unknown
<220> FEATURE:
```

```
<221> NAME/KEY: primer_bind
<223> OTHER INFORMATION: Artificial sequence

<400> SEQUENCE: 28
tttttctcga gcgataaacg ctcacttggt ta                                    32

<210> SEQ ID NO 29
<211> LENGTH: 32
<212> TYPE: DNA
<213> ORGANISM: Unknown
<220> FEATURE:
<221> NAME/KEY: primer_bind
<223> OTHER INFORMATION: Artificial sequence

<400> SEQUENCE: 29
tttttgtcga cacgttatgc tcacaacccc gg                                    32

<210> SEQ ID NO 30
<211> LENGTH: 679
<212> TYPE: DNA
<213> ORGANISM: Escherichia coli
<220> FEATURE:
<221> NAME/KEY: CDS
<222> LOCATION: (87)..(635)

<400> SEQUENCE: 30
```

| | | | | | | | | | | | | |
|---|---|---|---|---|---|---|---|---|---|---|---|---|
| ctcgagcgat aaacgctcac ttggttaatc atttcactct tcaattatct ataatgatga | | | | | | | | | | | | 60 |
| gtgatcagaa ttacatgtga gaaatt atg caa acg gaa cac gtc att tta ttg | | | | | | | | | | | | 113 |
| | | Met | Gln | Thr | Glu | His | Val | Ile | Leu | Leu | | |
| | | 1 | | | 5 | | | | | | | |
| aat gca cag gga gtt ccc acg ggt acg ctg gaa aag tat gcc gca cac | | | | | | | | | | | | 161 |
| Asn Ala Gln Gly Val Pro Thr Gly Thr Leu Glu Lys Tyr Ala Ala His | | | | | | | | | | | | |
| 10 | | | | 15 | | | | 20 | | | 25 | |
| acg gca gac acc cgc tta cat ctc gcg ttc tcc agt tgg ctg ttt aat | | | | | | | | | | | | 209 |
| Thr Ala Asp Thr Arg Leu His Leu Ala Phe Ser Ser Trp Leu Phe Asn | | | | | | | | | | | | |
| | | | 30 | | | | 35 | | | | 40 | |
| gcc aaa gga caa tta tta gtt acc cgc cgc gca ctg agc aaa aaa gca | | | | | | | | | | | | 257 |
| Ala Lys Gly Gln Leu Leu Val Thr Arg Arg Ala Leu Ser Lys Lys Ala | | | | | | | | | | | | |
| 45 | | | | | 50 | | | | | 55 | | |
| tgg cct ggc gtg tgg act aac tcg gtt tgt ggg cac cca caa ctg gga | | | | | | | | | | | | 305 |
| Trp Pro Gly Val Trp Thr Asn Ser Val Cys Gly His Pro Gln Leu Gly | | | | | | | | | | | | |
| | 60 | | | | | 65 | | | | | 70 | |
| gaa agc aac gaa gac gca gtg atc cgc cgt tgc cgt tat gag ctt ggc | | | | | | | | | | | | 353 |
| Glu Ser Asn Glu Asp Ala Val Ile Arg Arg Cys Arg Tyr Glu Leu Gly | | | | | | | | | | | | |
| 75 | | | | | 80 | | | | | 85 | | |
| gtg gaa att acg cct cct gaa tct atc tat cct gac ttt cgc tac cgc | | | | | | | | | | | | 401 |
| Val Glu Ile Thr Pro Pro Glu Ser Ile Tyr Pro Asp Phe Arg Tyr Arg | | | | | | | | | | | | |
| 90 | | | | 95 | | | | 100 | | | 105 | |
| gcc acc gat ccg agt ggc att gtg gaa aat gaa gtg tgt ccg gta ttt | | | | | | | | | | | | 449 |
| Ala Thr Asp Pro Ser Gly Ile Val Glu Asn Glu Val Cys Pro Val Phe | | | | | | | | | | | | |
| | | | 110 | | | | 115 | | | | 120 | |
| gcc gca cgc acc act agt gcg tta cag atc aat gat gat gaa gtg atg | | | | | | | | | | | | 497 |
| Ala Ala Arg Thr Thr Ser Ala Leu Gln Ile Asn Asp Asp Glu Val Met | | | | | | | | | | | | |
| | | 125 | | | | 130 | | | | 135 | | |
| gat tat caa tgg tgt gat tta gca gat gta tta cac ggt att gat gcc | | | | | | | | | | | | 545 |
| Asp Tyr Gln Trp Cys Asp Leu Ala Asp Val Leu His Gly Ile Asp Ala | | | | | | | | | | | | |
| | 140 | | | | 145 | | | | 150 | | | |
| acg ccg tgg gcg ttc agt ccg tgg atg gtg atg cag gcg aca aat cgc | | | | | | | | | | | | 593 |
| Thr Pro Trp Ala Phe Ser Pro Trp Met Val Met Gln Ala Thr Asn Arg | | | | | | | | | | | | |
| 155 | | | | 160 | | | | 165 | | | | |
| gaa gcc aga aaa cga tta tct gca ttt acc cag ctt aaa taa | | | | | | | | | | | | 635 |
| Glu Ala Arg Lys Arg Leu Ser Ala Phe Thr Gln Leu Lys | | | | | | | | | | | | |

```
                 170                 175                 180
aaaaaccccg acatttgccg gggttgtgag cataacgtgt cgac                     679

<210> SEQ ID NO 31
<211> LENGTH: 182
<212> TYPE: PRT
<213> ORGANISM: Escherichia coli

<400> SEQUENCE: 31

Met Gln Thr Glu His Val Ile Leu Leu Asn Ala Gln Gly Val Pro Thr
1               5                   10                  15

Gly Thr Leu Glu Lys Tyr Ala Ala His Thr Ala Asp Thr Arg Leu His
            20                  25                  30

Leu Ala Phe Ser Ser Trp Leu Phe Asn Ala Lys Gly Gln Leu Leu Val
        35                  40                  45

Thr Arg Arg Ala Leu Ser Lys Lys Ala Trp Pro Gly Val Trp Thr Asn
    50                  55                  60

Ser Val Cys Gly His Pro Gln Leu Gly Glu Ser Asn Glu Asp Ala Val
65                  70                  75                  80

Ile Arg Arg Cys Arg Tyr Glu Leu Gly Val Glu Ile Thr Pro Pro Glu
                85                  90                  95

Ser Ile Tyr Pro Asp Phe Arg Tyr Arg Ala Thr Asp Pro Ser Gly Ile
            100                 105                 110

Val Glu Asn Glu Val Cys Pro Val Phe Ala Ala Arg Thr Thr Ser Ala
        115                 120                 125

Leu Gln Ile Asn Asp Asp Glu Val Met Asp Tyr Gln Trp Cys Asp Leu
    130                 135                 140

Ala Asp Val Leu His Gly Ile Asp Ala Thr Pro Trp Ala Phe Ser Pro
145                 150                 155                 160

Trp Met Val Met Gln Ala Thr Asn Arg Glu Ala Arg Lys Arg Leu Ser
                165                 170                 175

Ala Phe Thr Gln Leu Lys
            180

<210> SEQ ID NO 32
<211> LENGTH: 31
<212> TYPE: DNA
<213> ORGANISM: Unknown
<220> FEATURE:
<221> NAME/KEY: primer_bind
<223> OTHER INFORMATION: Artificial sequence

<400> SEQUENCE: 32
tttttccatg gtgaaggagg aaatagcgaa a                                   31

<210> SEQ ID NO 33
<211> LENGTH: 32
<212> TYPE: DNA
<213> ORGANISM: Unknown
<220> FEATURE:
<221> NAME/KEY: primer_bind
<223> OTHER INFORMATION: Artificial sequence

<400> SEQUENCE: 33
tttttaagct tcactttttt tcttgtaacc aa                                  32

<210> SEQ ID NO 34
<211> LENGTH: 962
<212> TYPE: DNA
<213> ORGANISM: Archaeoglobus fulgidus
```

```
<220> FEATURE:
<221> NAME/KEY: CDS
<222> LOCATION: (3)..(956)

<400> SEQUENCE: 34 cc atg gtg aag gag gaa ata gcg aaa agg gcc gaa ata atc aac aaa         47
   Met Val Lys Glu Glu Ile Ala Lys Arg Ala Glu Ile Ile Asn Lys
   1               5                   10                  15 gcc att gaa gag ctt ctg ccc gaa agg gag ccg att gga ctc tac aaa        95
Ala Ile Glu Glu Leu Leu Pro Glu Arg Glu Pro Ile Gly Leu Tyr Lys
                20                  25                  30 gcc gca agg cat ctg atc aaa gca ggt ggc aag agg cta agg cct gta       143
Ala Ala Arg His Leu Ile Lys Ala Gly Gly Lys Arg Leu Arg Pro Val
            35                  40                  45 ata agc ctc tta gca gtc gaa gcc ctt ggg aaa gac tac aga aag att       191
Ile Ser Leu Leu Ala Val Glu Ala Leu Gly Lys Asp Tyr Arg Lys Ile
        50                  55                  60 atc ccg gct gct gtc agc att gaa aca atc cac aac ttc acc ctc gtg       239
Ile Pro Ala Ala Val Ser Ile Glu Thr Ile His Asn Phe Thr Leu Val
65                  70                  75 cat gac gac ata atg gac agg gac gag atg agg agg gga gtt ccg acg       287
His Asp Asp Ile Met Asp Arg Asp Glu Met Arg Arg Gly Val Pro Thr
80                  85                  90                  95 gta cac agg gtt tat ggg gaa gcg acg gcc att tta gca ggc gac aca       335
Val His Arg Val Tyr Gly Glu Ala Thr Ala Ile Leu Ala Gly Asp Thr
                100                 105                 110 ctc ttt gct gaa gcc ttc aag ctg ctg aca aag tgc gat gtt gag agc       383
Leu Phe Ala Glu Ala Phe Lys Leu Leu Thr Lys Cys Asp Val Glu Ser
            115                 120                 125 gag gga atc aga aaa gct aca gaa atg ctt tcg gac gtt tgc ata aaa       431
Glu Gly Ile Arg Lys Ala Thr Glu Met Leu Ser Asp Val Cys Ile Lys
        130                 135                 140 ata tgc gag ggg cag tac tac gac atg agc ttt gag aaa aag gag agc       479
Ile Cys Glu Gly Gln Tyr Tyr Asp Met Ser Phe Glu Lys Lys Glu Ser
145                 150                 155 gtt tcc gag gag gag tat ctc agg atg gtc gag ctg aag acc gga gtg       527
Val Ser Glu Glu Glu Tyr Leu Arg Met Val Glu Leu Lys Thr Gly Val
160                 165                 170                 175 ctg att gca gct tct gca gca tta cct gcg gtg ctt ttt ggg gag agc       575
Leu Ile Ala Ala Ser Ala Ala Leu Pro Ala Val Leu Phe Gly Glu Ser
                180                 185                 190 gag gaa att gta aag gcg ctg tgg gac tac gga gtt ctt agc ggt att       623
Glu Glu Ile Val Lys Ala Leu Trp Asp Tyr Gly Val Leu Ser Gly Ile
            195                 200                 205 ggc ttc cag atc cag gac gac ctg ctt gac ctg act gag gag acc gga       671
Gly Phe Gln Ile Gln Asp Asp Leu Leu Asp Leu Thr Glu Glu Thr Gly
        210                 215                 220 aag gac tgg gga agc gac ctg ctt aaa ggg aag aaa acc ctg att gtc       719
Lys Asp Trp Gly Ser Asp Leu Leu Lys Gly Lys Lys Thr Leu Ile Val
225                 230                 235 ata aag gcg ttc gaa aag gga gtg aag cta aag acg ttt gga aag gaa       767
Ile Lys Ala Phe Glu Lys Gly Val Lys Leu Lys Thr Phe Gly Lys Glu
240                 245                 250                 255 aag gcg gac gtc tct gag att aga gat gat atc gaa aag tta aga gag       815
Lys Ala Asp Val Ser Glu Ile Arg Asp Asp Ile Glu Lys Leu Arg Glu
                260                 265                 270 tgt ggt gcg att gat tac gct gcc agc atg gca aga aag atg gct gaa       863
Cys Gly Ala Ile Asp Tyr Ala Ala Ser Met Ala Arg Lys Met Ala Glu
            275                 280                 285 gag gcg aaa aga aag ctc gaa gtt ctg cct gaa agc aaa gcc aag gaa       911
```

| Glu | Ala | Lys | Arg | Lys | Leu | Glu | Val | Leu | Pro | Glu | Ser | Lys | Ala | Lys | Glu |
|---|---|---|---|---|---|---|---|---|---|---|---|---|---|---|---|
| | 290 | | | | 295 | | | | 300 | | | | | | |

```
aca ctg ctg gaa ctt acc gac ttc ttg gtt aca aga aaa aag tga        956
Thr Leu Leu Glu Leu Thr Asp Phe Leu Val Thr Arg Lys Lys
    305                 310                 315 aagctt                                                              962
```

<210> SEQ ID NO 35
<211> LENGTH: 317
<212> TYPE: PRT
<213> ORGANISM: Archaeoglobus fulgidus

<400> SEQUENCE: 35

| Met | Val | Lys | Glu | Glu | Ile | Ala | Lys | Arg | Ala | Glu | Ile | Ile | Asn | Lys | Ala |
|---|---|---|---|---|---|---|---|---|---|---|---|---|---|---|---|
| 1 | | | | 5 | | | | | 10 | | | | | 15 | |

| Ile | Glu | Glu | Leu | Leu | Pro | Glu | Arg | Glu | Pro | Ile | Gly | Leu | Tyr | Lys | Ala |
|---|---|---|---|---|---|---|---|---|---|---|---|---|---|---|---|
| | | | 20 | | | | | 25 | | | | | 30 | | |

| Ala | Arg | His | Leu | Ile | Lys | Ala | Gly | Gly | Lys | Arg | Leu | Arg | Pro | Val | Ile |
|---|---|---|---|---|---|---|---|---|---|---|---|---|---|---|---|
| | | 35 | | | | | 40 | | | | | 45 | | | |

| Ser | Leu | Leu | Ala | Val | Glu | Ala | Leu | Gly | Lys | Asp | Tyr | Arg | Lys | Ile | Ile |
|---|---|---|---|---|---|---|---|---|---|---|---|---|---|---|---|
| | 50 | | | | | 55 | | | | | 60 | | | | |

| Pro | Ala | Ala | Val | Ser | Ile | Glu | Thr | Ile | His | Asn | Phe | Thr | Leu | Val | His |
|---|---|---|---|---|---|---|---|---|---|---|---|---|---|---|---|
| 65 | | | | | 70 | | | | | 75 | | | | | 80 |

| Asp | Asp | Ile | Met | Asp | Arg | Asp | Glu | Met | Arg | Arg | Gly | Val | Pro | Thr | Val |
|---|---|---|---|---|---|---|---|---|---|---|---|---|---|---|---|
| | | | | 85 | | | | | 90 | | | | | 95 | |

| His | Arg | Val | Tyr | Gly | Glu | Ala | Thr | Ala | Ile | Leu | Ala | Gly | Asp | Thr | Leu |
|---|---|---|---|---|---|---|---|---|---|---|---|---|---|---|---|
| | | | | 100 | | | | | 105 | | | | | 110 | |

| Phe | Ala | Glu | Ala | Phe | Lys | Leu | Leu | Thr | Lys | Cys | Asp | Val | Glu | Ser | Glu |
|---|---|---|---|---|---|---|---|---|---|---|---|---|---|---|---|
| | | | 115 | | | | | 120 | | | | | 125 | | |

| Gly | Ile | Arg | Lys | Ala | Thr | Glu | Met | Leu | Ser | Asp | Val | Cys | Ile | Lys | Ile |
|---|---|---|---|---|---|---|---|---|---|---|---|---|---|---|---|
| | 130 | | | | | 135 | | | | | 140 | | | | |

| Cys | Glu | Gly | Gln | Tyr | Tyr | Asp | Met | Ser | Phe | Glu | Lys | Lys | Glu | Ser | Val |
|---|---|---|---|---|---|---|---|---|---|---|---|---|---|---|---|
| 145 | | | | | 150 | | | | | 155 | | | | | 160 |

| Ser | Glu | Glu | Glu | Tyr | Leu | Arg | Met | Val | Glu | Leu | Lys | Thr | Gly | Val | Leu |
|---|---|---|---|---|---|---|---|---|---|---|---|---|---|---|---|
| | | | | 165 | | | | | 170 | | | | | 175 | |

| Ile | Ala | Ala | Ser | Ala | Ala | Leu | Pro | Ala | Val | Leu | Phe | Gly | Glu | Ser | Glu |
|---|---|---|---|---|---|---|---|---|---|---|---|---|---|---|---|
| | | | 180 | | | | | 185 | | | | | 190 | | |

| Glu | Ile | Val | Lys | Ala | Leu | Trp | Asp | Tyr | Gly | Val | Leu | Ser | Gly | Ile | Gly |
|---|---|---|---|---|---|---|---|---|---|---|---|---|---|---|---|
| | 195 | | | | | 200 | | | | | 205 | | | | |

| Phe | Gln | Ile | Gln | Asp | Asp | Leu | Leu | Asp | Leu | Thr | Glu | Glu | Thr | Gly | Lys |
|---|---|---|---|---|---|---|---|---|---|---|---|---|---|---|---|
| 210 | | | | | 215 | | | | | 220 | | | | | |

| Asp | Trp | Gly | Ser | Asp | Leu | Leu | Lys | Gly | Lys | Lys | Thr | Leu | Ile | Val | Ile |
|---|---|---|---|---|---|---|---|---|---|---|---|---|---|---|---|
| 225 | | | | | 230 | | | | | 235 | | | | | 240 |

| Lys | Ala | Phe | Glu | Lys | Gly | Val | Lys | Leu | Lys | Thr | Phe | Gly | Lys | Glu | Lys |
|---|---|---|---|---|---|---|---|---|---|---|---|---|---|---|---|
| | | | | 245 | | | | | 250 | | | | | 255 | |

| Ala | Asp | Val | Ser | Glu | Ile | Arg | Asp | Asp | Ile | Glu | Lys | Leu | Arg | Glu | Cys |
|---|---|---|---|---|---|---|---|---|---|---|---|---|---|---|---|
| | | | 260 | | | | | 265 | | | | | 270 | | |

| Gly | Ala | Ile | Asp | Tyr | Ala | Ala | Ser | Met | Ala | Arg | Lys | Met | Ala | Glu | Glu |
|---|---|---|---|---|---|---|---|---|---|---|---|---|---|---|---|
| | | 275 | | | | | 280 | | | | | 285 | | | |

| Ala | Lys | Arg | Lys | Leu | Glu | Val | Leu | Pro | Glu | Ser | Lys | Ala | Lys | Glu | Thr |
|---|---|---|---|---|---|---|---|---|---|---|---|---|---|---|---|
| | 290 | | | | | 295 | | | | | 300 | | | | |

| Leu | Leu | Glu | Leu | Thr | Asp | Phe | Leu | Val | Thr | Arg | Lys | Lys |
|---|---|---|---|---|---|---|---|---|---|---|---|---|
| 305 | | | | | 310 | | | | | 315 | | |

<210> SEQ ID NO 36

```
<211> LENGTH: 1293
<212> TYPE: DNA
<213> ORGANISM: Archaeoglobus fulgidus
<220> FEATURE:
<221> NAME/KEY: CDS
<222> LOCATION: (206)..(1159)

<400> SEQUENCE: 36
```

| | |
|---|---:|
| taaaacgacg gccagtgagc gcgcgtaata cgactcacta tagggcgaat tgggtaccgg | 60 |
| gccccccctc gacgccgtcg ttcaatgaga atggataaga ggctcgtggg attgacgtga | 120 |
| ggggcaggg atggctatat ttctgggagc gaactccggg cgaggatcta gttgtaggga | 180 |
| gggattcatg acaccacaaa cagcc atg gtg aag gag gaa ata gcg aaa agg<br>                                        Met Val Lys Glu Glu Ile Ala Lys Arg<br>                                         1                  5 | 232 |
| gcc gaa ata atc aac aaa gcc att gaa gag ctt ctg ccc gaa agg gag<br>Ala Glu Ile Ile Asn Lys Ala Ile Glu Glu Leu Leu Pro Glu Arg Glu<br>10                  15                 20               25 | 280 |
| ccg att gga ctc tac aaa gcc gca agg cat ctg atc aaa gca ggt ggc<br>Pro Ile Gly Leu Tyr Lys Ala Ala Arg His Leu Ile Lys Ala Gly Gly<br>                  30                 35                 40 | 328 |
| aag agg cta agg cct gta ata agc ctc tta gca gtc gaa gcc ctt ggg<br>Lys Arg Leu Arg Pro Val Ile Ser Leu Leu Ala Val Glu Ala Leu Gly<br>                 45                 50                 55 | 376 |
| aaa gac tac aga aag att atc ccg gct gct gtc agc att gaa aca atc<br>Lys Asp Tyr Arg Lys Ile Ile Pro Ala Ala Val Ser Ile Glu Thr Ile<br>        60                 65                 70 | 424 |
| cac aac ttc acc ctc gtg cat gac gac ata atg gac agg gac gag atg<br>His Asn Phe Thr Leu Val His Asp Asp Ile Met Asp Arg Asp Glu Met<br>75                  80                 85 | 472 |
| agg agg gga gtt ccg acg gta cac agg gtt tat ggg gaa gcg acg gcc<br>Arg Arg Gly Val Pro Thr Val His Arg Val Tyr Gly Glu Ala Thr Ala<br>90                  95                100             105 | 520 |
| att tta gca ggc gac aca ctc ttt gct gaa gcc ttc aag ctg ctg aca<br>Ile Leu Ala Gly Asp Thr Leu Phe Ala Glu Ala Phe Lys Leu Leu Thr<br>                110               115               120 | 568 |
| aag tgc gat gtt gag agc gag gga atc aga aaa gct aca gaa atg ctt<br>Lys Cys Asp Val Glu Ser Glu Gly Ile Arg Lys Ala Thr Glu Met Leu<br>              125               130               135 | 616 |
| tcg gac gtt tgc ata aaa ata tgc gag ggg cag tac tac gac atg agc<br>Ser Asp Val Cys Ile Lys Ile Cys Glu Gly Gln Tyr Tyr Asp Met Ser<br>140                 145               150 | 664 |
| ttt gag aaa aag gag agc gtt tcc gag gag gag tat ctc agg atg gtc<br>Phe Glu Lys Lys Glu Ser Val Ser Glu Glu Glu Tyr Leu Arg Met Val<br>155                  160               165 | 712 |
| gag ctg aag acc gga gtg ctg att gca gct tct gca gca tta cct gcg<br>Glu Leu Lys Thr Gly Val Leu Ile Ala Ala Ser Ala Ala Leu Pro Ala<br>170                 175               180               185 | 760 |
| gtg ctt ttt ggg gag agc gag gaa att gta aag gcg ctg tgg gac tac<br>Val Leu Phe Gly Glu Ser Glu Glu Ile Val Lys Ala Leu Trp Asp Tyr<br>                190               195               200 | 808 |
| gga gtt ctt agc ggt att ggc ttc cag atc cag gac gac ctg ctt gac<br>Gly Val Leu Ser Gly Ile Gly Phe Gln Ile Gln Asp Asp Leu Leu Asp<br>              205               210               215 | 856 |
| ctg act gag gag acc gga aag gac tgg gga agc gac ctg ctt aaa ggg<br>Leu Thr Glu Glu Thr Gly Lys Asp Trp Gly Ser Asp Leu Leu Lys Gly<br>            220               225               230 | 904 |
| aag aaa acc ctg att gtc ata aag gcg ttc gaa aag gga gtg aag cta<br>Lys Lys Thr Leu Ile Val Ile Lys Ala Phe Glu Lys Gly Val Lys Leu<br>235                  240               245 | 952 |

-continued

```
aag acg ttt gga aag gaa aag gcg gac gtc tct gag att aga gat gat    1000
Lys Thr Phe Gly Lys Glu Lys Ala Asp Val Ser Glu Ile Arg Asp Asp
250                 255                 260                 265 atc gaa aag tta aga gag tgt ggt gcg att gat tac gcc agc atg        1048
Ile Glu Lys Leu Arg Glu Cys Gly Ala Ile Asp Tyr Ala Ala Ser Met
                270                 275                 280 gca aga aag atg gct gaa gag gcg aaa aga aag ctc gaa gtt ctg cct    1096
Ala Arg Lys Met Ala Glu Glu Ala Lys Arg Lys Leu Glu Val Leu Pro
            285                 290                 295 gaa agc aaa gcc aag gaa aca ctg ctg gaa ctt acc gac ttc ttg gtt    1144
Glu Ser Lys Ala Lys Glu Thr Leu Leu Glu Leu Thr Asp Phe Leu Val
        300                 305                 310 aca aga aaa aag tga aagcttcaat tgcatgctct agatgatcaa agaattcctg   1199
Thr Arg Lys Lys
    315 gcctagtcta taggaggttt tgaaaagaaa ggagcaataa tcattttctt gttctatcaa  1259 gagggtgcta ttgctccttt cttttttttct cgag                             1293

<210> SEQ ID NO 37
<211> LENGTH: 317
<212> TYPE: PRT
<213> ORGANISM: Archaeoglobus fulgidus

<400> SEQUENCE: 37

Met Val Lys Glu Glu Ile Ala Lys Arg Ala Glu Ile Ile Asn Lys Ala
1               5                   10                  15

Ile Glu Glu Leu Leu Pro Glu Arg Glu Pro Ile Gly Leu Tyr Lys Ala
            20                  25                  30

Ala Arg His Leu Ile Lys Ala Gly Gly Lys Arg Leu Arg Pro Val Ile
        35                  40                  45

Ser Leu Leu Ala Val Glu Ala Leu Gly Lys Asp Tyr Arg Lys Ile Ile
    50                  55                  60

Pro Ala Ala Val Ser Ile Glu Thr Ile His Asn Phe Thr Leu Val His
65                  70                  75                  80

Asp Asp Ile Met Asp Arg Asp Glu Met Arg Arg Gly Val Pro Thr Val
                85                  90                  95

His Arg Val Tyr Gly Glu Ala Thr Ala Ile Leu Ala Gly Asp Thr Leu
            100                 105                 110

Phe Ala Glu Ala Phe Lys Leu Leu Thr Lys Cys Asp Val Glu Ser Glu
        115                 120                 125

Gly Ile Arg Lys Ala Thr Glu Met Leu Ser Asp Val Cys Ile Lys Ile
    130                 135                 140

Cys Glu Gly Gln Tyr Tyr Asp Met Ser Phe Glu Lys Lys Glu Ser Val
145                 150                 155                 160

Ser Glu Glu Glu Tyr Leu Arg Met Val Glu Leu Lys Thr Gly Val Leu
                165                 170                 175

Ile Ala Ala Ser Ala Ala Leu Pro Ala Val Leu Phe Gly Glu Ser Glu
            180                 185                 190

Glu Ile Val Lys Ala Leu Trp Asp Tyr Gly Val Leu Ser Gly Ile Gly
        195                 200                 205

Phe Gln Ile Gln Asp Asp Leu Leu Asp Leu Thr Glu Glu Thr Gly Lys
    210                 215                 220

Asp Trp Gly Ser Asp Leu Leu Lys Gly Lys Lys Thr Leu Ile Val Ile
225                 230                 235                 240

Lys Ala Phe Glu Lys Gly Val Lys Leu Lys Thr Phe Gly Lys Glu Lys
                245                 250                 255
```

```
Ala Asp Val Ser Glu Ile Arg Asp Ile Glu Lys Leu Arg Glu Cys
            260                 265                 270

Gly Ala Ile Asp Tyr Ala Ala Ser Met Ala Arg Lys Met Ala Glu Glu
        275                 280                 285

Ala Lys Arg Lys Leu Glu Val Leu Pro Glu Ser Lys Ala Lys Glu Thr
    290                 295                 300

Leu Leu Glu Leu Thr Asp Phe Leu Val Thr Arg Lys Lys
305                 310                 315

<210> SEQ ID NO 38
<211> LENGTH: 35
<212> TYPE: DNA
<213> ORGANISM: Unknown
<220> FEATURE:
<221> NAME/KEY: primer_bind
<223> OTHER INFORMATION: Artificial sequence

<400> SEQUENCE: 38
gagctcttca ttatttcgat tttgatttcg tgacc                          35

<210> SEQ ID NO 39
<211> LENGTH: 38
<212> TYPE: DNA
<213> ORGANISM: Artificial sequence
<220> FEATURE:
<223> OTHER INFORMATION: Primer

<400> SEQUENCE: 39
aagcttggtt gatcagaaga agaagaagaa gatgaact                       38

<210> SEQ ID NO 40
<211> LENGTH: 647
<212> TYPE: DNA
<213> ORGANISM: Arabidopsis thaliana
<220> FEATURE:
<221> NAME/KEY: Promoter

<400> SEQUENCE: 40
gagctcttca ttatttcgat tttgatttcg tgaccagcga acgcagaata ccttgttgtg    60
taatacttta cccgtgtaaa tcaaaaacaa aaaggctttt gagcttttg tagttgaatt    120 tctctggctg atcttttctg tacagattca tatatctgca gagacgatat cattgattat   180
ttgagcttct tttgaactat ttcgtgtaat ttgggatgag agctctatgt atgtgtgtaa   240
actttgaaga caacaagaaa ggtaacaagt gagggaggga tgactccatg tcaaaataga   300
tgtcataaga ggcccatcaa taagtgcttg agcccattag ctagcccagt aactaccaga   360
ttgtgagatg gatgtgtgaa cagttttttt tttgatgtag gactgaaatg tgaacaacag   420
gcgcatgaaa ggctaaatta ggacaatgat aagcagaaat aacttatcct ctctaacact   480
tggcctcaca ttgcccttca cacaatccac acacatccaa tcacaacctc atcatatatc   540
tcccgctaat cttttttct tgatctttt ttttttgct tattatttt ttgactttga      600 tctcccatca gttcatcttc ttcttcttct tctgatcaac caagctt              647

<210> SEQ ID NO 41
<211> LENGTH: 28
<212> TYPE: DNA
<213> ORGANISM: Unknown
<220> FEATURE:
<221> NAME/KEY: primer_bind
<223> OTHER INFORMATION: Artificial sequence
```

-continued

```
<400> SEQUENCE: 41
gagctcactc actgatttcc attgcttg                                         28

<210> SEQ ID NO 42
<211> LENGTH: 23
<212> TYPE: DNA
<213> ORGANISM: Artificial sequence
<220> FEATURE:
<223> OTHER INFORMATION: Primer

<400> SEQUENCE: 42
aagcttttgt tgaagagatt tgg                                              23

<210> SEQ ID NO 43
<211> LENGTH: 37
<212> TYPE: DNA
<213> ORGANISM: Unknown
<220> FEATURE:
<221> NAME/KEY: primer_bind
<223> OTHER INFORMATION: Artificial sequence

<400> SEQUENCE: 43
cgccgttaag tcgatgtccg ttgatttaaa cagtgtc                               37

<210> SEQ ID NO 44
<211> LENGTH: 34
<212> TYPE: DNA
<213> ORGANISM: Unknown
<220> FEATURE:
<221> NAME/KEY: primer_bind
<223> OTHER INFORMATION: Artificial sequence

<400> SEQUENCE: 44
atcaacggac atcgacttaa cggcgtttgt aaac                                  34

<210> SEQ ID NO 45
<211> LENGTH: 777
<212> TYPE: DNA
<213> ORGANISM: Arabidopsis thaliana
<220> FEATURE:
<221> NAME/KEY: Promoter

<400> SEQUENCE: 45
gagctcactc actgatttcc attgcttgaa aattgatgat gaactaagat caatccatgt      60
tagtttcaaa acaacagtaa ctgtggccaa cttagttttg aaacaacact aactggtcga     120
agcaaaaaga aaaagagagtt tcatcatata tctgatttga tggactgttt ggagttagga    180
ccaaacatta tctacaaaca aagacttttc tcctaacttg tgattccttc ttaaacccta     240
ggggtaatat tctattttcc aaggatcttt agttaaaggc aaatccggga aattattgta     300
atcatttggg gaaacatata aaagatttga gttagatgga agtgacgatt aatccaaaca     360
tatatatctc tttcttctta tttcccaaat taacagacaa aagtagaata ttggctttta    420
acaccaatat aaaaacttgc ttcacaccta aacactttttg tttactttag ggtaagtgca   480
aaaagccaac caaatccacc tgcactgatt tgacgtttac aaacgccgtt aagtcgatgt    540
ccgttgattt aaacagtgtc ttgtaattaa aaaaatcagt ttacataaat ggaaaattta    600
tcacttagtt ttcatcaact tctgaactta cctttcatgg attaggcaat actttccatt    660
tttagtaact caagtggacc ctttacttct tcaactccat ctctctcttt ctatttcact    720
tctttcttct cattatatct cttgtcctct ccaccaaatc tcttcaacaa aaagctt       777
```

<210> SEQ ID NO 46
<211> LENGTH: 804
<212> TYPE: DNA
<213> ORGANISM: Synechococcus WH8102
<220> FEATURE:
<221> NAME/KEY: CDS

<400> SEQUENCE: 46

| atg | aaa | acg | aca | aga | tct | att | tcg | tgg | cca | tcg | act | tgc | tgg | cat | cac | 48 |
| Met | Lys | Thr | Thr | Arg | Ser | Ile | Ser | Trp | Pro | Ser | Thr | Cys | Trp | His | His | |
| 1 | | | | 5 | | | | | 10 | | | | | 15 | | |

| cag | ccg | agt | tgc | tca | agc | tgg | gtg | gca | aat | gag | ttc | agc | cct | cag | gcc | 96 |
| Gln | Pro | Ser | Cys | Ser | Ser | Trp | Val | Ala | Asn | Glu | Phe | Ser | Pro | Gln | Ala | |
| | | | 20 | | | | | 25 | | | | | 30 | | | |

| ctc | aaa | ggg | ttg | gct | ctg | gct | ggt | ctg | att | gga | tca | gcc | tgg | ctg | ctc | 144 |
| Leu | Lys | Gly | Leu | Ala | Leu | Ala | Gly | Leu | Ile | Gly | Ser | Ala | Trp | Leu | Leu | |
| | | 35 | | | | | 40 | | | | | 45 | | | | |

| tcc | ctg | ggc | ctg | agc | tac | acc | ctg | cca | ctt | gat | cag | acg | cct | ggg | ctg | 192 |
| Ser | Leu | Gly | Leu | Ser | Tyr | Thr | Leu | Pro | Leu | Asp | Gln | Thr | Pro | Gly | Leu | |
| | 50 | | | | | 55 | | | | | 60 | | | | | |

| ttg | att | ggc | agc | ttg | att | ctg | ctc | aga | gca | ttt | ctg | cac | acc | ggg | ctg | 240 |
| Leu | Ile | Gly | Ser | Leu | Ile | Leu | Leu | Arg | Ala | Phe | Leu | His | Thr | Gly | Leu | |
| 65 | | | | | 70 | | | | | 75 | | | | | 80 | |

| ttc | atc | gtt | gcc | cac | gat | tcc | atg | cac | gcc | agt | ctg | gtt | ccg | ggt | cat | 288 |
| Phe | Ile | Val | Ala | His | Asp | Ser | Met | His | Ala | Ser | Leu | Val | Pro | Gly | His | |
| | | | | 85 | | | | | 90 | | | | | 95 | | |

| ccc | gga | ttg | aac | cgc | tgg | atc | ggc | aaa | gtg | tat | ttg | ttg | gtg | tat | gca | 336 |
| Pro | Gly | Leu | Asn | Arg | Trp | Ile | Gly | Lys | Val | Tyr | Leu | Leu | Val | Tyr | Ala | |
| | | | 100 | | | | | 105 | | | | | 110 | | | |

| ggc | ttg | tct | tat | gag | cgt | tgt | tcc | cgc | aac | cac | aga | cgt | cat | cac | ctg | 384 |
| Gly | Leu | Ser | Tyr | Glu | Arg | Cys | Ser | Arg | Asn | His | Arg | Arg | His | His | Leu | |
| | | 115 | | | | | 120 | | | | | 125 | | | | |

| gca | ccg | gag | acg | ttc | cag | gat | cct | gac | tac | caa | cgt | tgc | acc | aat | aac | 432 |
| Ala | Pro | Glu | Thr | Phe | Gln | Asp | Pro | Asp | Tyr | Gln | Arg | Cys | Thr | Asn | Asn | |
| | 130 | | | | | 135 | | | | | 140 | | | | | |

| aac | atc | cta | gat | tgg | tat | gtt | cac | ttc | atg | ggc | aac | tat | ctg | ggc | atg | 480 |
| Asn | Ile | Leu | Asp | Trp | Tyr | Val | His | Phe | Met | Gly | Asn | Tyr | Leu | Gly | Met | |
| 145 | | | | | 150 | | | | | 155 | | | | | 160 | |

| cgg | caa | ctg | tta | aat | cta | agc | tgt | ctt | tgg | ctg | gcg | cta | atc | att | ctc | 528 |
| Arg | Gln | Leu | Leu | Asn | Leu | Ser | Cys | Leu | Trp | Leu | Ala | Leu | Ile | Ile | Leu | |
| | | | | 165 | | | | | 170 | | | | | 175 | | |

| aac | ggt | tct | gat | ctc | cct | gct | cag | atc | atg | cat | ctg | ctg | ttg | ttc | agc | 576 |
| Asn | Gly | Ser | Asp | Leu | Pro | Ala | Gln | Ile | Met | His | Leu | Leu | Leu | Phe | Ser | |
| | | | 180 | | | | | 185 | | | | | 190 | | | |

| gtt | ctg | ccg | ttg | atc | atc | agt | tcc | tgt | caa | ttg | ttt | cta | gtg | gga | acc | 624 |
| Val | Leu | Pro | Leu | Ile | Ile | Ser | Ser | Cys | Gln | Leu | Phe | Leu | Val | Gly | Thr | |
| | | 195 | | | | | 200 | | | | | 205 | | | | |

| tgg | tta | ccc | cac | cga | cgt | ggg | gcc | acg | aca | cga | ccg | ggc | gtg | aca | acg | 672 |
| Trp | Leu | Pro | His | Arg | Arg | Gly | Ala | Thr | Thr | Arg | Pro | Gly | Val | Thr | Thr | |
| | 210 | | | | | 215 | | | | | 220 | | | | | |

| cgc | agc | ctg | gct | ttg | cat | cca | gcc | ctc | tct | ttc | gca | gct | tgt | tac | aac | 720 |
| Arg | Ser | Leu | Ala | Leu | His | Pro | Ala | Leu | Ser | Phe | Ala | Ala | Cys | Tyr | Asn | |
| 225 | | | | | 230 | | | | | 235 | | | | | 240 | |

| ttt | ggc | tat | cat | cgt | gaa | cat | cat | gaa | tcg | cct | tcc | aca | ccc | tgg | ttt | 768 |
| Phe | Gly | Tyr | His | Arg | Glu | His | His | Glu | Ser | Pro | Ser | Thr | Pro | Trp | Phe | |
| | | | | 245 | | | | | 250 | | | | | 255 | | |

| cag | ctg | cca | caa | ctt | cga | aat | gaa | tca | ttc | act | tga | | | | | 804 |
| Gln | Leu | Pro | Gln | Leu | Arg | Asn | Glu | Ser | Phe | Thr | | | | | | |
| | | | 260 | | | | | 265 | | | | | | | | |

<210> SEQ ID NO 47

<211> LENGTH: 267
<212> TYPE: PRT
<213> ORGANISM: Synechococcus WH8102

<400> SEQUENCE: 47

Met Lys Thr Thr Arg Ser Ile Ser Trp Pro Ser Thr Cys Trp His His
1               5                   10                  15

Gln Pro Ser Cys Ser Ser Trp Val Ala Asn Glu Phe Ser Pro Gln Ala
            20                  25                  30

Leu Lys Gly Leu Ala Leu Ala Gly Leu Ile Gly Ser Ala Trp Leu Leu
        35                  40                  45

Ser Leu Gly Leu Ser Tyr Thr Leu Pro Leu Asp Gln Thr Pro Gly Leu
    50                  55                  60

Leu Ile Gly Ser Leu Ile Leu Arg Ala Phe Leu His Thr Gly Leu
65                  70                  75                  80

Phe Ile Val Ala His Asp Ser Met His Ala Ser Leu Val Pro Gly His
                85                  90                  95

Pro Gly Leu Asn Arg Trp Ile Gly Lys Val Tyr Leu Leu Val Tyr Ala
            100                 105                 110

Gly Leu Ser Tyr Glu Arg Cys Ser Arg Asn His Arg His His Leu
        115                 120                 125

Ala Pro Glu Thr Phe Gln Asp Pro Asp Tyr Gln Arg Cys Thr Asn Asn
130                 135                 140

Asn Ile Leu Asp Trp Tyr Val His Phe Met Gly Asn Tyr Leu Gly Met
145                 150                 155                 160

Arg Gln Leu Leu Asn Leu Ser Cys Leu Trp Leu Ala Leu Ile Ile Leu
                165                 170                 175

Asn Gly Ser Asp Leu Pro Ala Gln Ile Met His Leu Leu Leu Phe Ser
            180                 185                 190

Val Leu Pro Leu Ile Ile Ser Ser Cys Gln Leu Phe Leu Val Gly Thr
        195                 200                 205

Trp Leu Pro His Arg Arg Gly Ala Thr Thr Arg Pro Gly Val Thr Thr
    210                 215                 220

Arg Ser Leu Ala Leu His Pro Ala Leu Ser Phe Ala Ala Cys Tyr Asn
225                 230                 235                 240

Phe Gly Tyr His Arg Glu His His Glu Ser Pro Ser Thr Pro Trp Phe
                245                 250                 255

Gln Leu Pro Gln Leu Arg Asn Glu Ser Phe Thr
            260                 265

<210> SEQ ID NO 48
<211> LENGTH: 804
<212> TYPE: DNA
<213> ORGANISM: Unknown
<220> FEATURE:
<221> NAME/KEY: CDS
<223> OTHER INFORMATION: Artificial variant

<400> SEQUENCE: 48 atg aaa acg aca aga tct att tcg tgg cca tcg act tgc tgg cat cac      48
Met Lys Thr Thr Arg Ser Ile Ser Trp Pro Ser Thr Cys Trp His His
1               5                   10                  15 cag ccg agt tgc tca agc tgg gtg gca aat gag ttc agc cct cag gcc      96
Gln Pro Ser Cys Ser Ser Trp Val Ala Asn Glu Phe Ser Pro Gln Ala
            20                  25                  30 ctc aaa ggg ttg gct ctg gct ggt ctg att gga tca gcc tgg ctg ctc     144
Leu Lys Gly Leu Ala Leu Ala Gly Leu Ile Gly Ser Ala Trp Leu Leu
        35                  40                  45

```
tcc ctg ggc ctg agc tac acc ctg cca ctt gat cag acg cct ggg ctg      192
Ser Leu Gly Leu Ser Tyr Thr Leu Pro Leu Asp Gln Thr Pro Gly Leu
 50                  55                  60 ttg att ggc agc ttg att ctg tgg cag acc ttt ctg cac acc ggg ctg      240
Leu Ile Gly Ser Leu Ile Leu Trp Gln Thr Phe Leu His Thr Gly Leu
 65                  70                  75                  80 ttc atc gtt gcc cac gat tcc atg cac gcc agt ctg gtt ccg ggt cat      288
Phe Ile Val Ala His Asp Ser Met His Ala Ser Leu Val Pro Gly His
                 85                  90                  95 ccc gga ttg aac cgc tgg atc ggc aaa gtg tat ttg ttg gtg tat gca      336
Pro Gly Leu Asn Arg Trp Ile Gly Lys Val Tyr Leu Leu Val Tyr Ala
            100                 105                 110 ggc ttg tct tat gag cgt tgt tcc cgc aac cac aga cgt cat cac ctg      384
Gly Leu Ser Tyr Glu Arg Cys Ser Arg Asn His Arg Arg His His Leu
        115                 120                 125 gca ccg gag acg ttc cag gat cct gac tac caa cgt tgc acc aat aac      432
Ala Pro Glu Thr Phe Gln Asp Pro Asp Tyr Gln Arg Cys Thr Asn Asn
130                 135                 140 aac atc cta gat tgg tat gtt cac ttc atg ggc aac tat ctg ggc atg      480
Asn Ile Leu Asp Trp Tyr Val His Phe Met Gly Asn Tyr Leu Gly Met
145                 150                 155                 160 cgg caa ctg tta aat cta agc tgt ctt tgg ctg gcg cta atc att ctc      528
Arg Gln Leu Leu Asn Leu Ser Cys Leu Trp Leu Ala Leu Ile Ile Leu
                165                 170                 175 aac ggt tct gat ctc cct gct cag atc atg cat ctg ctg ttg ttc agc      576
Asn Gly Ser Asp Leu Pro Ala Gln Ile Met His Leu Leu Leu Phe Ser
            180                 185                 190 gtt ctg ccg ttg atc atc agt tcc tgt caa ttg ttt cta gtg gga acc      624
Val Leu Pro Leu Ile Ile Ser Ser Cys Gln Leu Phe Leu Val Gly Thr
        195                 200                 205 tgg tta ccc cac cga cgt ggg gcc acg aca cga ccg ggc gtg aca acg      672
Trp Leu Pro His Arg Arg Gly Ala Thr Thr Arg Pro Gly Val Thr Thr
    210                 215                 220 cgc agc ctg gct ttg cat cca gcc ctc tct ttc gca gct tgt tac aac      720
Arg Ser Leu Ala Leu His Pro Ala Leu Ser Phe Ala Ala Cys Tyr Asn
225                 230                 235                 240 ttt ggc tat cat cgt gaa cat cat gaa tcg cct tcc aca ccc tgg ttt      768
Phe Gly Tyr His Arg Glu His His Glu Ser Pro Ser Thr Pro Trp Phe
                245                 250                 255 cag ctg cca caa ctt cga aat gaa tca ttc act tga                      804
Gln Leu Pro Gln Leu Arg Asn Glu Ser Phe Thr
            260                 265

<210> SEQ ID NO 49
<211> LENGTH: 267
<212> TYPE: PRT
<213> ORGANISM: Unknown
<220> FEATURE:
<223> OTHER INFORMATION: Artificial variant

<400> SEQUENCE: 49

Met Lys Thr Thr Arg Ser Ile Ser Trp Pro Ser Thr Cys Trp His His
 1               5                  10                  15

Gln Pro Ser Cys Ser Ser Trp Val Ala Asn Glu Phe Ser Pro Gln Ala
                20                  25                  30

Leu Lys Gly Leu Ala Leu Ala Gly Leu Ile Gly Ser Ala Trp Leu Leu
            35                  40                  45

Ser Leu Gly Leu Ser Tyr Thr Leu Pro Leu Asp Gln Thr Pro Gly Leu
 50                  55                  60
```

```
Leu Ile Gly Ser Leu Ile Leu Trp Gln Thr Phe Leu His Thr Gly Leu
 65                  70                  75                  80

Phe Ile Val Ala His Asp Ser Met His Ala Ser Leu Val Pro Gly His
                 85                  90                  95

Pro Gly Leu Asn Arg Trp Ile Gly Lys Val Tyr Leu Leu Val Tyr Ala
            100                 105                 110

Gly Leu Ser Tyr Glu Arg Cys Ser Arg Asn His Arg Arg His His Leu
            115                 120                 125

Ala Pro Glu Thr Phe Gln Asp Pro Asp Tyr Gln Arg Cys Thr Asn Asn
    130                 135                 140

Asn Ile Leu Asp Trp Tyr Val His Phe Met Gly Asn Tyr Leu Gly Met
145                 150                 155                 160

Arg Gln Leu Leu Asn Leu Ser Cys Leu Trp Leu Ala Leu Ile Ile Leu
                165                 170                 175

Asn Gly Ser Asp Leu Pro Ala Gln Ile Met His Leu Leu Phe Ser
            180                 185                 190

Val Leu Pro Leu Ile Ile Ser Ser Cys Gln Leu Phe Leu Val Gly Thr
            195                 200                 205

Trp Leu Pro His Arg Arg Gly Ala Thr Thr Arg Pro Gly Val Thr Thr
    210                 215                 220

Arg Ser Leu Ala Leu His Pro Ala Leu Ser Phe Ala Ala Cys Tyr Asn
225                 230                 235                 240

Phe Gly Tyr His Arg Glu His His Glu Ser Pro Ser Thr Pro Trp Phe
                245                 250                 255

Gln Leu Pro Gln Leu Arg Asn Glu Ser Phe Thr
            260                 265

<210> SEQ ID NO 50
<211> LENGTH: 804
<212> TYPE: DNA
<213> ORGANISM: Unknown
<220> FEATURE:
<221> NAME/KEY: CDS
<223> OTHER INFORMATION: Artificial variant

<400> SEQUENCE: 50 atg aaa acg aca aga tct att tcg tgg cca tcg act tgc tgg cat cac        48
Met Lys Thr Thr Arg Ser Ile Ser Trp Pro Ser Thr Cys Trp His His
 1               5                  10                  15 cag ccg agt tgc tca agc tgg gtg gca aat gag ttc agc cct cag gcc        96
Gln Pro Ser Cys Ser Ser Trp Val Ala Asn Glu Phe Ser Pro Gln Ala
             20                  25                  30 ctc aaa ggg ttg gct ctg gct ggt ctg att gga tca gcc tgg ctg ctc       144
Leu Lys Gly Leu Ala Leu Ala Gly Leu Ile Gly Ser Ala Trp Leu Leu
         35                  40                  45 tcc ctg ggc ctg agc tac acc ctg cca ctt gat cag acg cct ggg ctg       192
Ser Leu Gly Leu Ser Tyr Thr Leu Pro Leu Asp Gln Thr Pro Gly Leu
     50                  55                  60 ttg att ggc agc ttg att ctg ctc aga gca ttt ctg cac acc ggg ctg       240
Leu Ile Gly Ser Leu Ile Leu Leu Arg Ala Phe Leu His Thr Gly Leu
 65                  70                  75                  80 ttc atc gtt gcc cac gat tcc atg cac gcc agt ctg gtt ccg ggt cat       288
Phe Ile Val Ala His Asp Ser Met His Ala Ser Leu Val Pro Gly His
                 85                  90                  95 ccc gga ttg aac cgc tgg atc ggc aaa gtg tat ttg ttg gtg tat gca       336
Pro Gly Leu Asn Arg Trp Ile Gly Lys Val Tyr Leu Leu Val Tyr Ala
            100                 105                 110 ggc ttg tct tat gag cgt tgt tcc cgc aac cac aga cgt cat cac gga       384
```

-continued

```
Gly Leu Ser Tyr Glu Arg Cys Ser Arg Asn His Arg Arg His His Gly
            115                 120                 125 cat cct ggt act gat tta gat cct gac tac caa cgt tgc acc aat aac    432
His Pro Gly Thr Asp Leu Asp Pro Asp Tyr Gln Arg Cys Thr Asn Asn
    130                 135                 140 aac atc cta gat tgg tat gtt cac ttc atg ggc aac tat ctg ggc atg    480
Asn Ile Leu Asp Trp Tyr Val His Phe Met Gly Asn Tyr Leu Gly Met
145                 150                 155                 160 cgg caa ctg tta aat cta agc tgt ctt tgg ctg gcg cta atc att ctc    528
Arg Gln Leu Leu Asn Leu Ser Cys Leu Trp Leu Ala Leu Ile Ile Leu
                165                 170                 175 aac ggt tct gat ctc cct gct cag atc atg cat ctg ctg ttg ttc agc    576
Asn Gly Ser Asp Leu Pro Ala Gln Ile Met His Leu Leu Leu Phe Ser
            180                 185                 190 gtt ctg ccg ttg atc atc agt tcc tgt caa ttg ttt cta gtg gga acc    624
Val Leu Pro Leu Ile Ile Ser Ser Cys Gln Leu Phe Leu Val Gly Thr
        195                 200                 205 tgg tta ccc cac cga cgt ggg gcc acg aca cga ccg ggc gtg aca acg    672
Trp Leu Pro His Arg Arg Gly Ala Thr Thr Arg Pro Gly Val Thr Thr
    210                 215                 220 cgc agc ctg gct ttg cat cca gcc ctc tct ttc gca gct tgt tac aac    720
Arg Ser Leu Ala Leu His Pro Ala Leu Ser Phe Ala Ala Cys Tyr Asn
225                 230                 235                 240 ttt ggc tat cat cgt gaa cat cat gaa tcg cct tcc aca ccc tgg ttt    768
Phe Gly Tyr His Arg Glu His His Glu Ser Pro Ser Thr Pro Trp Phe
                245                 250                 255 cag ctg cca caa ctt cga aat gaa tca ttc act tga                    804
Gln Leu Pro Gln Leu Arg Asn Glu Ser Phe Thr
            260                 265
```

<210> SEQ ID NO 51
<211> LENGTH: 267
<212> TYPE: PRT
<213> ORGANISM: Unknown
<220> FEATURE:
<223> OTHER INFORMATION: Artificial variant

<400> SEQUENCE: 51

```
Met Lys Thr Thr Arg Ser Ile Ser Trp Pro Ser Thr Cys Trp His His
1               5                   10                  15

Gln Pro Ser Cys Ser Ser Trp Val Ala Asn Glu Phe Ser Pro Gln Ala
            20                  25                  30

Leu Lys Gly Leu Ala Leu Ala Gly Leu Ile Gly Ser Ala Trp Leu Leu
        35                  40                  45

Ser Leu Gly Leu Ser Tyr Thr Leu Pro Leu Asp Gln Thr Pro Gly Leu
    50                  55                  60

Leu Ile Gly Ser Leu Ile Leu Leu Arg Ala Phe Leu His Thr Gly Leu
65                  70                  75                  80

Phe Ile Val Ala His Asp Ser Met His Ala Ser Leu Val Pro Gly His
                85                  90                  95

Pro Gly Leu Asn Arg Trp Ile Gly Lys Val Tyr Leu Leu Val Tyr Ala
            100                 105                 110

Gly Leu Ser Tyr Glu Arg Cys Ser Arg Asn His Arg Arg His His Gly
        115                 120                 125

His Pro Gly Thr Asp Leu Asp Pro Asp Tyr Gln Arg Cys Thr Asn Asn
    130                 135                 140

Asn Ile Leu Asp Trp Tyr Val His Phe Met Gly Asn Tyr Leu Gly Met
145                 150                 155                 160
```

```
Arg Gln Leu Leu Asn Leu Ser Cys Leu Trp Leu Ala Leu Ile Ile Leu
            165                 170                 175

Asn Gly Ser Asp Leu Pro Ala Gln Ile Met His Leu Leu Phe Ser
        180                 185                 190

Val Leu Pro Leu Ile Ile Ser Ser Cys Gln Leu Phe Leu Val Gly Thr
            195                 200                 205

Trp Leu Pro His Arg Arg Gly Ala Thr Thr Arg Pro Gly Val Thr Thr
    210                 215                 220

Arg Ser Leu Ala Leu His Pro Ala Leu Ser Phe Ala Ala Cys Tyr Asn
225                 230                 235                 240

Phe Gly Tyr His Arg Glu His His Glu Ser Pro Ser Thr Pro Trp Phe
                245                 250                 255

Gln Leu Pro Gln Leu Arg Asn Glu Ser Phe Thr
            260                 265

<210> SEQ ID NO 52
<211> LENGTH: 690
<212> TYPE: DNA
<213> ORGANISM: Nodularia spumigena NSOR10
<220> FEATURE:
<221> NAME/KEY: CDS

<400> SEQUENCE: 52 atg gcg atc gcc att att agt ata tgg gct atc agc cta ggt ttg tta      48
Met Ala Ile Ala Ile Ile Ser Ile Trp Ala Ile Ser Leu Gly Leu Leu
1               5                   10                  15 ctt tat att gat ata tcc caa ttc aag ttt tgg atg ttg tta ccg ctc      96
Leu Tyr Ile Asp Ile Ser Gln Phe Lys Phe Trp Met Leu Leu Pro Leu
            20                  25                  30 ata ttt tgg caa aca ttt tta tat acg gga tta ttt att aca gct cat    144
Ile Phe Trp Gln Thr Phe Leu Tyr Thr Gly Leu Phe Ile Thr Ala His
        35                  40                  45 gat gcc atg cat ggg gta gtt ttt ccc aaa aat ccc aaa atc aac cat    192
Asp Ala Met His Gly Val Val Phe Pro Lys Asn Pro Lys Ile Asn His
    50                  55                  60 ttc att ggc tca ttg tgc ctg ttt ctt tat ggt ctt tta cct tat caa    240
Phe Ile Gly Ser Leu Cys Leu Phe Leu Tyr Gly Leu Leu Pro Tyr Gln
65                  70                  75                  80 aaa ctt tta aaa aag cat tgg cta cat cac cat aat cca gcc agt gaa    288
Lys Leu Leu Lys Lys His Trp Leu His His His Asn Pro Ala Ser Glu
                85                  90                  95 aca gat cca gat ttt cac aac ggg aag cag aaa aac ttt ttt gct tgg    336
Thr Asp Pro Asp Phe His Asn Gly Lys Gln Lys Asn Phe Phe Ala Trp
            100                 105                 110 tat tta tat ttt atg aag cgt tac tgg agt tgg tta caa att atc aca    384
Tyr Leu Tyr Phe Met Lys Arg Tyr Trp Ser Trp Leu Gln Ile Ile Thr
        115                 120                 125 tta atg att att tat aac tta cta aaa tat ata tgg cat ttt cca gag    432
Leu Met Ile Ile Tyr Asn Leu Leu Lys Tyr Ile Trp His Phe Pro Glu
    130                 135                 140 gat aat atg act tat ttt tgg gta gtt ccc tca att tta agt tct tta    480
Asp Asn Met Thr Tyr Phe Trp Val Val Pro Ser Ile Leu Ser Ser Leu
145                 150                 155                 160 caa tta ttt tat ttt gga act ttt cta ccc cac agt gag cct gta gaa    528
Gln Leu Phe Tyr Phe Gly Thr Phe Leu Pro His Ser Glu Pro Val Glu
                165                 170                 175 ggt tat aaa gag cct cat cgt tcc caa act att agc cgt ccc att tgg    576
Gly Tyr Lys Glu Pro His Arg Ser Gln Thr Ile Ser Arg Pro Ile Trp
            180                 185                 190
```

```
tgg tca ttt ata act tgt tac cat ttt ggt tat cat tac gaa cat cat        624
Trp Ser Phe Ile Thr Cys Tyr His Phe Gly Tyr His Tyr Glu His His
        195                 200                 205 gaa tac ccc cat gtt cct tgg tgg caa tta cca gaa att tat aaa atg        672
Glu Tyr Pro His Val Pro Trp Trp Gln Leu Pro Glu Ile Tyr Lys Met
    210                 215                 220 tct aaa tca aat ttg tga                                                690
Ser Lys Ser Asn Leu
225

<210> SEQ ID NO 53
<211> LENGTH: 229
<212> TYPE: PRT
<213> ORGANISM: Nodularia spumigena NSOR10

<400> SEQUENCE: 53

Met Ala Ile Ala Ile Ile Ser Ile Trp Ala Ile Ser Leu Gly Leu Leu
1               5                   10                  15

Leu Tyr Ile Asp Ile Ser Gln Phe Lys Phe Trp Met Leu Leu Pro Leu
            20                  25                  30

Ile Phe Trp Gln Thr Phe Leu Tyr Thr Gly Leu Phe Ile Thr Ala His
        35                  40                  45

Asp Ala Met His Gly Val Val Phe Pro Lys Asn Pro Lys Ile Asn His
    50                  55                  60

Phe Ile Gly Ser Leu Cys Leu Phe Leu Tyr Gly Leu Leu Pro Tyr Gln
65                  70                  75                  80

Lys Leu Leu Lys Lys His Trp Leu His His Asn Pro Ala Ser Glu
                85                  90                  95

Thr Asp Pro Asp Phe His Asn Gly Lys Gln Lys Asn Phe Phe Ala Trp
            100                 105                 110

Tyr Leu Tyr Phe Met Lys Arg Tyr Trp Ser Trp Leu Gln Ile Ile Thr
        115                 120                 125

Leu Met Ile Ile Tyr Asn Leu Leu Lys Tyr Ile Trp His Phe Pro Glu
    130                 135                 140

Asp Asn Met Thr Tyr Phe Trp Val Val Pro Ser Ile Leu Ser Ser Leu
145                 150                 155                 160

Gln Leu Phe Tyr Phe Gly Thr Phe Leu Pro His Ser Glu Pro Val Glu
                165                 170                 175

Gly Tyr Lys Glu Pro His Arg Ser Gln Thr Ile Ser Arg Pro Ile Trp
            180                 185                 190

Trp Ser Phe Ile Thr Cys Tyr His Phe Gly Tyr His Tyr Glu His His
        195                 200                 205

Glu Tyr Pro His Val Pro Trp Trp Gln Leu Pro Glu Ile Tyr Lys Met
    210                 215                 220

Ser Lys Ser Asn Leu
225

<210> SEQ ID NO 54
<211> LENGTH: 37
<212> TYPE: DNA
<213> ORGANISM: Artificial sequence
<220> FEATURE:
<223> OTHER INFORMATION: Primer

<400> SEQUENCE: 54
gcgcatgcat ctagaaatga tccagttaga acaacca                                37

<210> SEQ ID NO 55
```

```
<211> LENGTH: 37
<212> TYPE: DNA
<213> ORGANISM: Artificial sequence
<220> FEATURE:
<223> OTHER INFORMATION: Primer

<400> SEQUENCE: 55
gcgcatgctc tagactattt tgctttgtaa atttctg                              37

<210> SEQ ID NO 56
<211> LENGTH: 792
<212> TYPE: DNA
<213> ORGANISM: Nostoc punctiforme ATCC 29133
<220> FEATURE:
<221> NAME/KEY: CDS
<222> LOCATION: (5)..(775)

<400> SEQUENCE: 56
```

| | | | | | | | | | | | | | | | |
|---|---|---|---|---|---|---|---|---|---|---|---|---|---|---|---|
| gcgc | atg | cat | cta | gaa | atg | atc | cag | tta | gaa | caa | cca | ctc | agt | cat caa | 49 |
| | Met | His | Leu | Glu | Met | Ile | Gln | Leu | Glu | Gln | Pro | Leu | Ser | His Gln | |
| | 1 | | | 5 | | | | | 10 | | | | | 15 | |
| gca | aaa | ctg | act | cca | gta | ctg | aga | agt | aaa | tct | cag | ttt | aag | ggg ctt | 97 |
| Ala | Lys | Leu | Thr | Pro | Val | Leu | Arg | Ser | Lys | Ser | Gln | Phe | Lys | Gly Leu | |
| | | | | 20 | | | | | 25 | | | | | 30 | |
| ttc | att | gct | att | gtc | att | gtt | agc | gca | tgg | gtc | att | agc | ctg | agt tta | 145 |
| Phe | Ile | Ala | Ile | Val | Ile | Val | Ser | Ala | Trp | Val | Ile | Ser | Leu | Ser Leu | |
| | | 35 | | | | | 40 | | | | | 45 | | | |
| tta | ctt | tcc | ctt | gac | atc | tca | aag | cta | aaa | ttt | tgg | atg | tta | ttg cct | 193 |
| Leu | Leu | Ser | Leu | Asp | Ile | Ser | Lys | Leu | Lys | Phe | Trp | Met | Leu | Leu Pro | |
| 50 | | | | | 55 | | | | | 60 | | | | | |
| gtt | ata | cta | tgg | caa | aca | ttt | tta | tat | acg | gga | tta | ttt | att | aca tct | 241 |
| Val | Ile | Leu | Trp | Gln | Thr | Phe | Leu | Tyr | Thr | Gly | Leu | Phe | Ile | Thr Ser | |
| 65 | | | | | 70 | | | | | 75 | | | | | |
| cat | gat | gcc | atg | cat | ggc | gta | gta | ttt | ccc | caa | aac | acc | aag | att aat | 289 |
| His | Asp | Ala | Met | His | Gly | Val | Val | Phe | Pro | Gln | Asn | Thr | Lys | Ile Asn | |
| 80 | | | | | 85 | | | | | 90 | | | | | 95 |
| cat | ttg | att | gga | aca | ttg | acc | cta | tcc | ctt | tat | ggt | ctt | tta | cca tat | 337 |
| His | Leu | Ile | Gly | Thr | Leu | Thr | Leu | Ser | Leu | Tyr | Gly | Leu | Leu | Pro Tyr | |
| | | | | 100 | | | | | 105 | | | | | 110 | |
| caa | aaa | cta | ttg | aaa | aaa | cat | tgg | tta | cac | cac | cac | aat | cca | gca agc | 385 |
| Gln | Lys | Leu | Leu | Lys | Lys | His | Trp | Leu | His | His | His | Asn | Pro | Ala Ser | |
| | | | | 115 | | | | | 120 | | | | | 125 | |
| tca | ata | gac | ccg | gat | ttt | cac | aat | ggt | aaa | cac | caa | agt | ttc | ttt gct | 433 |
| Ser | Ile | Asp | Pro | Asp | Phe | His | Asn | Gly | Lys | His | Gln | Ser | Phe | Phe Ala | |
| | | 130 | | | | | 135 | | | | | 140 | | | |
| tgg | tat | ttt | cat | ttt | atg | aaa | ggt | tac | tgg | agt | tgg | ggg | caa | ata att | 481 |
| Trp | Tyr | Phe | His | Phe | Met | Lys | Gly | Tyr | Trp | Ser | Trp | Gly | Gln | Ile Ile | |
| | 145 | | | | | 150 | | | | | 155 | | | | |
| gcg | ttg | act | att | att | tat | aac | ttt | gct | aaa | tac | ata | ctc | cat | atc cca | 529 |
| Ala | Leu | Thr | Ile | Ile | Tyr | Asn | Phe | Ala | Lys | Tyr | Ile | Leu | His | Ile Pro | |
| 160 | | | | | 165 | | | | | 170 | | | | | 175 |
| agt | gat | aat | cta | act | tac | ttt | tgg | gtg | cta | ccc | tcg | ctt | tta | agt tca | 577 |
| Ser | Asp | Asn | Leu | Thr | Tyr | Phe | Trp | Val | Leu | Pro | Ser | Leu | Leu | Ser Ser | |
| | | | | 180 | | | | | 185 | | | | | 190 | |
| tta | caa | tta | ttc | tat | ttt | ggt | act | ttt | tta | ccc | cat | agt | gaa | cca ata | 625 |
| Leu | Gln | Leu | Phe | Tyr | Phe | Gly | Thr | Phe | Leu | Pro | His | Ser | Glu | Pro Ile | |
| | | | | 195 | | | | | 200 | | | | | 205 | |
| ggg | ggt | tat | gtt | cag | cct | cat | tgt | gcc | caa | aca | att | agc | cgt | cct att | 673 |
| Gly | Gly | Tyr | Val | Gln | Pro | His | Cys | Ala | Gln | Thr | Ile | Ser | Arg | Pro Ile | |
| | | 210 | | | | | 215 | | | | | 220 | | | |
| tgg | tgg | tca | ttt | atc | acg | tgc | tat | cat | ttt | ggc | tac | cac | gag | gaa cat | 721 |
| Trp | Trp | Ser | Phe | Ile | Thr | Cys | Tyr | His | Phe | Gly | Tyr | His | Glu | Glu His | |

```
                225                 230                 235
cac gaa tat cct cat att tct tgg tgg cag tta cca gaa att tac aaa    769
His Glu Tyr Pro His Ile Ser Trp Trp Gln Leu Pro Glu Ile Tyr Lys
240                 245                 250                 255 gca aaa tagtctagag catgcgc                                         792
Ala Lys

<210> SEQ ID NO 57
<211> LENGTH: 257
<212> TYPE: PRT
<213> ORGANISM: Nostoc punctiforme ATCC 29133

<400> SEQUENCE: 57

Met His Leu Glu Met Ile Gln Leu Glu Gln Pro Leu Ser His Gln Ala
1               5                   10                  15

Lys Leu Thr Pro Val Leu Arg Ser Lys Ser Gln Phe Lys Gly Leu Phe
            20                  25                  30

Ile Ala Ile Val Ile Val Ser Ala Trp Val Ile Ser Leu Ser Leu Leu
        35                  40                  45

Leu Ser Leu Asp Ile Ser Lys Leu Lys Phe Trp Met Leu Leu Pro Val
50                  55                  60

Ile Leu Trp Gln Thr Phe Leu Tyr Thr Gly Leu Phe Ile Thr Ser His
65                  70                  75                  80

Asp Ala Met His Gly Val Val Phe Pro Gln Asn Thr Lys Ile Asn His
                85                  90                  95

Leu Ile Gly Thr Leu Thr Leu Ser Leu Tyr Gly Leu Leu Pro Tyr Gln
            100                 105                 110

Lys Leu Leu Lys Lys His Trp Leu His His His Asn Pro Ala Ser Ser
        115                 120                 125

Ile Asp Pro Asp Phe His Asn Gly Lys His Gln Ser Phe Phe Ala Trp
130                 135                 140

Tyr Phe His Phe Met Lys Gly Tyr Trp Ser Trp Gly Gln Ile Ile Ala
145                 150                 155                 160

Leu Thr Ile Ile Tyr Asn Phe Ala Lys Tyr Ile Leu His Ile Pro Ser
                165                 170                 175

Asp Asn Leu Thr Tyr Phe Trp Val Leu Pro Ser Leu Leu Ser Ser Leu
            180                 185                 190

Gln Leu Phe Tyr Phe Gly Thr Phe Leu Pro His Ser Glu Pro Ile Gly
        195                 200                 205

Gly Tyr Val Gln Pro His Cys Ala Gln Thr Ile Ser Arg Pro Ile Trp
210                 215                 220

Trp Ser Phe Ile Thr Cys Tyr His Phe Gly Tyr His Glu Glu His His
225                 230                 235                 240

Glu Tyr Pro His Ile Ser Trp Trp Gln Leu Pro Glu Ile Tyr Lys Ala
                245                 250                 255

Lys

<210> SEQ ID NO 58
<211> LENGTH: 26
<212> TYPE: DNA
<213> ORGANISM: Artificial sequence
<220> FEATURE:
<223> OTHER INFORMATION: Primer

<400> SEQUENCE: 58
gtcgaccctg ctttaatgag atatgc                                       26
```

<210> SEQ ID NO 59
<211> LENGTH: 27
<212> TYPE: DNA
<213> ORGANISM: Artificial sequence
<220> FEATURE:
<223> OTHER INFORMATION: Primer

<400> SEQUENCE: 59
ctcgagcttg gacaatcagt aaattga                                27

<210> SEQ ID NO 60
<211> LENGTH: 210
<212> TYPE: DNA
<213> ORGANISM: Agrobacterium tumefaciens
<220> FEATURE:
<221> NAME/KEY: Terminator

<400> SEQUENCE: 60
gtcgaccctg ctttaatgag atatgcgaga cgcctatgat cgcatgatat ttgctttcaa     60
ttctgttgtg cacgttgtaa aaaacctgag catgtgtagc tcagatcctt accgccggtt   120
tcggttcatt ctaatgaata tatcacccgt tactatcgta ttttttatgaa taatattctc   180 cgttcaattt actgattgtc caagctcgag                                    210

<210> SEQ ID NO 61
<211> LENGTH: 37
<212> TYPE: DNA
<213> ORGANISM: Artificial sequence
<220> FEATURE:
<223> OTHER INFORMATION: Primer

<400> SEQUENCE: 61
cccgggaatt cttcattatt tcgattttga tttcgtg                          37

<210> SEQ ID NO 62
<211> LENGTH: 38
<212> TYPE: DNA
<213> ORGANISM: Artificial sequence
<220> FEATURE:
<223> OTHER INFORMATION: Primer

<400> SEQUENCE: 62
aagcttggtt gatcagaaga agaagaagaa gatgaact                         38

<210> SEQ ID NO 63
<211> LENGTH: 652
<212> TYPE: DNA
<213> ORGANISM: Arabidopsis thaliana
<220> FEATURE:
<221> NAME/KEY: Promoter

<400> SEQUENCE: 63
cccgggaatt cttcattatt tcgattttga tttcgtgacc agcgaacgca gaataccttg     60
ttgtgtaata ctttacccgt gtaaatcaaa acaaaaagg cttttgagct ttttgtagtt    120
gaatttctct ggctgatctt ttctgtacag attcatatat ctgcagagac gatatcattg   180
attatttgag cttcttttga actatttcgt gtaatttggg atgagagctc tatgtatgtg   240
tgtaaacttt gaagacaaca agaaaggtaa caagtgaggg agggatgact ccatgtcaaa   300
atagatgtca taagaggccc atcaataagt gcttgagccc attagctagc ccagtaacta   360
ccagattgtg agatggatgt gtgaacagtt tttttttga tgtaggactg aaatgtgaac    420
aacaggcgca tgaaaggcta aattaggaca atgataagca gaaataactt atcctctcta   480

```
acacttggcc tcacattgcc cttcacacaa tccacacaca tccaatcaca acctcatcat    540
atatctcccg ctaatctttt tttctttgat cttttttttt ttgcttatta ttttttttgac    600 tttgatctcc catcagttca tcttcttctt cttcttctga tcaaccaagc tt             652

<210> SEQ ID NO 64
<211> LENGTH: 29
<212> TYPE: DNA
<213> ORGANISM: Artificial sequence
<220> FEATURE:
<223> OTHER INFORMATION: Primer

<400> SEQUENCE: 64
gagctctagc gcaatcttat gtggtacaa                                       29

<210> SEQ ID NO 65
<211> LENGTH: 29
<212> TYPE: DNA
<213> ORGANISM: Artificial sequence
<220> FEATURE:
<223> OTHER INFORMATION: Primer

<400> SEQUENCE: 65
aagcttttct tgaaagtaaa gattgagtc                                       29

<210> SEQ ID NO 66
<211> LENGTH: 1773
<212> TYPE: DNA
<213> ORGANISM: Petunia hybrida
<220> FEATURE:
<221> NAME/KEY: Promoter
<222> LOCATION: (1)..(1773)

<400> SEQUENCE: 66
gagctctagc gcaatcttat gtggtacaaa tcttgattag tcgggaaaaa atgatgtggc     60
cctacaaatg gttggaggat gggagatttg gctctatcta gagttatgtg gttgttgaag    120
catttggtta ctctctgctg tggtagttgg catatccaca ttgtctcctt ccactttttat   180 gacaattacg tgaaagttat gggttgtttt gtctatttt gtcgaggcct ttcttttcct    240
tccaggttgt tgaagatggt ccaattcgat tagaataatg ttttgagctt tagcatattc    300
tctctcgttt acacgattat agtaataatg atataggatg acagaagttg acacataaat    360 ttttattct ctccatttac tttaatccaa atctcaccta ccctaaactt ctttaatatg     420
tattcaatag tctatccgag taaattgtaa atttaacaac cattgataat attgacacct    480
actaacatat actagtaaag agaatattaa catggcacat ataatttgat gcaaaatgag    540
tatgatgaaa tttaaaccca aaatctcttg attttgacag tgtcaccttg acttgttaac    600
taataagtca tgttttagtg gcagaaagac aaactcatcc accaactgta tagcaataaa    660
aaatagaaga atcttcctga ggcaaagttt tggaaaaatt aagagtggct gagatttaat    720
ttcaacagga attagttcca cttaacttt aggttacgat acagtgctaa ttaaataact    780
taattgtatt agatatttct tgcacctaaa aaatttaaaa actgaaaaaa ggtagcaatc    840
aaaataaaca aaaggacaaa ataagtgaaa ggtacagcca ccaaccctgg cggctcactg    900
tttgttggtt aaaacgtaga cttacaccta ccaaaatcta caactaaaat gaggcaataa    960
tactttgccc aaaattacca agaaaagaaa aagaaaggaa tcccttaata ttactctcct   1020
ccatttcaca ataaatatcc tagttttgact taaattagag tttaaaaaat gaaagacgac   1080
ttttaaaact tgtaatctaa aataaatcat agttaaatgt gtggctataa atcattgtat   1140
```

-continued

```
taacggtaaa gtggtaagtt taaaagttaa ttgttttcaa atataaaatt gtactatcat    1200
tcttttggga atggactaat aagaaaacta tgacatccat tatggagcgg agggagtatc    1260 tcctttaac aataacctt gtcccttcaa ttcaattatc agtatgcaaa cattaaaaat      1320
tattattgat gttaagtacc acatcatcct taatgataga atcatcgtag aacgcttttc    1380
caggcacaca ttcaaactag ttagaccagt accacacatc gaatattcca gacttctttg    1440
tttgaatagt cgactacatt ggataatgga acttctcgaa ttaacttcga attagtcgag    1500
cccaaaataa tatatacgtc gggtggaaaa ctataaaatg tttgacaaaa atgtcaaatt    1560
aatatatcaa tctgcaacaa ccttttcacc ttgagaacac agctgaaatt ttttacaaag    1620
gtagttggtg aagctagtca gcgaatccca ttaccttcca ctctacctaa ccccttcac    1680 caacaacaaa tttctgtaat ttaaaaacta gccaaaaaag aactctcttt tacaaagagc    1740
caaagactca atctttactt tcaagaaaag ctt                                 1773
```

<210> SEQ ID NO 67
<211> LENGTH: 39
<212> TYPE: DNA
<213> ORGANISM: Artificial sequence
<220> FEATURE:
<223> OTHER INFORMATION: Primer

<400> SEQUENCE: 67
gcgcatgcat ctagaaatga attttttgtga taaaccagt                          39

<210> SEQ ID NO 68
<211> LENGTH: 37
<212> TYPE: DNA
<213> ORGANISM: Artificial sequence
<220> FEATURE:
<223> OTHER INFORMATION: Primer

<400> SEQUENCE: 68
gcgcatgctc tagattacga attggttact gaattgt                             37

<210> SEQ ID NO 69
<211> LENGTH: 819
<212> TYPE: DNA
<213> ORGANISM: Nostoc punctiforme ATCC 29133
<220> FEATURE:
<221> NAME/KEY: CDS
<222> LOCATION: (5)..(802)

<400> SEQUENCE: 69

```
gcgc atg cat cta gaa atg aat ttt tgt gat aaa cca gtt agc tat tat       49
     Met His Leu Glu Met Asn Phe Cys Asp Lys Pro Val Ser Tyr Tyr
      1               5                  10                  15 gtt gca ata gag caa tta agt gct aaa gaa gat act gtt tgg ggg ctg        97
Val Ala Ile Glu Gln Leu Ser Ala Lys Glu Asp Thr Val Trp Gly Leu
             20                  25                  30 gtg att gtc ata gta att att agt ctt tgg gta gct agt ttg gct ttt       145
Val Ile Val Ile Val Ile Ile Ser Leu Trp Val Ala Ser Leu Ala Phe
         35                  40                  45 tta cta gct att aat tat gcc aaa gtc cca att tgg ttg ata cct att       193
Leu Leu Ala Ile Asn Tyr Ala Lys Val Pro Ile Trp Leu Ile Pro Ile
     50                  55                  60 gca ata gtt tgg caa atg ttc ctt tat aca ggg cta ttt att act gca       241
Ala Ile Val Trp Gln Met Phe Leu Tyr Thr Gly Leu Phe Ile Thr Ala
 65                  70                  75 cat gat gct atg cat ggg tca gtt tat cgt aaa aat ccc aaa att aat       289
```

| | | |
|---|---|---|
| His Asp Ala Met His Gly Ser Val Tyr Arg Lys Asn Pro Lys Ile Asn<br>80                        85                        90                        95 | | |

```
aat ttt atc ggt tca cta gct gta gcg ctt tac gct gtg ttt cca tat      337
Asn Phe Ile Gly Ser Leu Ala Val Ala Leu Tyr Ala Val Phe Pro Tyr
                100                 105                 110 caa cag atg tta aag aat cat tgc tta cat cat cgt cat cct gct agc      385
Gln Gln Met Leu Lys Asn His Cys Leu His His Arg His Pro Ala Ser
        115                 120                 125 gaa gtt gac cca gat ttt cat gat ggt aag aga aca aac gct att ttc      433
Glu Val Asp Pro Asp Phe His Asp Gly Lys Arg Thr Asn Ala Ile Phe
    130                 135                 140 tgg tat ctc cat ttc atg ata gaa tac tcc agt tgg caa cag tta ata      481
Trp Tyr Leu His Phe Met Ile Glu Tyr Ser Ser Trp Gln Gln Leu Ile
145                 150                 155 gta cta act atc cta ttt aat tta gct aaa tac gtt ttg cac atc cat      529
Val Leu Thr Ile Leu Phe Asn Leu Ala Lys Tyr Val Leu His Ile His
160                 165                 170                 175 caa ata aat ctc atc tta ttt tgg agt att cct cca att tta agt tcc      577
Gln Ile Asn Leu Ile Leu Phe Trp Ser Ile Pro Pro Ile Leu Ser Ser
                180                 185                 190 att caa ctg ttt tat ttc gga aca ttt ttg cct cat cga gaa ccc aag      625
Ile Gln Leu Phe Tyr Phe Gly Thr Phe Leu Pro His Arg Glu Pro Lys
            195                 200                 205 aaa gga tat gtt tat ccc cat tgc agc caa aca ata aaa ttg cca act      673
Lys Gly Tyr Val Tyr Pro His Cys Ser Gln Thr Ile Lys Leu Pro Thr
        210                 215                 220 ttt ttg tca ttt atc gct tgc tac cac ttt ggt tat cat gaa gaa cat      721
Phe Leu Ser Phe Ile Ala Cys Tyr His Phe Gly Tyr His Glu Glu His
225                 230                 235 cat gag tat ccc cat gta cct tgg tgg caa ctt cca tct gta tat aag      769
His Glu Tyr Pro His Val Pro Trp Trp Gln Leu Pro Ser Val Tyr Lys
240                 245                 250                 255 cag aga gta ttc aac aat tca gta acc aat tcg taatctagag catgcgc      819
Gln Arg Val Phe Asn Asn Ser Val Thr Asn Ser
                260                 265

<210> SEQ ID NO 70
<211> LENGTH: 266
<212> TYPE: PRT
<213> ORGANISM: Nostoc punctiforme ATCC 29133

<400> SEQUENCE: 70

Met His Leu Glu Met Asn Phe Cys Asp Lys Pro Val Ser Tyr Tyr Val
1               5                   10                  15

Ala Ile Glu Gln Leu Ser Ala Lys Glu Asp Thr Val Trp Gly Leu Val
            20                  25                  30

Ile Val Ile Val Ile Ile Ser Leu Trp Val Ala Ser Leu Ala Phe Leu
        35                  40                  45

Leu Ala Ile Asn Tyr Ala Lys Val Pro Ile Trp Leu Ile Pro Ile Ala
    50                  55                  60

Ile Val Trp Gln Met Phe Leu Tyr Thr Gly Leu Phe Ile Thr Ala His
65                  70                  75                  80

Asp Ala Met His Gly Ser Val Tyr Arg Lys Asn Pro Lys Ile Asn Asn
                85                  90                  95

Phe Ile Gly Ser Leu Ala Val Ala Leu Tyr Ala Val Phe Pro Tyr Gln
            100                 105                 110

Gln Met Leu Lys Asn His Cys Leu His His Arg His Pro Ala Ser Glu
        115                 120                 125
```

-continued

```
Val Asp Pro Asp Phe His Asp Gly Lys Arg Thr Asn Ala Ile Phe Trp
    130                 135                 140
Tyr Leu His Phe Met Ile Glu Tyr Ser Ser Trp Gln Gln Leu Ile Val
145                 150                 155                 160
Leu Thr Ile Leu Phe Asn Leu Ala Lys Tyr Val Leu His Ile His Gln
                165                 170                 175
Ile Asn Leu Ile Leu Phe Trp Ser Ile Pro Pro Ile Leu Ser Ser Ile
            180                 185                 190
Gln Leu Phe Tyr Phe Gly Thr Phe Leu Pro His Arg Glu Pro Lys Lys
        195                 200                 205
Gly Tyr Val Tyr Pro His Cys Ser Gln Thr Ile Lys Leu Pro Thr Phe
    210                 215                 220
Leu Ser Phe Ile Ala Cys Tyr His Phe Gly Tyr His Glu Glu His His
225                 230                 235                 240
Glu Tyr Pro His Val Pro Trp Trp Gln Leu Pro Ser Val Tyr Lys Gln
                245                 250                 255
Arg Val Phe Asn Asn Ser Val Thr Asn Ser
                260                 265
```

<210> SEQ ID NO 71
<211> LENGTH: 33
<212> TYPE: DNA
<213> ORGANISM: Artificial sequence
<220> FEATURE:
<223> OTHER INFORMATION: Primer

<400> SEQUENCE: 71
gcgcatgcat ctagaaatgg cgatcgccat tat                                33

<210> SEQ ID NO 72
<211> LENGTH: 32
<212> TYPE: DNA
<213> ORGANISM: Artificial sequence
<220> FEATURE:
<223> OTHER INFORMATION: Primer

<400> SEQUENCE: 72
gcgcatgctc tagatcacaa atttgattta ga                                 32

<210> SEQ ID NO 73
<211> LENGTH: 720
<212> TYPE: DNA
<213> ORGANISM: Nodularia spumigena NSOR10
<220> FEATURE:
<221> NAME/KEY: CDS
<222> LOCATION: (5)..(703)

<400> SEQUENCE: 73

```
gcgc atg cat cta gaa atg gcg atc gcc att att agt ata tgg gct atc     49
     Met His Leu Glu Met Ala Ile Ala Ile Ile Ser Ile Trp Ala Ile
       1               5                  10                  15 agc cta ggt ttg tta ctt tat att gat ata tcc caa ttc aag ttt tgg     97
Ser Leu Gly Leu Leu Leu Tyr Ile Asp Ile Ser Gln Phe Lys Phe Trp
                 20                  25                  30 atg ttg tta ccg ctc ata ttt tgg caa aca ttt tta tat acg gga tta    145
Met Leu Leu Pro Leu Ile Phe Trp Gln Thr Phe Leu Tyr Thr Gly Leu
             35                  40                  45 ttt att aca gct cat gat gcc atg cat ggg gta gtt ttt ccc aaa aat    193
Phe Ile Thr Ala His Asp Ala Met His Gly Val Val Phe Pro Lys Asn
         50                  55                  60 ccc aaa atc aac cat ttc att ggc tca ttg tgc ctg ttt ctt tat ggt    241
```

| | | | | | | | | | | | | | | | |
|---|---|---|---|---|---|---|---|---|---|---|---|---|---|---|---|
|Pro|Lys|Ile|Asn|His|Phe|Ile|Gly|Ser|Leu|Cys|Leu|Phe|Leu|Tyr|Gly|
| |65| | | |70| | | |75| | | |  | |  |

```
ctt tta cct tat caa aaa ctt tta aaa aag cat tgg cta cat cac cat     289
Leu Leu Pro Tyr Gln Lys Leu Leu Lys Lys His Trp Leu His His His
 80              85              90              95 aat cca gcc agt gaa aca gat cca gat ttt cac aac ggg aag cag aaa     337
Asn Pro Ala Ser Glu Thr Asp Pro Asp Phe His Asn Gly Lys Gln Lys
            100             105             110 aac ttt ttt gct tgg tat tta tat ttt atg aag cgt tac tgg agt tgg     385
Asn Phe Phe Ala Trp Tyr Leu Tyr Phe Met Lys Arg Tyr Trp Ser Trp
                115             120             125 tta caa att atc aca tta atg att att tat aac tta cta aaa tat ata     433
Leu Gln Ile Ile Thr Leu Met Ile Ile Tyr Asn Leu Leu Lys Tyr Ile
        130             135             140 tgg cat ttt cca gag gat aat atg act tat ttt tgg gta gtt ccc tca     481
Trp His Phe Pro Glu Asp Asn Met Thr Tyr Phe Trp Val Val Pro Ser
    145             150             155 att tta agt tct tta caa tta ttt tat ttt gga act ttt cta ccc cac     529
Ile Leu Ser Ser Leu Gln Leu Phe Tyr Phe Gly Thr Phe Leu Pro His
160             165             170             175 agt gag cct gta gaa ggt tat aaa gag cct cat cgt tcc caa act att     577
Ser Glu Pro Val Glu Gly Tyr Lys Glu Pro His Arg Ser Gln Thr Ile
                180             185             190 agc cgt ccc att tgg tgg tca ttt ata act tgt tac cat ttt ggt tat     625
Ser Arg Pro Ile Trp Trp Ser Phe Ile Thr Cys Tyr His Phe Gly Tyr
            195             200             205 cat tac gaa cat cat gaa tac ccc cat gtt cct tgg tgg caa tta cca     673
His Tyr Glu His His Glu Tyr Pro His Val Pro Trp Trp Gln Leu Pro
        210             215             220 gaa att tat aaa atg tct aaa tca aat ttg tgatctagag catgcgc          720
Glu Ile Tyr Lys Met Ser Lys Ser Asn Leu
    225             230
```

<210> SEQ ID NO 74
<211> LENGTH: 233
<212> TYPE: PRT
<213> ORGANISM: Nodularia spumigena NSOR10

<400> SEQUENCE: 74

```
Met His Leu Glu Met Ala Ile Ala Ile Ile Ser Ile Trp Ala Ile Ser
1               5                   10                  15

Leu Gly Leu Leu Leu Tyr Ile Asp Ile Ser Gln Phe Lys Phe Trp Met
            20                  25                  30

Leu Leu Pro Leu Ile Phe Trp Gln Thr Phe Leu Tyr Thr Gly Leu Phe
        35                  40                  45

Ile Thr Ala His Asp Ala Met His Gly Val Val Phe Pro Lys Asn Pro
    50                  55                  60

Lys Ile Asn His Phe Ile Gly Ser Leu Cys Leu Phe Leu Tyr Gly Leu
65                  70                  75                  80

Leu Pro Tyr Gln Lys Leu Leu Lys Lys His Trp Leu His His His Asn
                85                  90                  95

Pro Ala Ser Glu Thr Asp Pro Asp Phe His Asn Gly Lys Gln Lys Asn
            100                 105                 110

Phe Phe Ala Trp Tyr Leu Tyr Phe Met Lys Arg Tyr Trp Ser Trp Leu
        115                 120                 125

Gln Ile Ile Thr Leu Met Ile Ile Tyr Asn Leu Leu Lys Tyr Ile Trp
    130                 135                 140

His Phe Pro Glu Asp Asn Met Thr Tyr Phe Trp Val Val Pro Ser Ile
```

-continued

```
            145                 150                 155                 160
       Leu Ser Ser Leu Gln Leu Phe Tyr Phe Gly Thr Phe Leu Pro His Ser
                           165                 170                 175

Glu Pro Val Glu Gly Tyr Lys Glu Pro His Arg Ser Gln Thr Ile Ser
                       180                 185                 190

Arg Pro Ile Trp Trp Ser Phe Ile Thr Cys Tyr His Phe Gly Tyr His
                   195                 200                 205

Tyr Glu His His Glu Tyr Pro His Val Pro Trp Trp Gln Leu Pro Glu
               210                 215                 220

Ile Tyr Lys Met Ser Lys Ser Asn Leu
       225                 230
```

PROCESS FOR PREPARING KETOCAROTENOIDS IN GENETICALLY MODIFIED ORGANISMS

RELATED APPLICATIONS

This application is a national stage application (under 35 U.S.C. 371) of PCT/EP2003/009106 filed Aug. 18, 2003 which claims benefit to German application 102 38 980.2 filed Aug. 20, 2002, German application 102 38 978.0, filed Aug. 20, 2002, German application 102 38 979.9 filed Aug. 20, 2002, German application 102 53 112.9 filed Nov. 13, 2002, and German application 102 58 971.2 filed Dec. 16, 2002.

BACKGROUND OF THE INVENTION

The present invention relates to a process for preparing ketocarotenoids by cultivation of genetically modified organisms which, compared with the wild type, have a modified ketolase activity, to the genetically modified organisms, and to the use thereof as human and animal foods and for producing ketocarotenoid extracts.

Carotenoids are synthesized de novo in bacteria, algae, fungi and plants. Ketocarotenoids, i.e. carotenoids containing at least one keto group, such as, for example, astaxanthin, canthaxanthin, echinenone, 3-hydroxyechinenone, 3'-hydroxyechinenone, adonirubin and adonixanthin, are natural antioxidants and pigments produced as secondary metabolites by some algae and microorganisms.

Because of their coloring properties, the ketocarotenoids and especially astaxanthin are used as pigmenting aids in livestock nutrition, especially in trout, salmon and shrimp rearing.

Astaxanthin is currently prepared for the most part by chemical synthesis processes. Natural ketocarotenoids such as, for example, natural astaxanthin are currently obtained in small quantities in biotechnological processes by cultivation of algae, for example *Haematococcus pluvialis* or by fermentation of genetically optimized microorganisms and subsequent isolation.

An economic biotechnological process for preparing natural ketocarotenoids is therefore of great importance.

Nucleic acids encoding a ketolase and the corresponding protein sequences have been isolated from various organisms and annotated, such as, for example, nucleic acids encoding a ketolase from *Agrobacterium aurantiacum* (EP 735 137, Accession No. D58420), from *Alcaligenes* sp. PC-1 (EP 735137, Accession No. D58422), *Haematococcus pluvialis Flotow em. Wille* and *Haematoccus pluvialis*, NIES-144 (EP 725137, WO 98/18910 and Lotan et al, FEBS Letters 1995, 364, 125-128, Accession No. X86782 and D45881, *Paracoccus marcusii* (Accession No. Y15112), *Synechocystis* sp. Strain PC6803 (Accession No. NP_442491), *Bradyrhizobium* sp. (Accession No. AF218415) and *Nostoc* sp. PCC 7120 (Kaneko et al., DNA Res. 2001, 8(5), 205-213; Accession No. AP003592, BAB74888).

EP 735 137 describes the preparation of xanthophylls in microorganisms such as, for example, *E. coli* by introducing ketolase genes (crtW) from *Agrobacterium aurantiacum* or *Alcaligenes* sp. PC-1 into microorganisms.

EP 725 137, WO 98/18910, Kajiwara et al. (Plant Mol. Biol. 1995, 29, 343-352) and Hirschberg et al. (FEBS Letters 1995, 364, 125-128) disclose the preparation of astaxanthin by introducing ketolase genes from *Haematococcus pluvialis* (crtw, crtO or bkt) into *E. coli*.

Hirschberg et al. (FEBS Letters 1997, 404, 129-134) describe the preparation of astaxanthin in *Synechococcus* by introducing ketolase genes (crtO) from *Haematococcus pluvialis*. Sandmann et al. (Photochemistry and Photobiology 2001, 73(5), 551-55) describe an analogous process which, however, leads to the preparation of canthaxanthin and provides only traces of astaxanthin.

WO 98/18910 and Hirschberg et al. (Nature Biotechnology 2000, 18(8), 888-892) describe the synthesis of ketocarotenoids in nectaries of tobacco flowers by introducing the ketolase gene from *Haematococcus pluvialis* (crtO) into tobacco.

WO 01/20011 describes a DNA construct for producing ketocarotenoids, especially astaxanthin, in seeds of oilseed crops such as rape, sunflower, soybean and mustard, using a seed-specific promoter and a ketolase from *Haematococcus pluvialis*.

All the processes described in the prior art for preparing ketocarotenoids and, in particular, the processes described for preparing astaxanthin have the disadvantage that the transgenic organisms provide a large quantity of hydroxylated byproducts, such as zeaxanthin and adonixanthin, for example.

DETAILED DESCRIPTION OF THE INVENTION

Figure 1:
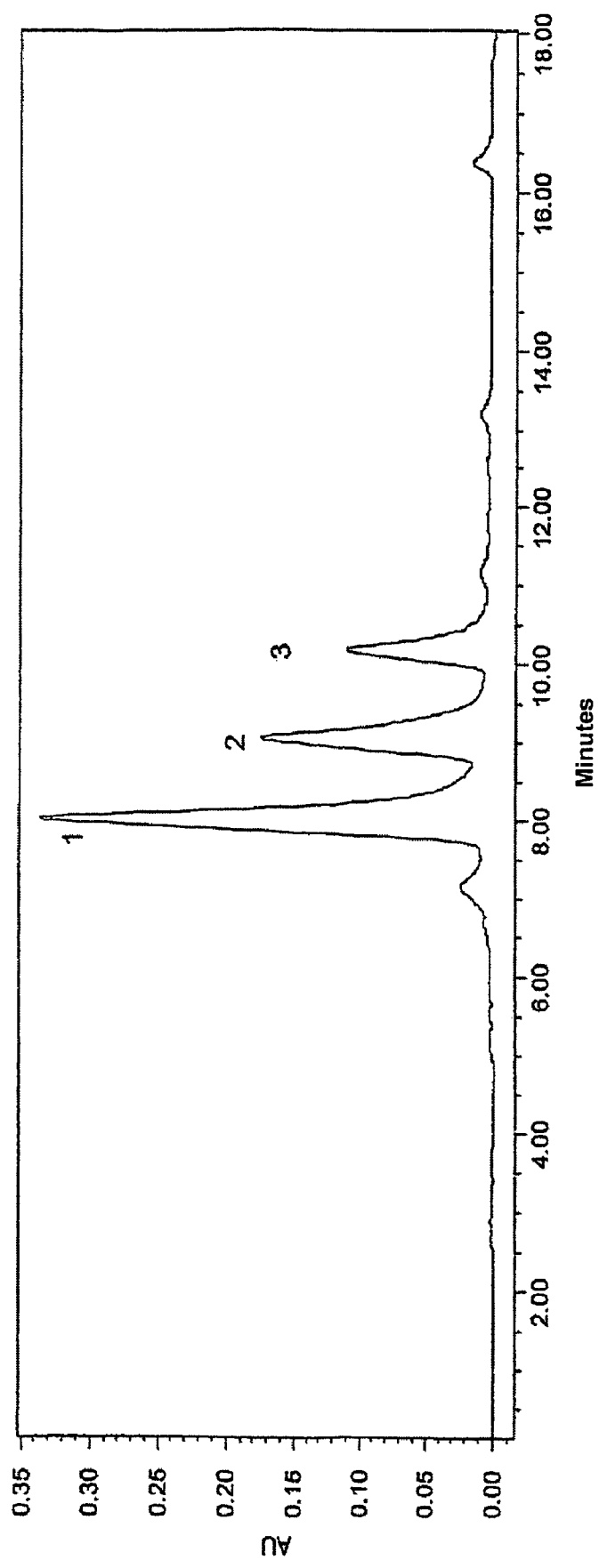
FIG. 1 depicts the chromiatographic analysis of a sample obtained from an *E. coli* strain transformed with pNOSTF-G and pMCL-CrtYIBZ/idilgps. This strain is shown to be able to synthesize various ketocarotenoids, owing to heterologous complementation. Astaxanthin (peak 1), adonirubin (peak 2) and canthaxanthin (peak 3) are eluted with increasing retention time.

It is an object of the present invention to provide a process for preparing ketocarotenoids by cultivation of genetically modified organisms, and to provide further genetically modified organisms which produce ketocarotenoids, which have the prior art disadvantages described above to a smaller extent or not at all.

We have found that this object is achieved by a process for preparing ketocarotenoids by cultivating genetically modified organisms which, compared with the wild type, have a modified ketolase activity, and the modified ketolase activity is caused by a ketolase comprising the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2.

The organisms of the invention, such as, for example, microorganisms or plants, are preferably able as starting organisms naturally to produce carotenoids such as, for example, β-carotene or zeaxanthin, or can be made able by genetic modification such as, for example, reregulation of metabolic pathways or complementation to produce carotenoids such as, for example, β-carotene or zeaxanthin.

Some organisms are already able as starting or wild-type organisms to produce ketocarotenoids such as, for example, astaxanthin or canthaxanthin. These organisms, such as, for example, *Haematococcus pluvialis, Paracoccus marcusii, Xanthophyllomyces dendrorhous, Bacillus circulans, Chlorococcum, Phaffia rhodozyma, adonis, Neochloris wimmeri, Protosiphon botryoides, Scotiellopsis oocystiformis, Scenedesmus vacuolatus, Chlorela zofingiensis, Ankistrodesmus braunii, Euglena sanguinea, Bacillus atrophaeus*, Blakeslea already have as starting or wild-type organism a ketolase activity.

In one embodiment of the process of the invention, therefore, the starting organisms used are those already having a ketolase activity as wild type or starting organism. In this embodiment, the genetic modification brings about an increase in the ketolase activity compared with the wild type or starting organism.

Ketolase activity means the enzymic activity of a ketolase. A ketolase means a protein which has the enzymatic activity of introducing a keto group on the, optionally substituted, β-ionone ring of carotenoids.

A ketolase means in particular a protein having the enzymatic activity of converting β-carotene into canthaxanthin.

Accordingly, ketolase activity means the amount of β-carotene converted or amount of canthaxanthin produced in a particular time by the ketolase protein.

Thus, when a ketolase activity is increased compared with the wild type, the amount of β-carotene converted or the amount of canthaxanthin produced in a particular time is increased by the ketolase protein compared with the wild type.

This increase in the ketolase activity is preferably at least 5%, more preferably at least 20%, more preferably at least 50%, more preferably at least 100%, preferably at least 300%, more preferably at least 500%, in particular at least 600%, of the ketolase activity of the wild type.

The term "wild type" means according to the invention the corresponding starting organism.

Depending on the context, the term "organism" may mean the starting organism (wild type) or a genetically modified organism of the invention, or both.

"Wild type" means, preferably and especially in cases where the organism or the wild type cannot be unambiguously assigned, in each case a reference organism for the increasing or causing of the ketolase activity, for the increasing, described hereinafter, of the hydroxylase activity, for the increasing, described hereinafter, of the β-cyclase activity and the increasing of the content of ketocarotenoids.

This reference organism for microorganisms which already have a ketolase activity as wild type is preferably *Haematococcus pluvialis*.

This reference organism for microorganisms which have no ketolase activity as wild type is preferably Blakeslea.

This reference organism for plants which already have a ketolase activity as wild type is preferably *Adonis aestivalis, Adonis flammeus* or *Adonis annuus*, particularly preferably *Adonis aestivalis*.

This reference organism for plants which have no ketolase activity in petals as wild type is preferably *Tagetes erecta, Tagetes patula, Tagetes lucida, Tagetes pringlei, Tagetes palmeri, Tagetes minuta* or *Tagetes campanulata*, particularly preferably *Tagetes erecta*.

Determination of the ketolase activity in the genetically modified organisms of the invention and in wild-type and reference organisms preferably takes place under the following conditions:

Determination of the ketolase activity in plant or microorganism material is based on the method of Frazer et al., (J. Biol. Chem. 272(10): 6128-6135, 1997). The ketolase activity in plant or microorganism extracts is determined using the substrates β-carotene and canthaxanthin in the presence of lipid (soybean lecithin) and detergent (sodium cholate). Substrate/product ratios from ketolase assays are measured by means of HPLC.

Various ways are possible for increasing the ketolase activity, for example by switching off inhibitory regulatory mechanisms at the translation and protein level or by increasing the gene expression of a nucleic acid encoding a ketolase compared with the wild type, for example by inducing the ketolase gene by activators or by introducing nucleic acids encoding a ketolase into the organism.

Increasing the gene expression of a nucleic acid encoding a ketolase also means according to the invention in this embodiment the manipulation of the expression of the organisms own endogenous ketolases. This can be achieved for example by modifying the promoter DNA sequence for ketolase-encoding genes. Such a modification, which results in a modified or, preferably, increased expression rate of at least one endogenous ketolase gene, can also be effected by deletion or insertion of DNA sequences.

It is possible as described above to modify the expression of at least one endogenous ketolase through application of exogenous stimuli. This can be effected by particular physiological conditions, i.e. through application of foreign substances.

A further possibility for achieving an increased expression of at least one endogenous ketolase gene is for a regulator protein which does not occur in the wild-type organism or is modified to interact with the promoter of these genes.

A regulator of this type may be a chimeric protein which consists of a DNA-binding domain and of a transcription activator domain as described, for example, in WO 96/06166.

In a preferred embodiment, the ketolase activity is increased by comparison with the wild type by increasing the gene expression of a nucleic acid encoding a ketolase comprising the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2.

In a further preferred embodiment, the gene expression of a nucleic acid encoding a ketolase is increased by introducing nucleic acids which encode ketolases, where the ketolases have the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2, into the organisms.

Thus, in this embodiment, at least one further ketolase gene encoding a ketolase comprising the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2, is present in the transgenic organisms of the invention compared with the wild type.

In this embodiment, the genetically modified organism of the invention accordingly has at least one exogenous (=heterologous) nucleic acid encoding a ketolase, or has at least two endogenous nucleic acids encoding a ketolase, where the ketolases comprise the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2.

In another, preferred embodiment of the process of the invention, the organisms used as starting organisms have no ketolase activity as wild type.

In this preferred embodiment, the genetic modification causes the ketolase activity in the organisms. The genetically modified organism of the invention thus has in this preferred embodiment a ketolase activity compared with the genetically unmodified wild type, and is thus preferably capable of transgenic expression of a ketolase comprising the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2.

In this preferred embodiment, the gene expression of a nucleic acid encoding a ketolase is caused, in analogy to the increasing, described above, of the gene expression of a nucleic acid encoding a ketolase, preferably by introducing nucleic acids which encode ketolases comprising the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2, into the starting organism.

It is possible to use for this purpose in both embodiments in principle all nucleic acids which encode a ketolase comprising the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2.

The use of the nucleic acids of the invention encoding a ketolase leads in the process of the invention surprisingly to ketocarotenoids having a smaller quantity of hydroxylated byproducts than on use of the ketolase genes used in the prior art.

All the nucleic acids mentioned in the description may be, for example, an RNA, DNA or cDNA sequence.

In the case of genomic ketolase sequences from eukaryotic sources which comprise introns, it is preferred to use nucleic acid sequences which have already been processed, such as the corresponding cDNAs, in the case where the host organism is unable or cannot be made able to express the corresponding ketolase.

Examples of nucleic acids encoding a ketolase, and the corresponding ketolases comprising the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2, which can be used advantageously in the process of the invention are, for example, sequences from

*Nostoc* sp. Strain PCC7120 (Accession No. AP003592, BAB74888; nucleic acid: SEQ ID NO: 1, protein: SEQ ID NO: 2),

*Nostoc punctiforme* ATTC 29133, nucleic acid: Acc. No. NZ_AABC01000195, base pairs 55,604 to 55,392 (SEQ ID NO: 3); protein: Acc. No. ZP_00111258 (SEQ ID NO: 4) (annotated as a putative protein) or

*Nostoc punctiforrne* ATTC 29133, nucleic acid: Acc. No. NZ_AABC01000196, base pairs 140,571 to 139,810 (SEQ ID NO: 5), protein: (SEQ ID NO: 6) (not annotated)

*Synechococcus* sp. WH 8102, nucleic acid: Acc. No. NZ_AABD01000001, base pairs 1,354,725-1,355,528 (SEQ ID NO: 46), protein: Acc. No. ZP_00115639 (SEQ ID NO: 47) (annotated as a putative protein),

*Nodularia spumigena* NSOR10, (Accession No. AY210783, AAO64399; nucleic acid: SEQ ID NO: 52, protein: SEQ ID NO: 53)

or ketolase sequences derived from said sequences, such as, for example, the ketolases of the sequence SEQ ID NO: 8 or 10 and the corresponding coding nucleic acid sequences SEQ ID NO: 7 or SEQ ID NO: 9 which arise, for example, from variation/mutation of the sequences SEQ ID NO: 4 and SEQ ID NO: 3, respectively, the ketolases of the sequence SEQ ID NO: 12 or 14 and the corresponding coding nucleic acid sequences SEQ ID NO: 11 or SEQ ID NO: 13 which arise, for example, from variation/mutation of the sequences SEQ ID NO: 6 and SEQ ID NO: 5, respectively, the ketolases of the sequence SEQ ID NO: 49 or 51 and the corresponding coding nucleic acid sequences SEQ ID NO: 48 or SEQ ID NO: 50 which arise, for example, from variation and mutation of the sequences SEQ ID NO: 47 and SEQ ID NO: 46, respectively, Further natural examples of ketolases and ketolase genes which can be used in the process of the invention can easily be found for example from various organisms whose genomic sequence is known through identity comparisons of the amino acid sequences or of the corresponding back-translated nucleic acid sequences from databases with the sequence SEQ ID NO: 2 described above.

Further natural examples of ketolases and ketolase genes can additionally be easily found starting from the nucleic acid sequences above, in particular starting from the sequence SEQ ID NO: 1 from various organisms whose genomic sequence is unknown through hybridization techniques in a manner known per se.

The hybridization can take place under moderate (low stringency) or preferably under stringent (high stringency) conditions.

Hybridization conditions of these types are described for example in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

For example, the conditions during the washing step can be selected from the range of conditions limited by those of low stringency (with 2×SSC at 50° C.) and those of high stringency (with 0.2×SSC at 50° C., preferably at 65° C.) (20×SSC: 0.3 M sodium citrate, 3 M sodium chloride, pH 7.0).

An additional possibility is to raise the temperature during the washing step from moderate conditions at room temperature, 22° C., up to stringent conditions at 65° C.

Both parameters, the salt concentration and temperature, can be varied simultaneously, and it is also possible to keep one of the two parameters constant and vary only the other one. It is also possible to employ denaturing agents such as, for example, formamide or SDS during the hybridization. Hybridization in the presence of 50% formamide is preferably carried out at 42° C.

Some examples of conditions for hybridization and washing step are given below:

(1) Hybridization conditions with for example
(i) 4×SSC at 65° C., or
(ii) 6×SSC at 45° C., or
(iii) 6×SSC at 68° C., 100 mg/ml denatured fish sperm DNA, or
(iv) 6×SSC, 0.5% SDS, 100 mg/ml denatured, fragmented salmon sperm DNA at 68° C., or
(v) 6×SSC, 0.5% SDS, 100 mg/ml denatured, fragmented salmon sperm DNA, 50% formamide at 42° C., or
(vi) 50% formamide, 4×SSC at 42° C., or
(vii) 50% (vol/vol) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C., or
(viii) 2× or 4×SSC at 50° C. (moderate conditions), or
(ix) 30 to 40% formamide, 2× or 4×SSC at 42° (moderate conditions).

(2) Washing step for 10 minutes each with for example
(i) 0.015 M NaCl/0.0015 M sodium citrate/0.1% SDS at 50° C., or
(ii) 0.1×SSC at 65° C., or
(iii) 0.1×SSC, 0.5% SDS at 68° C., or
(iv) 0.1×SSC, 0.5% SDS, 50% formamide at 42° C., or
(v) 0.2×SSC, 0.1% SDS at 42° C., or
(vi) 2×SSC at 65° C. (moderate conditions).

In a preferred embodiment of the process of the invention there is introduction of nucleic acids which encode a ketolase comprising the amino acid sequence SEQ ID NO: 2 or a sequence which is derived from this sequence by substitution, insertion or deletion of amino acids and which has an identity of at least 50%, preferably at least 60%, preferably at least 65%, preferably at least 70%, more preferably at least 75%, more preferably at least 80%, more preferably at least 85%, more preferably at least 90%, more preferably at least 95%, particularly preferably at least 98%, at the amino acid level with the sequence SEQ ID NO: 2.

It is moreover possible for the ketolase sequence to be a natural one which can be found as described above by identity comparison of the sequences from other organisms, or for the ketolase sequence to be an artificial one which has been modified starting from the sequence SEQ ID NO: 2 by artificial variation, for example by substitution, insertion or deletion of amino acids.

The term "substitution" means in the description substitution of one or more amino acids by one or more amino acids. So-called conservative substitutions are preferably carried out, in which the replaced amino acid has a similar property to the original amino acid, for example substitution of Glu by Asp, Gin by Asn, Val by Ile, Leu by Ile, Ser by Thr.

Deletion is the replacement of an amino acid by a direct linkage. Preferred positions for deletions are the termini of the polypeptide and the linkages between the individual protein domains.

Insertions are introductions of amino acids into the polypeptide chain, with formal replacement of a direct linkage by one or more amino acids.

Identity between two proteins means the identity of the amino acids over the entire length of each protein, in particular the identity calculated by comparison using the vector NTI suite 7.1 software supplied by Informax (USA) using the clustal method (Higgins D G, Sharp P M. Fast and sensitive multiple sequence alignments on a microcomputer. Comput Appl. Biosci. 1989 April; 5(2):151-1), setting the following parameters:

| Multiple alignment parameter: | |
| --- | --- |
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |
| Pairwise alignment parameter: | |
| FAST algorithm on | 1 |
| K-tuple size | |
| Gap penalty | 3 |
| Window size | 5 |
| Number of best diagonals | 5 |

The ketolase having an identity of at least 42% at the amino acid level with the sequence SEQ ID NO: 2 accordingly means a ketolase which, on comparison of its sequence with the sequence SEQ ID NO: 2, in particular using the above program logarithm with the above set of parameters, has an identity of at least 42%.

For example, using the above program logarithm with the above set of parameters, the sequence of the ketolase from *Nostoc punctiforme* ATTC 29133 (SEQ ID NO: 4) shows an identity of 64% with the sequence of the ketolase from *Nostoc* sp. Strain PCC7120 (SEQ ID NO: 2).

The sequence of the second ketolase from *Nostoc punctiforme* ATCC 29133 (SEQ ID NO: 6) has, for example, an identity of 58% with the sequence of the ketolase from *Nostoc* sp. Strain PCC7120 (SEQ ID NO: 2).

The sequence of the ketolase from *Synechococcus* sp. WH 8102 (SEQ ID NO: 47) has, for example, an identity of 44% with the sequence of the ketolase from *Nostoc* sp. Strain PCC7120 (SEQ ID NO: 2).

Suitable nucleic acid sequences can be obtained for example by back-translation of the polypeptide sequence in accordance with the genetic code.

The codons preferably used for this purpose are those frequently used in accordance with the organism-specific codon usage. The codon usage can easily be found by means of computer analyses of other, known genes in the relevant organisms.

In a particularly preferred embodiment, a nucleic acid comprising the sequence SEQ ID NO: 1 is introduced into the organism.

All the aforementioned ketolase genes can moreover be prepared in a manner known per se by chemical synthesis from the nucleotide units such as, for example, by fragment condensation of individual overlapping, complementary nucleic acid units of the double helix. Chemical synthesis of oligonucleotides is possible, for example, in a known manner by the phosphoramidite method (Voet, Voet, 2nd edition, Wiley Press New York, pages 896-897). Addition of synthetic oligonucleotides and filling in of gaps using the Klenow fragment of DNA polymerase and ligation reactions, and general cloning methods, are described in Sambrook et al. (1989), Molecular cloning: A laboratory manual, Cold Spring Harbor Laboratory Press.

The identity shown by the sequence of the ketolase from *Nostoc* sp. Strain PCC7120 (SEQ ID NO: 2) with the sequences of the ketolases used in the prior art processes is 39% (*Agrobacterium aurantiacum* (EP 735 137), Accession No. D58420), 40% (*Alcaligenes* sp. PC-1 (EP 735137), Accession No. D58422) and 20 to 21% (*Haematococcus pluvialis Flotow em. Wille* and *Haematoccus pluvialis*, NIES 144 (EP 725137, WO 98/18910 and Lotan et al, FEBS Letters 1995, 364, 125 128), Accession No. X86782 and D45881).

In a preferred embodiment, organisms which have an increased hydroxylase activity and/or β-cyclase activity in addition to the increased ketolase activity compared with the wild type are cultivated.

Hydroxylase activity means the enzymic activity of a hydroxylase.

A hydroxylase means a protein having the enzymatic activity of introducing a hydroxyl group on the, optionally substituted, β-ionone ring of carotenoids.

In particular, a hydroxylase means a protein having the enzymatic activity of converting β-carotene into zeaxanthin or canthaxanthin into astaxanthin.

Accordingly, hydroxylase activity means the amount of β-carotene or canthaxanthin converted, or amount of zeaxanthin or astaxanthin produced, by the hydroxylase protein.

Thus, when the hydroxylase activity is increased compared with the wild type, the amount of β-carotene or canthaxantin converted or the amount of zeaxanthin or astaxanthin produced in a particular time by the hydroxylase protein is increased compared with the wild type.

This increase in the hydroxylase activity is preferably at least 5%, further preferably at least 20%, further preferably at least 50%, further preferably at least 100%, more preferably at least 300%, even more preferably at least 500%, in particular at least 600%, of the hydroxylase activity of the wild type.

β-Cyclase activity means the enzymic activity of a β-cyclase.

A β-cyclase means a protein having the enzymatic activity of converting a terminal linear lycopene residue into a β-ionone ring.

In particular, a β-cyclase means a protein having the enzymatic activity of converting γ-carotene into β-carotene.

Accordingly, a β-cyclase activity means the amount of γ-carotene converted or the amount of β-carotene produced in a particular time by the β-cyclase protein.

Thus, when the β-cyclase activity is increased compared with the wild type, the amount of lycopene or γ-carotene converted or the amount of γ-carotene produced from lycopene or the amount of β-carotene produced from γ-carotene by the β-cyclase protein in a particular time is increased compared with the wild type.

This increase in the β-cyclase activity is preferably at least 5%, further preferably at least 20%, further preferably at least 50%, further preferably at least 100%, more preferably at least 300%, even more preferably at least 500%, in particular at least 600%, of the β-cyclase activity of the wild type.

The hydroxylase activity in the genetically modified organisms of the invention and in wild-type and reference organisms is preferably determined under the following conditions:

The hydroxylase activity is determined by the method of Bouvier et al. (Biochim. Biophys. Acta 1391 (1998), 320-328) in vitro. Ferredoxin, ferredoxin-NADP oxidoreductase, catalase, NADPH and β-carotene with mono- and digalactosyl glycerides are added to a defined amount of organism extract.

The hydroxylase activity is particularly preferably determined under the following conditions of Bouvier, Keller, d'Harlingue and Camara (Xanthophyll biosynthesis: molecular and functional characterization of carotenoid hydroxylases from pepper fruits (*Capsicum annuum* L.); Biochim. Biophys. Acta 1391 (1998), 320-328):

The in vitro assay is carried out in a volume of 0.250 ml. The mixture contains 50 mM potassium phosphate (pH 7.6), 0.025 mg of spinach ferredoxin, 0.5 units of spinach ferredoxin-NADP$^+$ oxidoreductase, 0.25 mM NADPH, 0.010 mg of beta-carotene (emulsified in 0.1 mg of Tween 80), 0.05 mM of a mixture of mono- and digalactosyl glycerides (1:1), 1 unit of catalysis, 200 mono- and digalactosyl glycerides (1:1), 0.2 mg of bovine serum albumin and organism extract in a different volume. The reaction mixture is incubated at 30° C. for 2 hours. The reaction products are extracted with organic solvents such as acetone or chloroform/methanol (2:1) and determined by HPLC.

The β-cyclase activity in the genetically modified organisms of the invention and in wild-type and reference organisms is preferably determined under the following conditions:

The β-cyclase activity is determined by the method of Fraser and Sandmann (Biochem. Biophys. Res. Comm. 185(1) (1992) 9 15) in vitro. Potassium phosphate is added as buffer (pH 7.6), lycopene as substrate, paprika stromal protein, NADP$^+$, NADPH and ATP to a defined amount of organism extract.

The β-cyclase activity is particularly preferably determined under the following conditions of Bouvier, d'Harlingue and Camara (Molecular Analysis of carotenoid cyclase inhibition; Arch. Biochem. Biophys. 346(1) (1997) 53-64):

The in vitro assay is carried out in a volume of 250 μl volume. The mixture contains 50 mM potassium phosphate (pH 7.6), various amounts of organism extract, 20 nM lycopene, 250 μg of paprika chromoplastid stromal protein, 0.2 mM NADP$^+$, 0.2 mM NADPH and 1 mM ATP. NADP/NADPH and ATP are dissolved in 10 ml of ethanol with 1 mg of Tween 80 immediately before addition to the incubation medium. After a reaction time of 60 minutes at 30°

C., the reaction is stopped by adding chloroform/methanol (2:1). The reaction products extracted into chloroform are analyzed by HPLC.

An alternative assay with radioactive substrate is described in Fraser and Sandmann (Biochem. Biophys. Res. Comm. 185(1) (1992) 9-15).

The hydroxylase activity and/or β-cyclase activity can be increased in various ways, for example by switching off inhibitory regulatory mechanisms at the expression and protein level or by increasing the gene expression of nucleic acids encoding a hydroxylase, and/or of nucleic acids encoding a β-cyclase, compared with the wild type.

The gene expression of nucleic acids encoding a hydroxylase, and/or the gene expression of the nucleic acid encoding a β-cyclase, compared with the wild type, can likewise be increased in various ways, for example by inducing the hydroxylase gene and/or β-cyclase gene by activators or by introducing one or more hydroxylase gene copies and/or β-cyclase gene copies, i.e. by introducing at least one nucleic acid encoding a hydroxylase, and/or at least one nucleic acid encoding a β-cyclase, into the organism.

Increasing the gene expression of a nucleic acid encoding a hydroxylase and/or β-cyclase also means according to the invention manipulation of the expression of the organism's own endogenous hydroxylase and/or β-cyclase.

This can be achieved for example by modifying the promoter DNA sequence for genes encoding hydroxylases and/or β-cyclases. Such a modification, resulting in an increased expression rate of the gene, can be effected for example by deletion or insertion of DNA sequences.

It is possible, as described above, to modify the expression of the endogenous hydroxylase and/or β-cyclase by application of exogenous stimuli. This can be effected by particular physiological conditions, i.e. by application of foreign substances.

A further possibility for achieving a modified or increased expression of an endogenous hydroxylase and/or β-cyclase gene is through interaction of a regulator protein which does not occur in the untransformed organism with the promoter of this gene.

Such a regulator may be a chimeric protein consisting of a DNA-binding domain and of a transcription activator domain as described, for example, in WO 96/06166.

In a preferred embodiment, the gene expression of a nucleic acid encoding a hydroxylase, and/or the gene expression of a nucleic acid encoding a β-cyclase, is increased by introducing at least one nucleic acid encoding a hydroxylase, and/or by introducing at least one nucleic acid encoding a β-cyclase, into the organism.

It is possible to use for this purpose in principle any hydroxylase gene or any β-cyclase gene, i.e. any nucleic acid which encodes a hydroxylase and any nucleic acid which encodes a β-cyclase.

In the case of genorhic hydroxylase or β-cyclase nucleic acid sequences from eukaryotic sources which comprise introns, it is preferred to use nucleic acid sequences which have already been processed, such as the corresponding cDNAs, in the case where the host organism is unable or cannot be made able to express the corresponding hydroxylase or β-cyclase.

One example of a hydroxylase gene is a nucleic acid encoding a hydroxylase from *Haematococcus pluvialis* (Accession AX038729, WO 0061764); (nucleic acid: SEQ ID NO: 15, protein: SEQ ID NO: 16).

One example of a β-cyclase gene is a nucleic acid encoding a β-cyclase from tomato (Accession X86452) (nucleic acid: SEQ ID NO: 17, protein: SEQ ID NO: 18).

Thus, in this preferred embodiment, at least one further hydroxylase gene and/or β-cyclase gene is present in the preferred transgenic organisms of the invention compared with the wild type.

In this preferred embodiment, the genetically modified organism has for example at least one exogenous nucleic acid encoding a hydroxylase, or at least two endogenous nucleic acids encoding a hydroxylase and/or at least one exogenous nucleic acid encoding a β-cyclase, or at least two endogenous nucleic acids encoding a β-cyclase.

The hydroxylase genes preferably used in the preferred embodiment described above are nucleic acids encoding proteins comprising the amino acid sequence SEQ ID NO: 16 or a sequence which is derived from this sequence by substitution, insertion or deletion of amino acids and which have an identity of at least 30%, preferably at least 50%, more preferably at least 70%, even more preferably at least 90%, most preferably at least 95%, at the amino acid level with the sequence SEQ ID NO: 16, and which have the enzymatic property of a hydroxylase.

Further examples of hydroxylases and hydroxylase genes can be easily found for example from various organisms whose genomic sequence is known as described above by homology comparisons of the amino acid sequences or of the corresponding back-translated nucleic acid sequences from databases with SEQ ID. NO: 16.

Further examples of hydroxylases and hydroxylase genes can easily be found in a manner known per se in addition for example starting from the sequence SEQ ID NO: 15 from various organisms whose genomic sequence is unknown, as described above, by hybridization and PCR techniques.

In a further particularly preferred embodiment, nucleic acids which encode proteins comprising the amino acid sequence of the hydroxylase of the sequence SEQ ID NO: 16 are introduced into organisms to increase the hydroxylase activity.

Suitable nucleic acid sequences can be obtained for example by back-translation of the polypeptide sequence in accordance with the genetic code.

The codons used for this purpose are preferably those frequently used in accordance with the organism-specific codon usage. This codon usage can easily be found by means of computer analyses of other, known genes of the relevant organisms.

In a particularly preferred embodiment, a nucleic acid comprising the sequence SEQ. ID. NO: 15 is introduced into the organism.

The β-cyclase genes preferably used in the preferred embodiment described above are nucleic acids which encode proteins comprising the amino acid sequence SEQ ID NO: 18 or a sequence which is derived from this sequence by substitution, insertion or deletion of amino acids and which has an identity of at least 30%, preferably at least 50%, more preferably at least 70%, even more preferably at least 90%, most preferably at least 95%, at the amino acid level with the sequence SEQ ID NO: 18, and which has the enzymatic property of a β-cyclase.

Further examples of β-cyclases and β-cyclase genes can easily be found for example from various organisms whose genomic sequence is known as described above by homology comparisons of the amino acid sequences or of the corresponding back-translated nucleic acid sequences from databases with the SEQ ID NO: 18.

Further examples of β-cyclases and β-cyclase genes can easily be found in a manner known per se in addition for example starting from the sequence SEQ ID NO: 17 from various organisms whose genomic sequence is unknown by hybridization and PCR techniques.

In a further particularly preferred embodiment, nucleic acids which encode proteins comprising the amino acid sequence of β-cyclase of the sequence SEQ. ID. NO: 18 are introduced into organisms to increase the β-cyclase activity.

Suitable nucleic acid sequences can be obtained for example by back-translation of the polypeptide sequence in accordance with the genetic code.

The codons preferably used for this purpose are those frequently used in accordance with the organ-specific codon usage. This codon usage can easily be found by means of computer analyses of other, known genes of the relevant organisms.

In a particularly preferred embodiment, a nucleic acid comprising the sequence SEQ. ID. NO: 17 is introduced into the organism.

All the aforementioned hydroxylase genes or β-cyclase genes can moreover be prepared in a manner known per se by chemical synthesis from the nucleotide units such as, for example, by fragment condensation of individual overlapping, complementary nucleic acid units of the double helix. Chemical synthesis of oligonucleotides is possible, for example, in a known manner by the phosphoramidite method (Voet, Voet, 2nd edition, Wiley Press New York, pages 896-897). Addition of synthetic oligonucleotides and filling in of gaps using the Klenow fragment of DNA polymerase and ligation reactions, and general cloning methods, are described in Sambrook et al. (1989), Molecular cloning: A laboratory manual, Cold Spring Harbor Laboratory Press.

The genetically modified organisms particularly preferably used in the process of the invention have the following combinations of genetic modifications:

genetically modified organisms which have, compared with the wild type, an increased or caused ketolase activity and an increased hydroxylase activity, genetically modified organisms which have, compared with the wild type, an increased or caused ketolase activity and an increased β-cyclase activity and genetically modified organisms which have, compared with the wild type, an increased or caused ketolase activity and an increased hydroxylase activity and an increased β-cyclase activity.

These genetically modified organisms can be produced as described hereinafter for example by introducing individual nucleic acid constructs (expression cassettes) or by introducing multiple constructs which comprise up to two or three of the described activities.

Organisms preferably mean according to the invention organisms which are able as wild-type or starting organisms naturally or through genetic complementation and/or reregulation of metabolic pathways to produce carotenoids, in particular β-carotene and/or zeaxanthin and/or neoxanthin and/or violaxanthin and/or lutein.

Further preferred organisms already have as wild-type or starting organisms a hydroxylase activity and are thus able as wild-type or starting organisms to produce zeaxanthin.

Preferred organisms are plants or microorganisms such as, for example, bacteria, yeasts, algae or fungi.

Bacteria which can be used are both bacteria which are able, because of the introduction of genes of carotenoid biosynthesis of a carotenoid-producing organism, to synthesize xanthophylls, such as, for example, bacteria of the genus *Escherichia*, which comprise for example crt genes from *Erwinia*, and bacteria which are intrinsically able to synthesize xanthophylls, such as, for example, bacteria of the genus *Erwinia*, *Agrobacterium*, *Flavobacterium*, *Alcaligenes*, *Paracoccus*, *Nostoc* or cyanobacteria of the genus *Synechocystis*.

Preferred bacteria are *Escherichia coli*, *Erwinia herbicola*, *Erwinia uredovora*, *Agrobacterium aurantiacum*, *Alcaligenes* sp. PC-1, *Flavobacterium* sp. strain R1534, the cyanobacterium *Synechocystis* sp. PCC6803, *Paracoccus marcusii* or *Paracoccus carotinifaciens*.

Preferred yeasts are *Candida*, *Saccharomyces*, *Hansenula*, *Pichia* or *Phaffia*. Particularly preferred yeasts are *Xanthophyllomyces dendrorhous* or *Phaffia rhodozyma*.

Preferred fungi are *Aspergillus*, *Trichoderma*, *Ashbya*, *Neurospora*, *Blakeslea*, *Phycomyces*, *Fusarium* or other fungi described in Indian Chem. Engr. Section B. Vol. 37, No. 1, 2 (1995) on page 15, table 6.

Preferred algae are green algae such as, for example, algae of the genus *Haematococcus*, *Phaedactylum tricomatum*, *Volvox* or *Dunaliella*. Particularly preferred algae are *Haematococcus pluvialis* or *Dunaliella bardawil*.

Further microorganisms which can be used and the production thereof for carrying out the process of the invention are disclosed for example in DE-A-199 16 140, which is incorporated herein by reference.

Particularly preferred plants are plants selected from the families Ranunculaceae, Berberidaceae, Papaveraceae, Cannabaceae, Rosaceae, Fabaceae, Linaceae, Vitaceae, Brassicaceae, Cucurbitaceae, Primulaceae, Caryophyllaceae, Amaranthaceae, Gentianaceae, Geraniaceae, Caprifoliaceae, Oleaceae, Tropaeolaceae, Solanaceae, Scrophulariaceae, Asteraceae, Liliaceae, Amaryllidaceae, Poaceae, Orchidaceae, Malvaceae, Illaceae or Lamiaceae.

Very particularly preferred plants are selected from the group of plant genera *Marigold*, *Tagetes erecta*, *Tagetes patula*, *Acacia*, *Aconitum*, *Adonis*, *Arnica*, *Aquilegia*, *Aster*, *Astragalus*, *Bignonia*, *Calendula*, *Caltha*, *Campanula*, *Canna*, *Centaurea*, *Cheiranthus*, *Chrysanthemum*, *Citrus*, *Crepis*, *Crocus*, *Curcurbita*, *Cytisus*, *Delonia*, *Delphinium*, *Dianthus*, *Dimorphotheca*, *Doronicum*, *Eschscholtzia*, *Forsythia*, *Fremontia*, *Gazania*, *Gelsemium*, *Genista*, *Gentiana*, *Geranium*, *Gerbera*, *Geum*, *Grevillea*, *Helenium*, *Helianthus*, *Hepatica*, *Heracleum*, *Hibiscus*, *Heliopsis*, *Hypericum*, *Hypochoeris*, *Impatiens*, *Iris*, *Jacaranda*, *Kerria*, *Laburnum*, *Lathyrus*, *Leontodon*, *Lilium*, *Linum*, *Lotus*, *Lycopersicon*, *Lysimachia*, *Maratia*, *Medicago*, *Mimulus*, *Narcissus*, *Oenothera*, *Osmanthus*, *Petunia*, *Photinia*, *Physalis*, *Phyteuma*, *Potentilla*, *Pyracantha*, *Ranunculus*, *Rhododendron*, *Rosa*, *Rudbeckia*, *Senecio*, *Silene*, *Silphium*, *Sinapsis*, *Sorbus*, *Spartium*, *Tecoma*, *Torenia*, *Tragopogon*, *Trollius*, *Tropaeolum*, *Tulipa*, *Tussilago*, *Ulex*, *Viola* or *Zinnia*, particularly preferably selected from the group of plant genera *Marigold*, *Tagetes erecta*, *Tagetes patula*, *Lycopersicon*, *Rosa*, *Calendula*, *Physalis*, *Medicago*, *Helianthus*, *Chrysanthemum*, *Aster*, *Tulipa*, *Narcissus*, *Petunia*, *Geranium*, *Tropaeolum* or *Adonis*.

In the process of the invention for preparing ketocarotenoids, the step of cultivating the genetically modified organisms is preferably followed by a harvesting of the organisms and further preferably in addition by an isolation of ketocarotenoids from the organisms.

The harvesting of the organisms takes place in a manner known per se appropriate for the particular organism. Microorganisms such as bacteria, yeasts, algae or fungi or plant cells cultivated by fermentation in liquid nutrient media can be removed for example by centrifugation, decantation or filtration. Plants are grown on nutrient media and appropriately harvested in a manner known per se.

The genetically modified microorganisms are preferably cultivated in the presence of oxygen at a cultivation temperature of at least about 20° C., such as for example, 20° C. to 40° C., and at a pH of about 6 to 9. In the case of genetically modified microorganisms, the microorganisms are preferably initially cultivated in the presence of oxygen and in a complex medium such as, for example, TB or LB medium at a cultivation temperature of about 20° C. or more, and at a pH of about 6 to 9, until a sufficient cell density is reached. In order to be able to control the oxidation reaction better, it is preferred to use an inducible promoter. The cultivation is continued after induction of ketolase expression in the presence of oxygen for example for 12 hours to 3 days.

The ketocarotenoids are isolated from the harvested biomass in a manner known per se, for example by extraction and, where appropriate, further chemical or physical purification processes such as, for example, precipitation methods, crystallography, thermal separation processes, such as rectification processes or physical separation processes such as, for example, chromatography.

As mentioned below, the ketocarotenoids can be specifically produced in the genetically modified plants of the invention preferably in various plant tissues such as, for example, seeds, leaves, fruits, flowers, especially in petals.

Ketocarotenoids are isolated from the harvested petals in a manner known per se, for example by drying and subsequent extraction and, where appropriate, further chemical or physical purification processes such as, for example, precipitation methods, crystallography, thermal separation processes such as rectification processes or physical separation processes such as, for example, chromatography. Ketocarotenoids are isolated from petals for example preferably by organic solvents such as acetone, hexane, ether or tert-methyl butyl ether.

Further processes for isolating ketocarotenoids, especially from petals, are described for example in Egger and Kleinig (Phytochemistry (1967) 6, 437-440) and Egger (Phytochemistry (1965) 4, 609-618).

The ketocarotenoids are preferably selected from the group of astaxanthin, canthaxanthin, echinenone, 3-hydroxyechinenone, 3'-hydroxyechinenone, adonirubin and adonixanthin.

Astaxanthin is a particularly preferred ketocarotenoid.

Depending on the organism used, the ketocarotenoids are obtained in free form or as fatty acid ester.

In plant petals, the ketocarotenoids are obtained in the process of the invention in the form of their mono- or diesters with fatty acids. Some examples of detected fatty acids are myristic acid, palmitic acid, stearic acid, oleic acid, linolenic acid and lauric acid (Kamata and Simpson (1987) Comp. Biochem. Physiol. Vol. 86B(3), 587-591).

The ketocarotenoids can be produced in the whole plant or, in a preferred embodiment, specifically in plant tissues containing chromoplasts. Examples of preferred plant tissues are roots, seeds, leaves, fruits, flowers and, in particular nectaries and petals.

In a particularly preferred embodiment of the process of the invention, genetically modified plants which show the highest rate of expression of a ketolase in flowers are used.

This is preferably achieved through the ketolase gene expression being under the control of a flower-specific promoter. For this purpose, for example, the nucleic acids described above are introduced into the plant, as described in detail below, in a nucleic acid construct functionally linked to a flower-specific promoter.

In a further, particularly preferred embodiment of the process of the invention, genetically modified plants which show the highest rate of expression of a ketolase in fruits are used.

This is preferably achieved through the ketolase gene expression being under the control of a fruit-specific promoter. For this purpose, for example, the nucleic acids described above are introduced into the plant, as described in detail below, in a nucleic acid construct functionally linked to a fruit-specific promoter.

In a further, particularly preferred embodiment of the process of the invention, genetically modified seeds which show the highest rate of expression of a ketolase in seeds are used.

This is preferably achieved through the ketolase gene expression being under the control of a seed-specific promoter. For this purpose, for example, the nucleic acids described above are introduced into the plant, as described in detail below, in a nucleic acid construct functionally linked to a seed-specific promoter.

The targeting into the chromoplasts is effected by a functionally linked plastid transit peptide.

The production of genetically modified plants with increased or caused ketolase activity is described by way of example below. Further activities such as, for example, the hydroxylase activity and/or the β-cyclase activity can be increased analogously using nucleic acid sequences encoding a hydroxylase or β-cyclase in place of nucleic acid sequences encoding a ketolase. The transformation can be effected in the combinations of genetic modifications singly or by multiple constructs.

The transgenic plants are preferably produced by transformation of the starting plants using a nucleic acid construct which comprises the nucleic acids described above encoding a ketolase, which are functionally linked to one or more regulatory signals which ensure transcription and translation in plants.

These nucleic acid constructs in which the coding nucleic acid sequence is functionally linked to one or more regulatory signals which ensure transcription and translation in plants are also called expression cassettes below.

The regulatory signals preferably comprise one or more promoters which ensure transcription and translation in plants.

The expression cassettes comprise regulatory signals, i.e. regulating nucleic acid sequences which control the expression of the coding sequence in the host cell. In a preferred embodiment, an expression cassette comprises a promoter upstream, i.e. at the 5' end of the coding sequence, and a polyadenylation signal downstream, i.e. at the 3' end, and, where appropriate, further regulatory elements which are operatively linked to the coding sequence, located in between, for at least one of the genes described above. Operative linkage means the sequential arrangement of promoter, coding sequence, terminator and, where appropriate, further regulatory elements in such a way that each of the regulatory elements is able to carry out its function as intended in the expression of the coding sequence.

The preferred nucleic acid constructs, expression cassettes and vectors for plants and processes for producing transgenic plants, and the transgenic plants themselves, are described by way of example below.

The sequences which are preferred for the operative linkage, but are not restricted thereto, are targeting sequences to ensure the subcellular localization in the apoplast, in the vacuole, in plastids, in the mitochondrion, in the endoplasmic reticulum (ER), in the cell nucleus, in elaioplasts or other compartments and translation enhancers such as the 5' leader sequence from tobacco mosaic virus (Gallie et al., Nucl. Acids Res. 15 (1987), 8693-8711).

A suitable promoter for the expression cassette is in principle any promoter able to control the expression of foreign genes in plants.

"Constitutive" promoter means promoters which ensure expression in numerous, preferably all, tissues over a relatively wide period during development of the plant, preferably at all times during development of the plant.

Preferably used is, in particular, a plant promoter or a promoter derived from a plant virus. Particular preference is given to the CaMV promoter of the 35S transcript of cauliflower mosaic virus (Franck et al. (1980) Cell 21:285-294; Odell et al. (1985) Nature 313:810-812; Shewmaker et al. (1985) Virology 140:281-288; Gardner et al. (1986) Plant Mol Biol 6:221-228), the 19S CaMV promoter (U.S. Pat. No. 5,352,605; WO 84/02913; Benfey et al. (1989) EMBO J 8:2195-2202), the triose phosphate translocator (TPT) promoter from *Arabidopsis thaliana* Acc. No. AB006698, base pair 53242 to 55281; the gene starting at bp 55282 is anotated as "phosphate/triose phosphate translocator", or the 34S promoter from figwort mosaic virus Acc. No. X16673, base pair 1 to 554.

A further suitable constitutive promoter is the pds promoter (Pecker et al. (1992) Proc. Natl. Acad. Sci USA 89: 4962-4966) or the rubisco small subunit (SSU) promoter (U.S. Pat. No. 4,962,028), the legumin B promoter (GenBank Acc. No. X03677), the *Agrobacterium* nopaline synthase promoter, the TR dual promoter, the *Agrobacterium* OCS (octopine synthase) promoter, the ubiquitin promoter (Holtorf S et al. (1995) Plant Mol Biol 29:637-639), the ubiquitin 1 promoter (Christensen et al. (1992) Plant Mol Biol 18:675-689; Bruce et al. (1989) Proc Natl Acad Sci USA 86:9692-9696), the Smas promoter, the cinnamyl alcohol dehydrogenase promoter (U.S. Pat. No. 5,683,439), the promoters of the vacuolar ATPase subunits or the promoter of a proline-rich protein from wheat (WO 91/13991), the Pnit promoter (Y07648.L, Hillebrand et al. (1998), Plant. Mol. Biol. 36, 89-99, Hillebrand et al. (1996), Gene, 170, 197-200) and further promoters of genes whose constitutive expression in plants is known to the skilled worker.

The expression cassettes may also comprise a chemically inducible promoter (review article: Gatz et al. (1997) Annu Rev Plant Physiol Plant Mol Biol 48:89-108) by which expression of the ketolase gene in the plant can be controlled at a particular time. Promoters of this type, such as, for example, the PRP1 promoter (Ward et al. (1993) Plant Mol Biol 22:361-366), a salicylic acid-inducible promoter (WO 95/19443), a benzenesulfonamide-inducible promoter (EP 0 388 186), a tetracycline-inducible promoter (Gatz et al. (1992) Plant J 2:397-404), an abscisic acid-inducible promoter (EP 0 335 528) or an ethanol- or cyclohexanone-inducible promoter (WO 93/21334), can likewise be used.

Promoters which are further preferred are those induced by biotic or abiotic stress, such as, for example, the pathogen-inducible promoter of the PRP1 gene (Ward et al. (1993) Plant Mol Biol 22:361-366), the heat-inducible tomato hsp70 or hsp80 promoter (U.S. Pat. No. 5,187,267), the cold-inducible potato alpha-amylase promoter (WO 96/12814), the light-inducible PPDK promoter or the wound-induced pinII promoter (EP375091).

Pathogen-inducible promoters include those of genes which are induced as a result of pathogen attack, such as, for example, genes of PR proteins, SAR proteins, β-1,3-glucanase, chitlnase etc. (for example Redolfi et al. (1983) Neth J Plant Pathol 89:245-254; Uknes, et al. (1992) The Plant Cell 4:645-656; Van Loon (1985) Plant Mol Viral 4:111-116; Marineau et al. (1987) Plant Mol Biol 9:335-342; Matton et al. (1987) Molecular Plant-Microbe Interactions 2:325-342; Somssich et al. (1986) Proc Natl Acad Sci USA 83:2427-2430; Somssich et al. (1988) Mol Gen Genetics 2:93-98; Chen et al. (1996) Plant J 10:955-966; Zhang and Sing (1994) Proc Natl Acad Sci USA 91:2507-2511; Warner, et al. (1993) Plant J 3:191-201; Siebertz et al. (1989) Plant Cell 1:961-968 (1989).

Also included as wound-inducible promoters such as that of the pinII gene (Ryan (1990) Ann Rev Phytopath 28:425-449; Duan et al. (1996) Nat Biotech 14:494498), of the wun1 and wun2 genes (U.S. Pat. No. 5,428,148), of the win1 and win2 genes (Stanford et al. (1989) Mol Gen Genet 215:200-208), of the systemin gene (McGurl et al. (1992) Science 225:1570-1573), of the WIP1 gene (Rohmeier et al. (1993) Plant Mol Biol 22:783-792; Ekelkamp et al. (1993) FEBS Letters 15 323:73-76), of the MPI gene (Corderok et al. (1994) The Plant J 6(2):141-150) and the like.

Examples of further suitable promoters are fruit ripening-specific promoters such as, for example, the tomato fruit ripening-specific promoter (WO 94/21794, EP 409 625). Development-dependent promoters include some of the tissue-specific promoters because the formation of some tissues naturally depends on development.

Further particularly preferred promoters are those which ensure expression in tissues or parts of plant in which, for example, the biosynthesis of ketocarotenoids or precursors thereof takes place. Preferred examples are promoters having specificities for anthers, ovaries, petals, sepals, flowers, leaves, stalks, seeds and roots and combinations thereof.

Examples of promoters specific for tubers, storage roots or roots are the patatin promoter class I (B33) or the potato cathepsin D inhibitor promoter.

Examples of leaf-specific promoters are the promoter of the potato cytosolic FBPase (WO 97/05900), the rubisco (ribulose-1,5-bisphosphate carboxylase) SSU promoter (small subunit) or the potato ST-LSI promoter (Stockhaus et al. (1989) EMBO J 8:2445-2451).

Examples of flower-specific promoters are the phytoene synthase promoter (WO 92/116635) or the promoter of the P-rr gene (WO 98/22593), the *Arabidopsis thaliana* AP3 promoter (see example 5), the CHRC promoter (chromoplast-specific carotenoid-associated protein (CHRC) gene promoter from *Cucumis sativus* Acc. No. AF099501, base pair 1 to 1532), the EPSP synthase promoter (5-enolpyruvylshikimate-3-phosphate synthase gene promoter from *Petunia hybrida*, Acc. No. M37029, base pair 1 to 1788), the PDS promoter (phytoene desaturase gene promoter from *Solanum lycopersicum*, Acc. No. U46919, base pair 1 to 2078), the DFR-A promoter (dihydroflavonol 4-reductase gene A promoter from *Petunia hybrida*, Acc. No. X79723, base pair 32 to 1902) or the FBP1 promoter (floral binding protein 1 gene promoter from *Petunia hybrida*, Acc. No. L10115, base pair 52 to 1069).

Examples of anther-specific promoters are the 5126 promoter (U.S. Pat. No. 5,689,049, U.S. Pat. No. 5,689,051), the glob-I promoter or the g-zein promoter.

Examples of seed-specific promoters are the ACP05 promoter (acyl carrier protein gene, WO 9218634), the *Arabidopsis* AtS1 and AtS3 promoters (WO 9920775), the *Vicia faba* LeB4 promoter (WO 9729200 and U.S. Pat. No. 0,640,3371), the *Brassica napus* napin promoter (U.S. Pat. No. 5,608,152; EP 255378; U.S. Pat. No. 5,420,034), the *Vicia faba* SBP promoter (DE 9903432) or the maize End1 and End2 promoters (WO 0011177).

Further promoters suitable for expression in plants are described in Rogers et al. (1987) Meth in Enzymol 153:253-277; Schardl et al. (1987) Gene 61:1-11 and Berger et al. (1989) Proc Natl Acad Sci USA 86:8402-8406.

Particularly preferred in the process of the invention are constitutive, seed-specific, fruit-specific, flower-specific and, in particular, petal-specific promoters.

The present invention therefore relates in particular to a nucleic acid construct comprising functionally linked a flower-specific or, in particular, a petal-specific promoter and a nucleic acid encoding a ketolase comprising the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2.

An expression cassette is preferably produced by fusing a suitable promoter to a nucleic acid, described above, encoding a ketolase, and preferably to a nucleic acid which is inserted between promoter and nucleic acid sequence and which codes for a plastid-specific transit peptide, and to a polyadenylation signal by conventional recombination and cloning techniques as described, for example in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley-Interscience (1987).

The preferably inserted nucleic acids encoding a plastid transit peptide ensure localization in plastids and, in particular, in chromoplasts.

It is also possible to use expression cassettes whose nucleic acid sequence codes for a ketolase fusion protein, where part of the fusion protein is a transit peptide which controls the translocaton of the polypeptide. Transit peptides which are specific for chromoplasts and which are eliminated enzymatically from the ketolase part after translocation of the ketolase into the chromoplasts.

The particularly preferred transit peptide is derived from the *Nicotiana tabacum* plastid transketolase or another transit peptide (e.g. the transit peptide of the small subunit of rubisco (rbcS) or of the ferredoxin NADP oxidoreductase, as well as the isopentenyl-pyrophosphate isomerase 2) or its functional equivalent.

Particular preference is given to nucleic acid sequences of three cassettes of the plastid transit peptide of the tobacco plastic transketolase in three reading frames as KpnI/BamHI fragments with an ATG codon in the NcoI cleavage site:

```
pTP09
KpnI_GGTACCATGGCGTCTTCTTCTTCTCTCACTCTCTCTCAAGCTATC
CTCTCTCGTTCTGTCCCTCGCCATGGCTCTGCCTCTTCTTCTCAACTTTC
CCCTTCTTCTCTCACTTTTTCCGGCCTTAAATCCAATCCCAATATCACCA
CCTCCCGCCGCCGTACTCCTTCCTCCGCCGCCGCCGCCGCCGTCGTAAGG
TCACCGGCGATTCGTGCCTCAGCTGCAACCGAAACCATAGAGAAAACTGA
GACTGCGGGATCC_BamHI (SEQ ID NO: 75)

pTP10
KpnI_GGTACCATGGCGTCTTCTTCTTCTCTCACTCTCTCTCAAGCTATC
CTCTCTCGTTCTGTCCCTCGCCATGGCTCTGCCTCTTCTTCTCAACTTTC
CCCTTCTTCTCTCACTTTTTCCGGCCTTAAATCCAATCCCAATATCACCA
CCTCCCGCCGCCGTACTCCTTCCTCCGCCGCCGCCGCCGCCGTCGTAAGG
TCACCGGCGATTCGTGCCTCAGCTGCAACCGAAACCATAGAGAAAACTGA
GACTGCGCTGGATCC_BamHI (SEQ ID NO: 76)
```

-continued
```
pTP11
KpnI_GGTACCATGGCGTCTTCTTCTTCTCTCACTCTCTCTCAAGCTATC
CTCTCTCGTTCTGTCCCTCGCCATGGCTCTGCCTCTTCTTCTCAACTTTC
CCCTTCTTCTCTCACTTTTTCCGGCCTTAAATCCAATCCCAATATCACCA
CCTCCCGCCGCCGTACTCCTTCCTCCGCCGCCGCCGCCGCCGTCGTAAGG
TCACCGGCGATTCGTGCCTCAGCTGCAACCGAAACCATAGAGAAAACTGA
GACTGCGGGGATCC_BamHI (SEQ ID NO: 77)
```

Further examples of a plastid transit peptide are the transit peptide of the *Arabidopsis thaliana* plastid isopentenyt-pyrophosphate isomerase 2 (IPP-2) and the transit peptide of the small subunit of ribulose-bisphosphate carboxylase (rbcS) from pea (Guerineau, F, Woolston, S, Brooks, L, Mullineaux, P (1988) An expression cassette for targeting foreign proteins into the chloroplasts. Nucl. Acids Res. 16: 11380).

The nucleic acids of the invention can be prepared synthetically or obtained naturally or comprise a mixture of synthetic and natural nucleic acid constituents, and consist of various heterologous gene sections from different organisms.

Preference is given, as described above, to synthetic nucleotide sequences with codons preferred by plants. These codons preferred by plants can be identified from codons with the highest protein frequency which are expressed in most plant species of interest.

For preparing an expression cassette it is possible to manipulate various DNA fragments in order to obtain a nucleotide sequence which expediently reads in the correct direction and is equipped with a correct reading frame. Adaptors or linkers can be attached to the fragments for connecting the DNA fragments to one another.

It is possible and expedient for the promoter and terminator regions to be provided in the direction of transcription with a linker or polylinker which contains one or more restriction sites for inserting this sequence. As a rule, the linker has 1 to 10, usually 1 to 8, preferably 2 to 6, restriction sites. The linker generally has a size of less than 100 bp, frequently less than 60 bp, but at least 5 bp, inside the regulatory regions. The promoter may be both native or homologous and foreign or heterologous to the host plant. The expression cassette preferably comprises in the 5'-3' direction of transcription the promoter, a coding nucleic acid sequence or a nucleic acid construct and a region for termination of transcription. Various termination regions are interchangeable as desired.

Examples of a terminator are the 35S terminator (Guerineau et al. (1988) Nucl Acids Res. 16: 11380), the nos terminator (Depicker A, Stachel S, Dhaese P, Zambryski P, Goodman H M. Nopaline synthase: transcript mapping and DNA sequence. J Mol Appl Genet. 1982;1(6):561-73) or the ocs terminator (Gielen, J, de Beuckeleer, M, Seurinck, J, Debroek, H, de Greve, H, Lemmers, M, van Montagu, M, Schell, J (1984) The complete sequence of the TL-DNA of the *Agrobacterium tumefaciens* plasmid pTiAch5. EMBO J. 3: 835-846).

It is furthermore possible to employ manipulations which provide appropriate restriction cleavage sites or delete the redundant DNA or restriction cleavage sites. It is possible in relation to insertions, deletions or substitutions, such as, for example, transitions and transversions, to use in vitro mutagenesis, primer repair, restriction or ligation.

It is possible with suitable manipulations, such as, for example, restriction, chewing back or filling in of overhangs for blunt ends, to provide complementary ends of the fragments for ligation.

Preferred polyadenylation signals are plant polyadenylation signals, preferably those which essentially correspond to T-DNA polyadenylation signals from *Agrobacterium tumefaciens*, especially of gene 3 of the T-DNA (octopine synthase) of the Ti plasmid pTiACH5 (Gielen et al., EMBO J. 3 (1984), 835 ff) or functional equivalents.

The transfer of foreign genes into the genome of a plant is referred to as transformation.

It is possible to use for this purpose methods known per se for the transformation and regeneration of plants from plant tissues or plant cells for transient or stable transformation.

Suitable methods for transforming plants are protoplast transformation by polyethylene glycol-induced DNA uptake, the biolistic method using the gene gun—called the particle bombardment method—electroporation, incubation of dry embryos in DNA-containing solution, microinjection and gene transfer mediated by *Agrobacterium* described above. Said processes are described, for example, in B. Jenes et al., Techniques for Gene Transfer, in: Transgenic Plants, Vol. 1, Engineering and Utilization, edited by S. D. Kung and R. Wu, Academic Press (1993), 128-143 and in Potrykus, Annu. Rev. Plant Physiol. Plant Molec. Biol. 42 (1991), 205-225.

The construct to be expressed is preferably cloned into a vector which is suitable for transforming *Agrobacterium tumefaciens*, for example pBin19 (Bevan et al., Nucl. Acids Res. 12 (1984), 8711) or particularly preferably, pSUN2, pSUN3, pSUN4 or pSUN5 (WO 02/00900).

Agrobacteria transformed with an expression plasmid can be used in a known manner for transforming plants, e.g. bathing wounded leaves or pieces of leaf in a solution of agrobacteria and subsequently cultivating in suitable media.

For the preferred production of genetically modified plants, also referred to as transgenic plants hereinafter, the fused expression cassette which expresses a ketolase is cloned into a vector, for example pBin19 or, in particular, pSUN5 and pSUN3, which is suitable for being transformed into *Agrobacterium tumefaciens*. Agrobacteria transformed with such a vector can then be used in a known manner for transforming plants, in particular crop plants, by bathing wounded leaves or pieces of leaf in a solution of agrobacteria and subsequently cultivating in suitable media.

The transformation of plants by agrobacteria is disclosed inter alia in F. F. White, Vectors for Gene Transfer in Higher Plants; in Transgenic Plants, Vol. 1, Engineering and Utilization, edited by S. D. Kung and R. Wu, Academic Press, 1993, pages 15-38. Transgenic plants which comprise a gene, integrated into the expression cassette for expression of a nucleic acid encoding a ketolase can be regenerated in a known manner from the transformed cells of the wounded leaves or pieces of leaf.

To transform a host cell with a nucleic acid coding for a ketolase, an expression cassette is incorporated and inserted into a recombinant vector whose vector DNA comprises additional functional regulatory signals, for example sequences for replication or integration. Suitable vectors are described inter alia in "Methods in Plant Molecular Biology and Biotechnology" (CRC Press), chapter 6/7, pages 71-119 (1993).

Using the recombination and cloning techniques quoted above, the expression cassettes can be cloned into suitable vectors which make replication thereof possible for example in *E. coli*. Suitable cloning vectors are, inter alia, pJIT117 (Guerineau et al. (1988) Nucl. Acids Res. 16 :11380), pBR332, pUC series, M13mp series and pACYC184. Binary vectors which are able to replicate both in *E. coli* and in agrobacteria are particularly suitable.

The production of the genetically modified microorganisms of the invention is described in more detail below:

The nucleic acids described above, encoding a ketolase or β-hydroxylase or β-cyclase, are preferably incorporated into expression constructs comprising, under the genetic control of regulatory nucleic acid sequences, a nucleic acid sequence coding for an enzyme of the invention; and vectors comprising at least one of these expression constructs.

Such constructs of the invention preferably include a promoter upstream, i.e. at the 5' end of the particular coding sequence, and a terminator sequence downstream, i.e. at the 3' end, and, where appropriate, further customary regulatory elements which are in each case operatively linked to the coding sequence. Operative linkage means the sequential arrangement of promoter, coding sequence, terminator and, where appropriate, further regulatory elements in such a way that each of the regulatory elements is able to carry out its function as intended in the expression of the coding sequence.

Examples of operatively linkable sequences are targeting sequences and translation enhancers, enhancers, polyadenylation signals and the lilke. Further regulatory elements include selectable markers, amplification signals, origins of replication and the like.

In addition to the artificial regulatory sequences it is possible for the natural regulatory sequence still to be present in front of the actual structural gene. This natural regulation can be switched off where appropriate, and the expression of the genes increased or reduced, by genetic modification. The gene construct may, however, also have a simpler structure, that is to say no additional regulatory signals are inserted in front of the structural gene, and the natural promoter with its regulation is not deleted. Instead, the natural regulatory sequence is mutated so that regulation no longer takes place, and gene expression is increased or reduced. The nucleic acid sequences may be present in one or more copies in the gene construct.

Examples of promoters which can be used are: cos, tac, trp, tet, trp-tet, lpp, lac, lpp-lac, laclq, T7, T5, T3, gal, trc, ara, SP6, lambda-PR or lambda-PL promoter, which are advantageously used in Gram-negative bacteria; and the Gram-positive promoters amy and SPO2 or the yeast promoters ADC1, MFα, AC, P-60, CYC1, GAPDH. The use of inducible promoters is particularly preferred, such as, for example, light- and, in particular, temperature-inducible promoters such as the $P_rP_l$ promoter.

It is possible in principle for all natural promoters with their regulatory sequences to be used. In addition, it is also possible advantageously to use synthetic promoters.

Said regulatory sequences are intended to make specific expression of the nucleic acid sequences and protein expression possible. This may mean, for example, depending on the host organism, that the gene is expressed or overexpressed only after induction or that it is immediately expressed and/or overexpressed.

The regulatory sequences or factors may moreover preferably influence positively, and thus increase or reduce, expression. Thus, enhancement of the regulatory elements can take place advantageously at the level of transcription by using strong transcription signals such as promoters and/or enhancers. However, it is also possible to enhance translation by, for example, improving the stability of the mRNA.

An expression cassette is produced by fusing a suitable promoter to the above described nucleic acid sequence which encodes a ketolase, β-hydroxylase or β-cyclase and to a terminator signal or polyadenylation signal. Conventional techniques of recombination and cloning are used for this purpose, as described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector, which makes optimal expression of the genes in the host possible. Vectors are well known to the skilled worker and can be found, for example, in "Cloning Vectors" (Pouwels P. H. et al., eds, Elsevier, Amsterdam-New York-Oxford, 1985). Vectors also mean not only plasmids but also all other vectors known to the skilled worker, such as, for example, phages, viruses, such as SV40, CMV, baculovirus and adenovirus, transposons, IS elements, phasmids, cosmids, and linear or circular DNA. These vectors may undergo autonomous replication in the host organism or chromosomal replication.

Examples of suitable expression vectors which may be mentioned are:

Conventional fusion expression vectors such as pGEX (Pharmacia Biotech Inc; Smith, D. B. and Johnson, K. S. (1988) Gene 67:3140), pMAL (New England Biolabs, Beverly, Mass.) and pRIT 5 (Pharmacia, Piscataway, N.J.), with which respectively glutathione S-transferase (GST), maltose E-binding protein and protein A are fused to the recombinant target protein.

Non-fusion protein expression vectors such as pTrc (Amann et al., (1988) Gene 69:301-315) and pET 11 d (Studier et al. Gene Expression Technology. Methods in Enzymology 185, Academic Press, San Diego, Calif. (1990) 60-89).

Yeast expression vector for expression in the yeast S. cerevisiae, such as pYepSec1 (Baldari et al., (1987) Embo J. 6:229-234), pMFα (Kurjan and Herskowitz (1982) Cell 30:933-943), pJRY88 (Schultz et al. (1987) Gene 54:113-123) and pYES2 (Invitrogen Corporation, San Diego, Calif.).

Vectors and methods for constructing vectors suitable for the use in other fungi such as filamentous fungi comprise those which are described in detail in: van den Hondel, C. A. M. J. J. & Punt, P. J. (1991) "Gene transfer systems and vector development for filamentous fungi, in: Applied Molecular Genetics of Fungi, J. F. Peberdy et al., eds, pp. 1-28, Cambridge University Press: Cambridge.

Baculovirus vectors which are available for expression of proteins in cultured insect cells (for example Sf9 cells) comprise the pAc series (Smith et al., (1983) Mol. Cell Biol. 3:2156-2165) and pVL series (Lucklow and Summers (1989) Virology 170:31-39).

Further suitable expression systems for prokaryotic and eukaryotic cells are described in chapters 16 and 17 of Sambrook, J., Fritsch, E. F. and Maniatis, T., Molecular cloning: A Laboratory Manual, 2nd edition, Cold Spring Harbor Laboratory, Cold Spring Harbor Laboratory Press, Cold Spring Harbor, N.Y., 1989.

The expression constructs or vectors of the invention can be used to produce genetically modified microorganisms which are transformed, for example, with at least one vector of the invention.

The recombinant constructs of the invention described above are advantageously introduced and expressed in a suitable host system. Cloning and transfection methods familiar to the skilled worker, such as, for example, coprecipitation, protoplast fusion, electroporation, retroviral transfection and the like, are preferably used to bring about expression of said nucleic acids in the particular expression system. Suitable systems are described, for example, in Current Protocols in Molecular Biology, F. Ausubel et al., eds, Wiley Interscience, New York 1997.

Successfully transformed organisms can be selected through marker genes which are likewise present in the vector or in the expression cassette. Examples of such marker genes are genes for antibiotic resistance and for enzymes which catalyze a color-forming reaction which causes staining of the transformed cell. These can then be selected by automatic cell sorting.

Microorganisms which have been successfully transformed with a vector and harbor an appropriate antibiotic resistance gene (for example G418 or hygromycin) can be selected by appropriate antibiotic-containing media or nutrient media. Marker proteins present on the surface of the cell can be used for selection by means of affinity chromatography.

The combination of the host organisms and the vectors appropriate for the organisms, such as plasmids, viruses or phages, such as, for example, plasmids with the RNA polymerase/promoter system, phages 8 or other temperate phages or transposons and/or other advantageous regulatory sequences forms an expression system.

The invention further relates to a process for producing genetically modified organisms, which comprises introducing a nucleic acid construct comprising functionally linked a promoter and nucleic acids encoding a ketolase comprising the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2, and, where appropriate, a terminator into the genome of the starting organism or extrachromosomally into the starting organism.

The invention further relates to the genetically modified organisms where the genetic modification A in the case where the wild-type organism already has a ketolase activity, increases the activity of a ketolase compared with the wild type and B in the case where the wild-type organism has no ketolase activity, causes the activity of a ketolase compared with the wild type, and the ketolase activity which has been increased as in A or caused as in B is caused by a ketolase comprising the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2.

As stated above, the increasing or causing of the ketolase activity is brought about by an increasing or causing of the gene expression of a nucleic acid encoding a ketolase comprising the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2, compared with the wild type.

In a further preferred embodiment, as stated above, the increasing or causing of the gene expression of a nucleic acid encoding a ketolase takes place by introducing nucleic acids encoding a ketolase into the plants and thus preferably by overexpression or transgenic expression of nucleic acids encoding a ketolase comprising the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2.

The invention further relates to a genetically modified organism comprising at least one transgenic nucleic acid encoding a ketolase comprising the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2. This is the case when the starting organism has no ketolase or an endogenous ketolase, and a transgenic ketolase is overexpressed.

The invention further relates to a genetically modified organism comprising at least two endogenous nucleic acids encoding a ketolase comprising the amino acid sequence SEQ. ID. NO. 2 or a sequence which is derived from this sequence by substitution, insertion or deletion of amino acids and which has an identity of at least 42% at the amino acid level with the sequence SEQ. ID. NO. 2. This is the case when the starting organism has an endogenous ketolase, and the endogenous ketolase is overexpressed.

Particularly preferred genetically modified organisms have, as mentioned above, additionally an increased hydroxylase activity and/or β-cyclase activity compared with a wild-type organism.

Further preferred embodiments are described above in the process of the invention. Organisms preferably mean according to the invention organisms which are able as wild-type or starting organisms naturally or through genetic complementation and/or reregulation of metabolic pathways to produce carotenoids, in particular β-carotene and/or zeaxanthin and/or neoxanthin and/or violaxanthin and/or luteine.

Further preferred organisms already have as wild-type or starting organisms a hydroxylase activity and are thus able as wild-type or starting organisms to produce zeaxanthin.

Preferred organisms are plants or microorganisms such as, for example, bacteria, yeasts, algae or fungi.

Bacteria which can be used are both bacteria which are able, because of the introduction of genes of carotenoid biosynthesis of a carotenoid-producing organism, to synthesize xanthophylls, such as, for example, bacteria of the genus *Escherichia*, which comprise for example crt genes from *Erwinia*, and bacteria which are intrinsically able to synthesize xanthophylls, such as, for example, bacteria of the genus *Erwinia, Agrobacterium, Flavobacterium, Alcaligenes, Paracoccus, Nostoc* or cyanobacteria of the genus *Synechocystis*.

Preferred bacteria are *Escherichia coli, Erwinia herbicola, Erwinia uredovora, Agrobacterium aurantiacum, Alcaligenes* sp. PC-1, *Flavobacterium* sp. strain R1534, the cyanobacterium *Synechocystis* sp. PCC6803, *Paracoccus marcusii* or *Paracoccus carotinifaciens*.

Preferred yeasts are *Candida, Saccharomyces, Hansenula, Pichia* or *Phaffia*. Particularly preferred yeasts are *Xanthophyllomyces dendrorhous* or *Phaffia rhodozyma*.

Preferred fungi are *Aspergillus, Trichoderna, Ashbya, Neurospora, Blakeslea, Phycomyces, Fusarium* or other fungi described in Indian Chem. Engr. Section B. Vol. 37, No. 1, 2 (1995) on page 15, table 6.

Preferred algae are green algae such as, for example, algae of the genus *Haematococcus, Phaedactylum tricornatum, Volvox* or *Dunaliella*. Particularly preferred algae are *Haematococcus pluvialis* or *Dunaliella bardawil*.

Further microorganisms which can be used and the production thereof for carrying out the process of the invention are disclosed for example in DE-A-199 16 140, which is incorporated herein by reference.

Particularly preferred plants are plants selected from the families Ranunculaceae, Berberidaceae, Papaveraceae, Cannabaceae, Rosaceae, Fabaceae, Linaceae, Vitaceae, Brassicaceae, Cucurbitaceae, Primulaceae, Caryophyllaceae, Amaranthaceae, Gentianaceae, Geraniaceae, Caprifoliaceae, Oleaceae, Tropaeolaceae, Solanaceae, Scrophulariaceae, Asteraceae, Liliaceae, Amaryllidaceae, Poaceae, Orchidaceae, Malvaceae, Illiaceae or Lamiaceae.

Very particularly preferred plants are selected from the group of plant genera *Marigold, Tagetes errecta, Tagetes patula, Acacia, Aconitum, Adonis, Amica, Aquilegia, Aster, Astragalus, Bignonia, Calendula, Caltha, Campanula, Canna, Centaurea, Cheiranthus, Chrysanthemum, Citrus, Crepis, Crocus, Curcurbita, Cytisus, Delonia, Delphinium, Dianthus, Dimorphotheca, Doronicum, Eschscholtzia, Forsythia, Fremontia, Gazania, Gelsemium, Genista, Gentiana, Geranium, Gerbera, Geum, Grevillea, Helenium, Helianthus, Hepatica, Heracleum, Hibiscus, Heliopsis, Hypericum, Hypochoeris, Impatiens, Iris, Jacaranda, Kerria, Labumum, Lathyrus, Leontodon, Lilium, Linum, Lotus, Lycopersicon, Lysimachia, Maratia, Medicago, Mimulus, Narcissus, Oenothera, Osmanthus, Petunia, Photinia, Physalis, Phyteuma, Potentilla, Pyracantha, Ranunculus, Rhododendron, Rosa, Rudbeckia, Senecio, Silene, Silphium, Sinapsis, Sorbus, Spartium, Tecoma, Torenia, Tragopogon, Trollius, Tropaeolum, Tulipa, Tussilago, Ulex, Viola* or *Zinnia*, particularly preferably selected from the group of plant genera *Marigold, Tagetes erecta, Tagetes patula, Lycopersicon, Rosa, Calendula, Physalis, Medicago, Helianthus, Chrysanthemum, Aster, Tulipa, Narcissus, Petunia, Geranium, Tropaeolum* or *Adonis*.

Very particularly preferred genetically modified plants are selected from the plant genera *Marigold, Tagetes erecta, Tagetes patula, Adonis, Lycopersicon, Rosa, Calendula, Physalis, Medicago, Helianthus, Chrysanthemum, Aster, Tulipa, Narcissus, Petunia, Geranium* or *Tropaeolum*, with the genetically modified plant comprising at least one transgenic nucleic acid encoding a ketolase.

The present invention further relates to the transgenic plants, their propagation material, and their plant cells, tissues or parts, especially their fruit, seeds, flowers and petals.

The genetically modified plants can, as described above, be used for preparing ketocarotenoids, especially astaxanthin.

Genetically modified organisms of the invention which can be consumed by humans and animals, especially plants or parts of plants, such as, in particular, petals with an increased content of ketocarotenoids, especially astaxanthin, can also be used directly or after processing known per se as human or animal foods or as animal and human food supplements.

The genetically modified organisms can also be used for producing ketocarotenoid-containing extracts of the organisms and/or for producing animal and human food supplements.

The genetically modified organisms have an increased content of ketocarotenoids compared with the wild type.

An increased content of ketocarotenoids usually means an increased total ketocarotenoid content.

However, an increased content of ketocarotenoid also means in particular an altered content of the preferred ketocarotenoids without the need for the total carotenoid content necessarily to be increased.

In a particularly preferred embodiment, the genetically modified plants of the invention have an increased astaxanthin content compared with the wild type.

An increased content means in this case also a caused content of ketocarotenoids such as astaxanthin.

The invention further relates to the novel ketolases and to the novel nucleic acids which encode the latter.

The invention relates in particular to ketolases comprising the amino acid sequence SEQ. ID. NO. 8 or a sequence which is derived from this sequence by substitution, insertion or deletion of amino acids and which has an identity of at least 70%, preferably at least 75%, particularly preferably at least 80%, more preferably at least 85%, more preferably at least 90%, more preferably at least 95% at the amino acid level with the sequence SEQ. ID. NO. 2, with the proviso that the amino acid sequence SEQ. ID NO. 8 is not present. The sequence SEQ ID NO: 4 is, as mentioned above, annotated as putative protein in databases.

The invention further relates to ketolases comprising the amino acid sequence SEQ. ID. NO. 6 or a sequence which is derived from this sequence by substitution, insertion or deletion of amino acids and which has an identity of at least 70% at the amino acid level with the sequence SEQ. ID. NO. 6. The sequence SEQ ID NO: 6 is, as mentioned above, not annotated in databases.

In a further embodiment, the invention relates to ketolases comprising the amino acid sequence SEQ ID NO: 12 or a sequence which is derived from this sequence by substitution, insertion or deletion of amino acids and which has an identity of at least 70%, preferably at least 75%, particularly preferably at least 80%, more preferably at least 85%, more preferably at least 90%, more preferably at least 95%, at the amino acid level with the sequence SEQ ID NO: 12, with the proviso that the amino acid sequence SEQ ID NO: 6 is not present.

The invention further relates to ketolases comprising the amino acid sequence SEQ ID NO: 49 or a sequence which is derived from this sequence by substitution, insertion or deletion of amino acids and which has an identity of at least 50%, preferably at least 60%, particularly preferably at least 70%, more preferably at least 80%, more preferably at least 90%, more preferably at least 95%, at the amino acid level with the sequence SEQ ID NO: 49, with the proviso that the amino acid sequence SEQ ID NO: 47 is not present. The sequence SEQ ID NO: 47 is, as mentioned above, annotated as a putative protein in databases.

The invention further relates to nucleic acids encoding a protein described above, with the proviso that the nucleic acid does not comprise the sequence SEQ ID NO: 5.

It has surprisingly been found that a protein comprising the amino acid sequence SEQ. ID. NO. 4 or a sequence which is derived from this sequence by substitution, insertion or deletion of amino acids and which has an identity of at least 70%, preferably at least 75%, particularly preferably at least 80%, more preferably at least 85%, more preferably at least 90%, more preferably at least 95%, at the amino acid level with the sequence SEQ. ID. NO. 4 and has the property of a ketolase, has a property as ketolase.

The invention therefore also relates to the use of a protein comprising the amino acid sequence SEQ. ID. NO. 4 or a sequence which is derived from this sequence by substitution, insertion or deletion of amino acids and which has an identity of at least 70%, preferably at least 75%, particularly preferably at least 80%, more preferably at least 85%, more preferably at least 90%, more preferably at least 95%, at the amino acid level with the sequence SEQ. ID. NO. 4, and has the property of a ketolase, as ketolase.

It has also surprisingly been found that a protein comprising the amino acid sequence SEQ. ID. NO. 6 or a sequence which is derived from this sequence by substitution, insertion or deletion of amino acids and which has an identity of at least 65%, preferably at least 70%, preferably at least 75%, particularly preferably at least 80%, more preferably at least 85%, more preferably at least 90%, more preferably at least 95%, at the amino acid level with the sequence SEQ. ID. NO. 6, and has the property of a ketolase, has a property as ketolase.

The invention therefore also relates to the use of a protein comprising the amino acid sequence SEQ. ID. NO. 6 or a sequence which is derived from this sequence by substitution, insertion or deletion of amino acids and which has an identity of at least 65%, preferably at least 70%, preferably at least 75%, particularly preferably at least 80%, more preferably at least 85%, more preferably at least 90%, more preferably at least 95%, at the amino acid level with the sequence SEQ. ID. NO. 6, and has the property of a ketolase, as ketolase.

It has also surprisingly been found that a protein comprising the amino acid sequence SEQ ID NO: 47 or a sequence which is derived from this sequence by substitution, insertion or deletion of amino acids and which has an identity of at least 50%, preferably at least 60%, preferably at least 70%, particularly preferably at least 80%, more preferably at least 85%, more preferably at least 90%, more preferably at least 95%, at the amino acid level with the sequence SEQ ID NO: 47 and which has the property of a ketolase, has a property as ketolase.

The invention therefore also relates to the use of a protein comprising the amino acid sequence SEQ ID NO: 47 or a sequence which is derived from this sequence by substitution, insertion or deletion of amino acids and which has an identity of at least 50%, preferably at least 60%, preferably at least 70%, particularly preferably at least 80%, more preferably at least 85%, more preferably at least 90%, more preferably at least 95%, at the amino acid level with the sequence SEQ ID NO: 47 and which has the property of a ketolase, as ketolase.

Compared with prior art processes, the process of the invention affords a larger quantity of ketocarotenoids, especially astaxanthin having a small quantity of hydroxylated byproducts.

The invention is now explained by the following examples, but is not restricted thereto:

General Experimental Conditions:

Sequence Analysis of Recombinant DNA

Recombinant DNA molecules were sequenced using a laser fluorescence DNA sequencer from Licor (sold by MWG Biotech, Ebersbach, Germany), following the method of Sanger (Sanger et al., Proc. Natl. Acad. Sci. USA 74 (1977), 5463-5467).

EXAMPLE 1

Amplification of a DNA which Encodes the Entire Primary Sequence of NOST Ketolase from *Nostoc* sp. PCC 7120

The DNA encoding the *Nostoc* sp. PCC 7120 NOST ketolase was amplified from *Nostoc* sp. PCC 7120 ("Pasteur Culture Collection of Cyanobacterium" strain) by means of PCR.

To prepare genomic DNA from a *Nostoc* sp. PCC 7120 suspension culture which had grown in BG 11 medium (1.5 g/l NaNO$_3$, 0.04 g/l K$_2$PO$_4$×3H$_2$O, 0.075 g/l MgSO$_4$×H$_2$O, 0.036 g/l CaCl$_2$×2H$_2$O, 0.006 g/l citric acid, 0.006 g/l ferric ammonium citrate, 0.001 g/l EDTA disodium magnesium, 0.04 g/l Na$_2$CO$_3$, 1 ml of trace metal mix A5+Co (2.86 g/l H$_3$BO$_3$, 1.81 g/l MnCl$_2$×4H$_2$O, 0.222 g/l ZnSO$_4$×7H$_2$O, 0.39 g/l NaMoO$_4$×2H$_2$O, 0.079 g/l CuSO$_4$×5H$_2$O, 0.0494 g/l Co(NO$_3$)$_2$×6H$_2$O) at 25° C. with constant shaking (150 rpm) and under continuous light for 1 week, the cells were harvested by centrifugation, frozen in liquid nitrogen and ground to a powder in a mortar.

Protocol for Isolating DNA from *Nostoc* PCC7120:

The bacteria cells were pelleted from a 10 ml liquid culture by centrifugation at 8000 rpm for 10 minutes. The bacterial cells were then crushed and ground in liquid nitrogen, using a mortar. The cell material was resuspended in 1 ml of 10 mM Tris HCl (pH 7.5) and transferred to an Eppendorf reaction vessel (volume: 2 ml). After addition of 100 μl of proteinase K (concentration: 20 mg/ml), the cell suspension was incubated at 37° C. for 3 hours. The suspension was then extracted with 500 μl of phenol. After centrifugation at 13 000 rpm for 5 minutes, the upper, aqueous phase was transferred to a new 2 ml Eppendorf reaction vessel. Extraction with phenol was repeated 3 times. The DNA was precipitated by adding 1/10 volume of 3 M sodium acetate (pH 5.2) and 0.6 volume of isopropanol and then washed with 70% ethanol. The DNA pellet was dried at room temperature, taken up in 25 μl of water and dissolved with heating to 65° C.

The nucleic acid encoding a *Nostoc* PCC 7120 ketolase was amplified from *Nostoc* sp. PCC 7120 by means of polymerase chain reaction (PCR) using a sense-specific primer (NOSTF, SEQ ID NO. 19) and an antisense-specific primer (NOSTG SEQ ID NO. 20).

The PCR conditions were as follows:

The PCR for amplifying the DNA encoding a ketolase protein consisting of the entire primary sequence was carried out in a 50 μl reaction mixture which contained:

- 1 μl of a *Nostoc* sp. PCC 7120 DNA (prepared as described above)
- 0.25 mM dNTPs
- 0.2 mM NOSTF (SEQ ID NO. 19)
- 0.2 mM NOSTG (SEQ ID NO. 20)
- 5 μl of 10×PCR buffer (TAKARA)
- 0.25 μl of R Taq polymerase (TAKARA)
- 25.8 μl of distilled water The PCR was carried out under the following cycle conditions:

| | |
|---|---|
| 1X | 94° C. for 2 minutes |
| 35X | 94° C. for 1 minute |
| | 55° C. for 1 minute |
| | 72° C. for 3 minutes |
| 1X | 72° C. for 10 minutes |

PCR amplification with SEQ ID NO. 19 and SEQ ID NO. 20 resulted in an 805 bp fragment encoding a protein consisting of the entire primary sequence (SEQ ID NO. 21). Using standard methods, the amplicon was cloned into the PCR cloning vector pGEM-T (Promega), producing the clone pNOSTF-G.

Sequencing of the pNOSTF-G clone with the M13F and M13R primers confirmed a sequence which is identical to the DNA sequence from 88,886-89,662 of database entry AP003592. This nucleotide sequence was reproduced in an independent amplification experiment and thus represents the nucleotide sequence in the *Nostoc* sp. PCC 7120 used.

Therefore, said clone, pNOSTF-G, was used for cloning into the expression vector pJIT117 (Guerineau et al. 1988, Nucl. Acids Res. 16: 11380). Cloning was carried out by isolating the 799 bp SphI fragment from pNOSTF-G and ligating it into the SphI-cut pJIT117 vector. The clone which contains the *Nostoc* sp. PCC 7120 ketolase in the correct orientation as an N-terminal translational fusion with the rbcS transit peptide is referred to as pJNOST.

EXAMPLE 2

Construction of the Plasmid pMCL-CrtYIBZ/idi/gps for the Synthesis of Zeaxanthin in *E. coli* pMCL-CrtYIBZ/idi/gps was constructed in three steps via the intermediates pMCL-CrtYIBZ and pMCL-CrtYIBZ/idi. The vector used was the plasmid pMCL200 which is compatible with high copy-number vectors (Nakano, Y., Yoshida, Y., Yamashita, Y. and Koga, T.; Construction of a series of pACYC-derived plasmid vectors; Gene 162 (1995), 157-158).

EXAMPLE 2.1

Construction of pMCL-CrtYIBZ

The biosynthesis genes crtY, crtB, crtI and crtZ are from the bacterium *Erwinia uredovora* and were amplified by means of PCR. *Erwinia uredovora* (DSM 30080) genomic DNA was prepared by the Deutsche Sammlung von Mikroorganismen und Zelikulturen (DSMZ, Brunswick, Germany) as part of a service. The PCR was carried out according to the manufacturer's information (Roche, Long Template PCR: Procedure for amplification of 5-20 kb targets with the Expand Long Template PCR system). The PCR conditions for amplifying the biosynthesis cluster of *Erwinia uredovora* were as follows Master Mix 1:
- 1.75 μl of dNTPs (final concentration 350 μM)
- 0.3 μM primer Crt1 (SEQ ID NO. 22)
- 0.3 μM primer Crt2 (SEQ ID NO. 23)
- 250-500 ng of DSM 30080 genomic DNA
- Distilled water to a total volume of 50 μl Master Mix 2:
- 5 μl of 10×PCR buffer 1 (final concentration 1×, with 1.75 mM Mg2+)
- 10×PCR buffer 2 (final concentration 1×, with 2.25 mM Mg2+)
- 10×PCR buffer 3 (final concentration 1×, with 2.25 mM Mg2+)
- 0.75 μl of Expand Long Template Enzyme Mix (final concentration 2.6 units)
- Distilled water to a total volume of 50 μl The two mixtures "Master Mix 1" and "Master Mix 2" were combined by pipetting. The PCR was carried out in a total volume of 50 µl under the following cycle conditions:

| 1X  | 94° C. for 2 minutes  |
|-----|-----------------------|
| 30X | 94° C. for 30 seconds |
|     | 58° C. for 1 minute   |
|     | 68° C. for 4 minutes  |
| 1X  | 72° C. for 10 minutes |

PCR amplification with SEQ ID NO. 22 and SEQ ID NO. 23 resulted in a fragment (SEQ ID NO. 24) encoding the genes CrtY (protein: SEQ ID NO. 25), CrtI (protein: SEQ ID NO. 26), crtB (protein: SEQ ID NO. 27) and CrtZ (iDNA). Using standard methods, the amplicon was cloned into the PCR cloning vector pCR2.1 (Invitrogen), producing the clone pCR2.1-CrtYIBZ.

The pCR2.1-CrtYIBZ plasmid was cut with SalI and HindIII, the resulting SalI/HindIII fragment was isolated and transferred by way of ligation into the SalI/HindIIII-cut vector pMCL200. The pCR2.1-CrtYIBZ SalI/HindIII fragment cloned into pMCL 200 is 4624 bp in length, encodes the genes CrtY, CrtI, crtB and CrtZ and corresponds to the sequence from position 2295 to position 6918 in D90087 (SEQ ID NO. 24). The resulting clone is referred to as pMCL-CrtYIBZ.

EXAMPLE 2.2

Construction of pMCL-CrtYIBZ/idi

The gene idi (isopentenyl-diphosphate isomerase; IPP isomerase) was amplified from *E. coli* by means of PCR. The nucleic acid which encodes the entire idi gene including the idi promoter and ribosomal binding site was amplified from *E. coli* by means of polymerase chain reaction (PCR) using a sense-specific primer (5'-idi SEQ ID NO. 28) and an antisense-specific primer (3'-idi SEQ ID NO. 29).

The PCR conditions were as follows:

The PCR for amplifying the DNA was carried out in a 50 µl reaction mixture which contained:

1 µl of an *E. coli* TOP10 suspension
0.25 mM dNTPs
0.2 mM 5'-idi (SEQ ID NO. 28)
0.2 mM 3'-idi (SEQ ID NO. 29)
5 µl of 10×PCR buffer (TAKARA)
0.25 µl of R Taq polymerase (TAKARA)
28.8 µl of distilled water The PCR was carried out under the following cycle conditions:

| 1X  | 94° C. for 2 minutes  |
|-----|-----------------------|
| 20X | 94° C. for 1 minute   |
|     | 62° C. for 1 minute   |
|     | 72° C. for 1 minute   |
| 1X  | 72° C. for 10 minutes |

PCR amplification with SEQ ID NO. 28 and SEQ ID NO. 29 resulted in a 679 bp fragment encoding a protein consisting of the entire primary sequence (SEQ ID NO. 30). Using standard methods, the amplicon was cloned into the PCR cloning vector pCR2.1 (Invitrogen), producing the clone pCR2.1-idi.

Sequencing of the pCR2.1-idi clone confirmed a sequence which does not differ from the published sequence AE000372 in positions 8774 to 9440. This region comprises the promoter region, the potential ribosomal binding site and the entire IPP isomerase open reading frame. The fragment cloned into pCR2.1-idi has a total length of 679 bp, due to insertion of an XhoI cleavage site at the 5' end and an SalI cleavage site at the 3' end of the idi gene.

This clone was therefore used for cloning the idi gene into the pMCL-CrtYIBZ vector. Cloning was carried out by isolating the XhoI/SalI fragment from pCR2.1-idi and ligating it into the XhoI/SalI cut pMCL-CrtYIBZ vector. The resulting clone is referred to as pMCL-CrtYIBZ/idi.

EXAMPLE 2.3

Construction of pMCL-CrtYIBZ/idi/gps

The gene gps (geranylgeranyl-pyrophosphate synthase; GGPP synthase) was amplified from *Archaeoglobus fulgidus* by means of PCR. The nucleic acid encoding *Archaeoglobus fulgidus* gps was amplified by means of polymerase chain reaction (PCR) using a sense-specific primer (5'-gps SEQ ID NO. 32) and an antisense-specific primer (3'-gps SEQ ID NO. 33).

The *Archaeoglobus fulgidus* DNA was prepared by the Deutsche Sammiung von Mikro-organismen und Zelikulturen (DSMZ, Brunswick, Germany) as part of a service. The PCR conditions were as follows:

The PCR for amplifying the DNA encoding a GGPP synthase protein consisting of the entire primary sequence was carried out in a 50 µl reaction mixture which contained:

1 µl of an *Archaeoglobus fulgidus* DNA
0.25 mM dNTPs
0.2 mM 5'-gps (SEQ ID NO. 32)
0.2 mM 3'-gps (SEQ ID NO. 33)
5 µof 10×PCR buffer (TAKARA)
0.25 µl of R Taq polymerase (TAKARA)
28.8 µl of distilled water The PCR was carried out under the following cycle conditions:

| 1X  | 94° C. for 2 minutes  |
|-----|-----------------------|
| 20X | 94° C. for 1 minute   |
|     | 56° C. for 1 minute   |
|     | 72° C. for 1 minute   |
| 1X  | 72° C. for 10 minutes |

The DNA fragment amplified by means of PCR and the primers SEQ ID NO. 32 and SEQ ID NO. 33 was eluted from the agarose gel by methods known per se and cut with the restriction enzymes NcoI and HindIII. This resulted in a 962 bp fragment which encodes a protein consisting of the entire primary sequence (SEQ ID NO. 34). Using standard methods, the NcoI/HindIII-cut amplicon was cloned into the pCB97-30 vector, producing the clone pCB-gps.

Sequencing of the pCB-gps clone confirmed a sequence for *A. fulgidus* GGPP synthase, which differs from the published sequence AF120272 in one nucleotide. Introducing an NcoI cleavage site in the gps gene altered the second codon of GGPP synthase. In the published sequence, AF120272, CTG (positions 4-6) codes for leucine. Amplificaton with the two primers SEQ ID NO. 32 and SEQ ID NO. 33 altered this second codon to GTG which codes for valine.

The clone pCB-gps was therefore used for cloning the gps gene into the pMCL-CrtYIBZ/idi vector. Cloning was carried out by isolating the KpnI/XhoI fragment from pCB-gps and ligating it into the pMCL-CrtYIBZ/idi vector cut with KpnI and XhoI. The cloned KpnI/XhoI fragment (SEQ ID NO. 34) carries the Prrn16 promoter together with a minimum 5' UTR sequence of rbcL, the first 6 rbcL codons which extend the GGPP synthase N-terminally, and, 3' from the gps gene, the psbA sequence. Thus, the N terminus of GGPP synthase has, instead of the natural amino acid sequence with Met-Leu-Lys-Glu (amino acids 1 to 4 of AF120272, SEQ ID NO: 78), the altered amino acid sequence Met-Thr-Pro-Gln-Thr-Ala-Met-Val-Lys-Glu (SEQ ID NO: 79). This leads to recombinant GGPP synthase, starting with Lys at position 3 (in AF120272), being identical and having no other changes in the amino acid sequence. The rbcL and psbA sequences were used according to a reference by Eibl et al. (Plant J. 19. (1999), 1-13). The resulting clone is referred to as pMCL-CrtYIBZ/idi/gps.

EXAMPLE 3

Biotransformation of Zeaxanthin in Recombinant *E. coli* Strains

Zeaxanthin biotransformation was carried out by preparing recombinant *E. coli* strains which are capable of zeaxanthin production due to heterologous complementation. *E. coli* TOP10 strains were used as host cells for complementation experiments with the plasmids pNOSTF-G and pMCL-CrtYIBZ/idi/gps.

In order to prepare *E. coli* strains which enable zeaxanthin to be synthesized at high concentrations, plasmid pMCL-CrtYIBZ/idi/gps was constructed. Said plasmid carries the biosynthesis genes crtY, crtB, crtI and crtY of *Erwinia uredovora*, the *Archaeoglobus fulgidus* gene gps (for geranylgeranyl-pyrophosphate synthatase) and the *E. coli* gene idi (isopentenyl-diphosphate isomerase). This construct was used to eliminate steps which limit high accumulation of carotenoids and of their biosynthetic precursors. This has been described previously by Wang et al. in a similar manner, using several plasmids (Wang, C.-W., Oh, M.-K. and Liao, J. C.; Engineered isoprenoid pathway enhances astaxanthin production in *Escherichia coli*, Biotechnology and Bioengineering 62 (1999), 235-241).

*E. coli* TOP10 cultures were transformed in a manner known per se with the two plasmids pNOSTF-G and pMCL-CrtYIBZ/idi/gps and cultured in LB medium at 30° C. and 37° C., respectively, overnight. Ampicillin (50 µg/ml), chloramphenicol (50 µg/ml) and isopropyl-β-thio-galactoside (1 mmol) were likewise added in a manner known per se overnight.

The carotenoids were isolated from the recombinant strains by extracting the cells with acetone, evaporating the organic solvent to dryness and fractionating said carotenoids by means of HPLC via a C30 column. The following process conditions were set.

| Separating column: | Prontosil C30 column, 250 × 4.6 mm (Bischoff, Leonberg, Germany) |
|---|---|
| Flow rate: | 1.0 ml/min |
| Eluents: | Eluent A - 100% methanol |
| | Eluent B - 80% methanol, 0.2% ammonium acetate |
| | Eluent C - 100% t-butyl methyl ether |

-continued

Gradient profile:

| Time | Flow rate | % eluent A | % eluent B | % eluent C |
|---|---|---|---|---|
| 1.00 | 1.0 | 95.0 | 5.0 | 0 |
| 1.05 | 1.0 | 80.0 | 5.0 | 15.0 |
| 14.00 | 1.0 | 42.0 | 5.0 | 53.0 |
| 14.05 | 1.0 | 95.0 | 5.0 | 0 |
| 17.00 | 1.0 | 95.0 | 5.0 | 0 |
| 18.00 | 1.0 | 95.0 | 5.0 | 0 |

Detection: 300-500 nm

The spectra were determined directly from the elution peaks, using a photodiode array detector. The isolated substances were identified by way of their absorption spectra and their retention times, in comparison with standard samples.

FIG. 1 depicts the chromatographic analysis of a sample obtained from an *E. coli* strain transformed with pNOSTF-G and pMCL-CrtYIBZ/idi/gps. This strain is shown to be able to synthesize various ketocarotenoids, owing to heterologous complementation. Astaxanthin (peak 1), adonirubin (peak 2) and canthaxanthin (peak 3) are eluted with increasing retention time.

EXAMPLE 3.1

Comparative Example

An *E. coli* strain expressing a ketolase from *Haematococcus pluvialis* Flotow em. Wille was prepared as a comparative example, similarly to the preceding examples. For this purpose, the cDNA encoding the entire primary sequence of *Haematococcus pluvialis* Flotow em. Wille ketolase was amplified and cloned according to example 1 into the same expression vector.

The cDNA encoding *Haematococcus pluvialis* ketolase was amplified from *Haematococcus pluvialis* (strain 192.80 of the "Sammlung von Algenkulturen der Universität Göttingen") suspension culture by means of PCR. To prepare total RNA from a *Haematococcus pluvialis* (strain 192.80) suspension culture which had grown in *Haematococcus* medium (1.2 g/l sodium acetate, 2 g/l yeast extract, 0.2 g/l MgCl2×6H2O, 0.02 CaCl2×2H2O; pH 6.8; after autoclaving, addition of 400 mg/l L-asparagine, 10 mg/l FeSO4× H2O) at room temperature with indirect daylight for 2 weeks, the cells were harvested, frozen in liquid nitrogen and ground to a powder in a mortar. Subsequently, 100 mg of the frozen algal cell powder were transferred to a reaction vessel and taken up in 0.8 ml of Trizol buffer (Life Technologies). The suspension was extracted with 0.2 ml of chloroform. After centrifugation at 12000 g for 15 minutes, the aqueous supernatant was removed and transferred to a new reaction vessel and extracted with one volume of ethanol. The RNA was precipitated with one volume of isopropanol, washed with 75% ethanol and the pellet was dissolved in DEPC water (water incubated overnight with 1/1000 volume of diethyl pyrocarbonate at room temperature, then autoclaved). The RNA concentration was determined photometrically.

For cDNA synthesis, 2.5 µg of total RNA were denatured at 60° C. for 10 min, cooled on ice for 2 min and transcribed into cDNA by means of a cDNA kit (Ready-to-go-you-prime-beads, Pharmacia Biotech), according to the manufacturer's information using an antisense-specific primer, PR1 (gcaagctcga cagctacaaa cc, SEQ ID NO: 80).

The nucleic acid encoding a ketolase from *Haematococcus pluvialis* (strain 192.80) was amplified by means of polymerase chain reaction (PCR) from *Haematococcus pluvialis*, using a sense-specific primer, PR2 (gaagcatgca gctagcagcg acag, SEQ ID NO: 81), and an antisense-specific primer, PR1.

The PCR conditions were as follows:

The PCR for amplifying the cDNA encoding a ketolase protein consisting of the entire primary sequence was carried out in a 50 ml reaction mixture containing:

4 ml of a *Haematococcus pluvialis* cDNA (prepared as described above)
0.25 mM dNTPs
0.2 mM PR1
0.2 mM PR2
5 ml of 10×PCR buffer (TAKARA)
0.25 ml of R Taq polymerase (TAKARA)
28.8 ml of distilled water The PCR was carried out under the following cycle conditions:

| | |
|---|---|
| 1X | 94° C. for 2 minutes |
| 35X | 94° C. for 1 minute |
| | 53° C. for 2 minutes |
| | 72° C. for 3 minutes |
| 1X | 72° C. for 10 minutes |

PCR amplification with PR1 and PR2 resulted in a 1155 bp fragment which encodes a protein consisting of the entire primary sequence:

Using standard methods, the amplicon was cloned into the PCR cloning vector pGEM-Teasy (Promega), producing the clone pGKETO2.

Sequencing of the pGKETO2 clone, using the T7 and SP6 primers, confirmed a sequence which differs from the published sequence, X86782, only in the three codons 73, 114 and 119 by one base each. These nucleotide substitutions were reproduced in an independent amplification experiment and thus represent the nucleotide sequence in the *Haematococcus pluvialis* strain used, 192.80.

This clone was used for cloning into the expression vector described in example 1. Cloning was carried out in a manner similar to that described in example 1. Transformation of the *E. coli* strains, culturing thereof and analysis of the carotenoid profile were carried out as described in example 3.

Figure 2:
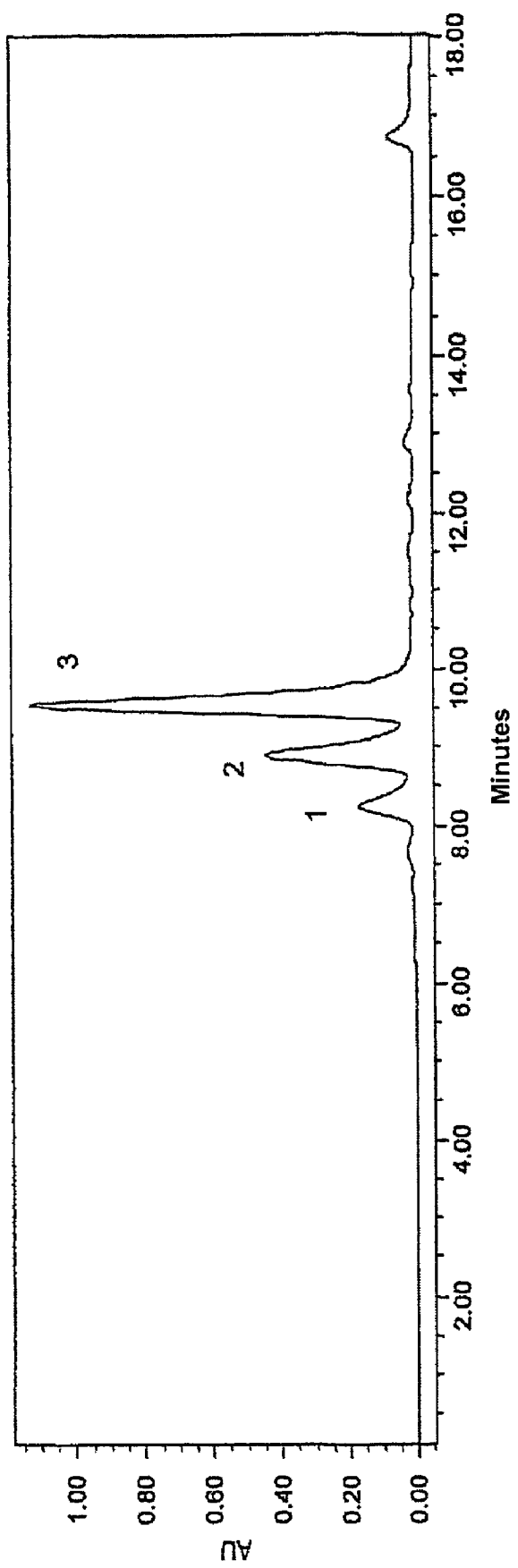
FIG. 2 depicts the chromatographic analysis of a sample obtained from an *E. coli* strain transformed with the expression vector as described in Example 3.1 and pMCL-CrtY-IBZ/idi/gps. With use of a *Haematococcus pluvialis* ketolase, as described, for example, in EP 725137, astaxanthin (peak 1), adonixanthin (peak 2) and unreacted zeaxanthin (peak 3) are eluted with increasing retention time.

FIG. 2 depicts the chromatographic analysis of a sample obtained from an *E. coli* strain transformed with said expression vector and pMCL-CrtYIBZ/idi/gps. With use of a *Haematococcus pluvialis* ketolase, as described, for example, in EP 725137, astaxanthin (peak 1), adonixanthin (peak 2) and unreacted zeaxanthin (peak 3) elute with increasing retention time. This carotenoid profile has already been described in EP 0725137.

Table 1 depicts a comparison of the bacterially produced carotenoid quantities:

```
gaagcatgca gctagcagcg acagtaatgt tggagcagct taccggaagc gctgaggcac      60
tcaaggagaa ggagaaggag gttgcaggca gctctgacgt gttgcgtaca tgggcgaccc     120
agtactcgct tccgtcagag gagtcagacg cggcccgccc gggactgaag aatgcctaca     180
agccaccacc ttccgacaca aagggcatca caatggcgct agctgtcatc ggctcctggg     240
ccgcagtgtt cctccacgcc atttttcaaa tcaagcttcc gacctccttg gaccagctgc     300
actggctgcc cgtgtcagat gccacagctc agctggttag cggcagcagc agcctgctgc     360
acatcgtcgt agtattcttt gtcctggagt tcctgtacac aggccttttt atcaccacgc     420
atgatgctat gcatggcacc atcgccatga gaaacaggca gcttaatgac ttcttgggca     480
gagtatgcat ctccttgtac gcctggtttg attacaacat gctgcaccgc aagcattggg     540
agcaccacaa ccacactggc gaggtgggca aggaccctga cttccacagg ggaaaccctg     600
gcattgtgcc ctggtttgcc agcttcatgt ccagctacat gtcgatgtgg cagtttgcgc     660
gcctcgcatg gtggacggtg tcatgcagc tgctgggtgc gccaatggcg aacctgctgg     720
tgttcatggc ggccgcgccc atcctgtccg ccttccgctt gttctacttt ggcacgtaca     780
tgccccacaa gcctgagcct ggcgccgcgt caggctcttc accagccgtc atgaactggt     840
ggaagtcgcg cactagccag gcgtccgacc tggtcagctt tctgacctgc taccacttcg     900
acctgcactg ggagcaccac cgctggccct ttgccccctg gtgggagctg cccaactgcc     960
gccgcctgtc tggccgaggt ctggttcctg cctagctgga cacactgcag tgggccctgc    1020
tgccagctgg gcatgcaggt tgtggcagga ctgggtgagg tgaaaagctg caggcgctgc    1080
tgccggacac gctgcatggg ctaccctgtg tagctgccgc cactagggga ggggtttgt    1140 agctgtcgag cttgc (SEQ ID NO: 82).
```

TABLE 1

Comparison of bacterial ketocarotenoid synthesis using two different ketolases, the
Nostoc sp. PCC7120 NOST ketolase according to the invention (example 3) and
Haematococcus pluvialis ketolase as a comparative example (example 3.1). Carotenoid
quantities are indicated in ng/ml culture liquid.

| Ketolase from | Astaxanthin | Adonirubin | Adonixanthin | Canthaxanthin | Zeaxanthin |
|---|---|---|---|---|---|
| Haematococcus pluvialis Flotow em. Wille (comparative example) | 13 | | 102 | | 738 |
| Nostoc sp. Strain PCC7120 | 491 | 186 | | 120 | |

Expression of *Nostoc* sp. strain PCC7120 ketolase according to the invention results in a carotenoid pattern which differs markedly from the carotenoid pattern after expression of a *Haematococcus pluvialis* ketolase. While the ketolase of the prior art provides the desired ketocarotenoid astaxanthin only in very limited amounts, astaxanthin is the main product when using the ketolase according to the invention. A distinctly lower amount of hydroxylated byproducts appears in the process of the invention.

EXAMPLE 4

Preparation of Expression Vectors for Constitutive Expression of *Nostoc* sp. PCC7120 NOST Ketolase in *Lycopersicon esculentum* and *Tagetes erecta*

The *Nostoc* sp. PCC7120 NOST ketolase is expressed in *L. esculentum* and in *Tagetes erecta* under the control of the constitutive promoter FNR (ferredoxin NADPH oxidoreductase, database entry AB011474, positions 70127 to 69493; WO03/006660) from *Arabidopsis thaliana*. The FNR gene starts at base pair 69492 and is annotated with "ferredoxin-NADP+ reductase". Expression was carried out using the pea transit peptide rbcS (Anderson et. al. 1986, Biochem J. 240: 709-715).

The DNA fragment comprising the *Arabidopsis thaliana* FNR promoter region was prepared by means of PCR using genomic DNA (isolated from *Arabidopsis thaliana* by standard methods) and the primers FNR-A (SEQ ID NO. 38) and FNR-B (SEQ ID NO. 39).

The PCR conditions were as follows:

The PCR for amplifying the DNA comprising the FNR promoter fragment FNR#1) was carried out in a 50 µl reaction mixture containing:

100 ng of *A. thaliana* genomic DNA
0.25 mM dNTPs
0.2 mM FNR-A (SEQ ID NO. 38)
0.2 mM FNR-B (SEQ ID NO. 39)
5 µl of 10×PCR buffer (Stratagene)
0.25 µl of Pfu polymerase (Stratagene)
28.8 µl of distilled water
The PCR was carried out under the following cycle conditions:

| 1X | 94° C. for 2 minutes |
| 35X | 94° C. for 1 minute |
| | 50° C. for 1 minute |
| | 72° C. for 1 minute |
| 1X | 72° C. for 10 minutes |

The 647 bp amplicon was cloned into the PCR cloning vector PCR 2.1 (Invitrogen) by using standard methods, producing the plasmid pFNR#1.

Sequencing of the pFNR#1 clone confirmed a sequence which corresponds to a sequence section on chromosome 5 of *Arabidopsis thaliana* (database entry AB011474; WO03/006660), from position 70127 to position 69493. The FNR gene starts at base pair 69492 and is annotated with "ferredoxin-NADP+ reductase".

pFNR was therefore used for cloning into the expression vector pJIT117 (Guerineau et al. 1988, Nucl. Acids Res. 16: 11380).

Cloning was carried out by isolating the 637 bp SacI-HindIII fragment from pFNR#1 (partial SacI hydrolysis) and ligating it into the SacI-HindIII-cut pJIT117 vector. The clone which contains the FNR#1 promoter instead of the original d35S promoter is referred to as pJITFNR.

An expression cassette, pJFNRNOST, was prepared by cloning the 799 bp SpHI fragment, NOSTF-G (described in example 1), into the SpHI-cut pJITFNR vector. The clone which contains the NOSTF-G fragment in the correct orientation as N-terminal fusion with the rbcS transit peptide is referred to as pJFNRNOST.

An expression cassette for *Agrobacterium*-mediated transformation of *Nostoc* ketolase into *L. esculentum* was prepared using the binary vector pSUN3 (WO02100900).

Figure 3:
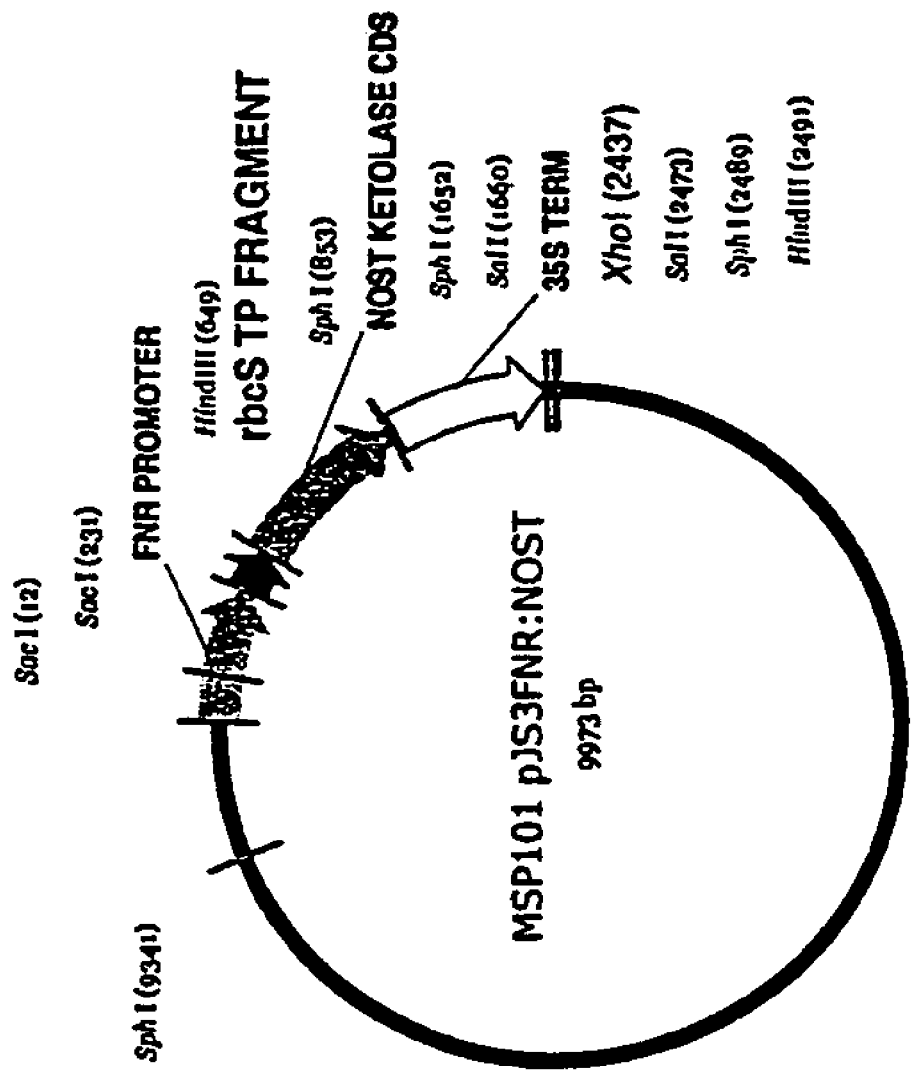
FIG. 3 shows the construct map of the expression vector pS3FNR:NOST (MSP101).

The expression vector pS3FNR:NOST (MSP101) was prepared by ligating the 2.425 bp SacI-XhoI fragment (partial SacI hydrolysis) from pJFNRNOST with the SacI-XhoI-cut pSUN3 vector (FIG. 3, construct map). In FIG. 3, the fragment FNR promoter comprises the FNR promoter (635 bp), the fragment rbcS TP fragment comprises the pea rbcS transit peptide (194 bp), the fragment Nost ketolase CDS (777 bp) comprises the entire primary sequence coding for *Nostoc* ketolase, and the fragment 35S Term (746 bp) comprises the CaMV polyadenylation signal.

An expression cassette for *Agrobacterium*-mediated transformation of the expression vector containing *Nostoc* ketolase into Tagetes erecta was prepared using the binary vector pSUN5 (WO02/00900).

Figure 4:
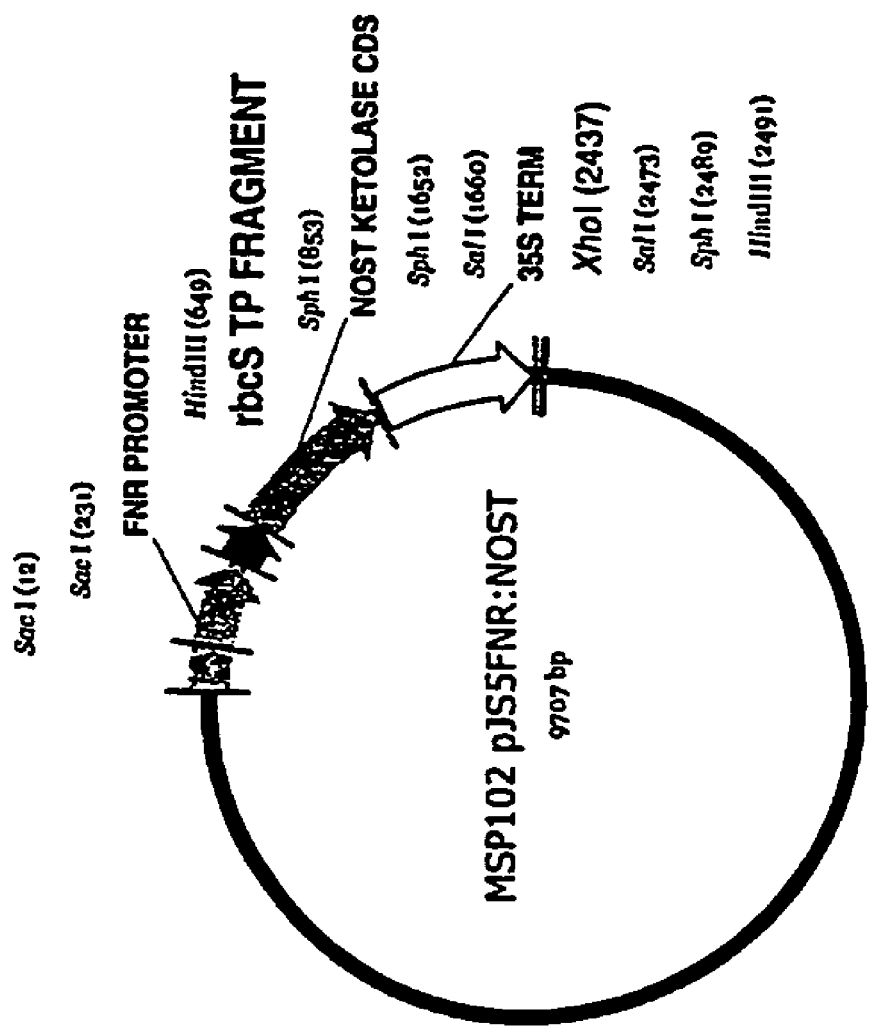
FIG. 4 shows the construct map of the expression vector pS5FNR:NOST (MSP102).

The Tagetes expression vector pS5FNR:NOST (MSP102) was prepared by ligating the 2.425 bp SacI-XhoI fragment (partial SacI hydrolysis) from pJFNRNOST with the SacI-XhoI-cut pSUN5 vector (FIG. 4, construct map). In FIG. 4, the fragment FNR promoter comprises the FNR promoter (635 bp), the fragment rbcS Transit Peptide comprises the pea rbcS transit peptide (194 bp), the fragment Nost ketolase (777 bp) comprises the entire primary sequence coding for *Nostoc* ketolase, and the fragment 35S Terminator (746 bp) comprises the CaMV polyadenylation signal.

EXAMPLE 5

Preparation of Expression Vectors for Flower-specific Expression of *Nostoc* sp. PCC 7120 NOST Ketolase in *Lycopersicon esculentum* and *Tagetes erecta*

Expression of *Nostoc* ketolase in *L. esculentum* and *Tagetes erecta* was carried out using the pea transit peptide rbcS (Anderson et al. 1986, Biochem J. 240: 709-715). Expression was carried out under the control of a modified version, AP3P, of the flower-specific *Arabidopsis thaliana* promoter AP3 (AL132971: nucleotide region 9298-10200; Hill et al. (1998) Development 125:1711-1721).

The DNA fragment which comprises the AP3 promoter region −902 to +15 from *Arabidopsis thaliana* was prepared by means of PCR using genomic DNA (isolated from *Arabidopsis thaliana* by standard methods) and the primers AP3-1 (SEQ ID NO. 41) and AP3-2 (SEQ ID NO. 42).

The PCR conditions were as follows:

The PCR for amplifying the DNA comprising the AP3 promoter fragment (−902 to +15) was carried out in a 50 μl reaction mixture containing:

100 ng of *A. thaliana* genomic DNA
0.25 mM dNTPs
0.2 mM AP3-1 (SEQ ID NO. 41)
0.2 mM AP3-2 (SEQ ID NO. 42)
5 μl of 10×PCR buffer (Stratagene)
0.25 μl of Pfu polymerase (Stratagene)
28.8 μl of distilled water The PCR was carried out under the following cycle conditions:

| | |
|---|---|
| 1X | 94° C. for 2 minutes |
| 35X | 94° C. for 1 minute |
| | 50° C. for 1 minute |
| | 72° C. for 1 minute |
| 1X | 72° C. for 10 minutes |

The 929 bp amplicon was cloned into the PCR cloning vector PCR 2.1 (Invitrogen) by using standard methods, producing the plasmid pAP3.

Sequencing of the pAP3 clone confirmed a sequence which differs from the published AP3 sequence (AL132971, nucleotide region 9298-10200) only by an insertion (a G in position 9765 of the sequence AL132971) and a base substitution (G for A in position 9726 of the sequence AL132971). These nucleotide differences were reproduced in an independent amplification experiment and thus represent the actual nucleotide sequence in the *Arabidopsis thaliana* plants used.

The modified version, AP3P, was prepared by means of recombinant PCR using the pAP3 plasmid. The region 10200-9771 was amplified using the primers AP3-1 (SEQ ID NO. 41) and primers AP3-4 (SEQ ID NO. 44) (amplicon A1/4), and the region 9526-9285 was amplified using AP3-3 (SEQ ID NO. 43) and AP3-2 (SEQ ID NO. 42) (amplicon A2/3).

The PCR conditions were as follows:

The PCRs for amplifying the DNA fragments comprising the regions region 10200-9771 and region 9526-9285 of the AP3 promoter were carried out in 50 μl reaction mixtures containing:

100 ng of AP3 amplicon (described above)
0.25 mM dNTPs
0.2 mM sense primer (AP3-1 SEQ ID NO. 41 or AP3-3 SEQ ID NO. 43)
0.2 mM antisense primer (AP3-4 SEQ ID NO. 44 or AP3-2 SEQ ID NO. 42)
5 μl of 10×PCR buffer (Stratagene)
0.25 μl of Pfu Taq polymerase (Stratagene)
28.8 μl of distilled water The PCR was carried out under the following cycle conditions:

| | |
|---|---|
| 1X | 94° C. for 2 minutes |
| 35X | 94° C. for 1 minute |
| | 50° C. for 1 minute |
| | 72° C. for 1 minute |
| 1X | 72° C. for 10 minutes |

The recombinant PCR comprises annealing of the amplicons A1/4 and A2/3 which overlap over a sequence of 25 nucleotides, completion to give a double strand and subsequent amplification. This results in a modified version of the AP3 promoter, AP3P, in which positions 9670-9526 have been deleted.

The two amplicons A1/4 and A2/3 were denatured (5 min at 95° C.) and annealed (slow cooling to 40° C. at room temperature) in a 17.6 μl reaction mixture which contained:

0.5 μg of A1/4 amplicon
0.25 μg of A2/3 amplicon

The 3' ends were filled in (30 min at 30° C.) in a 20 μl reaction mixture which contained:

17.6 μl of A1/4 and A2/3 annealing reaction (prepared as described above)
50 μm dNTPs
2 μl of 1× Klenow buffer
2 U of Klenow enzyme The nucleic acid coding for the modified promoter version, AP3P, was amplified by means of PCR using a sense-specific primer (AP3-1 SEQ ID NO. 41) and an antisense-specific primer (AP3-2 SEQ ID NO. 42).

The PCR conditions were as follows:

The PCR for amplifying the AP3P fragment was carried out in a 50 μl reaction mixture containing:

1 μl of annealing reaction (prepared as described above)
0.25 mM dNTPs
0.2 mM AP3-1 (SEQ ID NO. 41)
0.2 mM AP3-2 (SEQ ID NO. 42)
5 μl of 10×PCR buffer (Stratagene)
0.25 μl of Pfu Taq polymerase (Stratagene)
28.8 μl of distilled water The PCR was carried out under the following cycle conditions:

| | |
|---|---|
| 1X | 94° C. for 2 minutes |
| 35X | 94° C. for 1 minute |
| | 50° C. for 1 minute |
| | 72° C. for 1 minute |
| 1X | 72° C. for 10 minutes |

PCR amplification with SEQ ID NO. 41 (AP3-1) and SEQ ID NO. 42 (AP3-2) resulted in a 777 bp fragment encoding the modified promoter version, AP3P. The amplicon was cloned into the cloning vector pCR2.1 (Invitrogen), producing the plasmid pAP3P. Sequencing reactions using the primers T7 and M13 confirmed a sequence identical to the sequence AL132971, region 10200-9298, with the internal region 9285-9526 having been deleted. This clone was therefore used for cloning into the expression vector pJIT117 (Guerineau et al. 1988, Nucl. Acids Res. 16: 11380).

Cloning was carried out by isolating the 767 bp SacI-HindIII fragment from pAP3P and ligating it into the SacI-HindIII-cut pJIT117 vector. The clone which contains the AP3P promoter instead of the original d35S promoter is referred to as pJITAP3P. An expression cassette, pJAP3NOST, was prepared by cloning the 799 bp SpHI fragment, NOSTF-G (described in example 1), into the SpHI-cut pJITAP3P vector. The done which contains the NOSTF-G fragment in the correct orientation as an N-terminal fusion with the rbcS transit peptide is referred to as pJAP3PNOST.

An expression vector for *Agrobacterium*-mediated transformation of the AP3P-controlled *Nostoc* ketolase into *L. esculentum* was prepared using the binary vector pSUN3 (WO02/00900).

Figure 5:
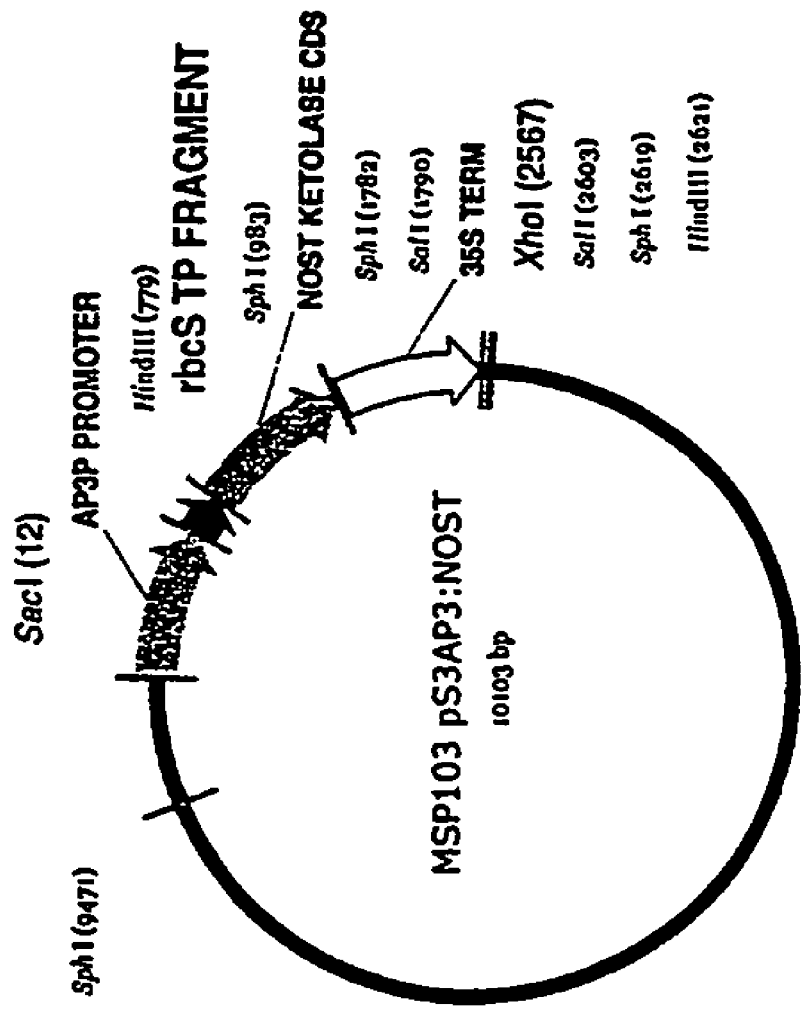
FIG. 5 shows the construct map of the expression vector pS3AP3:NOST (MSP103).

The expression vector pS3AP3:NOST (MSP103) was prepared by ligating the 2.555 bp SacI-XhoI fragment from pJAP3NOST with the SacI-XhoI-cut pSUN3 vector (FIG. 5, construct map). In FIG. 5, the fragment AP3P PROMOTER comprises the modified AP3P promoter (765 bp), the fragment rbcS TP FRAGMENT comprises the pea rbcS transit peptide (194 bp), the fragment NOST KETOLASE CDS (777 bp) comprises the entire primary sequence coding for *Nostoc* ketolase, and the fragment 35S TERM (746 bp) comprises the CaMV polyadenylation signal.

An expression vector for *Agrobacterium*-mediated transformation of the AP3P-controlled *Nostoc* ketolase into *Tagetes erecta* was prepared using the binary vector pSUN5 (WO02/00900).

Figure 6:
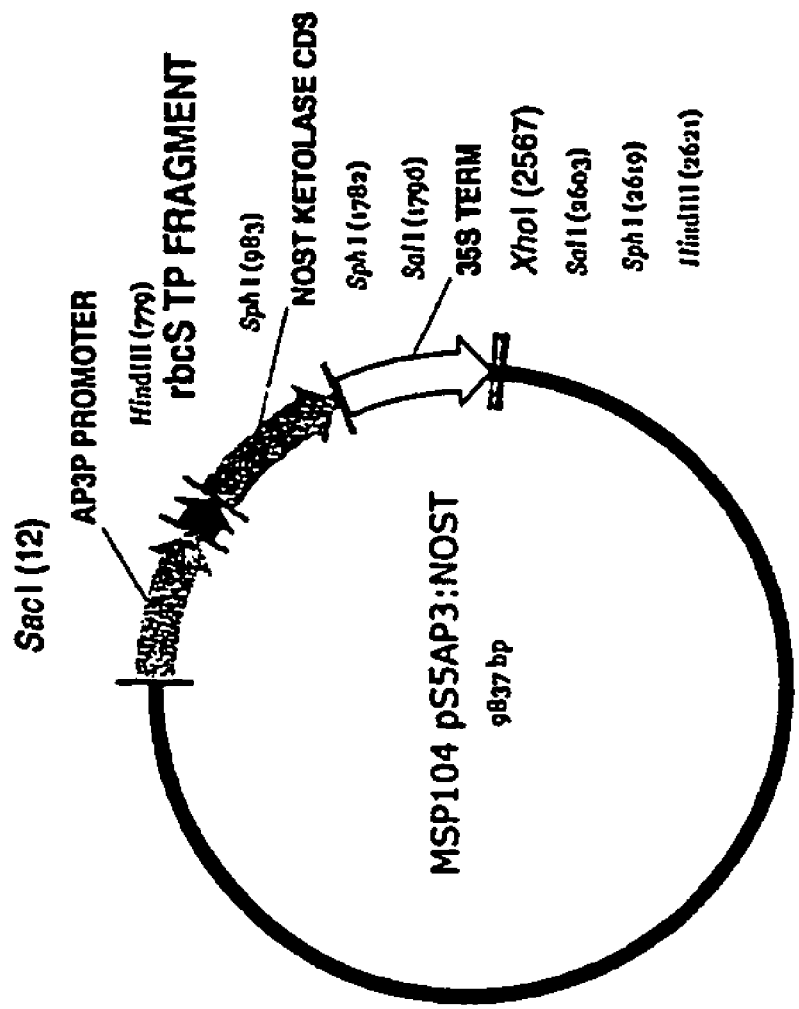
FIG. 6 shows the construct map of the expression vector pS5AP3:NOST (MSP104).

The expression vector pS5AP3:NOST (MSP104) was prepared by ligating the 2.555 bp SacI-XhoI fragment from pS5AP3PNOST with the SacI-XhoI-cut pSUN5 vector (FIG. 6, construct map). In FIG. 6, the fragment AP3P PROMOTER comprises the modified AP3P promoter (765 bp), the fragment rbcS TP FRAGMENT comprises the pea rbcS transit peptide (207 bp), the fragment NOST KETOLASE CDS (777 bp) comprises the entire primary sequence coding for *Nostoc* ketolase, and the fragment 35S TERM (746 bp) comprises the CaMV polyadenylation signal.

EXAMPLE 6

Amplification of a DNA Encoding the Entire Primary Sequence of NP196 Ketolase from *Nostoc punctiforme* ATCC 29133

The DNA encoding the *Nostoc punctiforme* ATCC 29133 NP196 ketolase was amplified from *Nostoc punctiforme* ATCC 29133 ("American Type Culture Collection" strain) by means of PCR.

To prepare genomic DNA from a *Nostoc punctiforme* ATCC 29133 suspension culture which had grown in BG 11 medium (1.5 g/l NaNO$_3$, 0.04 g/l K$_2$PO$_4$×3H$_2$O, 0.075 g/l MgSO$_4$×H$_2$O, 0.036 g/l CaCl$_2$×2H$_2$O, 0.006 g/l citric acid, 0.006 g/l ferric ammonium citrate, 0.001 g/l EDTA disodium magnesium, 0.04 g/l Na$_2$CO$_3$, 1 ml of trace metal mix A5+Co (2.86 g/l H$_3$BO$_3$, 1.81 g/l MnCl$_2$×4H$_2$O, 0.222 g/l ZnSO$_4$×7H$_2$O, 0.39 g/l NaMoO$_4$×2H$_2$O, 0.079 g/l CuSO$_4$× 5H$_{2O}$, 0.0494 g/l Co(NO$_3$)2×6H$_2$O) at 25° C. with constant shaking (150 rpm) and under continuous light for 1 week, the cells were harvested by centrifugation, frozen in liquid nitrogen and ground to a powder in a mortar.

Protocol for isolating DNA from *Nostoc punctiforme* ATCC 29133:

The bacteria cells were pelleted from a 10 ml liquid culture by centrifugation at 8000 rpm for 10 minutes. The bacterial cells were then crushed and ground in liquid nitrogen, using a mortar. The cell material was resuspended in 1 ml of 10 mM Tris HCl (pH 7.5) and transferred to an Eppendorf reaction vessel (volume: 2 ml). After addition of 100 µl of proteinase K (concentration: 20 mg/ml), the cell suspension was incubated at 37° C. for 3 hours. The suspension was then extracted with 500 µl of phenol. After centrifugation at 13000 rpm for 5 minutes, the upper, aqueous phase was transferred to a new 2 ml Eppendorf reaction vessel. Extraction with phenol was repeated 3 times. The DNA was precipitated by adding $\frac{1}{10}$ volume of 3 M sodium acetate (pH 5.2) and 0.6 volume of isopropanol and then washed with 70% ethanol. The DNA pellet was dried at room temperature, taken up in 25 µl of water and dissolved with heating to 65° C.

The nucleic acid encoding a *Nostoc punctiforme* ATCC 29133 ketolase was amplified from *Nostoc punctiforme* ATCC 29133 by means of polymerase chain reaction (PCR) using a sense-specific primer (NP196-1, SEQ ID NO. 54) and an antisense-specific primer (NP196-2 SEQ ID NO. 55).

The PCR conditions were as follows:

The PCR for amplifying the DNA encoding a ketolase protein consisting of the entire primary sequence was carried out in a 50 µl reaction mixture which contained:

1 µl of an *Nostoc punctiforme* ATCC 29133 DNA (prepared as described above)
0.25 mM dNTPs
0.2 mM NP196-1 (SEQ ID NO. 54)
0.2 mM NP196-2 (SEQ ID NO. 55)
5 µl of 10×PCR buffer (TAKARA)
0.25 µl of R Taq polymerase (TAKARA)
25.8 µl of distilled water The PCR was carried out under the following cycle conditions:

| | |
|---|---|
| 1X | 94° C. for 2 minutes |
| 35X | 94° C. for 1 minute |
| | 55° C. for 1 minute |
| | 72° C. for 3 minutes |
| 1X | 72° C. for 10 minutes |

PCR amplification with SEQ ID NO. 54 and SEQ ID NO. 55 resulted in a 792 bp fragment encoding a protein consisting of the entire primary sequence (NP196, SEQ ID NO. 56). Using standard methods, the amplicon was cloned into the PCR cloning vector pCR 2.1 (Invitrogen), producing the clone pNP196.

Sequencing of the pNP196 clone with the M13F and M13R primers confirmed a sequence which is identical to the DNA sequence from 140,571-139,810 of the database entry NZ_AABC01000196 (inversely oriented to the published database entry), except that G in position 140,571 was replaced by A in order to generate a standard ATG start codon. This nucleotide sequence was reproduced in an independent amplification experiment and thus represents the nucleotide sequence in the *Nostoc punctiforme* ATCC 29133 used.

This clone, pNP196, was therefore used for cloning into the expression vector pJIT117 (Guerineau et al. 1988, Nucl. Acids Res. 16:11380).

pJIT117 was modified by replacing the 35S terminator by the OCS terminator (octopine synthase) of the *Agrobacterium tumefaciens* Ti plasmid pTi15955 (database entry X00493, from position 12,541-12,350, Gielen et al. (1984) EMBO J. 3 835-846).

The DNA fragment which comprises the OCT terminator region was prepared by means of PCR using the plasmid pHELLSGATE (database entry AJ311874, Wesley et al. (2001) Plant J. 27 581-590, isolated from *E. coli* by standard methods) and the primers OCS-1 (SEQ ID NO. 58) and OCS-2 (SEQ ID NO. 59).

The PCR conditions were as follows:

The PCR for amplifying the DNA comprising the octopine synthase (OCS) terminator region (SEQ ID NO. 60) was carried out in a 50 µl reaction mixture containing:

1 ng of pHELLSGATE plasmid DNA
0.25 mM dNTPs
0.2 mM OCS-1 (SEQ ID NO. 58)
0.2 mM OCS-2 (SEQ ID NO. 59)
5 µl of 10×PCR buffer (Stratagene)
0.25 µl of Pfu polymerase (Stratagene)
28.8 µl of distilled water The PCR was carried out under the following cycle conditions:

| | |
|---|---|
| 1X | 94° C. for 2 minutes |
| 35X | 94° C. for 1 minute |
| | 50° C. for 1 minute |
| | 72° C. for 1 minute |
| 1X | 72° C. for 10 minutes |

The 210 bp amplicon was cloned into the PCR cloning vector pCR 2.1 (Invitrogen) by using standard methods, producing the plasmid pOCS.

Sequencing of the pOCS clone confirmed a sequence which corresponds to a sequence section on the *Agrobacterium tumefaciens* Ti plasmid pTi15955 (database entry X00493), from position 12,541 to position 12,350.

Cloning was carried out by isolating the 210 bp SalI-XhoI fragment from pOCS and ligating it into the SalI-XhoI-cut pJIT117 vector.

This clone is referred to as pJO and was therefore used for cloning into the expression vector pJONP196.

Cloning was carried out by isolating the 782 bp SphI fragment from pNP1 96 and ligating it into the SphI-cut pJO vector. The clone which contains the *Nostoc punctiforme* NP196 ketolase in the correct orientation as an N-terminal translational fusion with the rbcS transit peptide is referred to as pJONP196.

EXAMPLE 7

Preparation of Expression Vectors for Constitutive Expression of NP196 Ketolase from *Nostoc punctiforme* ATCC 29133 in *Lycopersicon esculentum* and *Tagetes erecta*

The *Nostoc punctiforme* NP196 ketolase is expressed in *L. esculentum* and in *Tagetes erecta* under the control of the constitutive promoter FNR (ferredoxin NADPH oxidoreductase, database entry AB011474, positions 70127 to 69493; WO03/006660) from *Arabidopsis thaliana*. The FNR gene starts at base pair 69492 and is annotated with "ferredoxin-NADP+ reductase". Expression was carried out using the pea transit peptide rbcS (Anderson et al. 1986, Biochem J. 240: 709-715).

The DNA fragment comprising the *Arabidopsis thaliana* FNR promoter region was prepared by means of PCR using genomic DNA (isolated from *Arabidopsis thaliana* by standard methods) and the primers FNR-1 (SEQ ID NO. 61) and FNR-2 (SEQ ID NO. 62).

The PCR conditions were as follows:

The PCR for amplifying the DNA comprising the FNR promoter fragment FNR (SEQ ID NO. 63) was carried out in a 50 µl reaction mixture containing:

100 ng of *A. thaliana* genomic DNA
0.25 mM dNTPs
0.2 mM FNR-1 (SEQ ID NO. 61)
0.2 mM FNR-2 (SEQ ID NO. 62)
5 µl of 10×PCR buffer (Stratagene)
0.25 µl of Pfu polymerase (Stratagene)
28.8 µl of distilled water The PCR was carried out under the following cycle conditions:

| | |
|---|---|
| 1X | 94° C. for 2 minutes |
| 35X | 94° C. for 1 minute |
| | 50° C. for 1 minute |
| | 72° C. for 1 minute |
| 1X | 72° C. for 10 minutes |

The 652 bp amplicon was cloned into the PCR cloning vector pCR 2.1 (Invitrogen) by using standard methods, producing the plasmid pFNR.

Sequencing of the pFNR clone confirmed a sequence which corresponds to a sequence section on chromosome 5 of *Arabidopsis thaliana* (database entry AB011474), from position 70127 to position 69493.

This clone is referred to as pFNR and was therefore used for cloning into the expression vector pJONP196 (described in example 6).

Cloning was carried out by isolating the 644 bp SmaI-HindIII fragment from pFNR and ligating it into the Ecl136II-HindIII-cut pJONP196 vector. The clone which contains the FNR promoter instead of the original d35S promoter and the fragment NP196 in the correct orientation as an N-terminal fusion with the rbcS transit peptide is referred to as pJOFNR:NP196.

An expression cassette for *Agrobacterium*-mediated transformation of the *Nostoc* NP196 ketolase into *L. esculentum* was prepared using the binary vector pSUN3 (WO02/00900).

Figure 7:
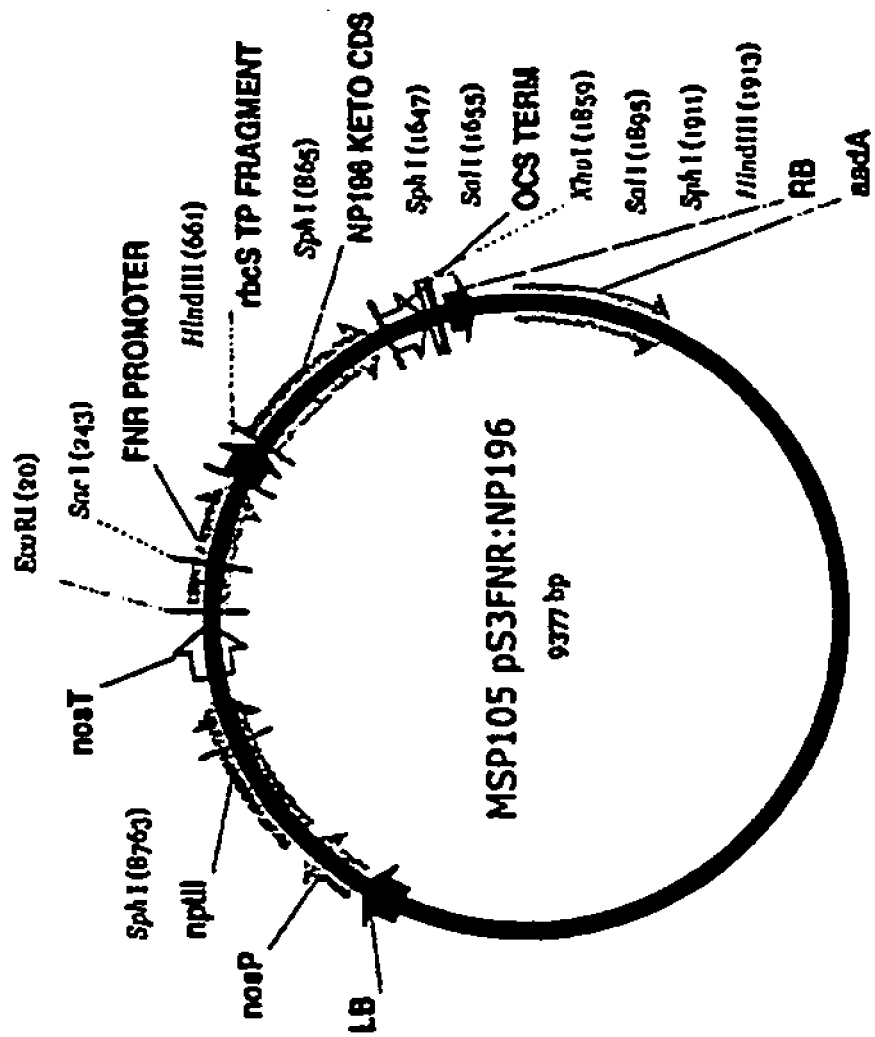
FIG. 7 shows the construct map of the expression vector pS3FNR:NP196 (MSP105).

The expression vector MSP105 was prepared by ligating the 1839 bp EcoRI-XhoI fragment from pJOFNR:NP196 with the EcoRI-XhoI-cut pSUN3 vector (FIG. 7, construct map). In FIG. 7, the fragment FNR promoter comprises the FNR promoter (635 bp), the fragment rbcS TP FRAGMENT comprises the pea rbcS transit peptide (194 bp), the fragment NP196 KETO CDS (761 bp) coding for *Nostoc punctiforme* NP196 ketolase, and the fragment OCS terminator (192 bp) comprises the polyadenylation signal of octopine synthase.

An expression cassette for *Agrobacterium*-mediated transformation of the expression vector containing the *Nostoc punctiforme* NP196 ketolase into *Tagetes erecta* was prepared using the binary vector pSUN5 (WO02/00900).

Figure 8:
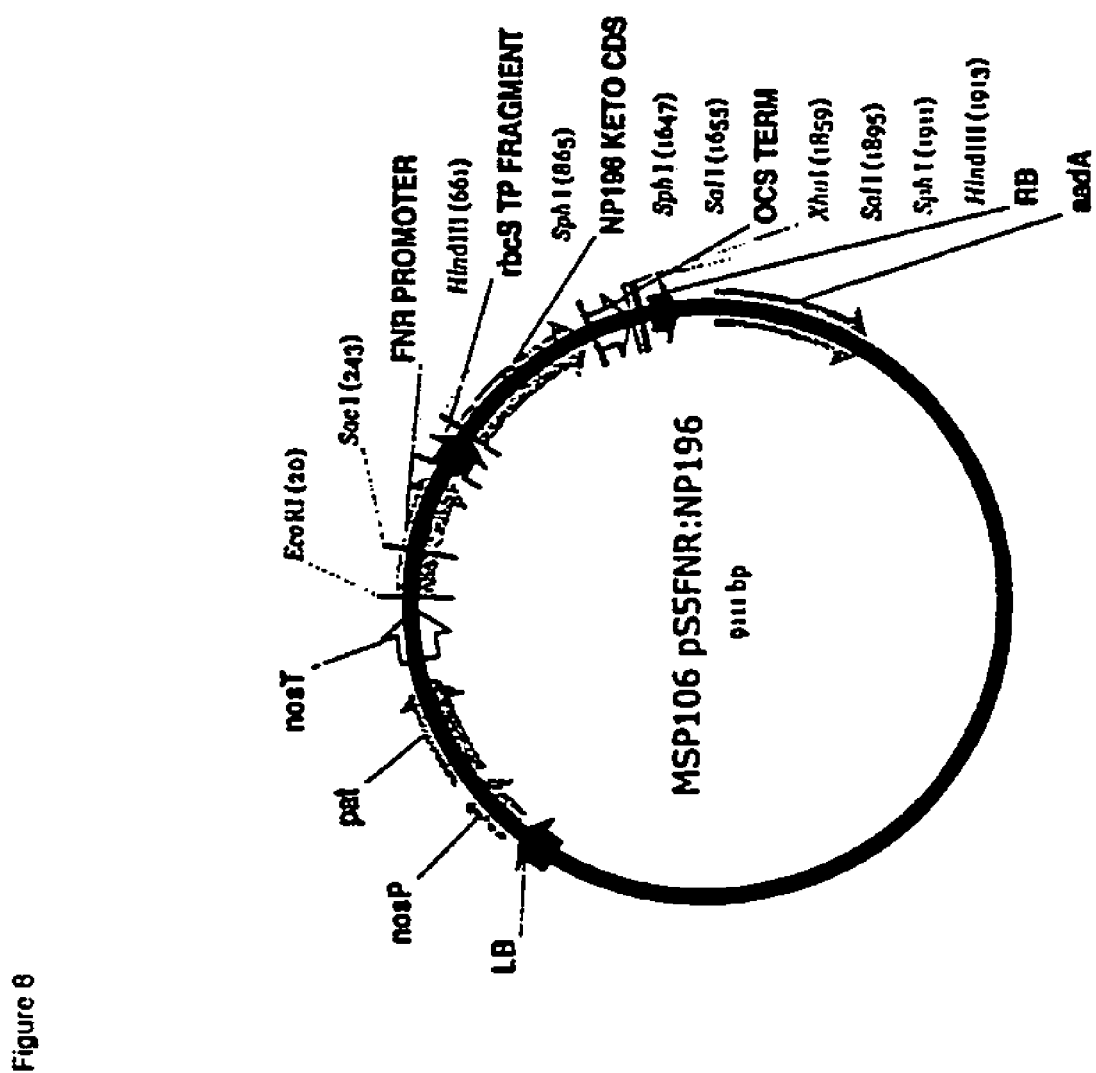
FIG. 8 shows the construct map of the expression vector pS5FNR:NP196 (MSP106).

The *Tagetes* expression vector MSP106 was prepared by ligating the 1839 bp EcoRI-XhoI fragment from pJOFNR:NP196 with the EcoRI-XhoI-cut pSUN5 vector (FIG. 8, construct map). In FIG. 8, the fragment FNR promoter comprises the FNR promoter (635 bp), the fragment rbcS TP FRAGMENT comprises the pea rbcS transit peptide (194 bp), the fragment NP196 KETO CDS (761 bp) coding for *Nostoc punctiforme* NP196 ketolase, and the fragment OCS terminator (192 bp) comprises the polyadenylation signal of octopine synthase.

EXAMPLE 8

Preparation of Expression Vectors for Flower-Specific Expression of NP196 Ketolase from *Nostoc punctiforme* ATCC 29133 in *Lycopersicon esculentum* and *Tagetes erecta*

*Nostoc punctiforme* NP196 ketolase was expressed in *L. esculentum* and *Tagetes erecta* by using the pea transit peptide rbcS (Anderson et al. 1986, Biochem J. 240: 709-715). Expression was carried out under the control of the flower-specific EPSPS promoter from *Petunia hybrida* (database entry M37029; nucleotide region 7-1787; Benfey et al. (1990) Plant Cell 2: 849-856).

The DNA fragment comprising the *Petunia hybrida* EPSPS promoter region (SEQ ID NO. 66) was prepared by means of PCR using genomic DNA (isolated from *Petunia hybrida* by standard methods) and the primers EPSPS-1 (SEQ ID NO. 64) and EPSPS-2 (SEQ ID NO. 65).

The PCR conditions were as follows:

The PCR for amplifying the DNA comprising the EPSPS promoter fragment (database entry M37029: nucleotide region 7-1787) was carried out in a 50 µl reaction mixture containing:

100 ng of *A. thaliana* genomic DNA
0.25 mM dNTPs
0.2 mM EPSPS-1 (SEQ ID NO. 64)
0.2 mM EPSPS-2 (SEQ ID NO. 65)
5 µl of 10×PCR buffer (Stratagene)
0.25 µl of Pfu polymerase (Stratagene)
28.8 µl of distilled water The PCR was carried out under the following cycle conditions:

| | |
|---|---|
| 1X | 94° C. for 2 minutes |
| 35X | 94° C. for 1 minute |
| | 50° C. for 1 minute |
| | 72° C. for 2 minutes |
| 1X | 72° C. for 10 minutes |

The 1773 bp amplicon was cloned into the PCR cloning vector pCR 2.1 (Invitrogen) by using standard methods, producing the plasmid pEPSPS.

Sequencing of the pEPSPS clone confirmed a sequence which differs from the published EPSPS sequence (database entry M37029: nucleotide region 7-1787) only by two deletions (bases ctaagtttcagga at positions 46-58 of the sequence M37029; bases aaaaatat at positions 1422-1429 of the sequence M37029) and the base substitutions (T for G at position 1447 of the sequence M37029; A for C at position 1525 of the sequence M37029; A for G at position 1627 of the sequence M37029). The two deletions and the two base substitutions at positions 1447 and 1627 of the sequence M37029 were reproduced in an independent amplification experiment and thus represent the actual nucleotide sequence in the *Petunia hybrida* plants used.

The pEPSPS clone was therefore used for cloning into the expression vector pJONP196 (described in example 6).

Cloning was carried out by isolating the 1763 bp SacI-HindIII fragment from pEPSPS and ligating it into the SacI-HindIII-cut pJONP196 vector. The clone which contains the EPSPS promoter instead of the original d35S promoter is referred to as pJOESP:NP196. This expression cassette contains the NP196 fragment in the correct orientation as an N-terminal fusion with the rbcS transit peptide.

An expression vector for *Agrobacterium*-mediated transformation of the EPSPS-controlled *Nostoc punctiforme* ATCC 29133 NP196 ketolase into *L. esculentum* was prepared using the binary vector pSUN3 (WO02/00900).

Figure 9:
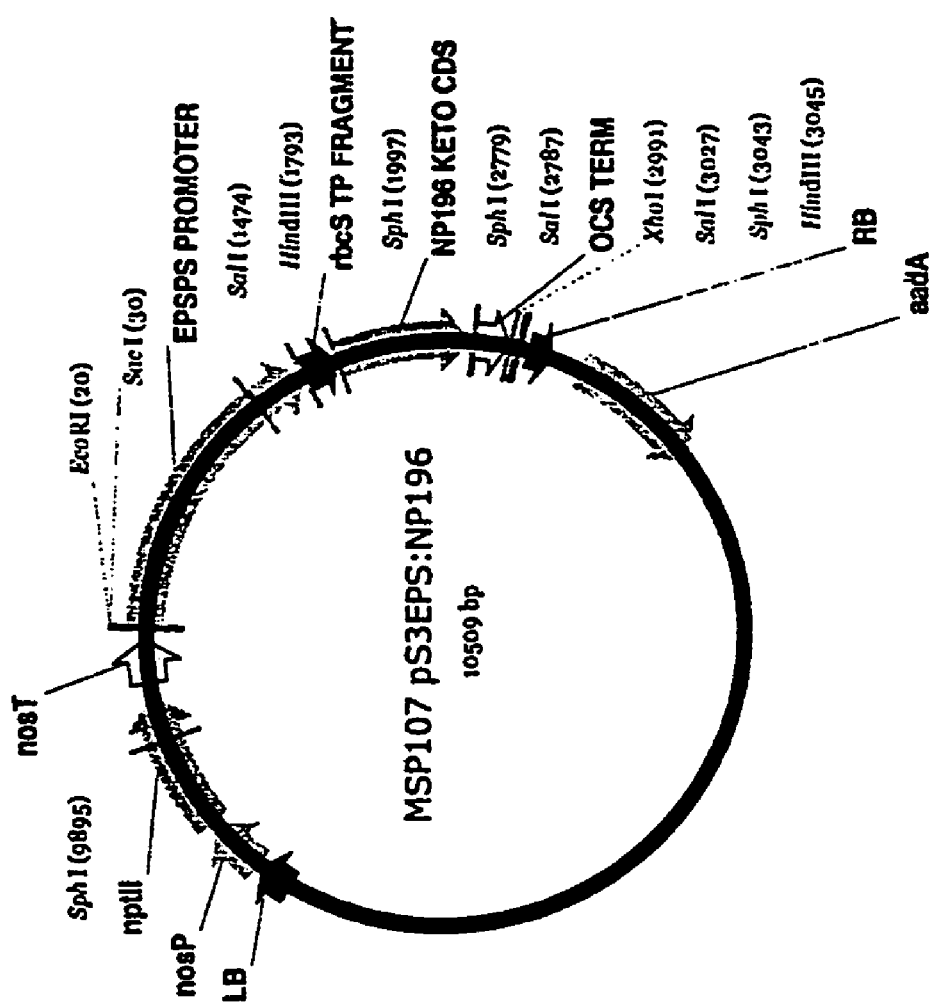
FIG. 9 shows the construct map of the expression vector pS3EPS:NP196 (MSP107).

The expression vector MSP107 was prepared by ligating the 2961 kbp SacI-XhoI fragment from pJOESP:NP196 with the SacI-XhoI-cut pSUN3 vector (FIG. 9, construct map). In FIG. 9, the fragment EPSPS comprises the EPSPS promoter (1761 bp), the fragment rbcS TP FRAGMENT comprises the pea rbcS transit peptide (194 bp), the fragment NP196 KETO CDS (761 bp) coding for *Nostoc punctiforme* NP196 ketolase, and the fragment OCS terminator (192 bp) comprises the polyadenylation signal of octopine synthase.

An expression vector for *Agrobacterium*-mediated transformation of the EPSPS-controlled *Nostoc punctiforme* NP196 ketolase into *Tagetes erecta* was prepared using the binary vector pSUN5 (WO02/00900).

Figure 10:
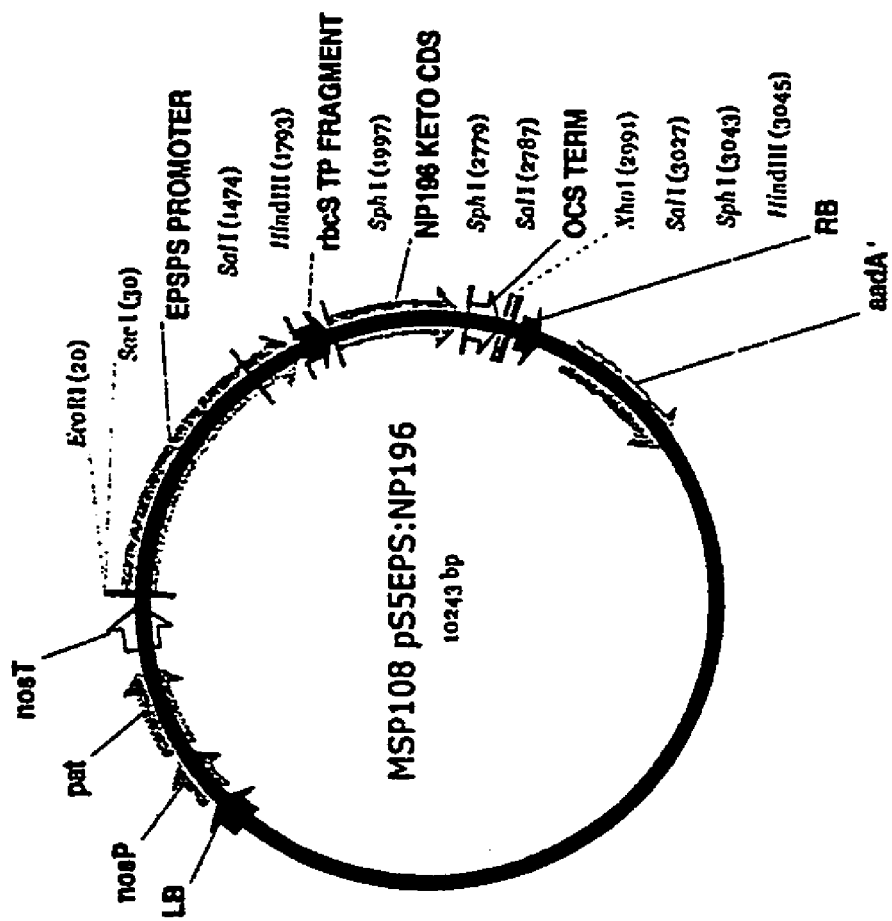
FIG. 10 shows the construct map of the expression vector pS5EPS:NP196 (MSP108).

The expression vector MSP108 was prepared by ligating the 2961 kbp SacI-XhoI fragment from pJOESP:NP196 with the SacI-XhoI-cut pSUN5 vector (FIG. 10, construct map). In FIG. 10, the fragment EPSPS comprises the EPSPS promoter (1761 bp), the fragment rbcS TP FRAGMENT comprises the pea rbcS transit peptide (194 bp), the fragment NP196 KETO CDS (761 bp) coding for *Nostoc punctiforme* NP196 ketolase, and the fragment OCS terminator (192 bp) comprises the polyadenylation signal of octopine synthase.

EXAMPLE 9

Amplification of a DNA Encoding the Entire Primary Sequence of NP195 Ketolase from *Nostoc punctiforme* ATCC 29133

The DNA coding for NP195 ketolase from *Nostoc punctiforme* ATCC 29133 was amplified from *Nostoc punctiforme* ATCC 29133 (strain of the American Type Culture Collection) by means of PCR. The preparation of genomic DNA from a *Nostoc punctiforme* ATCC 29133 suspension culture has been described in example 19.

The nucleic acid encoding a *Nostoc punctiforme* ATCC 29133 ketolase was amplified from *Nostoc punctiforne* ATCC 29133 by means of polymerase chain reaction (PCR) using a sense-specific primer (NP195-1, SEQ ID NO. 67) and an antisense-specific primer (NP195-2 SEQ ID NO. 68).

The PCR conditions were as follows:

The PCR for amplifying the DNA encoding a ketolase protein consisting of the entire primary sequence was carried out in a 50 µl reaction mixture which contained:

1 µl of a *Nostoc punctiforme* ATCC 29133 DNA (prepared as described above)
0.25 mM dNTPs
0.2 mM NP195-1 (SEQ ID NO. 67)
0.2 mM NP195-2 (SEQ ID NO. 68)
5 µl of 10×PCR buffer (TAKARA)
0.25 µl of R Taq polymerase (TAKARA)
25.8 µl of distilled water The PCR was carried out under the following cycle conditions:

| | |
|---|---|
| 1X | 94° C. for 2 minutes |
| 35X | 94° C. for 1 minute |
| | 55° C. for 1 minute |
| | 72° C. for 3 minutes |
| 1X | 72° C. for 10 minutes |

PCR amplification with SEQ ID NO. 67 and SEQ ID NO. 68 resulted in an 819 bp fragment encoding a protein consisting of the entire primary sequence (NP195, SEQ ID NO. 69). Using standard methods, the amplicon was cloned into the PCR cloning vector pCR 2.1 (Invitrogen), producing the clone pNP195.

Sequencing of the pNP195 clone with the M13F and M13R primers confirmed a sequence which is identical to the DNA sequence from 55,604-56,392 of the database entry NZ_AABC010001965, except that T at position 55,604 has been replaced with A in order to generate a standard ATG start codon. This nucleotide sequence was reproduced in an independent amplification experiment and thus represents the nucleotide sequence in the *Nostoc punctiforme* ATCC 29133 used.

This clone, pNP195, was therefore used for cloning into the expression vector pJO (described in example 6). Cloning was carried out by isolating the 809 bp SphI fragment from pNP195 and ligating it into the SphI-cut pJO vector. The clone which contains the *Nostoc punctiforme* NP195 ketolase in the correct orientation as an N-terminal translation fusion with the rbcS transit peptide is referred to as pJONP195.

EXAMPLE 10

Preparation of Expression Vectors for Constitutive Expression of NP195 Ketolase from *Nostoc punctiforme* ATCC 29133 in *Lycopersicon esculentum* and *Tagetes erecta*

The *Nostoc punctiforme* NP195 ketolase is expressed in *L. esculentum* and in *Tagetes erecta* under the control of the constitutive promoter FNR (ferredoxin NADPH oxidoreductase, database entry AB011474, positions 70127 to 69493; WO03/006660) from *Arabidopsis thaliana*. The FNR gene starts at base pair 69492 and is annotated with "ferredoxin-NADP+ reductase". Expression was carried out using the pea transit peptide rbcS (Anderson et al. 1986, Biochem J. 240: 709-715).

The clone pFNR (described in example 7) was therefore used for cloning into the expression vector pJONP195 (described in example 10).

Cloning was carried out by isolating the 644 bp SmaI-HindIII fragment from pFNR and ligating it into the Ecl136II-HindIII-cut pJONP195 vector. The clone which contains the FNR promoter instead of the original d35S promoter and the fragment NP195 in the correct orientation as an N-terminal fusion with the rbcS transit peptide is referred to as pJOFNR:NP195.

An expression cassette for *Agrobacterium*-mediated transformation of the *Nostoc punctiforme* NP195 ketolase in *L. esculentum* was prepared using the binary vector pSUN3 (WO02/00900).

Figure 11:
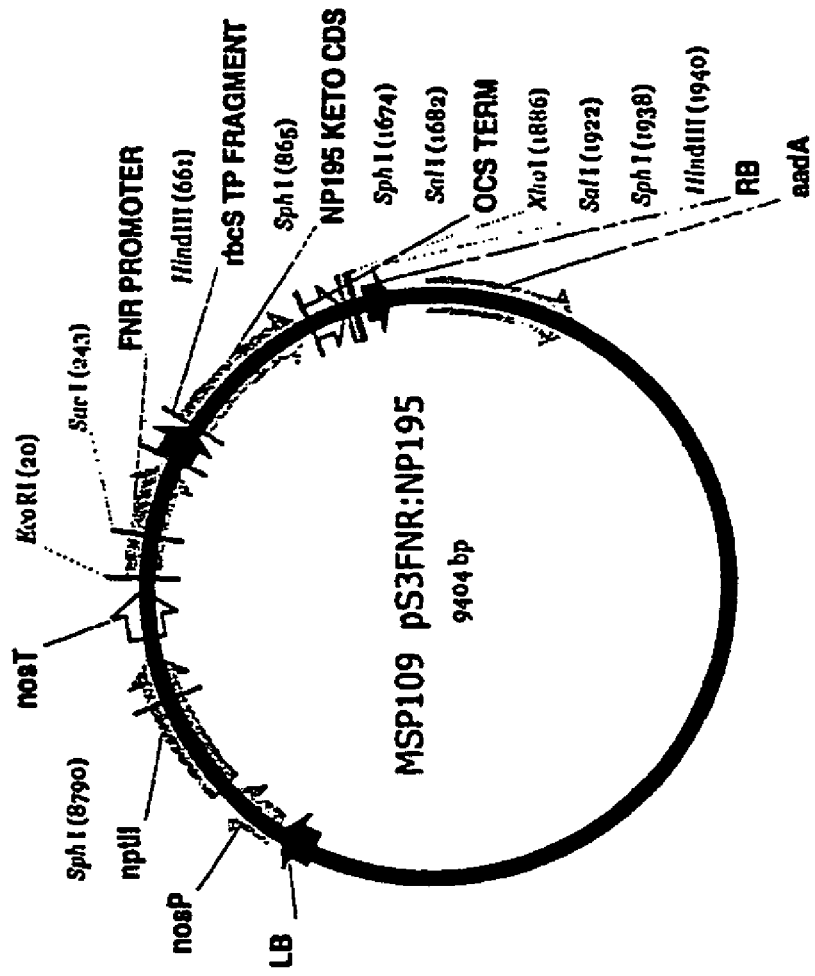
FIG. 11 shows the construct map of the expression vector pS3FNR:NP195 (MSP109).

The expression vector MSP109 was prepared by ligating the 1866 bp EcoRI-XhoI fragment from pJOFNR:NP195 with the EcoRI-XhoI-cut pSUN3 vector (FIG. 11, construct map). In FIG. 11, the fragment FNR promoter comprises the FNR promoter (635 bp), the fragment rbcS TP FRAGMENT comprises the pea rbcS transit peptide (194 bp), the fragment NP195 KETO CDS (789 bp) coding for *Nostoc punctiforme* NP195 ketolase, and the fragment OCS terminator (192 bp) comprises the polyadenylation signal of octopine synthase.

An expression cassette for *Agrobacterium*-mediated transformation of the expression vector containing the *Nostoc punctiforme* punctiforme NP195 ketolase into *Tagetes erecta* was prepared using the binary vector pSUN5 (WO02/00900).

Figure 12:
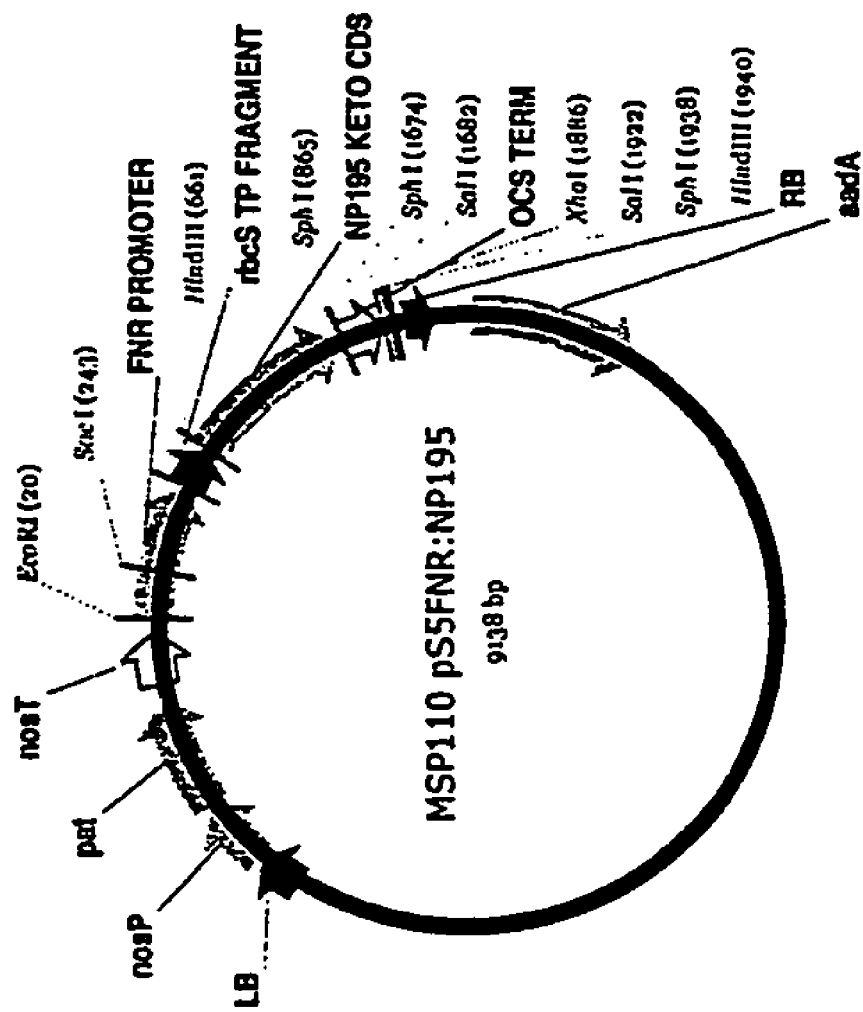
FIG. 12 shows the construct map of the expression vector pS5FNR:NP195 (MSP110).

The *Tagetes* expression vector MSP110 was prepared by ligating the 1866 bp EcoRI-XhoI fragment from pJOFNR:NP195 with the EcoRI-XhoI-cut pSUN5 vector (FIG. 12, construct map). In FIG. 12, the fragment FNR promoter comprises the FNR promoter (635 bp), the fragment rbcS TP FRAGMENT comprises the pea rbcS transit peptide (194 bp), the fragment NP195 KETO CDS (789 bp) coding for *Nostoc punctiforme* NP195 ketolase, and the fragment OCS terminator (192 bp) comprises the polyadenylation signal of octopine synthase.

EXAMPLE 11

Preparation of Expression Vectors for Flower-Specific Expression of NP195 Ketolase from *Nostoc punctiforme* ATCC 29133 in *Lycopersicon esculentum* and *Tagetes erecta*

*Nostoc punctiforme* NP195 ketolase was expressed in *L. esculentum* and *Tagetes erecta* by using the pea transit peptide rbcS (Anderson et al. 1986, Biochem J. 240: 709-715). Expression was carried out under the control of the flower-specific EPSPS promoter from *Petunia hybrida* (database entry M37029; nucleotide region 7-1787; Benfey et al. (1990) Plant Cell 2: 849-856).

The pEPSPS clone (described in example 8) was therefore used for cloning into the expression vector pJONP195 (described in example 10).

Cloning was carried out by isolating the 1763 bp SacI-HindIII fragment from pEPSPS and ligating it into the SacI-HindIII-cut pJONP195 vector. The clone which contains the EPSPS promoter instead of the original d35S promoter is referred to as pJOESP:NP195. This expression cassette contains the NP195 fragment in the correct orientation as an N-terminal fusion with the rbcS transit peptide.

An expression vector for *Agrobacterium*-mediated transformation of the EPSPS-controlled *Nostoc punctiforme* ATCC 29133 NP195 ketolase into *L. esculentum* was prepared using the binary vector pSUN3 (WO02/00900).

Figure 13:
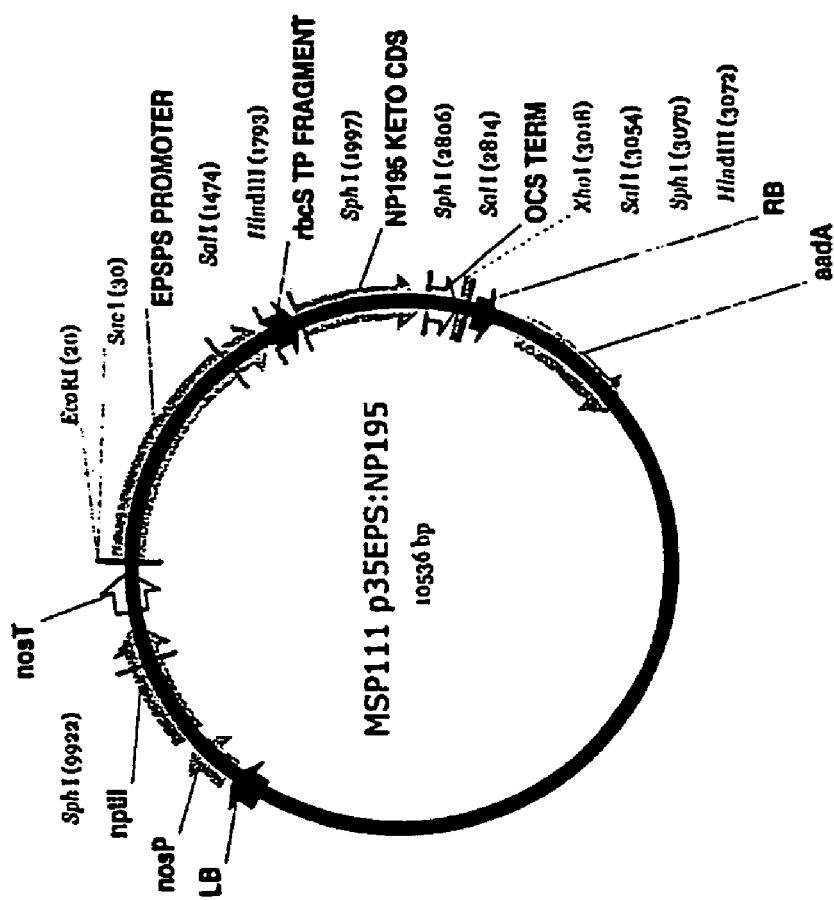
FIG. 13 shows the construct map of the expression vector p35EPS:NP195 (MSP111).

The expression vector MSP111 was prepared by ligating the 2988 kbp SacI-XhoI fragment from pJOESP:NP195 with the SacI-XhoI-cut pSUN3 vector (FIG. 13, construct map). In FIG. 13, the fragment EPSPS comprises the EPSPS promoter (1761 bp), the fragment rbcS TP FRAGMENT comprises the pea rbcS transit peptide (194 bp), the fragment NP195 KETO CDS (789 bp) coding for *Nostoc punctiforme* NP195 ketolase, and the fragment OCS terminator (192 bp) comprises the polyadenylation signal of octopine synthase.

An expression vector for *Agrobacterium*-mediated transformation of the EPSPS-controlled *Nostoc punctiforme* NP195 ketolase into *Tagetes erecta* was prepared using the binary vector pSUN5 (WO02/00900).

Figure 14:
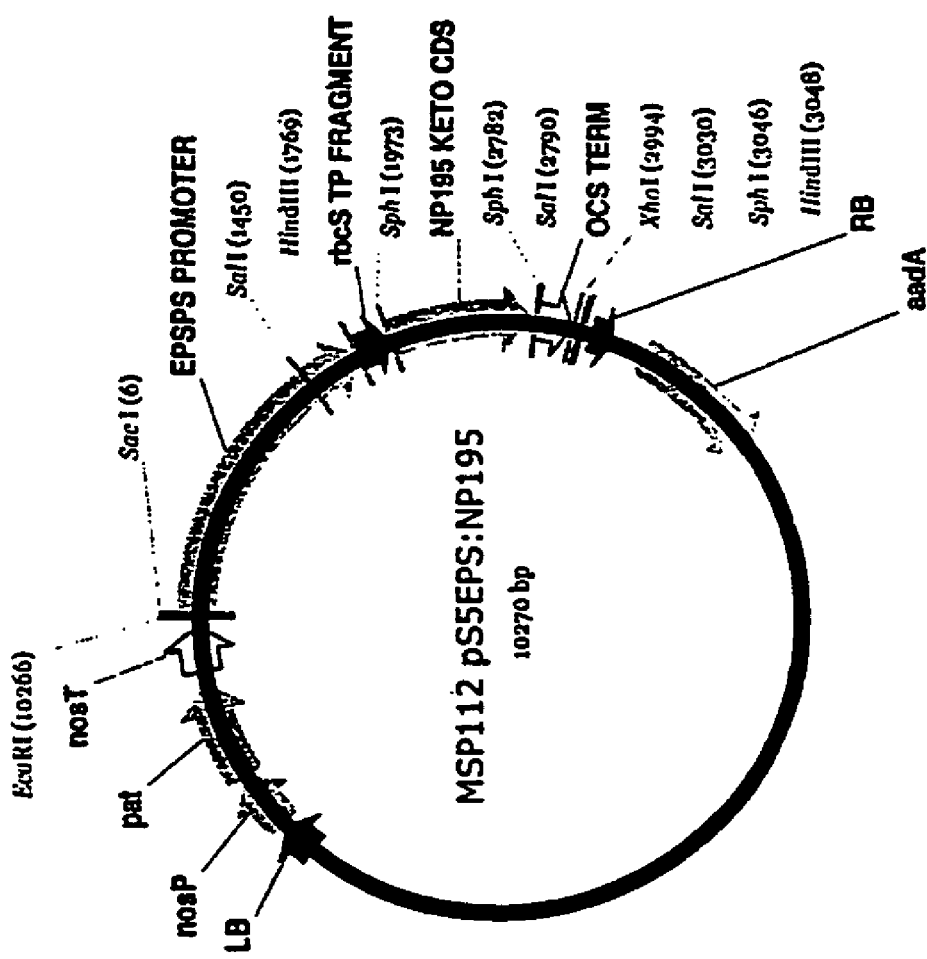
FIG. 14 shows the construct map of the expression vector pS5EPS:NP195 (MSP112).

The expression vector MSP112 was prepared by ligating the 2988 kbp SacI-XhoI fragment from pJOESP:NP195 with the SacI-XhoI-cut pSUN5 vector (FIG. 14, construct map). In FIG. 14, the fragment EPSPS comprises the EPSPS promoter (1761 bp), the fragment rbcS TP FRAGMENT comprises the pea rbcS transit peptide (194 bp), the fragment NP195 KETO CDS (789 bp) coding for *Nostoc punctiforme* NP195 ketolase, and the fragment OCS terminator (192 bp) comprises the polyadenylation signal of octopine synthase.

EXAMPLE 12

Amplification of a DNA Encoding the Entire Primary Sequence of NODK Ketolase from *Nodularia spumignea* NSOR10

The DNA coding for the *Nodularia spumignea* NSOR10 ketolase was amplified from *Nodularia spumignea* NSOR10 by means of PCR.

To prepare genomic DNA from a *Nodularia spumignea* NSOR10 suspension culture which had grown in BG 11 medium (1.5 g/l NaNO$_3$, 0.04 g/l K$_2$PO$_4$×3H$_2$O, 0.075 g/l MgSO$_4$×H$_2$O, 0.036 g/l CaCl$_2$×2H$_2$O, 0.006 g/l citric acid, 0.006 g/l ferric ammonium citrate, 0.001 g/l EDTA disodium magnesium, 0.04 g/l Na$_2$CO$_3$, 1 ml of trace metal mix A5+Co (2.86 g/l H$_3$BO$_3$, 1.81 g/l MnCl$_2$×4H$_2$O, 0.222 g/l ZnSO$_4$×7H$_2$O, 0.39 g/l NaMoO$_4$×2H$_2$O, 0.079 g/l CuSO$_4$× 5H$_2$O, 0.0494 g/l Co(NO$_3$)$_2$×6H$_2$O) at 25° C. with constant shaking (150 rpm) and under continuous light for 1 week, the cells were harvested by centrifugation, frozen in liquid nitrogen and ground to a powder in a mortar.

Protocol for Isolating DNA from *Nodularia spumignea* NSOR10:

The bacterial cells were pelleted from a 10 ml liquid culture by centrifugation at 8000 rpm for 10 minutes. The bacterial cells were then crushed and ground in liquid nitrogen, using a mortar. The cell material was resuspended in 1 ml of 10 mM Tris HCl (pH 7.5) and transferred to an Eppendorf reaction vessel (volume: 2 ml). After addition of 100 µl of proteinase K (concentration: 20 mg/ml), the cell suspension was incubated at 37° C. for 3 hours. The suspension was then extracted with 500 µl of phenol. After centrifugation at 13 000 rpm for 5 minutes, the upper, aqueous phase was transferred to a new 2 ml Eppendorf reaction vessel. Extraction with phenol was repeated 3 times. The DNA was precipitated by adding 1/10 volume of 3 M sodium acetate (pH 5.2) and 0.6 volume of isopropanol and then washed with 70% ethanol. The DNA pellet was dried at room temperature, taken up in 25 µl of water and dissolved with heating to 65° C.

The nucleic acid encoding a *Nodularia spumignea* NSOR10 ketolase was amplified from *Nodularia spumignea* NSOR10 by means of polymerase chain reaction (PCR) using a sense-specific primer (NODK-1, SEQ ID NO. 71) and an antisense-specific primer (NODK-2 SEQ ID NO. 72).

The PCR conditions were as follows:

The PCR for amplifying the DNA encoding a ketolase protein consisting of the entire primary sequence was carried out in a 50 µl reaction mixture which contained:

- 1 µl of a *Nodularia spumignea* NSOR10 DNA (prepared as described above)
- 0.25 mM dNTPs
- 0.2 mM NODK-1 (SEQ ID NO. 71)
- 0.2 mM NODK-2 (SEQ ID NO. 72)
- 5 µl of 10×PCR buffer (TAKARA)
- 0.25 µl of R Taq polymerase (TAKARA)
- 25.8 µl of distilled water The PCR was carried out under the following cycle conditions:

| | |
|---|---|
| 1X | 94° C. for 2 minutes |
| 35X | 94° C. for 1 minute |
| | 55° C. for 1 minute |
| | 72° C. for 3 minutes |
| 1X | 72° C. for 10 minutes |

PCR amplification with SEQ ID NO. 71 and SEQ ID NO. 72 resulted in a 720 bp fragment encoding a protein consisting of the entire primary sequence (NODK, SEQ ID NO. 73). Using standard methods, the amplicon was cloned into the PCR cloning vector pCR 2.1 (Invitrogen), producing the clone pNODK.

Sequencing of the pNODK clone with the M13F and M13R primers confirmed a sequence which is identical to the DNA sequence from 2130-2819 of the database entry AY210783 (inversely oriented to the published database entry). This nucleotide sequence was reproduced in an independent amplification experiment and thus represents the nucleotide sequence in the *Nodularia spumignea* NSOR10 used.

This clone, pNODK, was therefore used for cloning into the expression vector pJO (described in example 6). Cloning was carried out by isolating the 710 bp SphI fragment from pNODK and ligating it into the SphI-cut pJO vector. The clone which contains the *Nodularia spumignea* NODK ketolase in the correct orientation as an N-terminal translational fusion with the rbcS transit peptide is referred to as pJONODK.

EXAMPLE 13

Preparation of Expression Vectors for Constitutive Expression of NODK Ketolase from *Nodularia spumignea* NSOR10 in *Lycopersicon esculentum* and *Tagetes erecta*

The *Nodularia spumignea* NSOR10 NODK ketolase was expressed in *L. esculentum* and in *Tagetes erecta* under the control of the constitutive promoter FNR (ferredoxin NADPH oxidoreductase, database entry AB011474, positions 70127 to 69493; WO03/006660) from *Arabidopsis thaliana*. The FNR gene starts at base pair 69492 and is annotated with "ferredoxin-NADP+ reductase". Expression was carried out using the pea transit peptide rbcS (Anderson et al. 1986, Biochem J. 240: 709-715).

The clone pFNR (described in example 7) was therefore used for cloning into the expression vector pJONODK (described in example 12).

Cloning was carried out by isolating the 644 bp SmaI-HindIII fragment from pFNR and ligating it into the Ecl136II-HindIII-cut pJONODK vector. The clone which contains the FNR promoter instead of the original d35S promoter and the fragment NODK in the correct orientation as an N-terminal fusion with the rbcS transit peptide is referred to as pJOFNR:NODK.

An expression cassette for *Agrobacterium*-mediated transformation of the *Nodularia spumignea* NSOR10 NODK ketolase into *L. esculentum* was prepared using the binary vector pSUN3 (WO02/00900).

Figure 15:
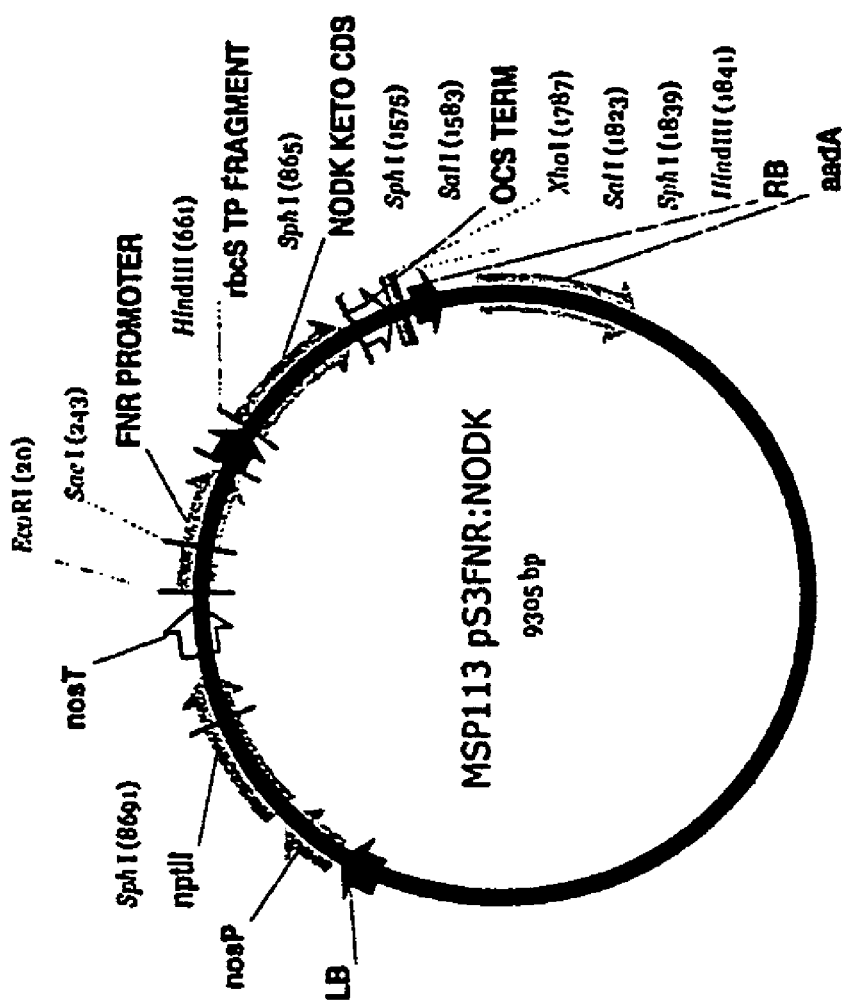
FIG. 15 shows the construct map of the expression vector pS3FNR:NODK (MSP113).
Figure 16:
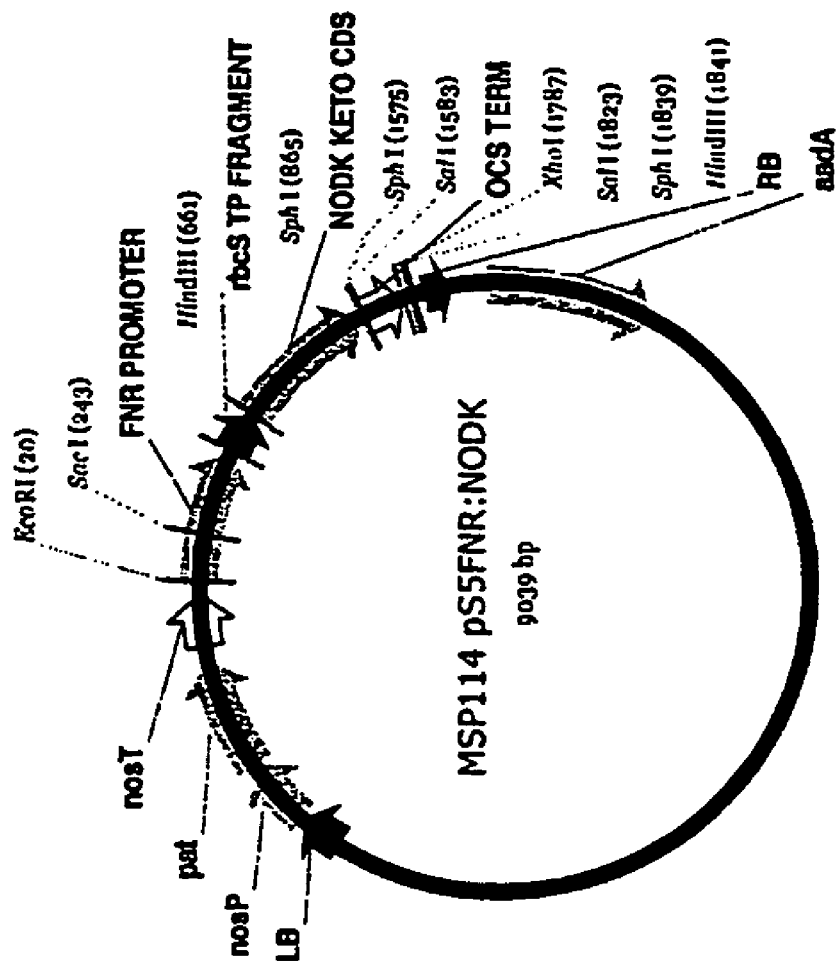
FIG. 16 shows the construct map of the expression vector pS5FNR:NODK (MSP114).
Figure 17:
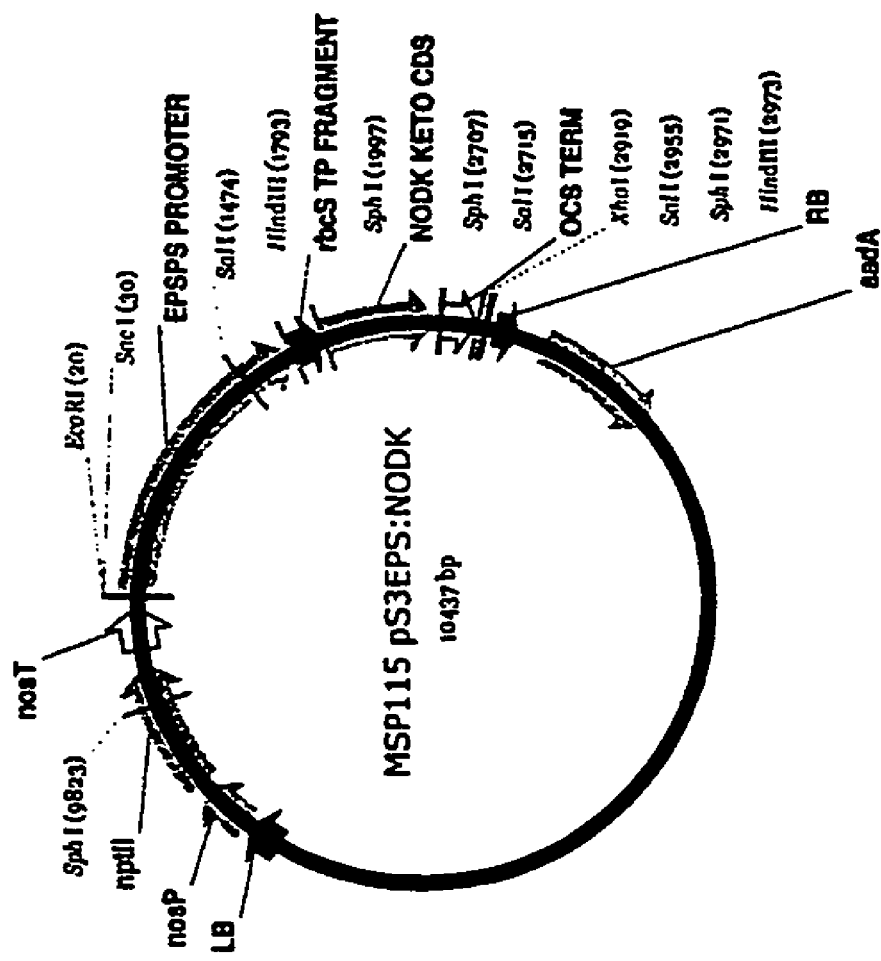
FIG. 17 shows the construct map of the expression vector pS3EPS:NODK (MSP115).
Figure 18:
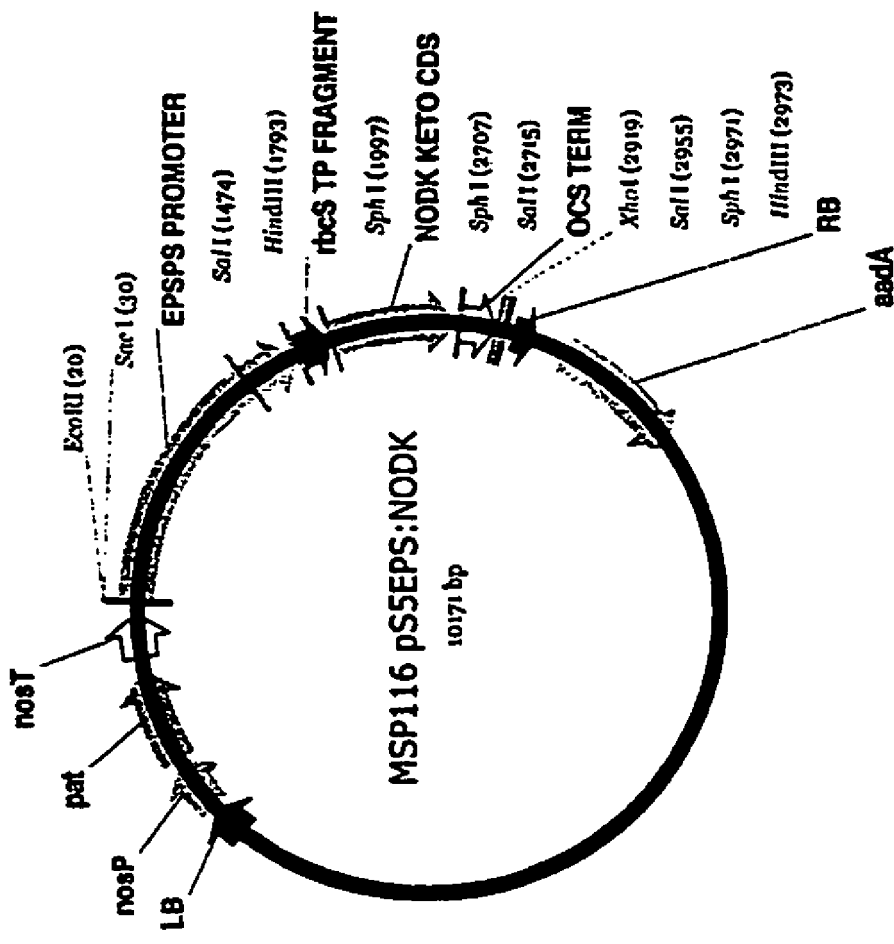
FIG. 18 shows the construct map of the expression vector pS5EPS:NODK (MSP116).

The expression vector MSP113 was prepared by ligating the 1767 bp EcoRI-XhoI fragment from pJOFNR:NODK with the EcoRI-XhoI-cut pSUN3 vector (FIG. 15, construct map). In FIG. 15, the fragment FNR promoter comprises the FNR promoter (635 bp), the fragment rbcS TP FRAGMENT comprises the pea rbcS transit peptide (194 bp), the fragment NODK KETO CDS (690 bp) coding for *Nodularia spumignea* NSOR10 NODK ketolase, and the fragment OCS terminator (192 bp) comprises the polyadenylation signal of octopine synthase.

An expression cassette for *Agrobacterium*-mediated transformation of the expression vector containing the *Nodularia spumignea* NSOR10 *punctiforme* NODK ketolase into *Tagetes erecta* was prepared using the binary vector pSUN5 (WO02/00900).

The *Tagetes* expression vector MSP114 was prepared by ligating the 1767 bp EcoRI-XhoI fragment from pJOFNR:NODK with the EcoRI-XhoI-cut pSUN5 vector (FIG. 16, construct map). In FIG. 16, the fragment FNR promoter comprises the FNR promoter (635 bp), the fragment rbcS TP FRAGMENT comprises the pea rbcS transit peptide (194 bp), the fragment NODK KETO CDS (690 bp) coding for *Nodularia spumignea* NSOR10 NODK ketolase, and the fragment OCS terminator (192 bp) comprises the polyadenylation signal of octopine synthase.

EXAMPLE 14

Preparation of Expression Vectors for Flower-Specific Expression of NODK Ketolase from *Nodularia spumignea* NSOR10 in *Lycopersicon esculentum* and *Tagetes erecta*

*Nodularia spumignea* NSOR10 NODK ketolase was expressed in *L. esculentum* and *Tagetes erecta* by using the pea transit peptide rbcS (Anderson et al. 1986, Biochem J. 240: 709-715). Expression was carried out under the control of the flower-specific EPSPS promoter from *Petunia hybrida* (database entry M37029; nucleotide region 7-1787; Benfey et al. (1990) Plant Cell 2: 849-856).

The pEPSPS clone (described in example 8) was therefore used for cloning into the expression vector pJONODK (described in example 12).

Cloning was carried out by isolating the 1763 bp SacI-HindIII fragment from pEPSPS and ligating it into the SacI-HindIII-cut pJONODK vector. The clone which contains the EPSPS promoter instead of the original d35S promoter is referred to as pJOESP:NODK. This expression cassette contains the NODK fragment in the correct orientation as an N-terminal fusion with the rbcS transit peptide.

An expression vector for *Agrobacterium*-mediated transformation of the EPSPS-controlled *Nodularia spumignea* NSOR10 NODK ketolase into *L. esculentum* was prepared using the binary vector pSUN3 (WO02/00900).

The expression vector MSP115 was prepared by ligating the 2889 kbp SacI-XhoI fragment from pJOESP:NODK with the SacI-XhoI-cut pSUN3 vector (FIG. 17, construct map). In FIG. 17, the fragment EPSPS comprises the EPSPS promoter (1761 bp), the fragment rbcS TP FRAGMENT comprises the pea rbcS transit peptide (194 bp), the fragment NODK KETO CDS (690 bp) coding for *Nodularia spumignea* NSOR10 NODK ketolase, and the fragment OCS terminator (192 bp) comprises the polyadenylation signal of octopine synthase.

An expression vector for *Agrobacterium*-mediated transformation of the EPSPS-controlled *Nodularia spumignea* NSORIO NODK ketolase into *Tagetes erecta* was prepared using the binary vector pSUN5 (WO02/00900).

The expression vector MSP116 was prepared by ligating the 2889 kbp SacI-XhoI fragment from pJOESP:NODK with the SacI-XhoI-cut pSUN5 vector (FIG. 18, construct map). In FIG. 18, the fragment EPSPS comprises the EPSPS promoter (1761 bp), the fragment rbcS TP FRAGMENT comprises the pea rbcS transit peptide (194 bp), the fragment NODK KETO CDS (690 bp) coding for *Nodularia spumignea* NSOR10 NODK ketolase, and the fragment OCS terminator (192 bp) comprises the polyadenylation signal of octopine synthase.

EXAMPLE 15

Preparation of Transgenic *Lycopersicon Esculentum* Plants

Tomato plants were transformed and regenerated according to the published method by Ling and coworkers (Plant Cell Reports (1998), 17: 843-847). In the case of the variety *Microtom*, selection was carried out using a higher kanamycin concentration (100 mg/l).

Cotyledons and hypocotyls of seedlings seven to ten days old of the *Microtom* line were used as initial explant for the transformation. The culture medium of Murashige and Skoog (1962: Murashige and Skoog, 1962, Physiol. Plant 15, 473-) containing 2% sucrose, pH 6.1 was used for germination. Germination took place at 21° C. with low light (20-100 μE). After seven to ten days, the cotyledons were divided transversely, and the hypocotyls were cut into sections about 5-10 mm long and placed on the MSBN medium (MS, pH 6.1, 3% sucrose+1 mg/l BAP, 0.1 mg/l NM) which had been charged the previous day with suspension-cultivated tomato cells. The tomato cells were covered, free of air bubbles, with sterile filter paper. The explants were precultured on the described medium for three to five days. Cells of the *Agrobacterium tumefaciens* strain LBA4404 were transformed individually with the plasmids pS3FNR:NOST, pS3AP3:NOST, pS3FNR:NP196, pS3EPS:NP196, pS3FNR:NP195, pS3EPS:NP195, pS3FNR:NODK and pS3EPS:NODK. In each case, an overnight culture of the individual *Agrobacterium* strains transformed with the binary vectors pS3FNRNOST, pS3AP3NOST, pS3FNR:NP196, pS3EPS:NP196, pS3FNR:NP195, pS3EPS:NP195, pS3FNR:NODK and pS3EPS:NODK was cultured in YEB medium with kanamycin (20 mg/l) at 28° C., and the cells were centrifuged. The bacterial pellet was resuspended in liquid MS medium (3% sucrose, pH 6.1) and adjusted to an optical density of 0.3 (at 600 nm). The precultured explants were transferred into the suspension and incubated at room temperature with gentle shaking for 30 minutes. Subsequently, the explants were dried with sterile filter paper and returned to their preculture medium for the three-day coculture (21° C.).

After the coculture, the explants were transferred to MSZ medium (MS pH 6.1+3% sucrose, 2 mg/l zeatin, 100 mg/l kanamycin, 160 mg/l timentin) and stored for the selective regeneration at 21° C. under weak light conditions (20-100 μE, light rhythm 16 h/8 h). The explants were transferred every two to three weeks until shoots formed. It was possible to detach small shoots from the explant and root them on MS (pH 6.1+3% sucrose), 160 mg/l timentin, 30 mg/l kanamycin, 0.1 mg/l IAA. Rooted plants were transferred into the glasshouse.

According to the transformation method described above, the following lines were obtained with the expression constructs below:

obtained with pS3FNR:NOST were: MSP101-1, MSP101-2, MSP101-3 obtained with pS3AP3:NOST were: MSP103-1, MSP103-2, MSP103-3 obtained with pS3FNR:NP196 were: MSP105-1, MSP105-2, MSP105-3 obtained with pS3EPS:NP196 were: MSP107-1, MSP107-2, MSP107-3 obtained with pS3FNR:NP195 were: MSP109-1, MSP109-2, MSP109-3 obtained with pS3EPS:NP195 were: MSP111-1, MSP111-2, MSP111-3 obtained with pS3FNR:NODK were: MSP113-1, MSP113-2, MSP113-3 obtained with pS3EPS:NODK were: MSP115-1, MSP115-2, MSP115-3

EXAMPLE 16

Preparation of Transgenic *Tagetes* Plants

*Tagetes* seeds are sterilized and placed on germination medium (MS medium; Murashige and Skoog, Physiol. Plant. 15 (1962), 473-497) pH 5.8, 2% sucrose). Germination takes place in a temperature/light/time interval of 18-28° C./20-200 μE/3-16 weeks, but preferably at 21° C., 20-70 μE, for 4-8 weeks.

All leaves of the plants which have developed in vitro by then are harvested and cut transverse to the middle. The leaf explants resulting therefrom, with a size of 10-60 mm², are stored during the preparation in liquid MS medium at room temperature for not more than 2 h.

Any *Agrobacterium tumefaciens* strain, but preferably a supervirulent strain such as, for example, EHA105 with an appropriate binary plasmid which may harbor a selection marker gene (preferably bar or pat) and one or more trait or reporter genes (pS5FNR:NOST, pS5AP3:NOST, pS5FNR:NP196, pS5EPS:NP196, pS5FNR:NP195, pS5EPS:NP195, pS5FNR:NODK and pS5EPS:NODK) cultivated overnight and used for cocultivation with the leaf material. The bacterial strain can be cultured as follows: a single colony of the appropriate strain is inoculated in YEB (0.1% yeast extract, 0.5% beef extract, 0.5% peptone, 0.5% sucrose, 0.5% magnesium sulfate×7 H₂O) with 25 mg/l kanamycin and cultured at 28° C. for 16 to 20 h. The bacterial suspension is then harvested by centrifugation at 6000 g for 10 min and resuspended in liquid MS medium so as to result in an $OD_{600}$ of approx. 0.1 to 0.8. This suspension is used for cocultivation with the leaf material.

Immediately before the cocultivation, the MS medium in which the leaves have been stored is replaced with the bacterial suspension. Incubation of the leaves in the agrobacterial suspension took place at room temperature with gentle shaking for 30 min. The infected explants are then put on an MS medium solidified with agar (e.g. 0.8% Plant Agar (Duchefa, NL)), with growth regulators such as, for example, 3 mg/l benzylaminopurin (BAP) and 1 mg/l indolylacetic acid (IAA). The orientation of the leaves on the medium is immaterial. Cultivation of the explants takes place for 1 to 8 days, but preferably for 6 days, during which the following conditions can be applied: light intensity 30-80 μmol/m²×sec, temperature: 22-24° C., 16/8 hours light/dark alternation. The cocultivated explants are then transferred to fresh MS medium, preferably with the same growth regulators, this second medium additionally containing an antibiotic to suppress bacterial growth. Timentin in a concentration of 200 to 500 mg/l is very suitable for this purpose. The second selective component employed is one for selecting for successful transformation. Phosphinothricin in a concentration of 1 to 5 mg/l selects very efficiently, but other selective components according to the method to be used are also conceivable.

After one to three weeks in each case, the explants are transferred to fresh medium until plumules and small shoots develop, which are then transferred to the same basal medium including timentin and PPT or alternative components with growth regulators, namely, for example, 0.5 mg/l indolylbutyric acid (IBA) and 0.5 mg/l gibberillic acid $GA_3$, for rooting. Rooted shoots can be transferred into the glasshouse.

In addition to the method described, the following advantageous modifications are possible:

Before the explants are infected with the bacteria, they may be preincubated on the medium described above for cocultivation for 1 to 12 days, preferably 3-4. This is followed by infection, cocultivation and selective regeneration as described above.

The pH for regeneration (normally 5.8) may be lowered to pH 5.2. This improves control of agrobacterial growth.

Addition of $AgNO_3$ (3-10 mg/l) to the regeneration medium improves the condition of the culture, including the regeneration itself.

Components which reduce phenol formation and are known to the skilled worker, such as, for example, citric acid, ascorbic acid, PVP and many others, have beneficial effects on the culture.

Liquid culture medium may also be used for the whole method. The culture may also be incubated on commercially available supports which are positioned on the liquid medium.

According to the above-described transformation method, the following lines were obtained with the expression constructs below:

obtained with pS5FNR:NOST were, for example: MSP102-1, MSP102-2, MSP102-3 obtained with pS5AP3:NOST were, for example: MSP104-1, MSP104-2, MSP104-3 obtained with pS5FNR:NP196 were: MSP106-1, MSP106-2, MSP106-3 obtained with pS5EPS:NP196 were: MSP108-1, MSP108-2, MSP108-3 obtained with pS5FNR:NP195 were: MSP110-1, MSP110-2, MSP110-3 obtained with pS5EPS:NP1 95 were: MSP112-1, MSP112-2, MSP112-3 obtained with pS5FNR:NODK were: MSP114-1, MSP114-2, MSP114-3 obtained with pS5EPS:NODK were: MSP116-1, MSP116-2, MSP116-3

EXAMPLE 17

Characterization of the Transgenic Plant Flowers

EXAMPLE 9.1

Separation of Carotenoid Esters in Petals of Transgenic Plants

General Protocol:

The petals of the transgenic plants are ground in liquid nitrogen and the petal powder (about 40 mg) is extracted with 100% acetone (three times with 500 μl each). The solvent is evaporated and the carotenoids are resuspended in 100-200 μl of petroleum ether/acetone (5:1, v/v).

The carotenoids are fractionated in concentrated form by means of thin layer chromatography (TLC) on Silica60 F254 plates (Merck) in an organic solvent (petroleum ether/acetone; 5:1), according to their phobicity. Yellow (xanthophyll esters), red (ketocarotenoid esters) and orange bands (mixture of xanthophyll and ketocarotenoid esters) on the TLC are scraped out.

The carotenoids bound to silica are eluted three times with 500 μl of acetone, the solvent is evaporated and the carotenoids are fractionated and identified by means of HPLC.

It is possible to distinguish between mono- and diesters of carotenoids by means of a C30 reverse phase column. HPLC run conditions were virtually identical to those of a published method (Frazer et al. (2000), Plant Journal 24(4): 551-558). The following process conditions were set.

| Separating column: | Prontosil C30 column, 250 × 4.6 mm (Bischoff, Leonberg, Germany) |
|---|---|
| Flow rate: | 1.0 ml/min |
| Eluents: | eluent A - 100% methanol |
| | Eluent B - 80% methanol, 0.2% ammonium acetate |
| | Eluent C - 100% t-butyl methyl ether |

Gradient profile:

| Time | Flow rate | % eluent A | % eluent B | % eluent C |
|---|---|---|---|---|
| 12.0 | 1.0 | 95.0 | 5.0 | 0 |
| 12.1 | 1.0 | 80.0 | 5.0 | 15.0 |
| 22.0 | 1.0 | 76.0 | 5.0 | 19.0 |
| 22.0 | 1.0 | 66.5 | 5.0 | 28.5 |
| 38.0 | 1.0 | 15.0 | 5.0 | 80.0 |
| 45.0 | 1.0 | 95.0 | 5.0 | 0 |
| 46.0 | 1.0 | 95.0 | 5.0 | 0 |
| 46.1 | 1.0 | 95.0 | 5.0 | 0 |

Detection: 300-500 nm

It is possible to identify carotenoids on the basis of UV-VIS spectra.

Petal material of the transgenic tomato plants is ground and extracted with acetone. Extracted carotenoids are fractionated by means of TLC. In the lines, mono- and diesters of keto-carotenoids may be detected; the monoesters are present at a distinctly lower concentration than the diesters.

EXAMPLE 18

Enzymatic Hydrolysis of Carotenoid Esters and Identification of Carotenoids

General Protocol

Ground petal material (30-100 mg fresh weight) is extracted with 100% acetone (three times 500 μl; shaking for about 15 minutes each time). The solvent is evaporated. Carotenoids are then taken up in 495 μl of acetone and, after addition of 4.95 ml of potassium phosphate buffer (100 mM, pH 7.4), thoroughly mixed. This is followed by addition of about 17 mg of bile salts (Sigma) and 149 μl of an NaCl/$CaCl_2$ solution (3M NaCl and 75 mM $CaCl_2$). The suspension is incubated at 37° C. for 30 minutes. For the enzymatic hydrolysis of the carotenoid esters, 595 μl of a lipase solution (50 mg/ml lipase type 7 from *Candida rugosa* (Sigma)) are added and incubated at 37° C. with shaking. After about 21 hours, a further 595 μl of lipase are added, with renewed incubation at 37° C. for at least 5 hours. Then about 700 mg of $Na_2SO_4 \times 10H_2O$ are dissolved in the solution. After addition of 1800 μl of petroleum ether, the carotenoids are extracted into the organic phase by vigorous mixing. This extraction is repeated until the organic phase remains colorless. The petroleum ether fractions are combined and the petroleum ether is evaporated. Free carotenoids are taken up in 100-120 μl of acetone. Free carotenoids can be identified on the basis of retention time and UV-VIS spectra by means of HPLC and a C30 reverse phase column.

We claim:

1. A process for preparing ketocarotenoids by cultivating a genetically transformed plant which, compared with an untransformed wild type plant, has an introduced or increased ketolase activity caused by transformation with a polynucleotide encoding a ketolase comprising the amino acid sequence of SEQ ID NO: 2 or a sequence which is derived from this sequence by substitution, insertion or deletion of amino acids and which has an identity of at least 95% at the amino acid level with the sequence of SEQ ID NO: 2; wherein said transformed plant produces ketocarotenoids and the ketocarotenoids are harvested.

2. The process as claimed in claim 1, wherein the plant is additionally transformed with a polynucleotide encoding a polypeptide that introduces or increases the activity, compared with the untransformed wild type plant, of at least one of the activities selected from the group of hydroxylase activity and β-cyclase activity.

3. The process as claimed in claim 2, wherein the polynucleotide which encodes a hydroxylase comprises the amino acid sequence of SEQ ID NO: 16 or a sequence which is derived from this sequence by substitution, insertion or deletion of amino acids and which has an identity of at least 95% at the amino acid level with the sequence of SEQ ID NO: 16.

4. The process as claimed in claim 3, wherein the polynucleotide comprises the sequence of SEQ ID NO: 15.

5. The process as claimed in claim 2, wherein the polynucleotide which encodes a β-cyclase comprises the amino acid sequence of SEQ ID NO: 18 or a sequence which is derived from this sequence by substitution, insertion or deletion of amino acids and which has an identity of at least 95% at the amino acid level with the sequence of SEQ ID NO: 18.

6. The process as claimed in claim 5, wherein the polynucleotide comprises the sequence of SEQ ID NO: 17.

7. The process as claimed in claim 1, wherein a plant selected from the families Ranunculaceae, Berberidaceae, Papaveraceae, Cannahaceae, Rosaceac, Fabaceae, Linaceae, Vitaceae, Brassiceae, Cucurbitaceae, Primulaceac, Caryophyllaceae, Amaranthaceae, Gentianaceae, Geraniaceae, Caprifoliaceae, Oleaceae, Tropaeolaceae, Solanaceae, Scrophulariaccac, Asteraccue, Liliaceae, Amaryllidaceae, Poaceae, Orchidaceae, Malvaceae, Illiaceae or Lamiaceae is used as plant.

8. The process as claimed in claim 7, wherein a plant selected from the plant genera Marigold, Tagetes erecta, Tagetes patula, Acacia, Aconitum, Adunis, Amica, Aquilegia, Aster, Bignonia, Calendula, Caltha, Campanula, Canna, Centaurea, Cheiranthus, Chrysanthemum, Citrus, Crepis, Crocus, Curcurbita, Cytisus, Delonia, Delphinium, Dianthus, Dimorphotheca, Doronicum, Eschscholtzia, Forsythia, Fremontia, Gazania, Gelsemium, Genista, Gentiana, Geranium, Gerbera, Geum, Grevillea, Helenium, Helianthus, Hepatica, Heracleum, Hibiscus, Heliopsis, Hypericum, Hypochoeris, Impatiens, Iris, Jacaranda, Kerria, Laburnum, Lathyrus, Leontodon, Lilium, Linum, Lotus, Lycopersicon, Lysimachia, Maratia, Medicago, Mimulus, Narcissus, Oenothera, Osmanthus, Petunia, Photinia, Physalis, Phyteuma, Potentilla, Pyracantha, Ranunculus, Rhododendron, Rosa, Rudbeckia, Senecio, Silene, Silphium, Sinapsis, Sorbus, Spartium, Tecoma, Torenia, Tragopogon, Trollius, Tropaeolum, Tulipa, Tussilago, Ulex, Viola or Zinnia is used as plant.

9. The process as claimed in claim 1, wherein the ketocarotenoids are selected from the group of astaxanthin, canthaxanthin, echinenone, 3-hydroxyechinenone, 3'-hydroxyechinenone, adonirubin and adonixanthin.

10. The genetically transformed plant of claim 1.

11. The genetically transformed plant of claim 3.

12. The genetically transformed plant as claimed in claim 10, wherein the plant is selected from the families Ranunculaceae, Berberidaceae, Papaveraceae, Cannabaceae, Rosaceae, Fabaceae, Linaceae, Vitaceae, Brassiceae, Cucurbitaceae, Primulaceae, Caryophyllaceae, Amaranthaceae, Gentianaceae, Geraniaceae, Caprifoliaceae, Oleaceae, Tropaeolaceae, Solanaceae, Scrophulariaceac, Asteraceae, Liliaceae, Amaryllidaceae, Poaceae, Orchidaceae, Malvaceae, Illiaceae or Lamiaceac.

13. The genetically modified plant as claimed in claim 12, wherein the plants are selected from the plant genera Marigold, Tagetes erecta, Tagetes patula, Acacia, Aconitum, Adonis, Arnica, Aquilegia, Aster, Astragalus, Bignonia, Calendula, Caltha, Campanula, Canna, Centaurea, Cheiranthus, Chrysanthemum, Citrus, Crepis, Crocus, Curcurbita, Cytisus, Delonia, Delphinium, Dianthus, Dimorphotheca, Doronicum, Eschscholtzia, Forsythia, Fremontia, Gazania, Gelsemium, Genista, Gentiana, Geranium, Gerbera, Geum, Grevillea, Helenium, Helianthus, Hepatica, Heracleum, Hibiscus, Heliopsis, Hypericum, Hypochocris, Impatiena, Iris, Jacaranda, Kerria, Laburnum, Lathyrus, Leontodon, Lilium, Linuin, Lotus, Lycopersicon, Lysimachia, Maratia, Medicago, Mimulus, Narcissus, Oenothera, Osmanthus, Petunia, Photinia, Physalis, Phyteuma, Potentilla, Pyracantha, Ranunculus, Rhododendron, Rosa, Rudbeckia, Senecio, Silene, Silphium, Sinapsis, Sorbus, Spartium, Tecoma, Torenia, Tragopogon, Trollius, Tropaeolum, Tulipa, Tussilago, Ulex, Viola or Zinnia.

14. The genetically transformed plant as claimed in claim 10, where the plant is used as animal or human food.

15. The genetically transformed plant as claimed in claim 10, where the plant produces ketocarotenoid-containing extracts or animal or human food supplements.

16. The process as claimed in claim 7, wherein the plant is a plant from the family Asteraceae.

17. The process as claimed in claim 8, wherein the plant is Tagetes erecta.

18. The process as claimed in claim 1, wherein the nucleic acid encoding a ketolase comprises the amino acid sequence of SEQ ID NO: 2.

19. The process as claimed in claim 1, wherein the nucleic acids which encode ketolases comprise the amino acid sequence of SEQ ID NO: 2.

20. The process as claimed in claim 3, wherein the nucleic acids which encode a hydroxylase comprise the amino acid sequence of SEQ ID NO: 16.

21. The process as claimed in claim 5, wherein the nucleic acids which encode a β-cyclase comprise the amino acid sequence of SEQ ID NO: 18.

22. The genetically transformed plant of claim 5.

23. The genetically transformed plant as claimed in claim 11, where the plant is used as animal or human food.

24. The genetically transformed plant as claimed in claim 11, where the plant produces ketocarotenoid-containing extracts or animal or human food supplements.

25. The genetically transformed plant as claimed in claim 22, where the plant is used as animal or human food.

26. The genetically transformed plant as claimed in claim 22, where the plant produces ketocarotenoid-containing extracts or animal or human food supplements.

27. The genetically transformed plant as claimed in claim 11, wherein the plant is selected from the families Ranunculaceae, Berberidaceae, Papaveraceae, Cannabaceae, Rosaceae, Fabaceae, Linaceae, Vitaceae, Brassiceae, Cucurbitaceae, Primulaceae, Caryophyllaceae, Amaranthaceae, Gentianaceae, Geraniaceae, Caprifoliaceae, Oleaceae, Tropaeolaceae, Solanaceae, Scrophulariaceae, Asteraceae, Liliaceae, Amaryllidaceac, Poaceae, Orchidaceae, Malvaceae, Illiaceae or Lamiaceae.

28. The genetically modified plant as claimed in claim 27, wherein the plants are selected from the plant genera Marigold, Tagetes erecta, Tagetes patula, Acacia, Aconitum, Adonis, Amica, Aquilegia, Aster, Astragalus, Bignonia, Calendula, Caltha, Campanula, Canna, Centaurea, Cheiranthus, Chrysanthemum, Citrus, Crepis, Crocus, Curcurbita, Cytisus, Delonia, Delphinium, Dianthus, Dimorphotheca, Doronicum, Esch scholtzia, Forsythia, Fremontia, Gazania, Gelsemium, Genista, Gentiana, Geranium, Gerbera, Geum, Grevillea, Helenium, Helianthus, Hepatica, Heracleum, Hibiscus, Heliopsis, Hypericum, Hypochoeris, Impatiens, Iris, Jacaranda, Kerria, Laburnim, Lathyrus, Leontodon, Lilium, Linum, Lotus, Lycopersicon, Lysimachia, Maratia, Medicago, Mimulus, Narcissus, Oenothera, Osmanthus, Petunia, Photinia, Physalis, Phyteuma, Potentilla, Pyracantha, Ranunculus, Rhododendron, Rosa, Rudbeckia, Senecio, Silene, Silphium, Sinapsis, Sorbus, Spartium, Tecoma, Torenia, Tragopogon, Trollius, Tropaeolum, Tulipa, Tussilago, Ulex, Viola or Zinnia.

29. The genetically transformed plant as claimed in claim 22, wherein the plant is selected from the families Ranunculaceac, Berberidaceae, Papaveraceae, Cannabaceae, Rosaceae, Fabaceae, Linaceae, Vitaceac, Brassiceae, Cucurbitaceae, Primulaceae, Caryophyllaceae, Amaranthaceae, Gentianaoeae, Geraniaceae, Caprifoliaceae, Oleaceae, Tropaeolaceae, Solanaceae, Scrophulariaceae, Asteraceae, Liliaceae, Amaryllidaceae, Poaceae, Orchidaceae, Malvaceae, Illiaceae or Lamiaceae.

30. The genetically modified plant as claimed in claim 29, wherein the plants are selected from the plant genera Marigold, Tagetes erecta, Tagetes patula, Acacia, Aconitum, Adonis, Arnica, Aquilegia, Aster, Astragalus, Bignonia, Calendula, Caltha, Campanula, Canna, Centaurca, Cheiranthus, Chrysanthemum, Citrus, Crepis, Crocus, Curcubita, Cytisus, Delonia, Delphinium, Dianthus, Dimorphotheca, Doronicum, Eschscholtzia, Forsythia, Fremontia, Gazania, Gelsemium, Genista, Gentiana, Geranium, Gerbera, Geum, Grevillea, Helenium, Helianthus, Hepatica, Heracleum, Hibiscus, Heliopsis, Hypericum, Hypochoeris, Impatiens, Iris, Jacaranda, Kerria, Laburnum, Lathyrus, Leontodon, Lilium, Linum, Lotus, Lycopersicon, Lysimachia, Maratia, Medicago, Mimulus, Narcissus, Oenothera, Osmanthus, Petunia, Photinia, Physalis, Phyteuma, Potentilla, Pyracantha, Ranunculus, Rhododendron, Rosa, Rudbeckia, Senecio, Silene, Silphium, Sinapsis, Sorbus, Spartium, Tecoma, Torenia, Tragopogon, Trollius, Tropaeolum, Tulipa, Tussilago, Ulex, Viola or Zinnia.

\* \* \* \* \*